United States Patent
Vasudevan et al.

(10) Patent No.: US 6,531,599 B2
(45) Date of Patent: Mar. 11, 2003

(54) COMPOUNDS HAVING ACTIVITY AS INHIBITORS OF CYTOCHROME P450RAI

(75) Inventors: Jayasree Vasudevan, Irvine, CA (US); Alan T. Johnson, San Diego, CA (US); Dehua Huang, San Diego, CA (US); Roshantha A. Chandraratna, Laguna Hills, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 10/004,914

(22) Filed: Dec. 5, 2001

(65) Prior Publication Data

US 2002/0193578 A1 Dec. 19, 2002

Related U.S. Application Data

(62) Division of application No. 09/829,098, filed on Apr. 9, 2001, now Pat. No. 6,359,135, which is a division of application No. 09/651,235, filed on Aug. 29, 2000, now Pat. No. 6,252,090.

(51) Int. Cl.[7] .................. C07D 237/08; C07D 403/06; C07D 215/02
(52) U.S. Cl. ................ 544/230; 544/333; 544/405; 546/165; 546/166
(58) Field of Search .................. 544/230, 333, 544/405; 546/165, 166; 534/775

(56) References Cited

U.S. PATENT DOCUMENTS

| | | | |
|---|---|---|---|
| 4,740,519 A | 4/1988 | Shroot et al. | 514/443 |
| 4,826,984 A | 5/1989 | Berlin et al. | 546/134 |
| 4,980,369 A | 12/1990 | Chandraratna | 514/432 |
| 5,015,658 A | 5/1991 | Chandraratna | 514/432 |
| 5,023,341 A | 6/1991 | Chandraratna | 549/23 |
| 5,037,825 A | 8/1991 | Klaus et al. | 514/233.8 |
| 5,045,551 A | 9/1991 | Chandraratna | 514/337 |
| 5,089,509 A | 2/1992 | Chandraratna | 514/337 |
| 5,130,335 A | 7/1992 | Chandraratna | 514/510 |
| 5,134,159 A | 7/1992 | Chandraratna | 514/456 |
| 5,149,705 A | 9/1992 | Chandraratna | 514/356 |
| 5,264,578 A | 11/1993 | Chandraratna | 546/269 |
| 5,346,895 A | 9/1994 | Chandraratna | 514/247 |
| 5,346,915 A | 9/1994 | Chandraratna | 514/432 |
| 5,399,561 A | 3/1995 | Chandraratna | 514/252 |
| 5,455,265 A | 10/1995 | Chandraratna | 514/448 |
| 5,466,861 A | 11/1995 | Dawson et al. | 560/100 |
| 5,616,597 A | 4/1997 | Chandraratna | 514/365 |
| 5,648,503 A | 7/1997 | Vuligonda et al. | 549/13 |
| 5,663,347 A | 9/1997 | Chandraratna | 546/152 |
| 5,675,024 A | 10/1997 | Teng et al. | 549/405 |
| 5,723,666 A | 3/1998 | Vuligonda et al. | 564/253 |
| 5,773,594 A | 6/1998 | Johnson et al. | 534/298 |
| 5,952,345 A | 9/1999 | Klein et al. | 514/311 |
| 5,965,606 A | 10/1999 | Teng et al. | 514/456 |
| 6,025,388 A | 2/2000 | Nagpal et al. | 514/460 |
| 6,291,677 B1 * | 9/2001 | Vasudevan et al. | 546/165 |
| 6,303,785 B1 * | 10/2001 | Vasudevan et al. | 546/144 |
| 6,369,261 B1 * | 4/2002 | Johnson et al. | 560/59 |

FOREIGN PATENT DOCUMENTS

| | | | | |
|---|---|---|---|---|
| DE | 3316932 | 11/1983 | | C07D/311/58 |
| DE | 3708060 | 9/1987 | | C07D/311/04 |
| EP | 0130795 | 1/1985 | | C07D/311/58 |
| WO | 85/00806 | 2/1985 | | C07C/69/78 |
| WO | 93/11755 | 6/1993 | | A61K/31/07 |

OTHER PUBLICATIONS

Kuijper, et al., "The effects of oral liarozole on epidermal proliferation and differentiation in severe plaque psoriasis are comparable with those of acitretin", *British Journal of Dermatology*, (1998) 139: pp 380–389.

Kang, et al., "Liarozole Inhibits Human Epidermal Retinoid Acid 4–Hydroxylase Activity and Differentially Augments Human Skin Responses to Retinoic Acid and Retinol In Vivo", *The Journal of Investigative Dermatology*, (Aug. 1996) vol. 107, No. 2: pp 183–187.

VanWauwe, et al., "Liarozole, an Inhibitor of Retinoic Acid Metabolism, Exerts Retinoid–Mimetic Effects in Vivo", *The Journal of Pharmacology and Experimental Therapeutics*, (1992) vol. 261, No. 2: pp 773–779.

De Porre, et al., "Second Generation Retinoic Acid Metabolism Blocking Agent (Ramba) R116010: Dose Finding in Healthy Male Volunteers", University of Leuven, Belgium, pp 30. (1993).

VanWauwe, et al., "Ketoconazole Inhibits the in Vitro and in Vivo Metabolism of All–Trans–Retinoic Acid", *The Journal of Pharmacology and Experimental Therapeutics*, (1988) vol. 245, No. 2: pp 718–722.

White, et al., "cDNA Cloning of Human Retinoic Acid–metabolizing Enzyme (hP450RAI) Identifies a Novel Family of Cytochromes P450 (CYP26)*", *The Journal of Biological Chemistry*, (1997) vol. 272, No. 30, Issue of Jul. 25 pp 18538–18541.

(List continued on next page.)

Primary Examiner—Cecilia Tsang
Assistant Examiner—Ebenezer Sackey
(74) Attorney, Agent, or Firm—Gabor L. Szekeres; Carlos A. Fisher; Martin A. Voet

(57) ABSTRACT

Compounds having Formula 1 wherein the symbols have the meaning defined in the specification are inhibitors of the cytochrome P450RAI (retinoic acid inducible) enzyme, and are used for treating diseases responsive to treatment by retinoids.

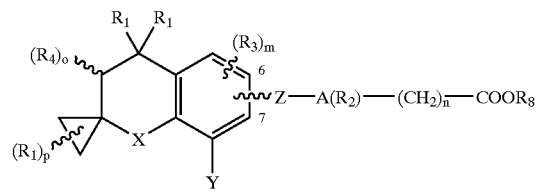

Formula 1

13 Claims, 1 Drawing Sheet

OTHER PUBLICATIONS

Figure 1:
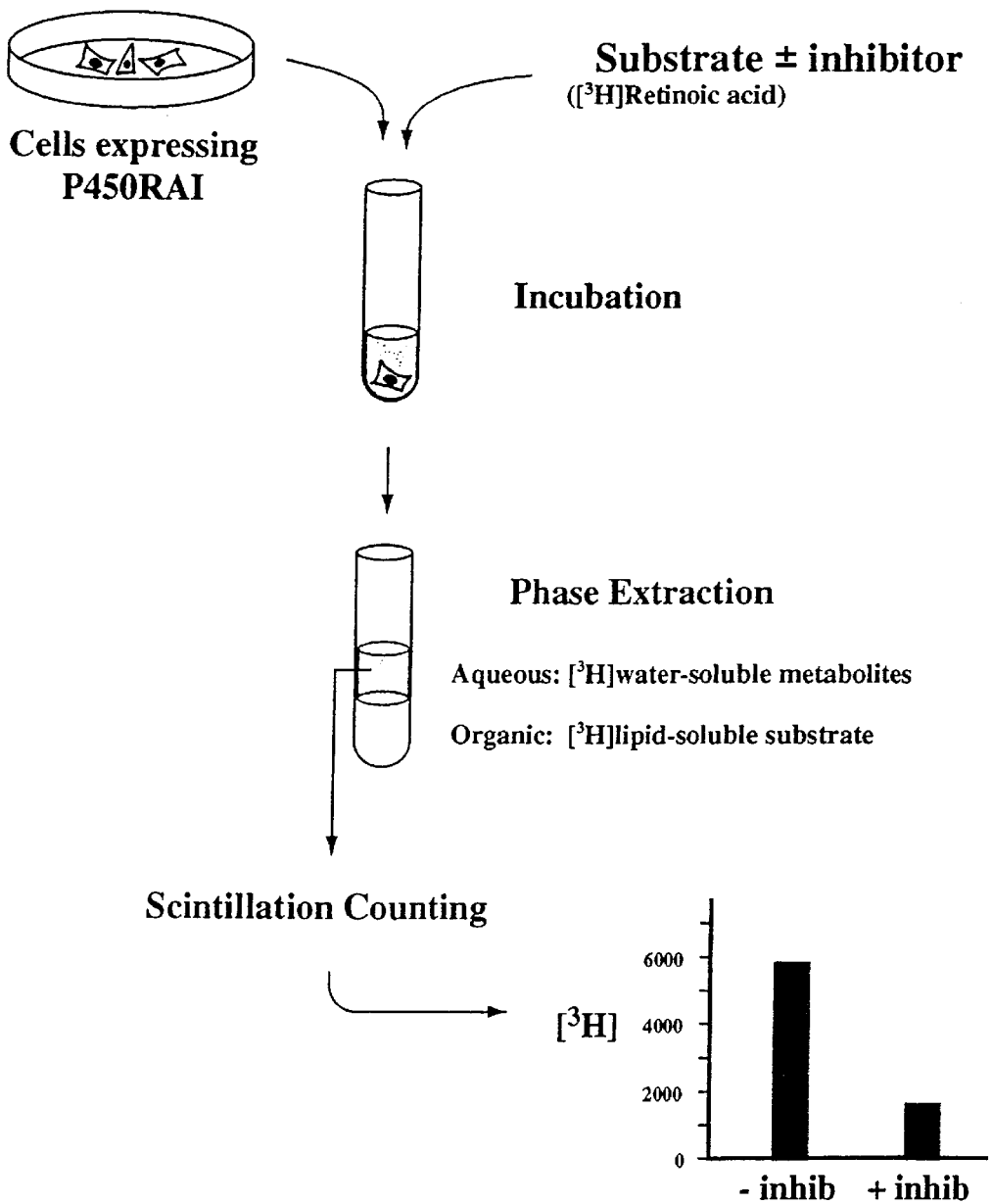

Hanzlik, et al., "Cyclopropylamines as Suicide Substrates for Cytochromes P450RAI", *Journal of Medicinal Chemistry* (1979), vol. 22, No. 7, pp 759–761.

Ortiz de Montellano, "Topics in Biology—The Inactivation of Cytochrome P450RAI", *Annual Reports in Medicinal Chemistry*, (1984), Chapter 20, pp 201–210.

Hanzlik, et al., "Suicidal Inactivation of Cytochrome P450RAI by Cyclopropylamines Evidence for Cation–Radical Intermediates", *J. Am. Chem. Soc.,* (1982), vol. 104, No. 107, pp. 2048–2052.

Dawson, et al., "Chemistry and Biology of Synthetic Retinoids", published by *CRC Press, Inc.,* (1990), pp. 324–356.

Bligh et al., (1959) Canadian Journal of Biochemistry 37, pp. 911–917.

Feigner P. L. and Holm M. (1989) Focus, 112.

Heyman, et al., Cell 68, 397–406 (1992).

Allegretto, et al., J. Biol. Chem. 268, 26625–26633. (1993).

Mangelsdorf, et al., The Retinoids: Biology, Chemistry and Medicine, pp 319–349, Raven Press Ltd., New York. (1994).

Cheng, et al., Biochemical Pharmacology vol. 22 pp 3099–3108. (1973).

Standeven et al., "Specific antagonist of retinoid toxicity in mice", *Toxicol. Appl. Pharmacol.* 138: 169–175, (1996).

Thacher, et al., "Receptor specificity of retinoid–induced hyperplasia. Effect of RXR–selective agonist and correlation with topical irritation", *J. Pharm. Exp. Ther.,* 282:528–534 (1997).

* cited by examiner

COMPOUNDS HAVING ACTIVITY AS INHIBITORS OF CYTOCHROME P450RAI

CROSS-REFERENCE TO RELATED APPLICATION

The present application is a divisional of application Ser. No. 09/829,098, filed on Apr. 9, 2001 now U.S. Pat. No. 6,359,135 which is a divisional of application Ser. No. 09/651,235 filed on Aug. 29, 2000, now U.S. Pat. No. 6,252,090.

BACKGROUND OF THE INVENTION

1. Field of the Invention

The present invention is directed to novel compounds which inhibit the enzyme cytochrome P450RAI. More particularly, the present invention is directed to compounds many of which are derivatives of phenylacetic or heteroarylacetic acid, and which inhibit the enzyme cytochrome P450RAI. Several compounds of the invention that have an inhibitory effect on the enzyme cytochrome P450RAI include a cyclopropyl aryl, cyclopropylheteroaryl, cyclopropylaminoaryl, or (1-imidazolyl) methylaryl structure.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

Several compounds having retinoid-like activity are actually marketed under appropriate regulatory approvals in the United States of America and elsewhere as medicaments for the treatment of several diseases responsive to treatment with retinoids. Retinoic acid (RA) itself is a natural product, biosynthesized and present in a multitude of human and mammalian tissues and is known to play an important rule in the regulation of gene expression, tissue differentiation and other important biological processes in mammals including humans. Relatively recently it has been discovered that a catabolic pathway in mammals, including humans, of natural retinoic acid includes a step of hydroxylation of RA catalyzed by the enzyme Cytochrome P450RAI (retinoic acid inducible).

Several inhibitors of CP450RAI have been synthesized or discovered in the prior art, among the most important ones ketoconazole, liarozole and R116010 are mentioned. The chemical structures of these prior art compounds are provided below. It has also been noted in the prior art, that administration to mammals, including humans, of certain inhibitors of CP-450RAI results in significant increase in endogeneous RA levels, and further that treatment with CP450RAI inhibitors, for example with liarozole, gives rise to effects similar to treatment by retinoids, for example amelioration of psoriasis.

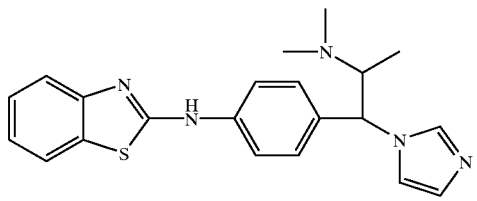

R116010

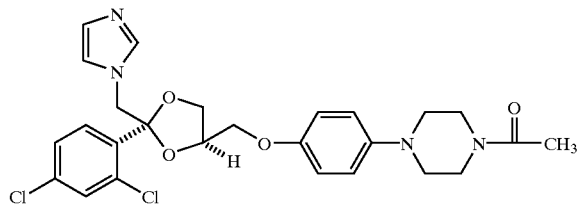

KETOCONAZOLE

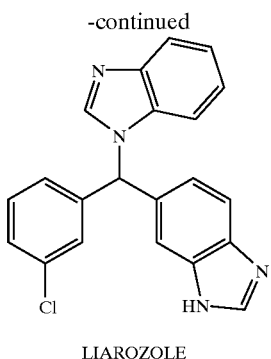

LIAROZOLE

The following publications describe or relate to the above-summarized role of CP450RAI in the natural catabolism of RA, to inhibitors of CP-450RAI and to in vitro and in vivo experiments which demonstrate that inhibition of CP450RAI activity results in a increases endogeneous RA levels and potential therapeutic benefits:

Kuijpers, et al., "The effects of oral liarozole on epidermal proliferation and differentiation in severe plaque psoriasis are comparable with those of acitretin", *British Journal of Dermatology*, (1998) 139: pp 380–389.

Kang, et al., "Liarozole Inhibits Human Epidermal Retinoid Acid 4-Hydroxylase Activity and Differentially Augments Human Skin Responses to Retinoic Acid and Retinol In Vivo", *The Journal of Investigative Dermatology*, (August 1996) Vol.107, No.2: pp 183–187.

Van Wauwe, et al., "Liarozole, an Inhibitor of Retinoic Acid Metabolism, Exerts Retinoid-Mimetic Effects in Vivo", *The Journal of Pharmacology and Experimental Therapeutics*, (1992) Vol. 261, No 2: pp 773–779.

De Porre, et al., "Second Generation Retinoic Acid Metabolism Blocking Agent (Ramba) R116010: Dose Finding in Healthy Male Volunteers", University of Leuven, Belgium, pp 30.

Wauwe, et al., "Ketoconazole Inhibits the in Vitro and in Vivo Metabolism of All-Trans-Retinoic Acid", *The Journal of Pharmacology and Experimental Therapeutics*, (1988) Vol. 245, No. 2: pp 718–722.

White, et al., "cDNA Cloning of Human Retinoic Acid-metabolizing Enzyme (hP450RAI) Identifies a Novel Family of Cytochromes P450 (CYP26)*", *The Journal of Biological Chemistry*, (1997) Vol. 272, No. 30, Issue of July 25 pp 18538–18541.

Hanzlik, et al., "Cyclopropylamines as Suicide Substrates for Cytochromes P450RAI", *Journal of Medicinal Chemistry* (1979), Vol. 22, No. 7, pp 759–761.

Ortiz de Montellano, "Topics in Biology—The Inactivation of Cytochrome P450RAI", *Annual Reports in Medicinal Chemistry*, (1984), Chapter 20, pp 201–210.

Hanzlik, et al. "Suicidal Inactivation of Cytochrome P450RAI by Cyclopropylamines> Evidence for Cation-Radical Intermediates", *J. Am. Chem. Soc.*, (1982), Vol. 104, No. 107, pp. 2048–2052.

The present invention provides several new chemical compounds which act as inhibitors of CP450RAI, and as such potentially provide therapeutic benefit in the treatment or prevention of the diseases and conditions which respond to treatment by retinoids and or which in healthy mammals, including humans, are controlled by natural retinoic acid. The perceived mode of action of these compounds is that by inhibiting the enzyme CP450RAI that catabolyzes natural RA, endogenous RA level is elevated to a level where desired therapeutic benefits are attained. The chemical structures of the compounds of the invention and of compounds with similar biological activity are summarized by Formulas 1 through 8 which are provided in the Summary Section of this application for patent. Based on these chemical structures the following art is of interest as background to the novel structures of Formula 1.

U.S. Pat. Nos. 5,965,606; 6,025,388; 5,773,594; 5,675,024; 5,663,347; 5,045,551; 5,023,341; 5,264,578; 5,089,509; 5,616,712; 5,134,159; 5,346,895; 5,346,915; 5,149,705; 5,399,561; 4,980,369; 5,015,658; 5,130,335; 4,740,519; 4,826,984; 5,037,825; 5,466,861; WO 85/00806; EP 0 130,795; DE 3316932; DE 3708060; Dawson, et al. "Chemistry and Biology of Synthetic Retinoids", published by CRC Press. Inc., (1990), pages 324–356; are of interest to compounds of Formula 1.

SUMMARY OF THE INVENTION

The present invention relates to compounds of Formula 1. The remaining formulas in this Summary section are of compounds having the same or similar biological activity. Those compounds are disclosed herein because their preparation involves synthetic routes, which are illustrative of synthetic methodology that can be used as appliable for the synthesis of the compounds of Formula 1 as well.

Formula 1

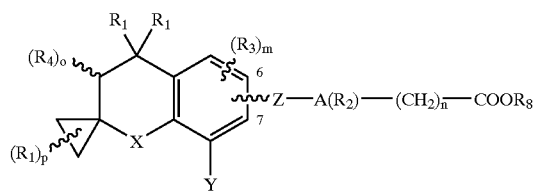

wherein

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S or NR where R is H, alkyl of 1 to 6 carbons or benzyl;

Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 3 to 6 carbons, Cl, Br, or I;

Z is
—C≡C—,
—(CR$_1$=CR$_1$)$_n$—, where n' is an integer having the value 1–5,
—CO—NR$_1$—,
NR$_1$—CO—;
—CO—O—,
—O—CO—,
—CS—NR$_1$—,
NR$_1$—CS—,
—CO—S—,
—S—CO—,
—N=N—;

$R_1$ is independently H or alkyl of 1 to 6 carbons;

p is an integer having the values of 0 to 4;

$R_2$ is independently H, alkyl of 1 to 6 carbons, F, Cl, Br, I, $CF_3$, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 2;

$R_4$ is independently H, alkyl of 1 to 6 carbons, or F; fluorosubstituted alkyl of 1 to 6 carbons, or halogen;

o is an integer having the values of 0 to 2;

n is an integer having the values of 0 to 4, and $R_8$ is H, alkyl of 1 to 6 carbons, —CH$_2$O(C$_{1-6}$-alkyl), or a cation of a pharmaceutically acceptable base.

Compounds of Formula 2 are disclosed

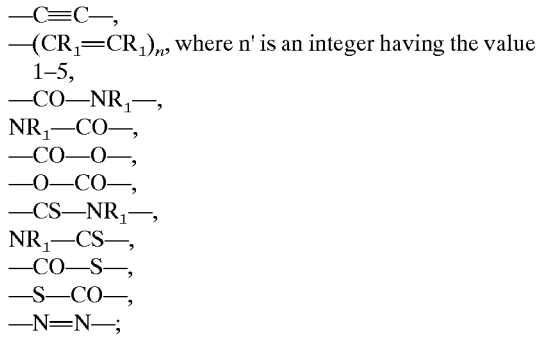

Formula 2 wherein

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S or NR where R is H, alkyl of 1 to 6 carbons or benzyl;

Z is
—C≡C—,
—(CR$_1$=CR$_1$)$_{n'}$, where n' is an integer having the value 1–5,
—CO—NR$_1$—,
NR$_1$—CO—,
—CO—O—,
—O—CO—,
—CS—NR$_1$—,
NR$_1$—CS—,
—CO—S—,
—S—CO—,
—N=N—;

$R_1$ is independently H or alkyl of 1 to 6 carbons;

p is an integer having the values of 0 to 4;

$R_2$ is independently H, alkyl of 1 to 6 carbons, F, Cl, Br, I, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 4;

$R_5$ is H, alkyl of 1 to 6 carbons, fluorosubstituted alkyl of 1 to 6 carbons, benzyl, or lower alkyl or halogen substituted benzyl;

n is an integer having the values of 0 to 4, and $R_8$ is H, alkyl of 1 to 6 carbons, —CH$_2$O(C$_{1-6}$-alkyl), or a cation of a pharmaceutically acceptable base.

Compounds of Formula 3 are disclosed

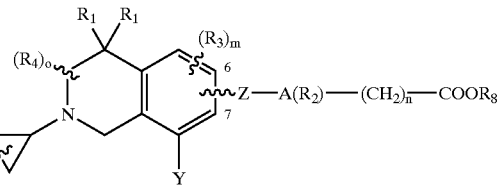

Formula 3 wherein

A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 1 to 6 carbons, Cl, Br, or I;

Z is
—C≡C—,
—(CR$_1$=CR$_1$)$_{n'}$, where n' is an integer having the value 1–5,
—CO—NR$_1$—,
NR$_1$—CO—,
—CO—O—,
—O—CO—,
—CS—NR$_1$—,
NR$_1$—CS—,
—CO—S—,
—S—CO—,
—N=N—;

$R_1$ is independently H or alkyl of 1 to 6 carbons;

p is an integer having the values of 0 to 5;

$R_2$ is independently H, alkyl of 1 to 6 carbons, F, Cl, Br, I, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 2;

$R_4$ is independently H, alkyl of 1 to 6 carbons, or F; fluorosubstituted alkyl of 1 to 6 carbons, or halogen;

o is an integer having the values of 0 to 4;

n is an integer having the values of 0 to 4, and $R_8$ is H, alkyl of 1 to 6 carbons, —CH$_2$O(C$_{1-6}$-alkyl), or a cation of a pharmaceutically acceptable base.

Compounds of Formula 4 are disclosed

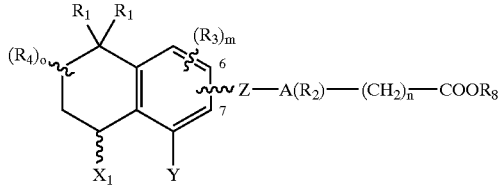

Formula 4 wherein
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

$X_1$ is 1-imidazolyl, or lower alkyl or halogen substituted 1-imidazolyl, OR, SR, $NRR_6$ where R is H, alkyl of 1 to 6 carbons or benzyl;

Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 3 to 6 carbons, Cl, Br, or I;

Z is
—C≡C—,
—$(CR_1=CR_1)_{n'}$, where n' is an integer having the value 1–5,
—CO—$NR_1$—,
$NR_1$—CO—,
—CO—O—,
—O—CO—,
—CS—$NR_1$—,
$NR_1$—CS—,
—CO—S—,
—S—CO—,
—N=N—;

$R_1$ is independently H or alkyl of 1 to 6 carbons;

$R_2$ is independently H, alkyl of 1 to 6 carbons, F, Cl, Br, I, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 2;

$R_4$ is independently H, alkyl of 1 to 6 carbons, or F; fluorosubstituted alkyl of 1 to 6 carbons, or halogen;

o is an integer having the values of 0 to 4;

$R_6$ is H, lower alkyl, cycloalkyl of 3 to 6 carbons, lower alkyl substituted cycloalkyl of 3 to 6 carbons;

n is an integer having the values of 0 to 4, and $R_8$ is H, alkyl of 1 to 6 carbons, —$CH_2O(C_{1-6}$-alkyl), or a cation of a pharmaceutically acceptable base, with the proviso that when Y is H, A is phenyl and $X_1$ is OH then n is 1 to 4.

Compounds of Formula 5 are disclosed

Formula 5

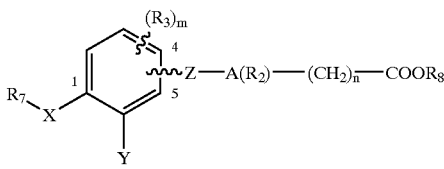

wherein
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

X is O, S or NR where R is H, alkyl of 1 to 6 carbons, $C_{1-6}$-trialkylsilyl or benzyl;

Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 3 to 6 carbons, Cl, Br, or I;

Z is
—C≡C—,
—$(CR_1=CR_1)_{n'}$, where n' is an integer having the value 1–5,
—CO—$NR_1$—,
$NR_1$—CO—,
—CO—O—,
—O—CO—,
—CS—$NR_1$—,
$NR_1$—CS—,
—CO—S—,
—S—CO—,
—N=N—;

$R_1$ is independently H or alkyl of 1 to 6 carbons;

$R_2$ is independently H, alkyl of 1 to 6 carbons, F, Cl, Br, I, fluoro substituted alkyl of 1 to 6 carbons, alkoxy of 1 to 6 carbons, or alkylthio of 1 to 6 carbons;

$R_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 3;

$R_7$ is H, alkyl of 1 to 6 carbons, cycloalkyl of 3 to 6 carbons or lower alkyl substituted cycloalkyl of 1 to 6 carbons;

n is an integer having the values of 1 to 4, and $R_8$ is H, alkyl of 1 to 6 carbons, —$CH_2O(C_{1-6}$-alkyl), or a cation of a pharmaceutically acceptable base.

Compounds of Formula 6 are disclosed

Formula 6

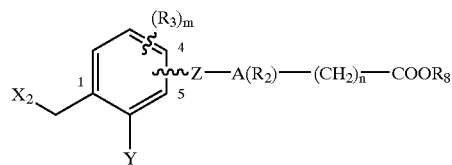

wherein
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two $R_2$ groups;

$X_2$ is 1-imidazolyl, lower alkyl or halogen substituted 1-imidazolyl, $OR_7$, $SR_7$ or $NRR_7$ where R is H, alkyl of 1 to 6 carbons or benzyl;

Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 3 to 6 carbons, Cl, Br, or I;

Z is
—C≡C—,
—$(CR_1=CR_1)_{n'}$, where n' is an integer having the value 1–5,
—CO—$NR_1$—,
$NR_1$—CO—,
—CO—O—,
—O—CO—, —CS—NR$_1$—,
NR$_1$—CS—,
—CO—S—,
—S—CO—,
—N=N—;
R$_1$ is independently H or alkyl of 1 to 6 carbons;
R$_2$ is independently H, alkyl of 1 to 6 carbons, F, Cl, Br, I, fluoro substituted alkyl of 1 to 6 carbons, alkoxy of 1 to 6 carbons, or alkylthio of 1 to 6 carbons;
R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;
m is an integer having the values 0 to 3;
R$_7$ is H, alkyl of 1 to 6 carbons, cycloalkyl of 3 to 6 carbons, lower alkyl substituted cycloalkyl of 3 to 6 carbons or C$_{1-6}$-trialkylsilyl.
n is an integer having the values of 0 to 4, and
R$_8$ is H, alkyl of 1 to 6 carbons, —CH$_2$O(C$_{1-6}$-alkyl), or a cation of a pharmaceutically acceptable base.
Compounds of Formula 7 are disclosed Formula 7

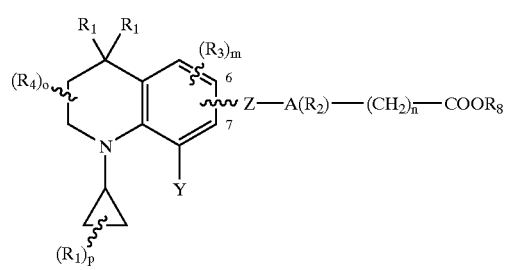

wherein
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;
Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 3 to 6 carbons, F, Cl, Br, or I;
Z is
—C≡C—,
—(CR$_1$=CR$_1$)$_{n'}$, where n' is an integer having the value 1–5,
—CO—NR$_1$—,
NR$_1$—CO—,
—CO—O—,
—O—CO—,
—CS—NR$_1$—,
NR$_1$—CS—,
—CO—S—,
—S—CO—,
—N=N—;
R$_1$ is independently H or alkyl of 1 to 6 carbons;
p is an integer having the values of 0 to 5;
R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;
R$_3$ is independently alkyl of 1 to 6 carbons, F, Cl, Br, I, CF$_3$, fluoro substituted alkyl of 1 to 6 carbons, OH, SH, alkoxy of 1 to 6 carbons, alkylthio of 1 to 6 carbons or benzyl;

m is an integer having the values 0 to 2;
R$_4$ is independently H, alkyl of 1 to 6 carbons, or F; fluorosubstituted alkyl of 1 to 6 carbons, or halogen;
o is an integer having the values of 0 to 4;
n is an integer having the values of 0 to 4, and
R$_8$ is H, alkyl of 1 to 6 carbons, —CH$_2$O(C$_{1-6}$-alkyl), or a cation of a pharmaceutically acceptable base.
Compounds of Formula 8 are disclosed Formula 8

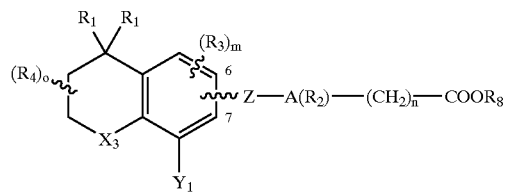

wherein
A is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R$_2$ groups;
X$_3$ is S, or O, C(R$_1$)$_2$, or CO;
Y$_1$ is H, lower alkyl of 1 to 6 carbons, cycloalkyl of 3 to 6 carbons, benzyl, lower alkyl substituted cycloalkyl of 3 to 6 carbons;
Z is
—C≡C—,
—(CR$_1$=CR$_1$)$_{n'}$, where n' is an integer having the value 1–5,
—CO—NR$_1$—,
NR$_1$—CO—,
—CO—O—,
—O—CO—,
—CS—NR$_1$—,
NR$_1$—CS—,
—CO—S—,
—S—CO—,
—N=N—;
R$_1$ is independently H or alkyl of 1 to 6 carbons;
R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;
R$_3$ is independently alkyl of 1 to 6 carbons, F, Cl, Br, I, CF$_3$, fluoro substituted alkyl of 1 to 6 carbons, OH, SH, alkoxy of 1 to 6 carbons, alkylthio of 1 to 6 carbons or benzyl;
m is an integer having the values 0 to 2;
R$_4$ is independently H, alkyl of 1 to 6 carbons, or F; fluorosubstituted alkyl of 1 to 6 carbons, or halogen;
o is an integer having the values of 0 to 4;
n is an integer having the values of 0 to 4, and
R$_8$ is H, alkyl of 1 to 6 carbons, —CH$_2$O(C$_{1-6}$-alkyl), or a cation of a pharmaceutically acceptable base, the compound meeting at least one of the provisos selected from the group consisting of:
Y$_1$ is cycloalkyl,
when Y$_1$ is not cycloalkyl then X$_3$ is O or S and n is 1,
when Y$_1$ is not cycloalkyl then X$_3$ is CO, and n is 1,
when Y$_1$ is not cycloalkyl then X$_3$ is CO and the moiety A is substituted with at least one F group.

In a second aspect, this invention relates to the use of the compounds of Formula 1 for the prevention or treatment of diseases and conditions in mammals, including humans, which diseases or conditions are prevented, treated, ameliorated, or the onset of which is delayed by administration of retinoid compounds or by the mammalian organism's naturally occurring retinoic acid. Because the compounds act as inhibitors of the breakdown of retinoic acid, the invention also relates to the use of the compounds of Formula 1 in conjunction with retinoic acid or other retinoids. In this regard it is noted that retionoids are usefull for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The retinoids are also useful for the prevention and treatment of metabolic diseases such as type II non-insulin dependent diabetes mellitus (NIDDM) and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. Retinoids can also be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoids include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

This invention also relates to a pharmaceutical formulation comprising one or more compounds of Formula 1 in admixture with a pharmaceutically acceptable excipient, said formulation being adapted for administration to a mammal, including a human being, to treat or alleviate the conditions which were described above as treatable by retinoids, or which are controlled by or responsive to the organism's native retinoic acid. These formulations can also be co-administered with retinoids to enhance or prolong the effects of medications containing retinoids or of the organism's native retinoic acid.

BRIEF DESCRIPTION OF THE DRAWING FIGURE

FIG. 1 is a schematic representation of the P450RAI cell based assay utilized to evaluate the ability of the compounds of the invention to inhibit the Cytochrome P450RAI enzyme.

Biological Activity, Modes of Administration
P450RAI-1 Cell-Based Inhibitor Assay FIG. 1 shows a schematic diagram of the P450RAI-1 cell based assay. P450RAI-1 stably transfected HeLa cells are maintained in 100 millimolar tissue culture dishes in Modified Eagle's Medium (MEM) containing 10% Fetal Bovine Serum (FBS) and 100 µg/ml hygromycin. Exponentially growing cells are harvested by incubating in trypsin. Cells are then washed with 1× Phosphate Buffered Saline (PBS) and plated in a 48-well plate at $5\times10^5$ cells in 0.2 ml MEM medium containing 10% FBS and 0.05 µCi [$^3$H]-RA in the presence or absence of increasing concentrations of the test compounds. The compounds are diluted in 100% DMSO and then added in triplicate wells at either 10, 1 or 0.1 µM final concentration. As a positive control for RA metabolism inhibition, cells are also incubated with ketoconazole at 100, 10 and 1 µM. Cell are incubated for 3 hours at 37° C. The retinoids are then extracted using the procedure of Bligh et al. (1959) Canadian Journal of Biochemistry 37, 911–917, modified by using methylenechloride instead of chloroform. The publication Bligh et al. (1959) Canadian Journal of Biochemistry 37, 911–917 is specifically incorporated herein by reference. The water soluble radioactivity is quantified using a β-scintillation counter. $IC_{50}$ values represent the concentration of inhibitor required to inhibit all-trans-RA metabolism by 50 percent and are derived manually from log-transformed data. The $IC_{50}$ values obtained in this assay several preferred compounds of the invention are disclosed in Table 1 below.

Assays of Retinoid-like or Retinoid Antagonist and Inverse Agonist-like Biological Activity Assays described below measure the ability of a compound to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR_\beta$, and $RXR_\gamma$ receptors, and the ability or inability of the compounds to activate transcription of a reporter gene through these receptor subtypes can be tested.

As far as specific assays are concerned, a chimeric receptor transactivation assay which tests for agonist-like activity in the $RAR_\alpha$, $RAR_\beta$ and $RAR_\gamma$, receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference. The numeric results obtained with several preferred compounds of this invention in this assay are shown below in Table 1. These data demonstrate that generally speaking the compounds are not agonists (or only weak agonists) of RAR retinoic receptors, and also that they do not bind, or in some cases bind only weakly to RAR retinoid receptors.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

The results if the ligand binding assay for several preferred compounds of the invention are included in Table 1. In the holoreceptor transactivation assay, tested for $RXR_\alpha$, $RXR_\beta$, and $RXR_\gamma$ receptors, the compounds of the present invention are, generally speaking, entirely devoid of activity, demonstrating that the compounds of the invention do not act as RXR agonists.

TABLE 1

| Compound # | General Formula | Table #[1] | RAR $EC_{50}$/ (EFFICACY)/$K_d$nM α | β | γ | P450RAI INHIBITION DATA INTACT HELA $IC_{50}$μM |
|---|---|---|---|---|---|---|
| 110 | 2 | 3 | NA<br>(44)<br>2058 | 74<br>(42)<br>409 | 262<br>>10K | >10 |
| 112 | 2 | 3 | NA<br>5853 | 335<br>(37)<br>704 | NA<br>685 | >10 |
| 3 | 4 | 5 | 280<br>(28)<br>145 | 4.8<br>(54)<br>0.8 | 9.8<br>(52)<br>158 | 3 |
| 114 | 2 | 3 | NA<br>>10K | NA<br>>10K | NA<br>>10K | >10 |
| 108 | 2 | 3 | 6.6<br>(15)<br>21K | 283<br>(36)<br>547 | 141<br>(10)<br>13K | >10 |
| 116 | 2 | 3 | NA<br>3269 | WA<br>732 | NA<br>886 | >10 |
| 77 | 2 | 3 | NA<br>2207 | WA<br>225 | NA<br>16 | >10 |
| 78 | 2 | 3 | NA<br>>10K | NA<br>>10K | NA<br>>10K | >10 |
| 40 | 1 | 2 | 33<br>(207)<br>69 | 1.2<br>(126)<br>1.3 | 6.8<br>(140)<br>363 | 1.7 |
| 42 | 1 | 2 | NA<br>15K | NA<br>3636 | NA<br>>10K | 0.19 |
| 28 | 8 | 9 | NA<br>21K | NA<br>4272 | NA<br>>10K | 0.34 |
| 70 | 2 | 3 | NA<br>>10K | NA<br>>10K | NA<br>>10K | >10 |
| 69 | 2 | 3 | 313<br>(10)<br>469 | 12<br>(50)<br>133 | 52.6<br>(31)<br>501 | >10 |
| 73 | 2 | 3 | WA<br>(39)<br>486 | 22.5<br>(24)<br>26 | 91<br>351 | >10 |
| 74 | 2 | 3 | NA<br>11K | NA<br>14K | NA<br>>10K | 3.5 |
| 30 | 8 | 9 | 14 | 2.2 | 84 | 0.28 |
| 44 | 1 | 2 | 49<br>(138)<br>37 | 1.7<br>(100)<br>1.9 | 7.5<br>(116)<br>392 | 0.27 |
| 82 | 2 | 3 | NA<br>>10K | NA<br>>10K | NA<br>>10K | >10 |
| 81 | 2 | 3 | NA<br>4210 | 490<br>(80)<br>846 | 183<br>(67)<br>1058 | >10 |

TABLE 1-continued

| Compound # | General Formula | Table #[1] | RAR $EC_{50}$/ (EFFICACY)/$K_d$nM α | β | γ | P450RAI INHIBITION DATA INTACT HELA $IC_{50}$μM |
|---|---|---|---|---|---|---|
| 89 | 2 | 3 | 268<br>(20)<br>3407 | 26<br>(50)<br>980 | 12<br>(46)<br>475 | >10 |
| 90 | 2 | 3 | NA<br>>10K | NA<br>>10K | NA<br>>10K | 0.95 |
| 94 | 2 | 3 | NA<br>>10K | NA<br>>10K | NA<br>>10K | >10 |
| 93 | 2 | 3 | 4821<br>(114)<br>3450 | 20<br>(39)<br>554 | 10<br>(55)<br>358 | >10 |
| 5 | 8 | 9 | NA<br>9148 | 11<br>(36)<br>2815 | NA<br>>10K | 0.55 |
| 8 | 4 | 5 | NA<br>10K | 363<br>(96)<br>3781 | NA<br>25K | 0.4 |
| 86 | 2 | 3 | NA<br>>10K | NA<br>>10K | NA<br>>10K | 1.4 |
| 85 | 2 | 3 | 976<br>(60)<br>1861 | 3.5<br>(77)<br>240 | 2.5<br>(65)<br>302 | >10 |
| 98 | 2 | 3 | NA | NA | NA | 0.8 |
| 13 | 4 | 5 | NA | 3.2<br>(6.6) | 116<br>(9) | 3.1<br>3.1 |
| 10 | 8 | 9 | 57<br>(146) | 0.3<br>(86) | 6<br>(94) | 0.7 |
| 36 | 8 | 9 | 13K | 4896 | 492 | 0.033 |
| 38 | 8 | 9 | 10K | 5317 | 2884 | 0.025 |
| 34 | 8 | 9 | 61.5 | 15 | 2.5 | 0.13 |
| 119 | 6 | 7 | >10K | >10K | >10K | 0.4 |
| 121 | 6 | 7 | >10K | >100K | >100K | 0.18 |
| 46 | 8 | 9 | >10K | >10K | >10K | 2.2 |
| 20 | 8 | 9 | | | | >10 |
| 18 | 4 | 5 | | | | 1.1 |
| 32 | 8 | 9 | 27K | 4225 | 13K | 0.18 |
| 139 | 4 | 5 | | | | 0.05 |
| 22 | 3 | 4 | | | | 1.6 |
| 24 | 3 | 4 | | | | 3 |
| 137 | 4 | 5 | | | | 0.1 |
| 26 | 4 | 5 | | | | 10 |
| 127 | 6 | 7 | | | | 0.4 |
| 126 | 6 | 7 | | | | 0.09 |
| 48 | 1 | 2 | | | | 0.03 |
| 50 | 1 | 2 | | | | 0.014 |
| 52 | 1 | 2 | | | | 0.05 |
| 54 | 1 | 2 | | | | 0.022 |
| 62 | 7 | 8 | | | | >10 |
| 56 | 8 | 9 | | | | 0.13 |
| 134 | 6 | 7 | | | | 5 |
| 58 | 1 | 2 | | | | 0.18 |
| 60 | 1 | 2 | | | | 1.6 |
| 143 | | | | | | 0.8 |
| 145 | | | | | | 0.2 |

[1]The "Table #" refers to the Table provided below where the compound is identified with reference to a corresponding specific formula of Formulas 9 through 16.

Topical Skin Irritation Tests

As is known the topical retinoid all-trans-retinoic acid (ATRA) and oral retinoids such as 13-cis RA and etretinate are known to induce substantial skin irritation in humans. This irritation is a direct result of activation of the RAR nuclear receptors. Analysis of retinoid topical irritation is also a highly reproducible method of determining in vivo retinoid potency. The SKH1-hrBR or hairless mouse provides a convenient animal model of topical irritation, since retinoid-induced skin flaking and abrasion can be readily scored by eye (Standeven et al., "Specific antagonist of retinoid toxicity in mice." Toxicol. Appl. Pharmacol., 138:169–175, (1996); Thacher, et al., "Receptor specificity of retinoid-induced hyperplasia. Effect of RXR-selective agonists and correlation with topical irritation". *J. Pharm. Exp. Ther.*, 282:528–534, (1997)). As is demonstrated below the topical application of P450RAI inhibitors of the present invention also causes an increase in the endogenous levels of ATRA that results in ATRA-induced irritation in skin of hairless mice. The attached data table discloses the retinoid-mimetic effects of some P450RAI inhibitor compounds of the present invention on the skin of hairless mice.

Methods

Female hairless mice (Crl:SKH1-hrBR), 5–7 weeks old, were obtained from Charles River Breeding Labs (Wilmington, Mass.). Animals were about 6 weeks old at the start of the experiments. Food (Purina Rodent Chow 5001) and reverse osmosis water were provided ad libitum. Mice were housed individually throughout the dosing period. In some experiments, mice that fit within a defined weight range, e.g., 21–25 g, were selected from the available stock and then randomly assigned to the various treatment groups, using body weight as the randomization variable.

The compounds to be tested were dissolved in acetone for application to the backs of the mice.

Mice were treated topically on the back in a volume of 4.0 ml/kg (0.07–0.12 ml) adjusted daily so as to deliver a fixed dose of test compound per g body weight. Doses are disclosed as nmol/25g.

Unless indicated otherwise, mice were treated with retinoids once daily on days 1 through 5 and observed on days 2, 3, 4, 5, 6, 7 and 8.

The mice were weighed daily and the dorsal skin was graded daily using separate semi-quantitative scales to determine flaking and abrasion. These flaking and abrasion scores were combined with weight change (if any) to create a cutaneous toxicity score (Blackjack score).

Cutaneous Toxicity Score

A visual grading scale was used for characterizing topical irritation on a daily basis. The grading scale used is as follows:

| Flaking | Abrasions |
|---|---|
| 0 = none | 0 = none |
| 1 = slight (small flakes, <50% coverage) | 1 = slight (one or two abrasions with a light pink color) |
| 2 = mild (small flakes, 50% coverage) | 2 = mild (several abrasions with a pink color) |
| 3 = moderate (small flakes, >50% coverage & large flakes, <25% coverage) | 3 = moderate (one or two deep abrasions with red color, <25% coverage) |
| 4 = severe (small flakes, >50% coverage & large flakes, 25–50% coverage) | 4 = severe (multiple deep abrasions with red color, >25% coverage) |
| 5 = very severe (large flakes, >50% coverage) | |

Topical Toxicity Score

The flaking and abrasion observations were combined with body weight observations to calculate a single, semi-quantitative topical or cutaneous "toxicity score" as detailed below. The toxicity score (also known as "blackjack score" since the theoretical maximum is 21) takes into account the maximal severity, and the time of onset of skin flaking and abrasions and the extent of weight between the first and last days of the experiment. Below are listed the seven numerical components of the toxicity score and an explanation of how those values are combined to calculate the toxicity score.

1. Flaking-Maximal Severity:
   Highest flaking score attained during observation period.
2. Flaking-Day of Onset of grade 2 or worse:
   0—>8 days
   1—day 8
   2—day 6 or 7
   3—day 4 or 5
   4—day 2 or 3
3. Flaking-Average Severity:
   Flaking severity scores are summed and divided by the number of observation days.
4. Abrasion-Maximal Severity:
   Highest abrasion score attained during observation period.
5. Abrasion-Day of Onset of grade 2 or worse:
   Same scale as (2) above.
6. Abrasion-Average Severity:
   Abrasion severity scores are summed and divided by the number of observation days.
7. Systemic Toxicity (weight loss):
   0—<1 g
   1—1 to 2 g
   2—2 to 4 g
   3—4 to 6 g
   4—>6 g or dead Calculation of Composite Flaking Score Flaking onset score (2) and average severity score (3) are summed and divided by two. The quotient is added to the maximal severity score (1). Composite flaking scores are calculated for each individual animal in a group, averaged, and rounded to the nearest integer. Values can range from 0–9.

Calculation of Composite Abrasion Score

Abrasion onset score (5) and average severity score (6) are summed and divided by two. The quotient is added to the maximal severity score (4). Composite abrasion scores are calculated for each individual animal in a group, averaged and rounded to the nearest integer. Values can range from 0–8.

Calculation of Toxicity Score

Composite flaking score, composite abrasion score, and systemic toxicity score are summed to give the "toxicity score." Toxicity scores are calculated for each individual animal in a group, averaged, and rounded to the nearest integer. Values can range from 0–21 and are expressed in Table 1A below as the mean ±SD of the values for a group.

Calculation of Percentage Change in Body Weight

The body weight at the time of the last weighing (day 8, 11, or 12) was subtracted from the initial body weight. The difference was divided by the initial body weight, multiplied by 100%, and rounded to the nearest integer. Values were calculated for each individual animal and the mean and standard deviation for each group are shown.

TABLE 1A

| | Cutaneous Toxicity Score (Blackjack Score) | | |
|---|---|---|---|
| Compound No. | 100 nmole | 300 nmole | 1000 nmole |
| 5 | 0 | | 6 ± 3 |
| 15 | 1 ± 1 | | 5 ± 2 |
| 36 | 1 ± 1 | | 11 ± 0 |
| 38 | 1 ± 1 | | 10 ± 1 |

TABLE 1A-continued

| Compound No. | Cutaneous Toxicity Score (Blackjack Score) | | |
| --- | --- | --- | --- |
| | 100 nmole | 300 nmole | 1000 nmole |
| 8 | 5 ± 2 | 8 ± 3 | 12 ± 1 |
| 22 | 0 ± 0 | 0 ± 0 | 1 ± 1 |
| 137 | 1 ± 1 | 1 ± 1 | 5 ± 2 |
| 48 | 1 ± 1 | 3 ± 1 | 7 ± 2 |
| 50 | 1 ± 0 | 3 ± 2 | 8 ± 2 |
| 58 | 0 ± 0 | 0 ± 0 | 0 ± 0 |
| 131 | 1 ± 1 | 0 ± 1 | 1 ± 1 |
| 127 | 0 ± 0 | 0 ± 0 | 0 ± 0 |
| 18 | 0 ± 0 | 5 ± 2 | 10 ± 2 |

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds, or to control by naturally occurring retinoic acid will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

In some applications pharmaceutical formulations containing the CP-450RAI inhibitory compounds of the invention may be co-administered with formulations containing retinoids.

General Embodiments and Synthetic Methodology
Definitions

The term alkyl refers to and covers any and all groups which are known as normal alkyl and branched-chain alkyl. Unless specified otherwise, lower alkyl means the above-defined broad definition of alkyl groups having 1 to 6 carbons in case of normal lower alkyl, and 3 to 6 carbons for lower branch chained alkyl groups. A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Some compounds of the present invention may have trans and cis (E and Z) isomers. Unless specific orientation of substituents relative to a double bond or a ring is indicated in the name of the respective compound, and/or by specifically showing in the structural formula the orientation of the substituents relative to the double bond or ring the invention covers trans as well as cis isomers.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well. A bond drawn with a wavy line indicates that the carbon to which the bond is attached can be in any of the applicable possible configurations.

General Synthetic Methodology

The compounds of the invention are encompassed by the general Formulas 1 through 8 provided above. As it can be seen, in each of these formulas a linker or tethering group designated Z covalently connects an aromatic or heteroaromatic moiety designated $A(R_2)$—$CH_2)_n$—$COOR_8$ and another cyclic moiety which in accordance with these formulas is a substituted phenyl, substituted tetrahydronaphthalene, substituted chroman, thiochroman, tetrahydroquinoline or tetrahydroisoquinoline moiety. Generally speaking a compound such as $X_4$—$A(R_2)$—$(CH_2)_n$—$COOR_8$ is commercially available, or can be made in accordance with the chemical literature, or with such modification of known chemical processes which are within the skill of the practicing organic chemist. The group $X_4$ represents a reactive group, which is suitable for coupling the $X_4$-$A(R_2)$—$(CH_2)_n$—$COOR_8$ compound to a derivative of the substituted phenyl, substituted tetrahydronaphthalene, substituted chroman, thiochroman, tetrahydroquinoline or tetrahydroisoquinoline moiety so that as a result of the coupling the linker or tether moiety Z is formed. In many instances the group $X_4$ is a leaving group such as halogen, or trifluoromethanesulfonyloxy, or a group capable of participating in a Wittig or Horner Emmons reaction. In some instances the group $X_4$ is an ethynyl group capable of undergoing a coupling reaction with a leaving group (such as a halogen or a trifluoromethanesulfonyloxy group) attached to the substituted phenyl, substituted tetrahydronaphthalene, substituted chroman, thiochroman, tetrahydroquinoline or tetrahydroisoquinoline moiety. The group $X_4$ can also represent an OH or an $NH_2$ group that forms an ester (COO) or amide (CONH) linker, respectively, when reacted with an activated carboxyl derivative of the substituted phenyl, substituted tetrahydronaphthalene, substituted chroman, thiochroman, tetrahydroquinoline or tetrahydroisoquinoline moiety. Examples for the compounds of formula $X_4$-$A(R_2)$—$(CH_2)_n$-$COOR_8$ are provided in the specific examples below. Further examples where the $X_4$ group is halogen are ethyl 4-iodobenzoate, ethyl 6-iodonicotinate, ethyl 5-iodofuran-3-carboxylate, ethyl 5-iodothiophen-3-carboxylate, ethyl 5-iodofuran-2-carboxylate, ethyl 5-iodothiophen-2-carboxylate, and analogous halogenated derivatives of the respective pyridazine, pyrazine and other heteroaryl carboxylic acid esters. The analogous aryl and and heteroaryl hydroxyl compounds and amines, wherein the halogen of the above-listed compounds is replaced by $OH$ or $NH_2$ respectively, also serve as additional examples for the reagents of the formula $X_4$—$A(R_2)$—$(CH_2)_n$—$COOR_8$. In these examples $X_4$ is OH or $NH_2$, respectively.

Still further in accordance with the general synthetic methodology to provide the compounds of the present invention, a derivative of the substituted phenyl, substituted tetrahydronaphthalene, substituted chroman, thiochroman, tetrahydroquinoline or tetrahydroisoquinoline moiety is synthesized first, having a covalently attached $X_5$ group. The $X_5$ group reacts with the $X_4$ group of the reagent $X_4$—$A(R_2)$—$CH_2)_n$—$COOR_8$ to form the linker designated Z in Formulas 1 through 8. The $X_5$ group is one that is capable of participating in a catalyzed coupling reaction, (such as an ethynyl group when $X_4$ is a leaving group), or a leaving group (such as halogen or trifluoromethanesulfonyloxy when $X_4$ is an ethynyl group) , or an activated carboxylic acid function (when $X_4$ is OH or $NH_2$). The $X_5$ group can also be an OH, SH or $NH_2$ group when the $X_4$ group is an activated carboxylic acid function. Specific examples for substituted phenyl, substituted tetrahydronaphthalene, substituted chroman, thiochroman, tetrahydroquinoline or tetrahydroisoquinoline intermediates having an $X_5$ functionality are provided below, and are also available in the chemical scientific and patent literature. Generally speaking, for reagents and reactions covalently joining a substituted tetrahydronaphthalene, substituted chroman, thiochroman, or tetrahydroquinoline intermediate with a substituted aryl or heteroaryl group, such as $X_4$—$A(R_2)$—$(CH_2)_n$—$COOR_8$, to form a compound including the linker designated Z, reference is made to U.S. Pat. Nos. 5,648,503; 5,723,666 and 5,952,345 the specification of each of which are expressly incorporated herein by reference.

The substituted phenyl, tetrahydronaphthalene, chroman, thiochroman, tetrahydroquinoline or tetrahydroisoquinoline moiety of the novel compounds of the invention are derivatized in a manner to include the specific substituents (such as for example the cycloalkyl substituents) encompassed within the scope of the invention, either before or after the —$A(R_2)$—$(CH_2)_n$—$COOR_8$ moiety has been attached and the linker Z has formed, as illustrated by the below described specific examples. The —$(CH_2)_n$—$COOR_8$ moiety of the compounds of the invention can be modified in order to obtain still further compounds of the invention. One such modification is saponification of compounds where the $R_8$ group is an alkyl or —$CH_2O(C_{1-6}$-alkyl) group. Another modification is esterification of the carboxylic acid function when the $R_8$ group is H or a cation. Such saponification and esterification reactions are well known in the art and within the skill of the practicing organic chemist. Still another modification of the compounds of the invention (or of the intermediates $X_4$—$A(R_2)$—$(CH_2)_n$—$COOR_8$, or of precursors to these intermediates) is the homologation of the $(CH_2)_n$ group. The latter can be accomplished, for example, by the well known Arndt-Eistert method of homologation, or other known methods of homologation.

Specific Embodiments

With reference to the symbol A in Formulas 1 through 8, the preferred compounds of the invention are those where A is phenyl, naphthyl, pyridyl, thienyl or furyl. Even more preferred are compounds where A is phenyl. As far as substitutions on the A (phenyl) and A (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention either there is no $R_2$ substituent on the A group, or the $R_2$ substituent is preferably a fluoro group that is preferably located on the aromatic carbon adjacent (ortho) to the carbon bearing the —$(CH_2)_n$—$COOR_8$ group.

As far as the —$(CH_2)_n$—$COOR_8$ is concerned compounds are preferred where n is 0, 1 or 2, and even more preferred where n is 1. In Formulas 5 and 8 only compounds where n is 1 or 2 are preferred, with n=1 being most preferred. For the $R_8$ group H, lower alkyl of 1 to 3 carbons, and —$CH_2O(C_{1-6}$-alkyl) groups are preferred, as well as the pharmaceutically acceptable salts of the free acids when $R_8$ is H. Among the lower alkyl and —$CH_2O(C_{1-6}$-alkyl) groups ethyl and $OCH_2CH_3$, respectively, are presently most preferred.

The linker group Z in all the compounds of the invention is preferably ethynyl (—C≡C—), ester (CO—O), ethenyl, (—$CR_1$=$CR_1$—) or amide ($CONR_1$). Among these the ethynyl (—C≡C—) and ester (CO—O) linkers are most preferred. Moreover, in the preferred compounds of the invention the linker Z is attached to the 6 position in Formula 1, to the 4 position in Formula 2, to the 6 position in Formula 3, to the 6 position in Formula 4, to the 4 position in Formula 5, to the 4 position in Formula 6, to the 6 position in Formula 7, and to the 6 position in Formula 8. These positions are indicated by arabic numerals in Formulas 1 through 8.

The $R_1$ group substituting the non-aromatic rings in Formulas 1, 3, 4, 7 and 8 is preferably alkyl, more preferably alkyl of 1 to 3 carbons, and most preferably methyl. The $R_1$ group substituting the cyclopropane ring in Formulas 1, 2, 3 and 7 is preferably non-existent (p is 0), or is alkyl of 1 to 3 carbons, even more preferably methyl.

The X group in Formulas 1 and 5 is preferably O, and in Formula 2 X is preferably O or NR.

The $X_1$ group in Formula 4 is preferably 1-imidazolyl, substituted 1-imidazolyl, or $NRR_6$, where $R_6$ is preferably cyclopropyl or branched-chain alkyl. The $X_2$ group in Formula 6 is preferably 1-imidazolyl or substituted 1-imidazolyl.

The $X_3$ group in Formula 8 is preferably O or C=O.

The Y group is preferably H, lower alkyl of 1 to 3 carbons, cycloalkyl, lower alkyl substituted cycloalkyl, or halogen. Among these, H, Cl, and cyclopropyl are most preferred.

The $Y_1$ group of Formula 8 is preferably H, lower alkyl of 1 to 3 carbons, cycloalkyl, or lower alkyl substituted cycloalkyl. Among these H, ethyl and cyclopropyl are presently most preferred.

The most preferred compounds of the invention are disclosed in Tables 2 through 9 with reference to Formulas 9 through 16. The compounds specifically shown in Tables 2 through 9 are carboxylic acids, but it should be understood that the $C_{1-3}$alkyl esters, methoxymethyl ($OCH_2CH_3$) esters and pharmaceutically acceptable salts of the acids shown in these tables are also highly preferred.

It should also be apparent that the preferred compounds shown in Table 2 with reference to the more specific Formula 9 are within the scope of Formula 1.

Similarly, the preferred compounds shown in Table 3 with reference to the more specific Formula 10 are within the scope of Formula 2;

the preferred compounds shown in Table 4 with reference to the more specific Formula 11 are within the scope of Formula 3;

the preferred compounds shown in Table 5 with reference to the more specific Formula 12 are within the scope of Formula 4;

the preferred compounds shown in Table 6 with reference to the more specific Formula 13 are within the scope of Formula 5;

the preferred compounds shown in Table 7 with reference to the more specific Formula 14 are within the scope of Formula 6;

the preferred compounds shown in Table 8 with reference to the more specific Formula 15 are within the scope of Formula 7, and the preferred compounds shown in Table 9 with reference to the more specific Formula 16 are within the scope of Formula 8.

TABLE 2

| Compound No. | X | Y | Z | $R_2$ | n | Position of $(CH_2)_nCOOH$ |
|---|---|---|---|---|---|---|
| 40 | O | H | —C≡C— | H | 0 | 4 |
| 42 | O | H | —C≡C— | H | 1 | 4 |
| 44 | O | H | —C≡C— | F | 0 | 4 |
| 48 | O | cyclopropyl | —C≡C— | H | 1 | 4 |
| 50 | O | cyclopropyl | —C≡C— | F | 1 | 4 |
| 52 | O | cyclopropyl | —C≡C— | H | 0 | 4 |
| 54 | O | cyclopropyl | —C≡C— | F | 0 | 4 |
| 58 | O | cyclopropyl | —CO—O— | H | 1 | 4 |
| 60 | O | cyclopropyl | —CO—O— | H | 1 | 3 |
| 66 | $CH_3N$ | H | —C≡C— | H | 0 | 4 |

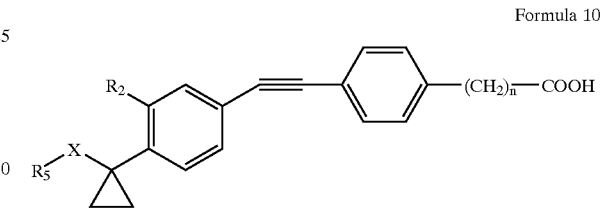

Formula 10

TABLE 3

| Compound No. | $R_5$ | X | $R_3$ | n |
|---|---|---|---|---|
| 110 | n-propyl | (n-propyl)N | H | 0 |
| 112 | benzyl | NH | H | 0 |
| 114 | benzyl | (n-benzyl)N | H | 0 |
| 108 | n-propyl | NH | H | 0 |
| 116 | benzyl | methylN | H | 0 |
| 77 | benzyl | O | H | 0 |
| 78 | benzyl | O | H | 1 |
| 70 | methyl | O | H | 1 |
| 69 | methyl | O | H | 0 |
| 73 | isopropyl | O | H | 0 |
| 74 | isopropyl | O | H | 1 |
| 82 | benzyl | O | methyl | 1 |
| 81 | benzyl | O | methyl | 0 |
| 89 | $(CH_3)_3C—CH_2—$ | O | methyl | 0 |
| 90 | $(CH_3)_3C—CH_2—$ | O | methyl | 1 |
| 94 | benzyl | O | ethyl | 1 |
| 93 | benzyl | O | ethyl | 0 |
| 86 | isopropyl | O | methyl | 1 |
| 85 | isopropyl | O | methyl | 0 |
| 105 | ethyl | O | t-butyl | 0 |
| 106 | ethyl | O | t-butyl | 1 |
| 98 | isopropyl | O | ethyl | 1 |

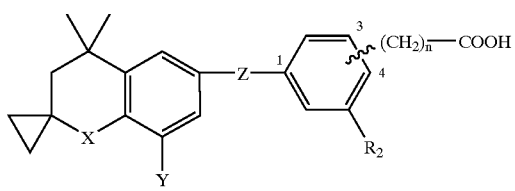

Formula 9

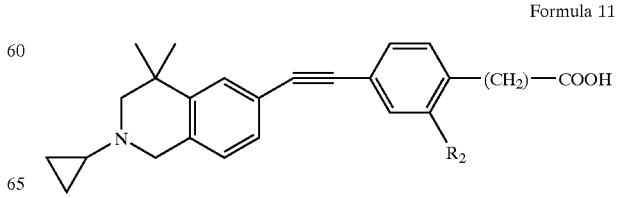

Formula 11

TABLE 4

| Compound No. | R₂ |
|---|---|
| 22 | F |
| 24 | H |

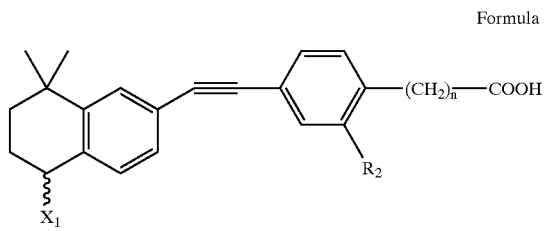

Formula 12

TABLE 5

| Compound No. | X₁ | R₂ | n |
|---|---|---|---|
| 3 | methyl,cyclopropyl-N | H | 0 |
| 8 | methyl,cyclopropyl-N | H | 1 |
| 13 | methyl,cyclopropyl-N | F | 0 |
| 18 | methyl,cyclopropyl-N | F | 1 |
| 139 | 1-imidazolyl | H | 0 |
| 137 | 1-imidazolyl | H | 1 |
| 26 | methyl,isopropyl-N | H | 0 |

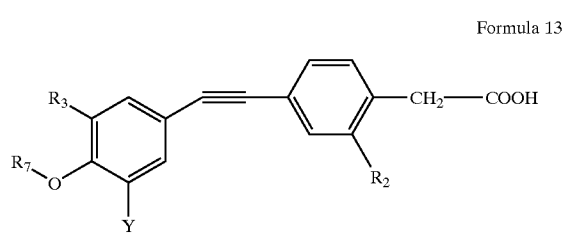

Formula 13

TABLE 6

| Compound No. | R₂ | R₇ | Y | R₃ |
|---|---|---|---|---|
| 143 | H | methyl | t-butyl | t-butyl |
| 145 | F | methyl | t-butyl | t-butyl |

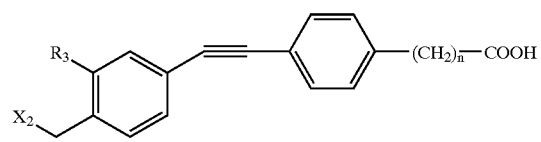

Formula 14

TABLE 7

| Compound No. | X₂ | R₃ | n |
|---|---|---|---|
| 119 | 1-imidazolyl | methyl | 0 |
| 121 | 1-imidazolyl | methyl | 1 |
| 127 | 1-imidazolyl | iso-propyl | 1 |
| 126 | 1-imidazolyl | iso-propyl | 0 |
| 134 | ethyl,cyclopropyl-N | iso-propyl | 0 |

TABLE 7-continued

| Compound No. | X₂ | R₃ | n |
|---|---|---|---|
| 130 | ethyl,cyclopropyl-N | methyl | 0 |
| 131 | ethyl,cyclopropyl-N | methyl | 1 |
| 141 | (1-methyl)cyclopropyl-oxy | iso-propyl | 1 |

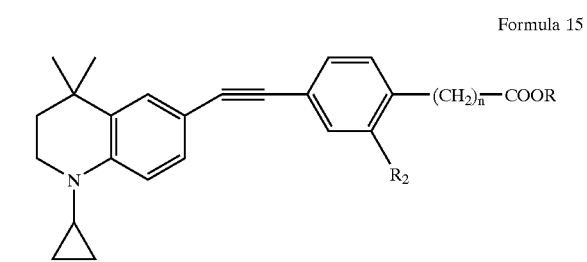

Formula 15

TABLE 8

| Compound No. | R | R₂ | n |
|---|---|---|---|
| 62 | H | H | 0 |
| 63 | Me | H | 1 |

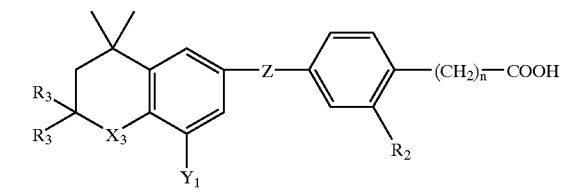

Formula 16

TABLE 9

| Compound No. | X₃ | Y₁ | R₃ | Z | R₂ | n |
|---|---|---|---|---|---|---|
| 28 | O | H | methyl | —C≡C— | H | 1 |
| 30 | O | H | methyl | —C≡C— | F | 0 |
| 5 | CO | H | H | —C≡C— | H | 1 |
| 10 | CO | H | H | —C≡C— | F | 0 |
| 36 | O | cyclopropyl | methyl | —C≡C— | H | 1 |
| 38 | O | cyclopropyl | methyl | —C≡C— | F | 1 |
| 46 | O | H | methyl | —CO—O— | H | 1 |
| 20 | CO | H | H | —CO—O— | H | 1 |
| 32 | O | H | methyl | —C≡C— | F | 1 |
| 56 | O | ethyl | methyl | —C≡C— | H | 1 |
| 34 | O | cyclopropyl | methyl | —C≡C— | H | 0 |
| 15 | CO | H | H | —C≡C— | F | 1 |

The compounds of the invention can be synthesized by applying the general synthetic methodology described above, and by such modifications of the hereinafter described specific synthetic routes which will become readily apparent to the practicing synthetic organic chemist in light of this disclosure and in view of general knowledge available in the art. The hereinafter disclosed specific reaction schemes are directed to the synthesis of exemplary and preferred compounds of the invention. Whereas each of the specific and exemplary synthetic routes shown in these schemes may describe specific compounds of the invention only within the scope of one or two of the general Formulas 1 through 8, the synthetic processes and methods used therein are adaptable within the skill of the practicing organic chemist and can be used with such adaptation for the synthesis of compounds of the invention which are not specifically described herein as examples.

Reaction Scheme 1 discloses a presently preferred synthetic route to certain intermediates or reagents having the general formula $X_4$—$A(R_2)$—$(CH_2)_n$—$COOR_8$, where the symbol A represents a di-, or tri-substituted phenyl moiety. These intermediates are utilized in the synthesis of the compounds of the invention.

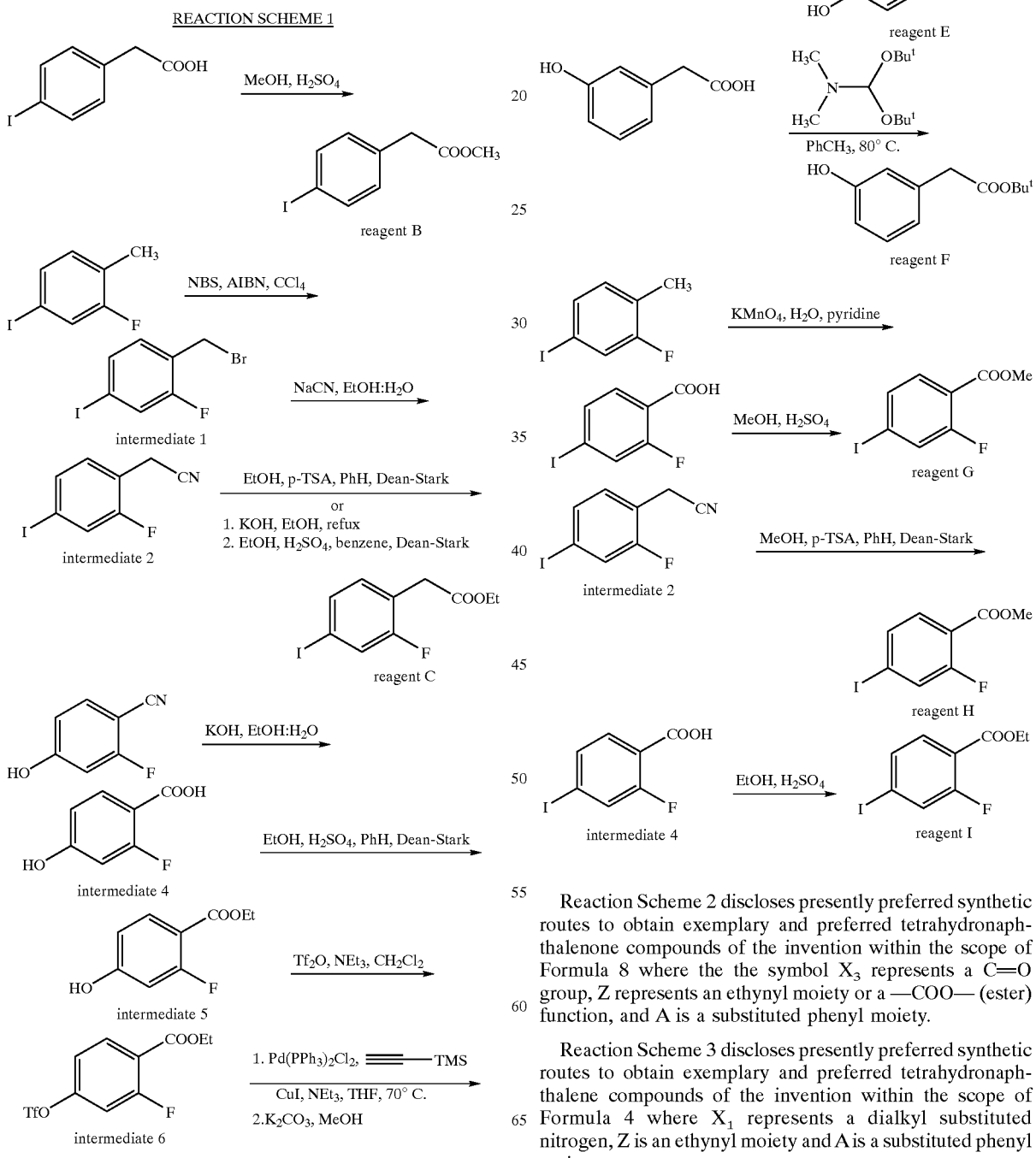

Reaction Scheme 2 discloses presently preferred synthetic routes to obtain exemplary and preferred tetrahydronaphthalenone compounds of the invention within the scope of Formula 8 where the the symbol $X_3$ represents a C=O group, Z represents an ethynyl moiety or a —COO— (ester) function, and A is a substituted phenyl moiety.

Reaction Scheme 3 discloses presently preferred synthetic routes to obtain exemplary and preferred tetrahydronaphthalene compounds of the invention within the scope of Formula 4 where $X_1$ represents a dialkyl substituted nitrogen, Z is an ethynyl moiety and A is a substituted phenyl moiety.

Reaction Scheme 4 discloses presently preferred synthetic routes to obtain exemplary and preferred isoquinoline compounds of the invention within the scope of Formula 3 where the symbol Y represents hydrogen, Z is an ethynyl moiety and A is a substituted phenyl moiety.

Reaction Scheme 5 discloses presently preferred synthetic routes to obtain exemplary and preferred chroman compounds of the invention within the scope of Formula 8 where the symbol $Y_1$ represents hydrogen, Z is an ethynyl moiety or an ester (COO) function, and A is a substituted phenyl moiety.

REACTION SCHEME 2

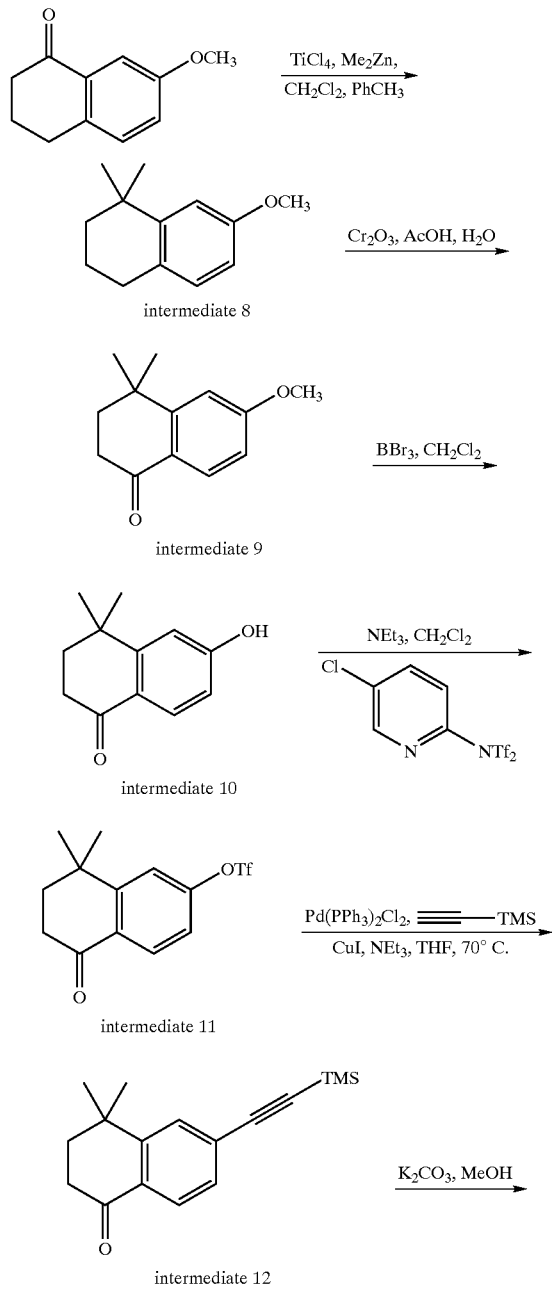

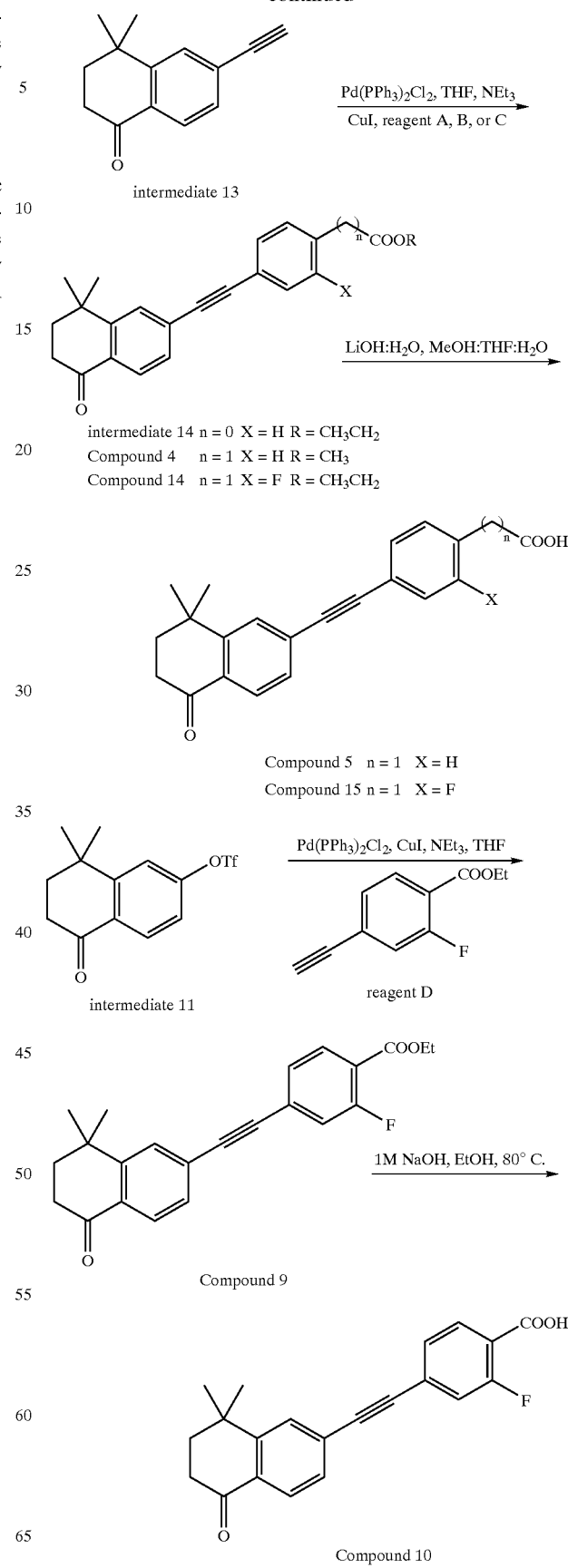

29

-continued

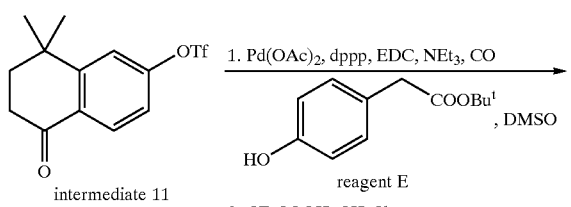

intermediate 11 reagent E

1. Pd(OAc)$_2$, dppp, EDC, NEt$_3$, CO, DMSO
2. CF$_3$COOH, CH$_2$Cl$_2$

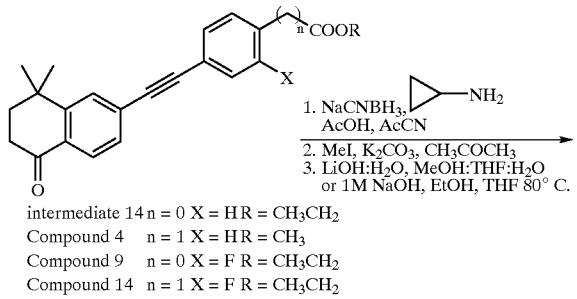

Compound 20

REACTION SCHEME 3

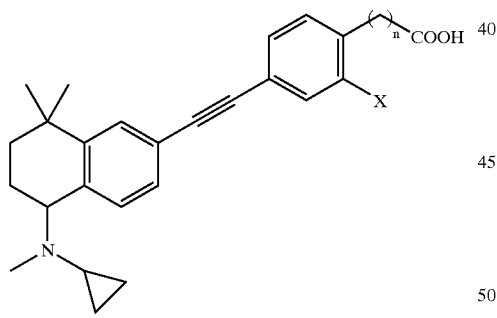

1. NaCNBH$_3$, AcOH, AcCN
2. MeI, K$_2$CO$_3$, CH$_3$COCH$_3$
3. LiOH:H$_2$O, MeOH:THF:H$_2$O or 1M NaOH, EtOH, THF 80° C.

intermediate 14  n = 0  X = H  R = CH$_3$CH$_2$
Compound 4      n = 1  X = H  R = CH$_3$
Compound 9      n = 0  X = F  R = CH$_3$CH$_2$
Compound 14     n = 1  X = F  R = CH$_3$CH$_2$ Compound 3   n = 0  X = H
Compound 8   n = 1  X = H
Compound 13  n = 0  X = F
Compound 18  n = 1  X = F

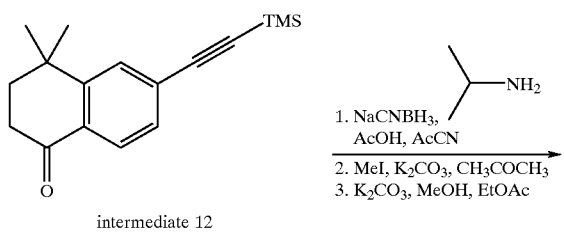

intermediate 12

1. NaCNBH$_3$, AcOH, AcCN
2. MeI, K$_2$CO$_3$, CH$_3$COCH$_3$
3. K$_2$CO$_3$, MeOH, EtOAc

30

-continued

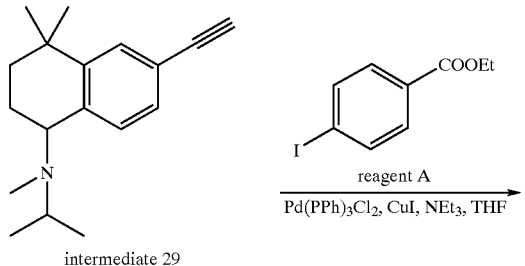

intermediate 29 reagent A

Pd(PPh$_3$)$_3$Cl$_2$, CuI, NEt$_3$, THF

Compound 25

1M NaOH, EtOH, THF, 80° C.

Compound 26

REACTION SCHEME 4

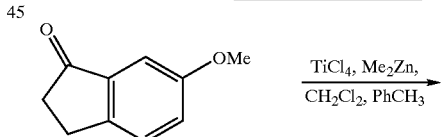

TiCl$_4$, Me$_2$Zn, CH$_2$Cl$_2$, PhCH$_3$ intermediate 15

Cr$_2$O$_3$, AcOH, H$_2$O intermediate 16

NaN$_3$, H$_2$SO$_4$, PhH
(reference 1)

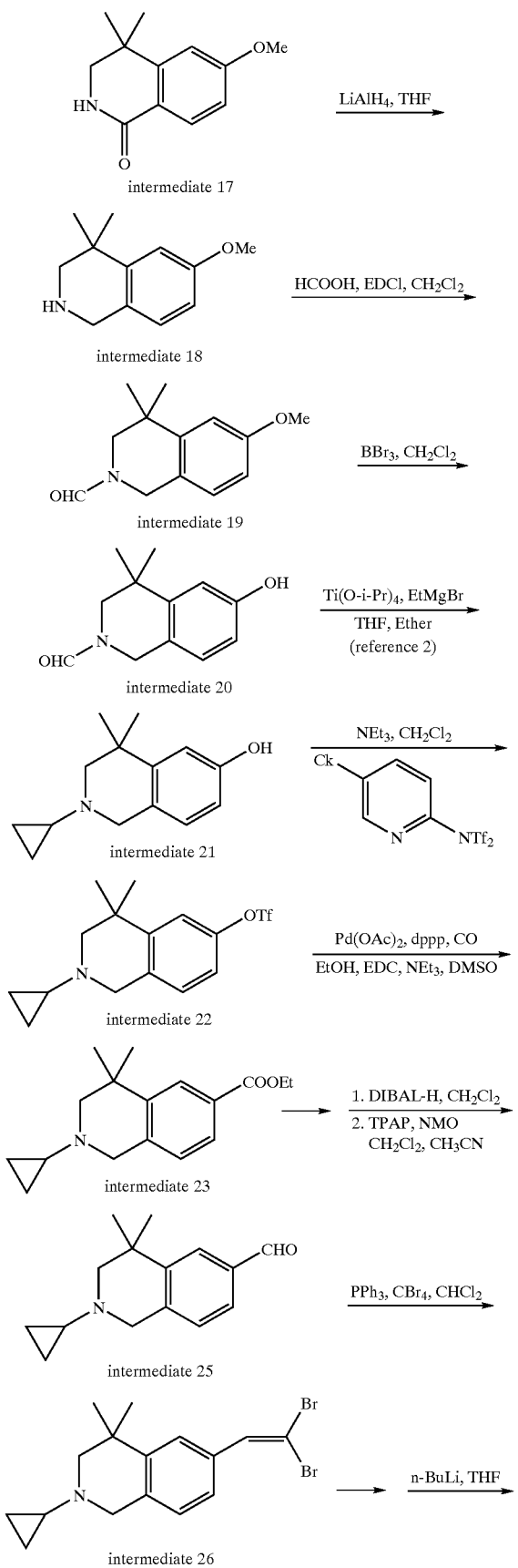
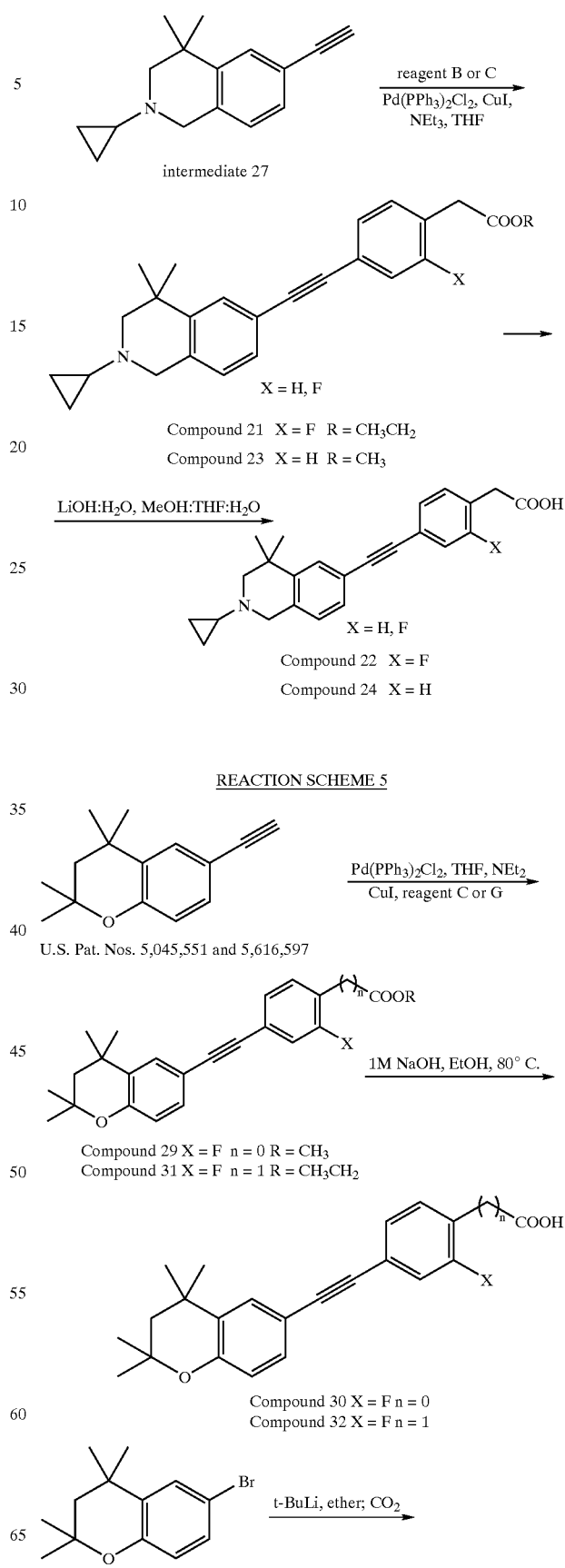

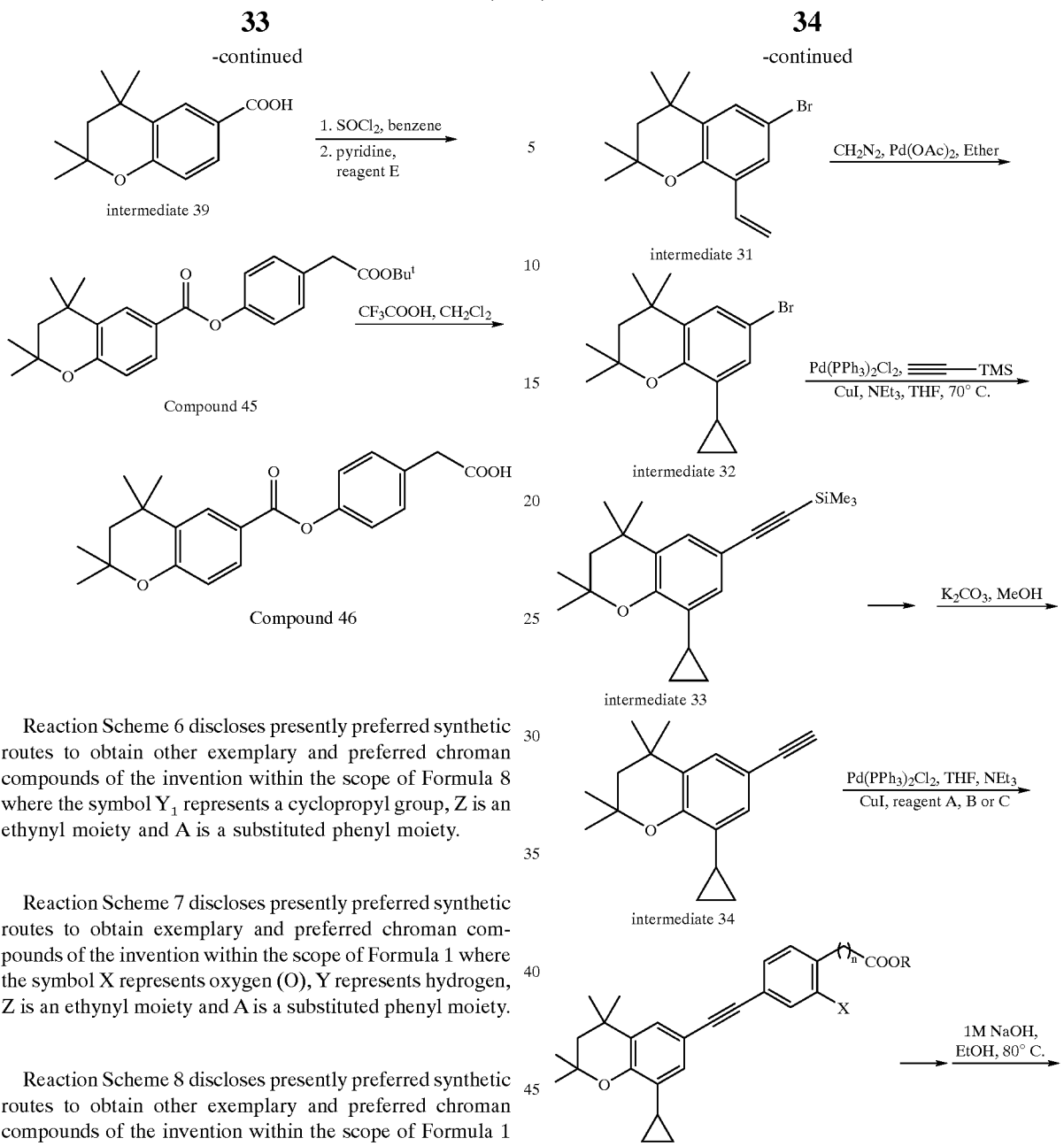

Reaction Scheme 6 discloses presently preferred synthetic routes to obtain other exemplary and preferred chroman compounds of the invention within the scope of Formula 8 where the symbol $Y_1$ represents a cyclopropyl group, Z is an ethynyl moiety and A is a substituted phenyl moiety.

Reaction Scheme 7 discloses presently preferred synthetic routes to obtain exemplary and preferred chroman compounds of the invention within the scope of Formula 1 where the symbol X represents oxygen (O), Y represents hydrogen, Z is an ethynyl moiety and A is a substituted phenyl moiety.

Reaction Scheme 8 discloses presently preferred synthetic routes to obtain other exemplary and preferred chroman compounds of the invention within the scope of Formula 1 where the symbol X represents oxygen (O), Y represents a cyclopropyl group, Z is an ethynyl moiety and A is a substituted phenyl moiety.

REACTION SCHEME 6

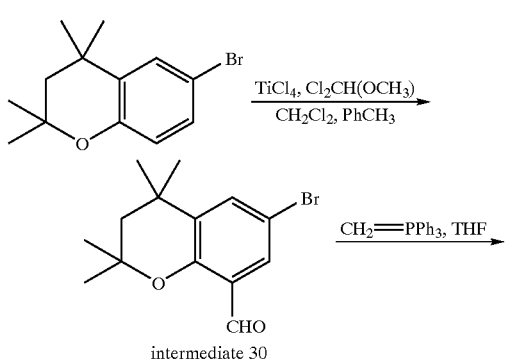

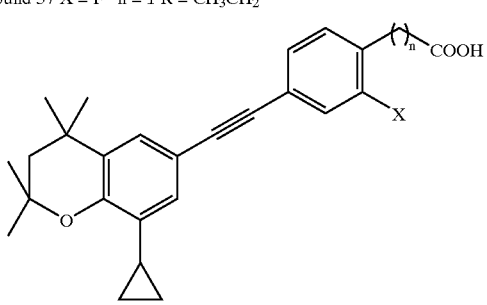

Compound 33 X = H  n = 0  R = CH$_3$CH$_2$
Compound 35 X = H  n = 1  R = CH$_3$
Compound 37 X = F  n = 1  R = CH$_3$CH$_2$ Compound 34 X = H  n = 0
Compound 36 X = H  n = 1
Compound 38 X = F  n = 1

REACTION SCHEME 7
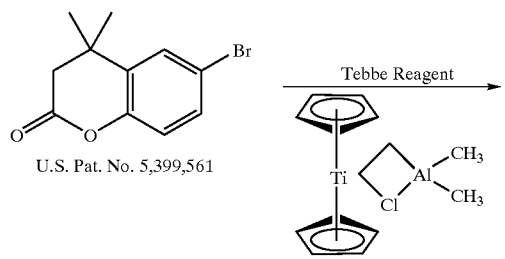
U.S. Pat. No. 5,399,561
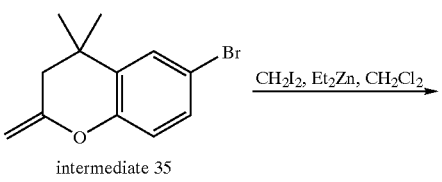
intermediate 35
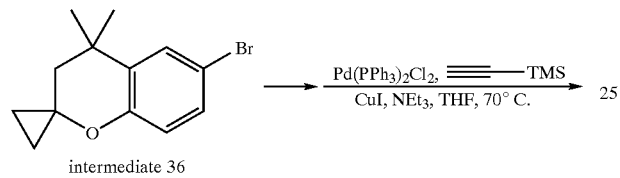
intermediate 36
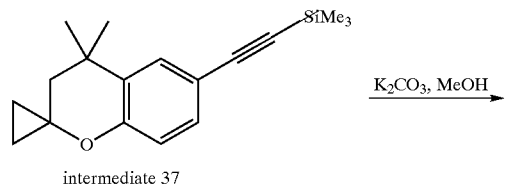
intermediate 37
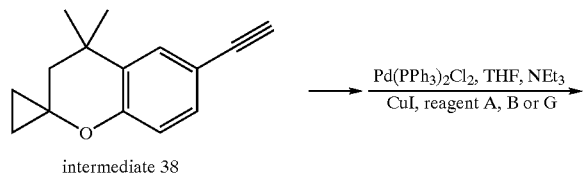
intermediate 38
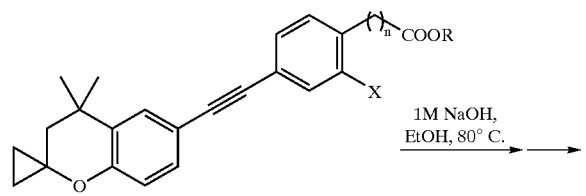
Compound 39 X = H  n = 0  R = CH$_3$CH$_2$
Compound 41 X = H  n = 1  R = CH$_3$
Compound 43 X = F  n = 0  R = CH$_3$
Compound 40 X = H  n = 0
Compound 42 X = H  n = 1
Compound 44 X = F  n = 0
REACTION SCHEME 8
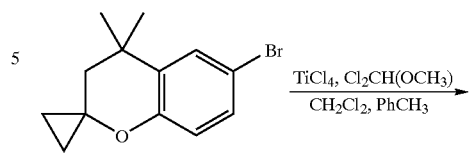
intermediate 36
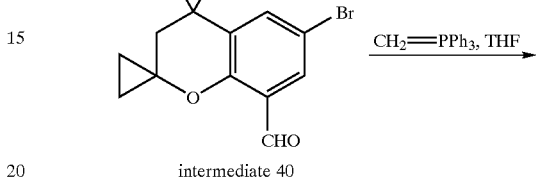
intermediate 40
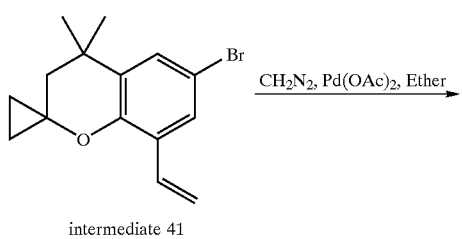
intermediate 41
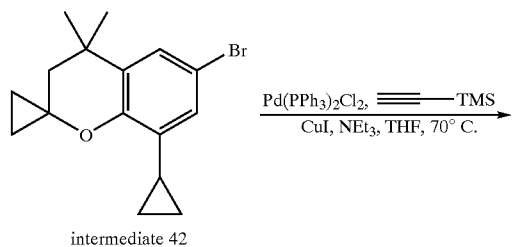
intermediate 42
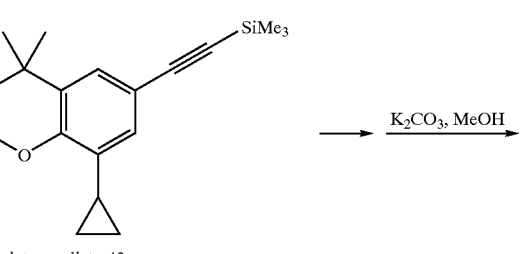
intermediate 43
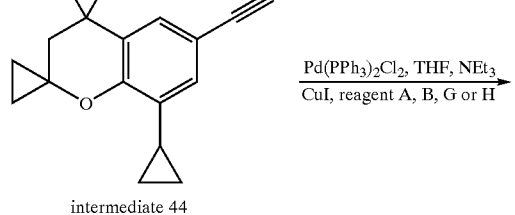
intermediate 44

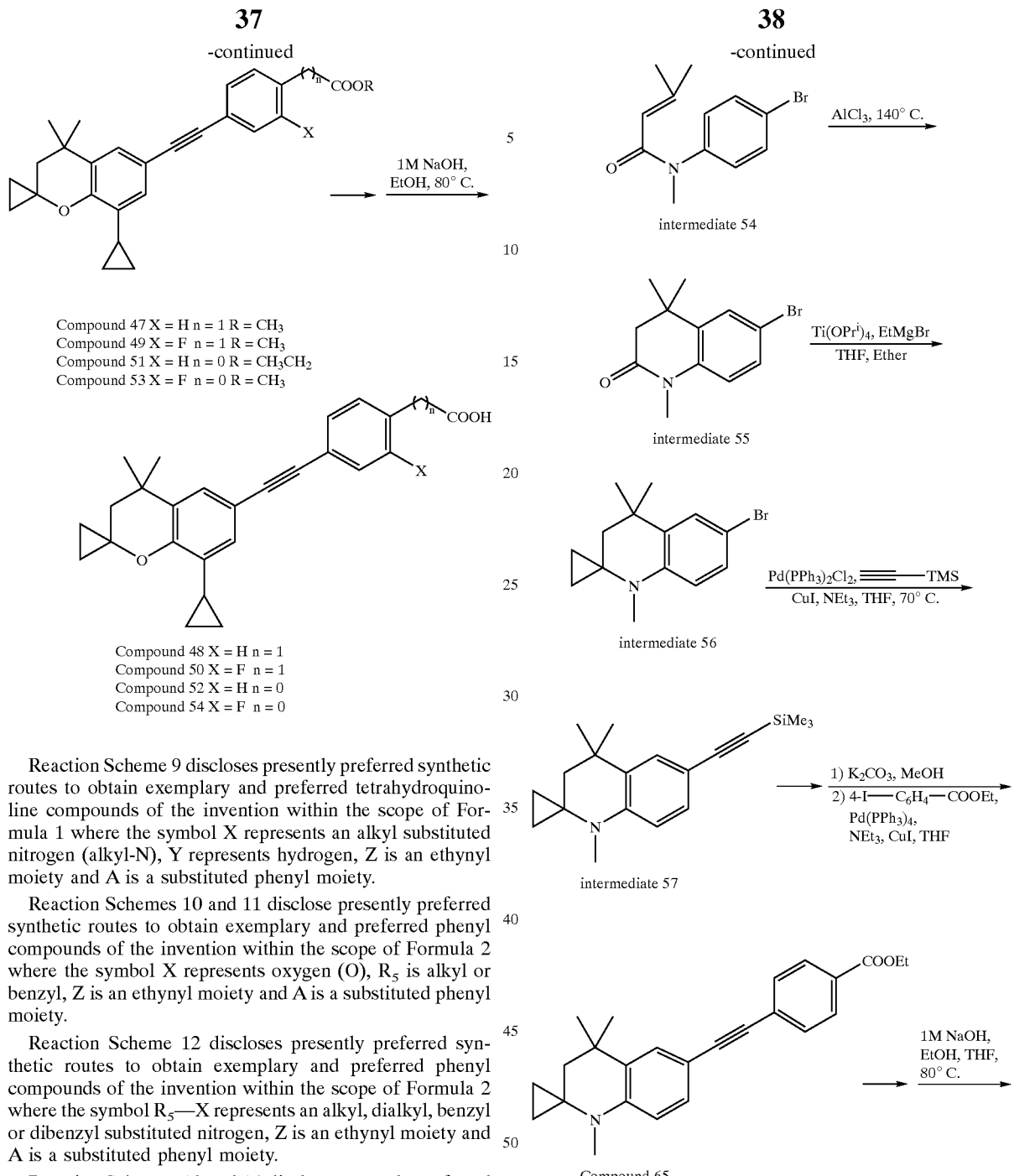

Compound 47 X = H n = 1 R = CH₃
Compound 49 X = F n = 1 R = CH₃
Compound 51 X = H n = 0 R = CH₃CH₂
Compound 53 X = F n = 0 R = CH₃

Compound 48 X = H n = 1
Compound 50 X = F n = 1
Compound 52 X = H n = 0
Compound 54 X = F n = 0

Reaction Scheme 9 discloses presently preferred synthetic routes to obtain exemplary and preferred tetrahydroquinoline compounds of the invention within the scope of Formula 1 where the symbol X represents an alkyl substituted nitrogen (alkyl-N), Y represents hydrogen, Z is an ethynyl moiety and A is a substituted phenyl moiety.

Reaction Schemes 10 and 11 disclose presently preferred synthetic routes to obtain exemplary and preferred phenyl compounds of the invention within the scope of Formula 2 where the symbol X represents oxygen (O), $R_5$ is alkyl or benzyl, Z is an ethynyl moiety and A is a substituted phenyl moiety.

Reaction Scheme 12 discloses presently preferred synthetic routes to obtain exemplary and preferred phenyl compounds of the invention within the scope of Formula 2 where the symbol $R_5$—X represents an alkyl, dialkyl, benzyl or dibenzyl substituted nitrogen, Z is an ethynyl moiety and A is a substituted phenyl moiety.

Reaction Schemes 13 and 14 disclose presently preferred synthetic routes to obtain exemplary and preferred phenyl compounds of the invention within the scope of Formula 6 where the symbol $X_2$ represents a (1-imidazolyl) moiety, Z is an ethynyl moiety and A is a substituted phenyl moiety.

REACTION SCHEME 9

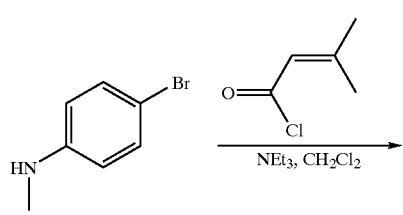

REACTION SCHEME 10
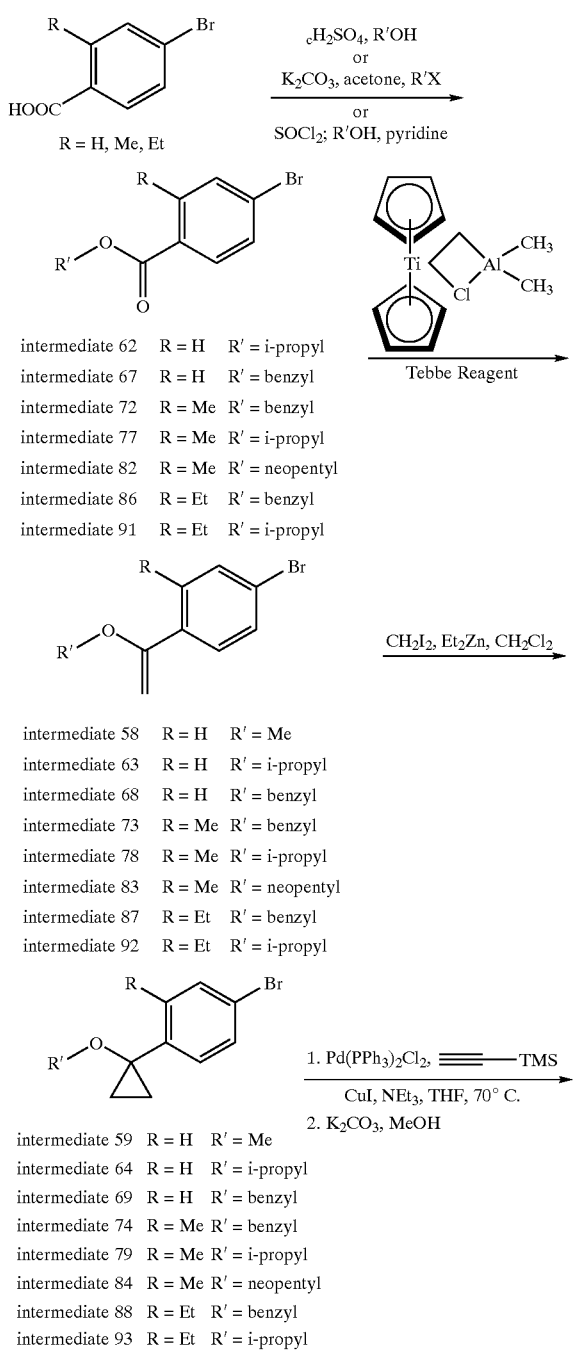
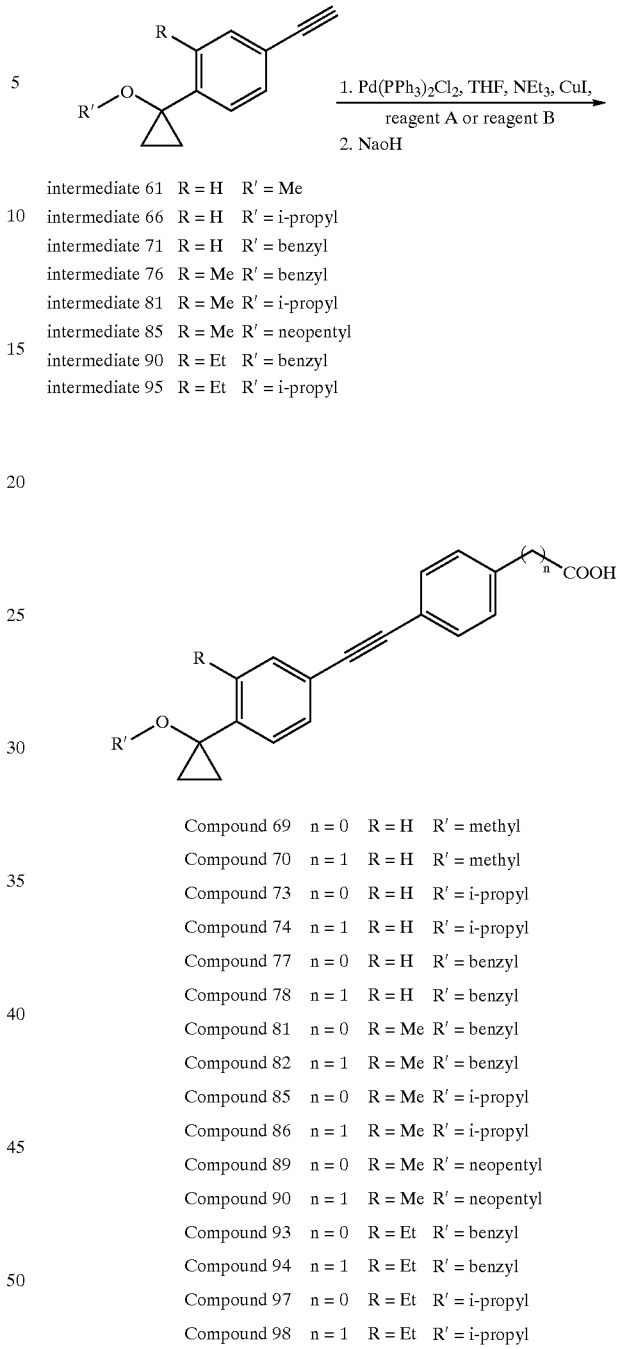
REACTION SCHEME 11
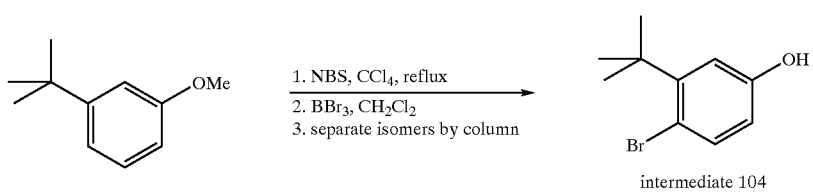

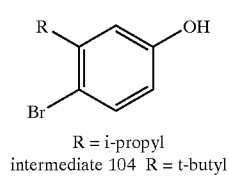

R = i-propyl
intermediate 104  R = t-butyl

1. TIPSCl, DMF, imidazole
2. t-BuLi, Et$_2$O; ClCOOEt

-continued

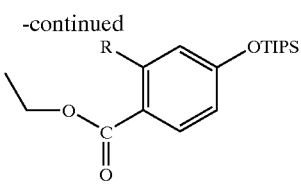

intermediate 97   R = i-propyl
intermediate 106  R = t-butyl

Tebbe Reagent

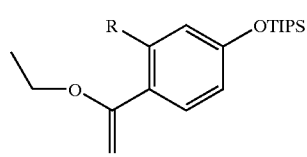

intermediate 98   R = i-propyl
intermediate 107  R = t-butyl

CH$_2$I$_2$, Et$_2$Zn, CH$_2$Cl$_2$

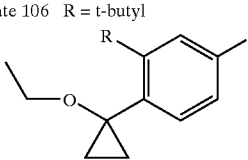

intermediate 99   R = i-propyl
intermediate 108  R = t-butyl

TBAF, THF

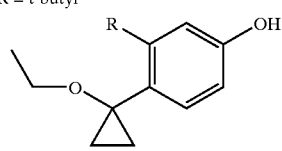

intermediate 100  R = i-propyl
intermediate 109  R = t-butyl 1. 5-Cl—C$_3$H$_5$N-2-NTf$_2$, NEt$_3$, CH$_2$Cl$_2$
2. Pd(PPh$_3$)$_2$Cl$_2$, ≡—TMS, CuI, NEt$_3$, THF, 70° C.
3. K$_2$CO$_3$, MeOH

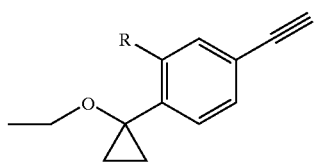

intermediate 103  R = i-propyl
intermediate 112  R = t-butyl

1. Pd(PPh$_3$)$_2$Cl$_2$, THF, NEt$_3$, CuI, reagent A or reagent B
2. NaOH

TIPS = tri-iso-propylsilyl
TBAF = tetra-n-butyl ammonium fluoride

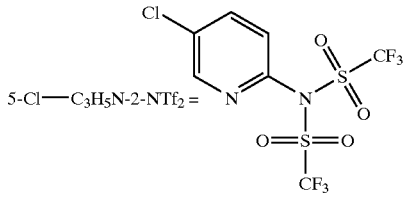

5-Cl—C$_3$H$_5$N-2-NTf$_2$ =

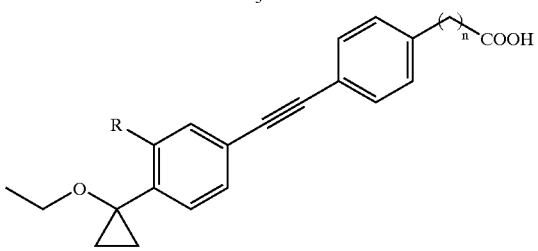

Compound 101  n = 0   R = i-propyl
Compound 102  n = 1   R = i-propyl
Compound 105  n = 0   R = t-butyl
Compound 106  n = 1   R = t-butyl

REACTION SCHEME 12

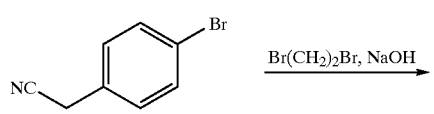

Br(CH$_2$)$_2$Br, NaOH

-continued

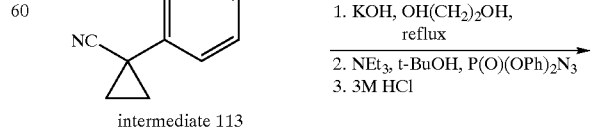

intermediate 113

1. KOH, OH(CH$_2$)$_2$OH, reflux
2. NEt$_3$, t-BuOH, P(O)(OPh)$_2$N$_3$
3. 3M HCl -continued
REACTION SCHEME 13
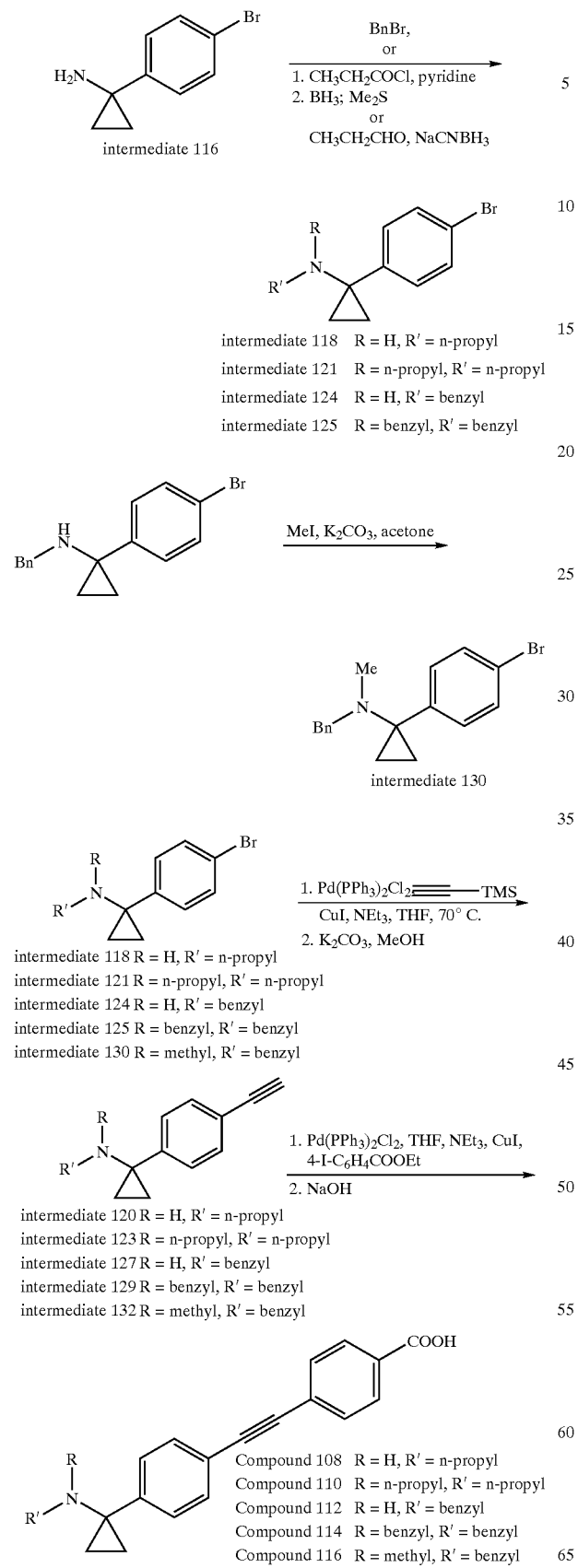
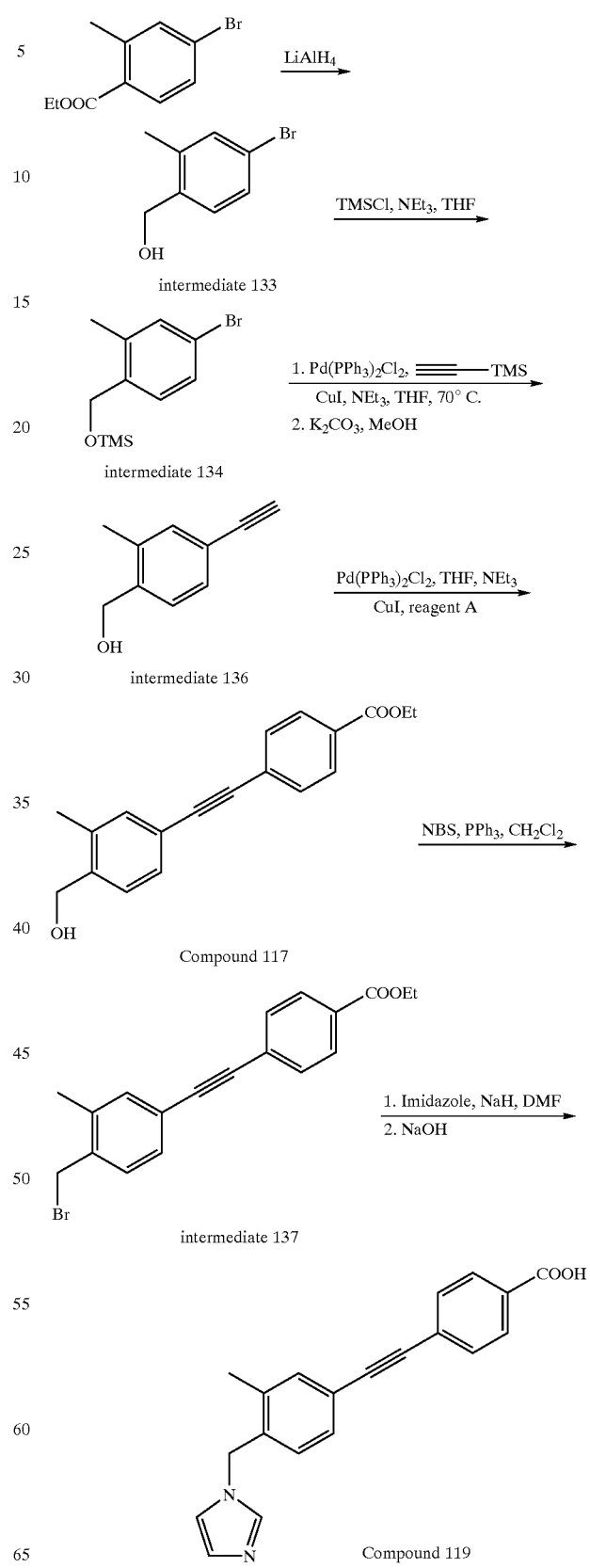

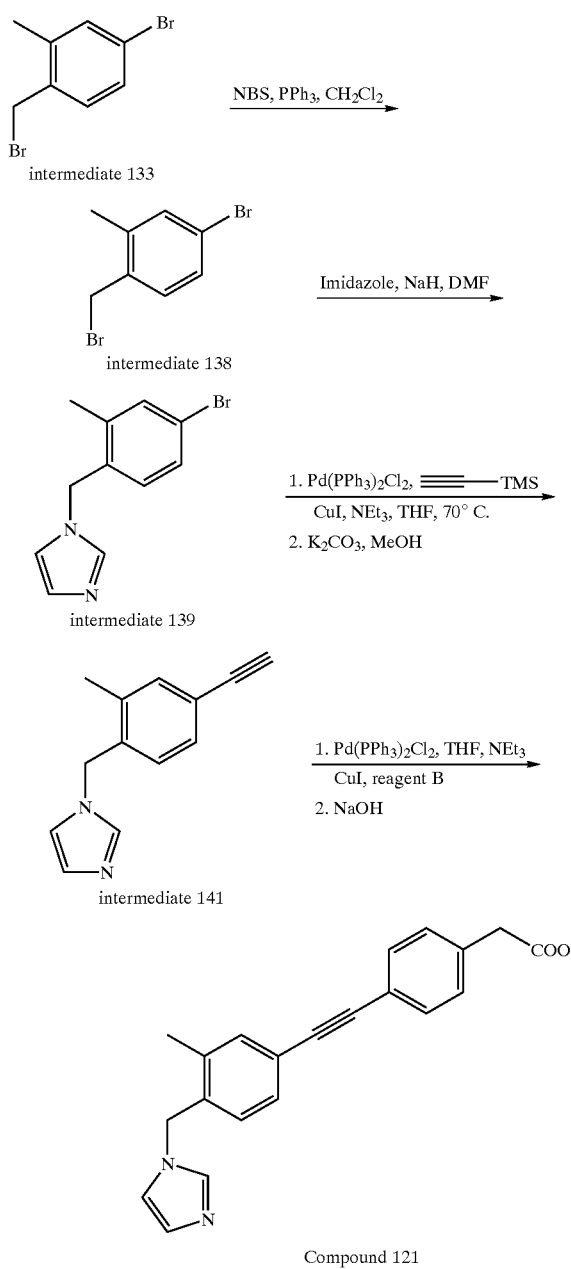
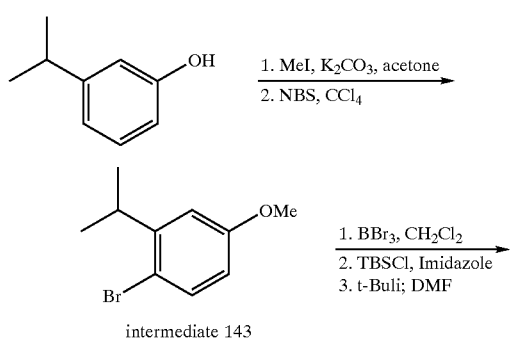
REACTION SCHEME 14
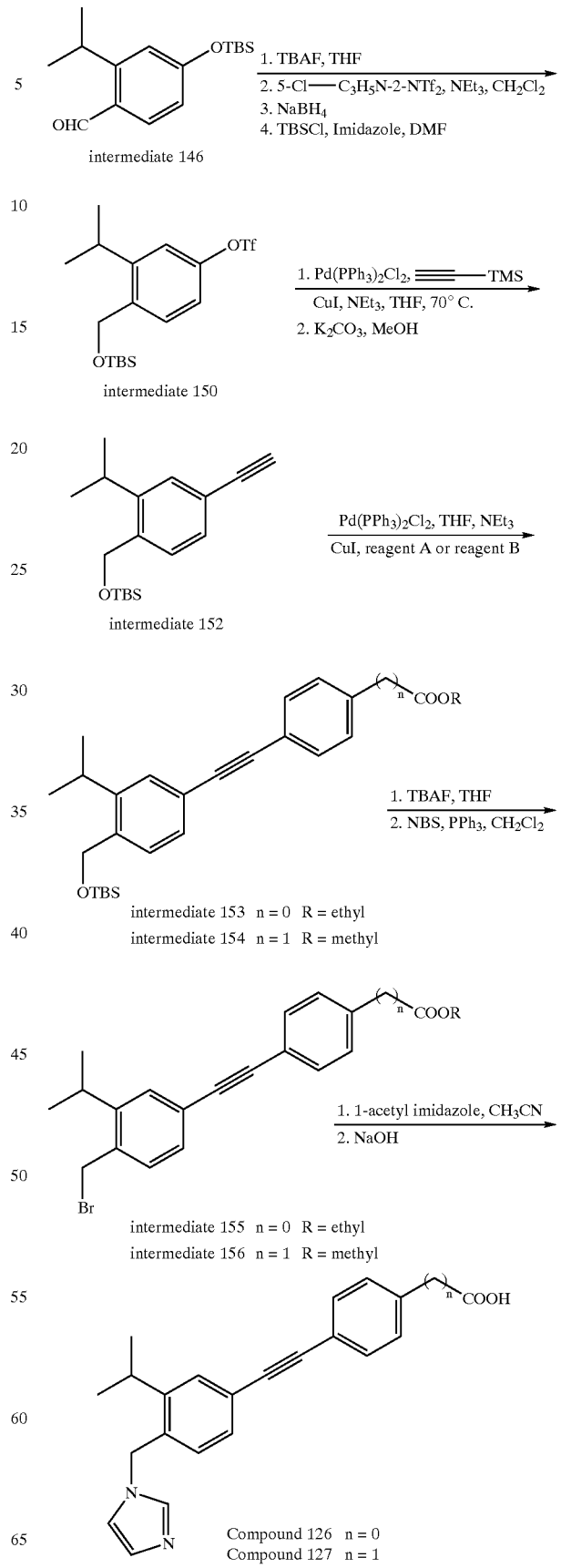

-continued

TBS = t-butyldimethylsilyl

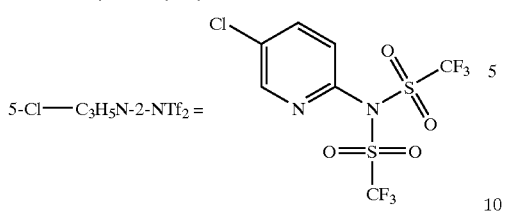

5-Cl—C₃H₅N-2-NTf₂ =

-continued

Compound 128 n = 0 R = Et
Compound 129 n = 1 R = Me

Reaction Scheme 15 disclose presently preferred synthetic routes to obtain exemplary and preferred phenyl compounds of the invention within the scope of Formula 6 where $X_2$ represents an alkyl and cyclopropyl substituted nitrogen ($X_2$=(alkyl,cycloalkyl)N), Y represents hydrogen, Z is an ethynyl moiety and A is a substituted phenyl moiety.

Reaction Scheme 16 discloses presently preferred synthetic routes to obtain exemplary and preferred tetrahydronaphthalene compounds of the invention within the scope of Formula 4 where the symbol $X_1$ represents a (1-imidazolyl) moiety, Y represents hydrogen, Z is an ethynyl moiety and A is a substituted phenyl moiety.

Reaction Scheme 17 discloses presently preferred synthetic routes to obtain exemplary and preferred phenyl compounds of the invention within the scope of Formula 6 where the symbol $X_2$ represents a 1-methyl-cyclopropoxy moiety, Y represents hydrogen, Z is an ethynyl moiety and A is a substituted phenyl moiety.

Reaction Scheme 18 discloses presently preferred synthetic routes to obtain exemplary and preferred phenyl compounds of the invention within the scope of Formula 5 where the symbol X represents oxygen (O), Y represents a tertiary-butyl group, Z is an ethynyl moiety and A is a substituted phenyl moiety.

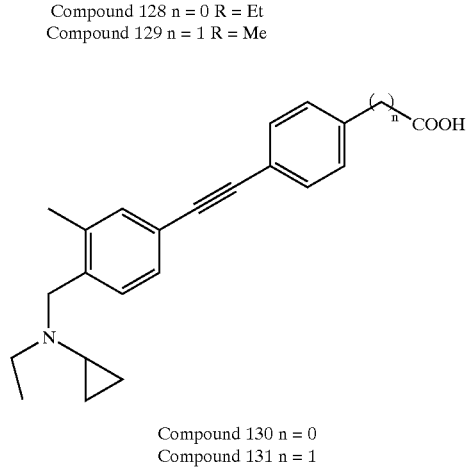

Compound 130 n = 0
Compound 131 n = 1

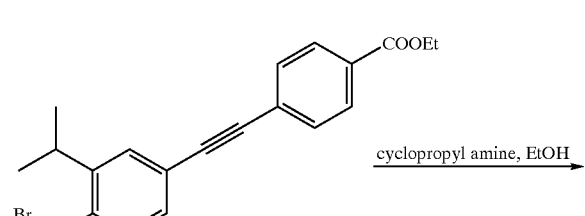

intermediate 155

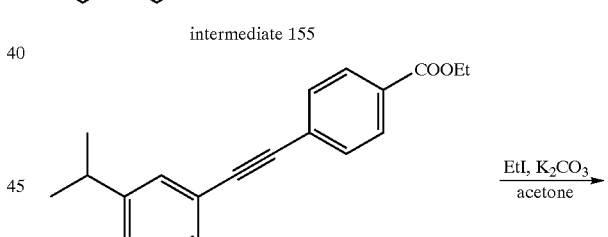

Compound 132

REACTION SCHEME 15

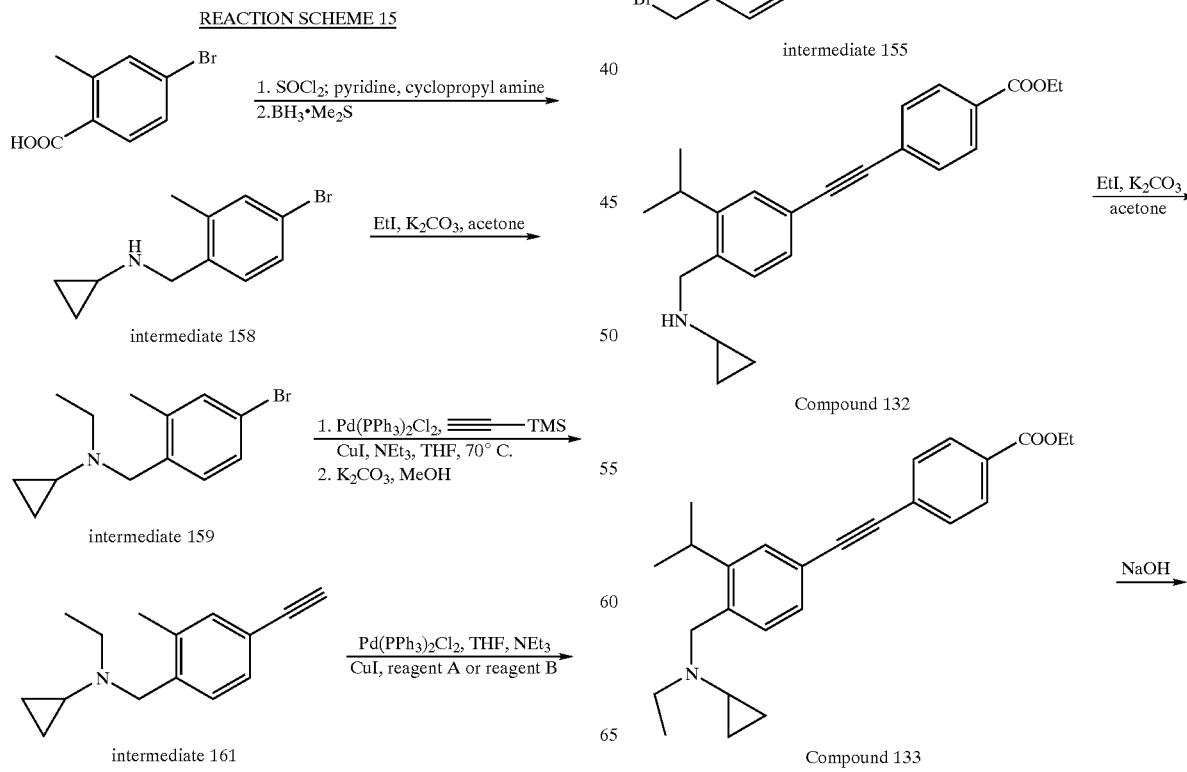

Compound 133

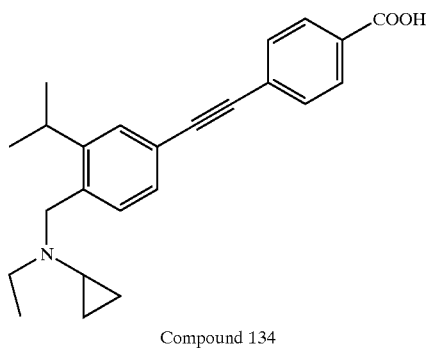
Compound 134
REACTION SCHEME 16
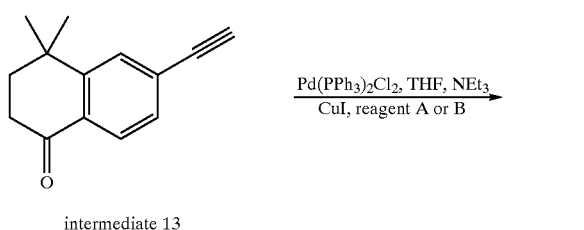
intermediate 13
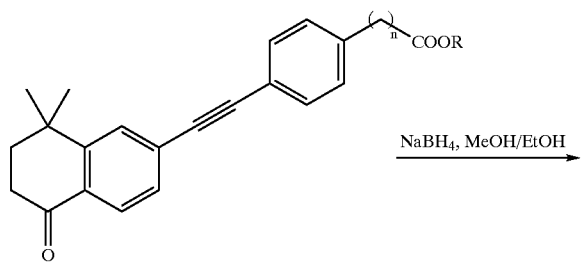
n = 0 R = Et
Compound 4 n = 1 R = Me
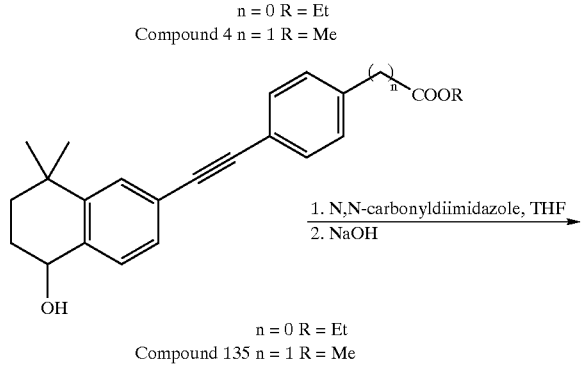
n = 0 R = Et
Compound 135 n = 1 R = Me
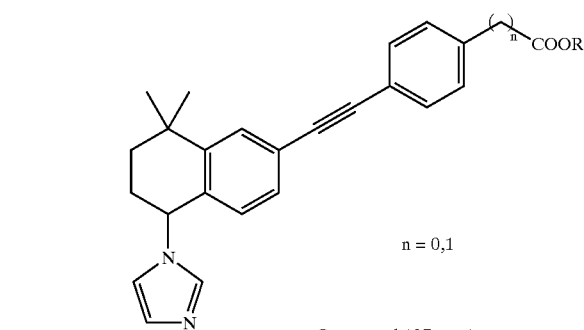
n = 0,1
Compound 137 n = 1
Compound 139 n = 0
REACTION SCHEME 17
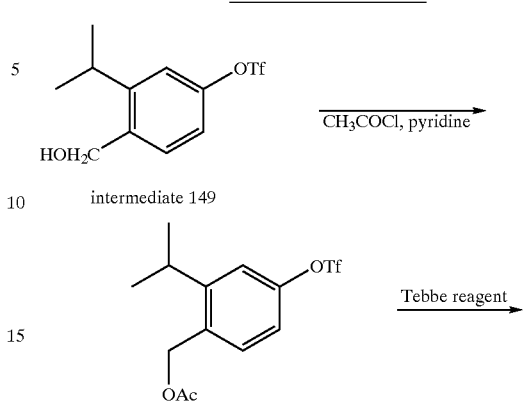
intermediate 149
intermediate 162
intermediate 163
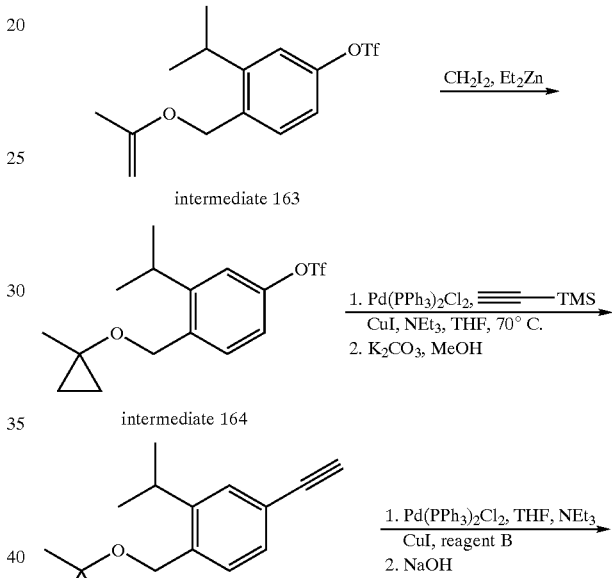
intermediate 164
intermediate 166
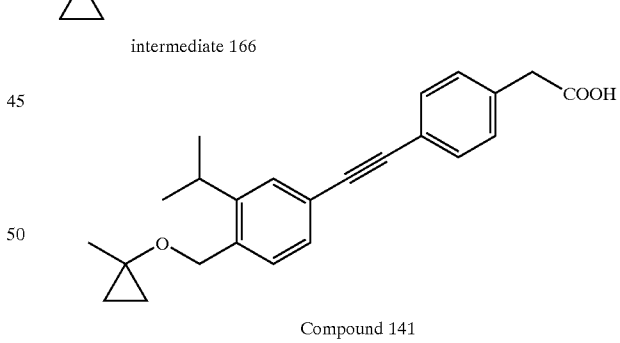
Compound 141
REACTION SCHEME 18
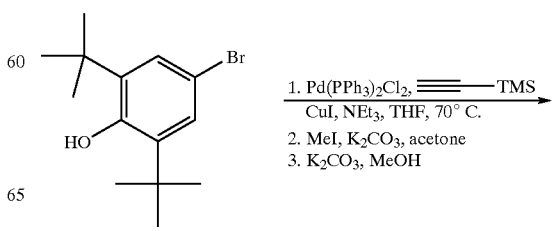

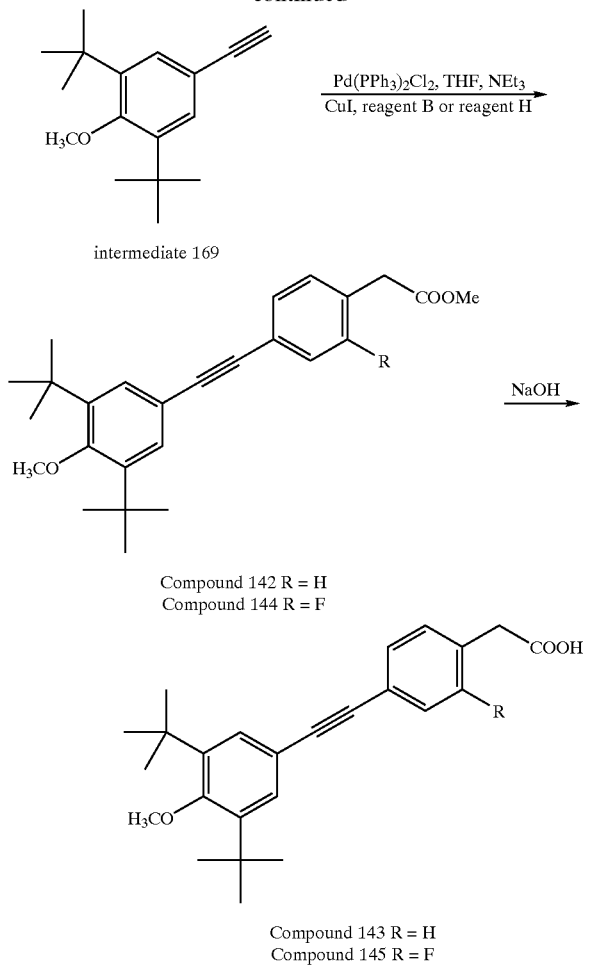

intermediate 169

Compound 142 R = H
Compound 144 R = F

Compound 143 R = H
Compound 145 R = F

SPECIFIC EXAMPLES

4-Hydroxy phenyl acetic acid-t-butyl ester
(Reagent E)

A stirred suspension of 4-hydroxy-phenyl acetic acid (0.152 g, 1 mmol) in anhydrous toluene (5 mL) was heated at 80° C. and N,N-dimethyl formamide-di-t-butyl acetal (1 mL, 4.17 mmol) was added when the solution became homogenous. After 0.5 h, the reaction mixture was cooled to ambient temperature and the volatiles were distilled off in vacuo. The residue was diluted with water and extracted with diethyl ether (×2). The combined organic extract was dried over anhydrous sodium sulfate, filtered and evaporated in vacuo to afford an oil which was subjected to flash column chromatography over silica gel (230–400 mesh) using 16% ethyl acetate in hexane as the eluent to afford the title compound as a solid (0.11 g, 56%).

$^1$H-NMR (300 MHz, CDCl$_3$): δ 1.44(s, 9H), 3.45(s, 2H), 6.55(s, 1H), 6.69(d, J=8.8Hz, 2H), 7.06(d, J=8.5Hz, 2H).

3-Hydroxy phenyl acetic acid-t-butyl ester
(Reagent F)

A stirred suspension of 3-hydroxy-phenyl acetic acid (1.52 g, 10 mmol) in anhydrous toluene (2 mL) was heated at 80° C. and N,N-dimethyl formamide-di-t-butyl acetal (9.6 mL, 40 mmol) was added when the solution became homogenous. After 0.5 h, the reaction mixture was cooled to ambient temperature and the volatiles were distilled off in vacuo. Th residue was diluted with water and extracted with diethyl ether (×2). The combined organic extract was dried over anhydrous sodium sulfate, filtered and evaporated in vacuo to afford an oil which was subjected to flash column chromatography over silica gel (230–400 mesh) using 16% ethyl acetate in hexane as the eluent to afford the title compound as a solid (1.17 g, 56%).

$^1$H-NMR (300 MHz, CDCl$_3$): δ 1.47(s, 9H), 3.49(s, 2H), 6.30(s, 1H), 6.70–6.79 (m, 2H), 6.81(d, J=7.6 Hz, 1H), 7.16(t, J=7.7 Hz, 1H).

Methyl-2-fluoro-4-iodo benzoate (Reagent G)

A solution of 2-fluoro-4-iodo toluene (5 g, 26.6 mmol) in pyridine (2 mL) and water (20 mL) was treated with potassium permanganate (16.6 g, 105 mmol) and heated at 150° C. overnight. The reaction mixture was then cooled to room temperature and filtered and the filtrate was extracted with hexane. The aqueous phase was acidified with 10% hydrochloric acid and extracted with ethyl acetate. The organic phase was dried over anhydrous sodium sulfate, filtered and evaporated in vacuo. The residue was dissolved in 20 mL of methanol, treated with concentrated sulfuric acid (1 mL) and refluxed overnight. The volatiles were distilled off in vacuo and the residue was dissolved in diethyl ether, washed with brine, dried over anhydrous sodium sulfate, filtered and evaporated in vacuo to an oil. Flash column chromatography over silica gel (230–400 mesh) using 10% ethyl acetate in hexane as the eluent afforded the title compound as an oil (0.26 g, 5%).

$^1$H NMR (300 MHz, CDCl$_3$): δ 7.60 (m, 4H), 3.93 (s, 3H).

Ethyl-2-fluoro-4-hydroxy benzoate (Reagent I)

A solution of 2-fluoro-4-hydroxy benzoic acid (Intermediate 4, 3 g, 9.2 mmol) in ethanol (65 mL) and benzene (90 mL) was treated with concentrated sulfuric acid (1.5 mL) and heated at reflux overnight using a Dean-Stark water trap. The volatiles were distilled off in vacuo and the residue was diluted with water and diethyl ether. The phases were separated and the organic phase was washed with saturated aqueous sodium bicarbonate (×1), water (×1) and brine (×1), dried over anhydrous magnesium sulfate, filtered and evaporated in vacuo to afford the title compound as a solid (3.07 g, 86%).

$^1$H-NMR (300 MHz, CD$_3$COCD$_3$): δ 1.34 (t, J=7.1 Hz, 3H), 4.32 (q, J=7.1 Hz, 2H), 6.66(dd, J=2.6, 10.9 Hz, 1H), 6.76 (dd, J=2.3, 8.5 Hz, 1H), 7.83(d, J=8.4 Hz, 1H), 9.91 (s, 1H).

Ethyl-2-fluoro-4-trifluoromethylsulfonyloxy-benzoate (Intermediate 6)

A stirred, cooled (ice bath) solution of ethyl-2-fluoro-4-hydroxy-benzoate (Intermediate 5, 0.368 g, 2 mmol) and 2,6-di-tert-butyl-4-methyl-pyridine (0.81 g, 8 mmol) in 8 mL of dichloromethane was treated with trifluoromethane-sulfonic anhydride (0.1 g, 4 mmol). The reaction mixture was allowed to warm to ambient temperature and stirred overnight. The reaction mixture was subjected to flash column chromatography over silica gel (230–400 mesh) using 5–10% ethyl acetate in hexane as the eluent to afford the title compound (0.53 g, 85%).

$^1$H-NMR (300 MHz, CDCl$_3$): δ 1.41 (t, J=7.3 Hz, 3H), 4.42 (q, J=7.1 Hz, 2H), 7.12–7.20(m, 2H), 8.08(t, J=8.3 Hz, 1H).

Ethyl-2-fluoro-4-trimethylsilanylethynyl-benzoate
(Intermediate 7)

A solution of ethyl-2-fluoro-4-trifluoromethylsulfonyloxy-benzoate (Intermediate 6, 1.82 g, 6 mmol) in triethyl amine (12 mL) and anhydrous tetrahydrofuran (30 mL) was treated with copper(I)iodide (0.12 g, 0.6 mmol) and sparged with argon. Dichlorobis (triphenylphosphine)palladium(II) (0.43 g, 0.6 mmol) was added followed by (trimethylsilyl)acetylene (3.6 mL, 24 mmol) and the resulting reaction mixture was heated at 70° C. overnight. It was then cooled to ambient temperature, diluted with diethyl ether and filtered over a bed of celite. The filtrate was evaporated in vacuo to an oil which was subjected to flash column chromatography over silica gel (230–400 mesh) using 5% ethyl acetate in hexane as the eluent to afford the title compound as an orange oil (1.5 g, quantitative).

$^1$H-NMR (300 MHz, CDCl$_3$): δ 0.011 (s, 9H), 1.13(t, J=7.1 Hz, 3H), 4.13 (q, J=7.1 Hz, 2H), 6.93–7.02(m, 2H), 7.07 (s, 1H), 7.61(t, J=7.9 Hz, 1H).

Ethyl-4-ethynyl-2-fluoro benzoate (Reagent D)

A solution of ethyl-2-fluoro-4-trimethylsilanylethynyl-benzoate (Intermediate 7, 1.5 g, 6 mmol) in ethanol (16 mL) was treated with potassium carbonate (1.485 g, 10.74 mmol) and stirred overnight at room temperature. The reaction mixture was then diluted with water and extracted with diethyl ether (×2). The combined organic phase was dried over anhydrous magnesium sulfate, filtered and evaporated in vacuo to afford an orange oil. Flash column chromatography over silica gel (230–400 mesh) using 5% ethyl acetate in hexane as the eluent afforded the title compound (1 g, 86%).

$^1$H-NMR (300 MHz, CDCl$_3$): δ 1.39 (t, J=7.1 Hz, 3H), 3.26 (s, 1H), 4.39 (q, J=7.1 Hz, 2H), 7.22–7.33 (m, 2H), 7.88(t, J=7.7 Hz, 1H).

Methyl-4-iodo-phenyl acetate (Reagent B)

A solution of 4-iodo phenyl acetic acid (5 g, 19 mmol) in methanol was treated with concentrated sulfuric acid (0.5 mL) and refluxed overnight. The volatiles were distilled off in vacuo and the residue was dissolved in ethyl acetate, washed with brine, dried over anhydrous sodium sulfate, filtered and evaporated in vacuo to an oil which was subjected to flash column chromatography over silica gel (230–400 mesh) using 5% ethyl acetate in hexane as the eluent to afford the title compound as a clear oil (5 g, 95%).

$^1$H NMR (300 MHz, CDCl$_3$): δ 7.63 (d, 2H, J=8.5 Hz), 7.01 (d, 2H, J=8.0 Hz), 3.67 (s, 3H), 3.55 (s, 2H).

2-Fluoro-4-iodo-phenyl acetonitrile (Intermediate 2)

A solution of 2-fluoro-4-iodo-benzyl bromide (Intermediate 1, 2.56 g, 8.15 mmol) in ethanol (55 mL and water (10 mL) was treated with sodium cyanide (2.15 g, 43.86 mmol) and refluxed for 0.5 h. The volatiles were distilled off in vacuo and the residue was diluted with water and extracted with diethyl ether (×2). The combined organic extract was washed with water (×1) and brine (×1), dried over anhydrous magnesium sulfate, filtered and evaporated in vacuo to afford the title compound as a pale yellow solid (2.05 g, 96%).

$^1$H-NMR (300 MHz, CDCl$_3$): δ 3.71(s, 3H), 7.16(t, J=8.2 Hz, 1H), 7.45(dd, J=1.7, 9.1 Hz, 1H), 7.51(dd, J=1.5, 8.2 Hz, 1H).

2-Fluoro-4-iodo-phenyl acetic acid (Intermediate 3)

A solution of 2-fluoro-4-iodo-phenyl acetonitrile (Intermediate 2, 2.05 g, 7.83 mmol) in ethanol (50 mL and water (15 mL) was treated with potassium hydroxide (3.4 g, 60.7 mmol) and refluxed for 4 h. The volatiles were distilled off in vacuo and the residue was diluted with water and poured into cold, dilute hydrochloric acid and the precipitated solid was filtered. The solid was dissolved in diethyl ether, and the organic solution was dried over anhydrous magnesium sulfate, filtered and evaporated in vacuo to afford the title compound a pale yellow solid (1.75 g, 79%).

$^1$H-NMR (300 MHz, CDCl$_3$): δ 3.64 (s, 2H), 6.98(t, J=7.9 Hz, 1H), 7.25–7.46 (m, 2H), 9.60–10.40(br s, 1H).

Ethyl-2-fluoro-4-iodo-phenyl acetate (Reagent C)

A solution of 2-fluoro-iodo-phenyl acetic acid (Intermediate 3, 1.75 g, 6.22 mmol) in ethanol (50 mL) and benzene (100 mL) was treated with concentrated sulfuric acid (1.4 mL) and heated at reflux overnight using a Dean-Stark water trap. The volatiles were distilled off in vacuo and the residue was diluted with water and diethyl ether. The phases were separated and the organic phase was washed with saturated aqueous sodium bicarbonate (×1), water (×1) and brine (×1), dried over anhydrous magnesium sulfate, filtered and evaporated in vacuo to afford an oil which was subjected to flash column chromatography over silica gel (230–400 mesh) using 5%–10% ethyl acetate in hexane as the eluent to afford the title compound as a pale yellow solid (1.4 g, 73%).

$^1$H-NMR (300 MHz, CDCl$_3$): δ 1.25 (t, J=7.1 Hz, 3H), 3.60 (s, 2H), 4.16 (q, J=7.1 Hz, 2H), 6.99(t, J=8.0 Hz, 1H), 7.39–7.44(m, 2H).

Methyl-2-fluoro-4-iodo-phenyl acetate (Reagent H)

A solution of 2-fluoro-4-iodo-phenyl acetonitrile (Intermediate 2, 3 g, 11.45 mmol) in methanol (50 mL) and benzene (50 mL) was treated with p-toluene sulfonic acid (2.5 g, 13.15 mmol) and heated at reflux overnight using a Dean-Stark water trap. The volatiles were distilled off in vacuo and the residue was diluted with water and diethyl ether. The phases were separated and the organic phase was washed with saturated aqueous sodium bicarbonate (×1), water (×1) and brine (×1), dried over anhydrous magnesium sulfate, filtered and evaporated in vacuo to afford an oil which was subjected to flash column chromatography over silica gel (230–400 mesh) using 6% ethyl acetate in hexane as the eluent to afford the title compound as a colorless oil (2.7 g, 80%).

$^1$H-NMR (300 MHz, CDCl$_3$): δ 3.62 (s, 2H), 3.70 (s, 3H), 6.99(t, J=7.9 Hz, 1H), 7.39–7.45(m, 2H).

General Procedure A

7-Methoxy-1,1-dimethyl- 1,2,3,4-tetrahydronaphthalene (Intermediate 8)

A stirred, cooled (−40° C.) solution of titanium tetrachloride in anhydrous dichloromethane (1M, 20 mL) under argon, was treated with a solution of dimethyl zinc (2M, 40 mL) in toluene. After 0.5 h, a solution of 7-methoxy-1-tetralone (1.76 g, 10 mmol) in anhydrous dichloromethane (5 mL) was cannulated into the reaction mixture and the resulting solution was allowed to warm to ambient temperature and stirred overnight. The reaction mixture was then cooled to −40° C. and cautiously quenched with methanol (11 mL). It was diluted with dichloromethane and saturated aqueous ammonium chloride solution. The phases were separated and the aqueous phase was extracted with dichloromethane (×2 mL). The combined organic phase was dried over anhydrous sodium sulfate, filtered and evaporated in vacuo to the title compound (1.75 g, 92%) as an oil.

¹H-NMR (300 MHz, CDCl₃): δ 1.33(s, 6H), 1.67–1.71(m, 2H), 1.79–1.90(m, 2H), 2.75(t, J=6.2 Hz, 2H), 3.83(s, 3H), 6.72(dd, J=2.6, 8.3 Hz, 1H), 6.93(d, J=2.6 Hz, 1H), 7.02(d, J=8.3 Hz, 1H).

General Procedure B

6-Methoxy-4,4-dimethyl-1,2,3,4-tetrahydronaphthalene-1-one (Intermediate 9)

A solution of 7-methoxy-1,1-dimethyl-1,2,3,4-tetrahydronaphthalene (Intermediate 8, 1.65 g, 8.7 mmol) in 7.5 mL of glacial acetic acid was cooled to 0° C. and treated with a solution of chromium trioxide (2 g, 20 mmol) in 8 mL of acetic acid and 7 mL of water. The reaction mixture was then allowed to warn to ambient temperature and stirred overnight. It was diluted with water and extracted with diethyl ether (×2). The combined organic phase was washed with water (×1), saturated aqueous sodium bicarbonate (×1) and brine (×1), dried over anhydrous magnesium sulfate, filtered and evaporated in vacuo to afford the title compound (1.64 g, 93%) as a yellow oil.

¹H-NMR (300 MHz, CDCl₃): δ 1.34(s, 6H), 1.96(t, J=7.1 Hz, 2H), 2.64(t, J=7.1 Hz, 2H), 3.83(s, 3H), 6.77(dd, J=2.6, 8.7 Hz, 1H), 6.83(d, J=2.5 Hz, 1H), 7.98(d, J=8.7 Hz, 1H).

6-Hydroxy-4,4-dimethyl-1,2,3,4-tetrahydronaphthalene-1-one (Intermediate 10)

A stirred, cooled (−78° C.) solution of 6-methoxy-4,4-dimethyl-1,2,3,4-tetrahydronaphthalene-1-one (Intermediate 9, 0.8, 3 mmol) under argon was treated with a 1M solution of boron tribromide (10 mL). The reaction mixture was allowed to warm to ambient temperature and stirred overnight. The reaction mixture was cooled to −78° C., quenched and diluted with saturated aqueous sodium bicarbonate solution and the aqueous phase was extracted with dichloromethane (×2). The combined organic phase was dried over anhydrous sodium sulfate, filtered and evaporated in vacuo to an oil. Flash column chromatography over silica gel (230–400 mesh) using 30% ethyl acetate in hexane as the eluent afforded the title compound (0.3 g, 52%) as a yellow viscous oil.

¹H-NMR (300 MHz, CDCl₃): δ 1.33(s, 6H), 1.97(t, J=6.8 Hz, 2H), 2.71(t, J=6.7 Hz, 2H), 6.81(dd, J=2.3, 8.5 Hz, 1H), 6.94(d, J=2.3 Hz, 1H), 7.98(d, J=8.7 Hz, 1H), 9.35(s, 1H).

General Procedure C 4,4-Dimethyl-6-trifluoromethylsulfonyloxy-1,2,3,4-tetrahydronaphthalene-1-one (Intermediate 11)

A stirred, cooled (0° C.) solution of 6-hydroxy-4,4-dimethyl-1,2,3,4-terahydronaphthalene-1-one (Intermediate 10, 0.3 g, 1.6 mmol) in anhydrous dichloromethane (10 mL) was treated with 4-(dimethylamino)pyridine (0.36 g, 3.27 mmol) followed by 2-[N,N'-bis(trifluoromethylsulfonyl) amino]-5-chloropyridine (0.79 g, 2 mmol). After stirring at ambient temperature for 0.75 h, the reaction mixture was diluted with dichloromethane and washed with water (×1). The organic phase was dried over anhydrous sodium sulfate, filtered and evaporated in vacuo to an oil. Flash column chromatography over silica gel (230–400 mesh) using 8–10% ethyl acetate in hexane as the eluent afforded the title compound (0.462 g, 90%) as an off-white solid.

¹H-NMR (300 MHz, CDCl₃): δ 1.36(s, 6H), 2.01(t, J=6.8 Hz, 2H), 2.70(t, J=6.7 Hz, 2H), 7.15(dd, J=2.5, 8.7 Hz, 1H), 7.28(d, J=2.4 Hz, 1H), 8.06(d, J=8.7 Hz, 1H).

General Procedure D 4,4-Dimethyl-6-trimethylsilanyl-ethynyl-1,2,3,4-tetrahydronaphthalene-1-one (Intermediate 12)

A solution of 4,4-dimethyl-6-trifluoromethylsulfonyloxy-1,2,3,4-tetrahydronaphthalene-1-one (Intermediate 11, 0.46 g, 1.43 mmol) in triethyl amine (3 mL) and anhydrous tetrahydrofuran (8 mL) was treated with copper(I)iodide (0.1 g, 0.53 mmol) and sparged with argon for 5 minutes. Trimethylsilyl acetylene (0.85 mL, 6 mmol) was then added followed by dichlorobis(triphenylphosphine)palladium(II) (0.25 g, 0.36 mmol). The resulting reaction mixture was heated at 70° C. for 17 h. It was then cooled to ambient temperature, diluted with diethyl ether and filtered over a bed of celite. The filtrate was evaporated vacuo to an oil which was subjected to flash column chromatography over silica gel (230–400 mesh) using 5% ethyl acetate in hexane as the eluent to afford the title compound (0.28 g, 72%).

¹H-NMR (300 MHz, CDCl₃): δ 0.26(s, 9H), 1.36(s, 6H), 1.99(t, J=6.8 Hz, 2H), 2.69(t, J=6.7 Hz, 2H), 7.35(dd, J=1.7, 8.2 Hz, 1H), 7.49 (unresolved d, 1H), 7.93(d, J=8.1 Hz, 1H).

General Procedure E

6-Ethynyl-4,4-dimethyl-1,2,3,4-tetrahydronaphthalene-l-one (Intermediate 13)

A solution of 4,4-dimethyl-6-trimethylsilanylethynyl-1,2,3,4-tetrahydronaphthalene-1-one (Intermediate 12, 0.28 g, 1.03 mmol) in methanol (10 mL) was treated with potassium carbonate (0.74 g, 5.35 mmol) and stirred at ambient temperature for 4 h. The volatiles were distilled off in vacuo and the residue was diluted with water and extracted with diethyl ether (×2). The combined organic extract was dried over anhydrous magnesium sulfate, filtered and evaporated in vacuo to afford the title compound (0.19 g, 89%) as an oil that solidified on standing.

¹H-NMR (300 MHz, CDCl₃): δ 1.33(s, 6H), 1.96(t, J=6.8 Hz, 2H), 2.67(t, J=6.8 Hz, 2H), 3.25(S, 1H), 7.33(dd, J=1.5, 8.1 Hz, 1H), 7.49 (d, J=1.5 Hz, 1H), 7.13(d, J=8.1 Hz, 1H).

General Procedure F 4-(8,8-Dimethyl-5-oxo-5,6,7,8-tetrahydro-naphthalene-2-yl-ethynyl)-benzoic acid ethyl ester (Intermediate 14)

A solution of 6-ethynyl-4,4-dimethyl-1,2,3,4-tetrahydronaphthalene-1-one (Intermediate 13, 0.23 g, 1.1 mmol) and ethyl-4-iodo benzoate (Reagent A, 0.36 g, 1.3 mmol) in triethyl amine (7 mL) and anhydrous tetrahydrofuran (3 mL) was treated with copper(I)iodide (0.114 g, 0.6 mmol) and sparged with argon for 5 minutes. Dichlorobis(triphenylphosphine)palladium(II) (0.23 g, 0.33 mmol) was added and the reaction mixture was stirred overnight at room temperature. It was diluted with diethyl ether and filtered over a bed of celite. The filtrate was evaporated in vacuo to a brown oil that was subjected to flash column chromatography over silica gel (230–400 mesh) using 6–7% ethyl acetate in hexane as the eluent to afford the title compound (0.29 g, 72%) as a pale brown solid.

¹H-NMR (300 MHz, CDCl₃): δ 1.3(t, J=7.1 Hz, 3H), 1.37(s, 6H), 1.80 (t, J=6.8 Hz, 2H), 2.69(t, J=6.8 Hz, 2H), 4.35(q, J=7.1 Hz, 2H), 7.40(dd, J=1.5, 8.2 Hz, 1H), 7.51 (d, J=1.6 Hz, 1H), 7.57 (d, J=8.3 Hz, 2H), 7.96(d, J=8.2 Hz, 1H), 7.99(d, J=8.5 Hz, 2H).

General Procedure G 4-(5-Cyclopropylamino-8,8-dimethyl-5,6,7,8-tetrahydro-naphthalene-2yl-ethynyl)-benzoic acid ethyl ester (Compound 1, General Formula 4)

A solution of 4-(8,8-dimethyl-5-oxo-5,6,7,8-tetrahydro-naphthalene-2-ylethynyl)-benzoic acid ethyl ester (Intermediate 14, 0.14 g, 0.4 mmol) in 3 mL of dichloromethane and 2 mL of acetonitrile was treated with cyclopropyl amine(1 mL, 14.45 mmol). After 5 minutes, acetic acid (1 mL) was added followed by sodium cyanoborohydride (0.13 g, 2 mmol). The reaction was stirred overnight at ambient temperature. It was then diluted with water and saturated aqueous sodium carbonate solution and extracted with dichloromethane (×2). The combined organic extract was dried over anhydrous sodium sulfate, filtered and evaporated in vacuo to an oil. Flash column chromatography over silica gel (230–400 mesh) using 20% ethyl acetate in hexane as the eluent afforded the title compound (0.1 g, 62%) as a pale yellow solid.

$^1$H-NMR (300 MHz, CDCl$_3$): δ 0.30–0.60(m, 4H), 1.28(s, 3H), 1.35 (s, 3H), 1.30(t, J=7.1 Hz, 3H), 1.55–1.61(m, 1H), 1.83–2.05(m, 3H), 2.25 (quintet, J=3.0 Hz, 1H), 3.80 (t, J=4.9 Hz, 1H), 4.39(q, J=7.1 Hz, 2H), 7.27–7.36(m, 2H), 7.52 (s, 1H), 7.55(d, J=8.3 Hz, 2H), 8.03(d, J=8.5 Hz, 2H).

General Procedure H

4-[(5-Cyclopropyl-methyl-amino)-8,8-dimethyl-5,6, 7,8-tetrahydro-naphthalene-2-ylethynyl]-benzoic acid ethyl ester (Compound 2, General Formula 4)

A solution of 4-(5-cyclopropylamino-8,8-dimethyl-5,6,7, 8-tetrahydro-naphthalene-2-ylethynyl)-benzoic acid ethyl ester (Compound 1, 0.064 g, 0.16 mmol) in acetone (2 mL) was treated with potassium carbonate (0.6 g, 4.34 mmol) and methyl iodide (1 mL, 16 mmol) and stirred overnight at ambient temperature. The volatiles were distilled off in vacuo and the residue was diluted with water and extracted with dichloromethane (×2). The combined organic extract was dried over anhydrous sodium sulfate, filtered and evaporated in vacuo to afford the title compound (0.065 g, 99%).

$^1$H-NMR (300 MHz, CDCl$_3$): δ 0.28–0.49 (m, 4H), 1.21(s, 3H), 1.26 (s, 3H), 1.33 (t, J=7.1 Hz, 3H), 1.58–1.73 (m, 2H), 1.83–1.89 (m, 2H), 2.02–2.08 (m, 1H), 2.06 (s, 3H), 3.88 (t, J=8.1 Hz, 1H), 4.32(q, J=7.1 Hz, 2H), 7.20(d, J=7.8 Hz, 1H), 7.41 (s, 1H), 7.46 (d, J=7.8 Hz, 1H), 7.52(d, J=8.4 Hz, 2H), 8.03(d, J=8.3 Hz, 2H).

General Procedure I

4-[(5-Cyclopropyl-methyl-amino)-8,8-dimethyl-5,6, 7,8-tetrahydro-naphthalene-2yl-ethynyl]-benzoic acid (Compound 3, General Formula 4)

A solution of 4-[(5-cyclopropyl-methyl-amino)-8,8-dimethyl-5,6,7,8-tetrahydro-naphthalene-2-ylethynyl]-benzoic acid ethyl ester (Compound 2, 0.065 g, 0.158 mmol) in ethanol (1 mL) and tetrahydrofuran (1 mL) was treated with 1M aqueous sodium hydroxide solution (1 mL) and heated at 80° C. for 1 h. The volatiles were distilled off in vacuo and the residue was diluted with saturated aqueous ammonium chloride solution and extracted with ethyl acetate (×2). The combined organic extract was dried over anhydrous sodium sulfate, filtered and evaporated in vacuo to afford a solid that was washed with dichoromethane and dried to afford the title compound (0.029 g, 38%) as a white solid.

$^1$H-NMR (300 MHz, CD$_3$COCD$_3$): δ 0.35–0.51(m, 4H), 1.26(s, 3H), 1.29 (s, 3H), 1.60–1.82(m, 2H), 1.88–2.02(m, 2H), 2.02–2.15 (m, 1H), 2.10 (s, 3H), 3.93 (t, J=8.0 Hz, 1H), 7.26(dd, J=1.5, 8.2 Hz, 1H), 7.51 (d, J=1.5 Hz, 1H), 7.52(d, J=8.2 Hz, 1H), 7.62(d, J=8.5 Hz, 2H), 8.02(d, J=8.2 Hz, 2H).

4-[(8,8-Dimethyl-5-oxo-5,6,7,8-tetrahydro-naphthalene-2-yl-ethynyl)-phenyl]-acetic acid methyl ester (Compound 4, General Formula 8)

Following general procedure F and using 6-ethynyl-4,4-dimethyl-1,2,3,4-tetrahydronaphthalene-1-one (Intermediate 13, 0.312 g, 1.5 mmol), 4-iodo phenyl acetic acid methyl ester (Reagent B, 0.50 g, 1.8 mmol), triethyl amine (7 mL), anhydrous tetrahydrofuran (3 mL), copper(I) iodide (0.04 g, 0.2 mmol) and dichlorobis (triphenylphosphine)palladium(II) (0.15 g, 0.213 mmol) followed by flash column chromatography over silica gel (230–400 mesh) using 16–20% ethyl acetate in hexane as the eluent, the title compound was obtained as a pale yellow solid (0.42 g, 76%).

$^1$H-NMR (300 MHz, CDCl$_3$): δ 1.42(s, 6H), 2.04(t, J=6.7 Hz, 2H), 2.74(t, J=6.7 Hz, 2H), 3.66(s, 2H), 3.71(s, 3H), 7.29 (d, J=8.2 Hz, 2H), 7.43(dd, J=1.5, 7.9 Hz, 1H), 7.52 (d, J=8.2 Hz, 2H), 7.57 (d, J=1.5 Hz, 1H), 8.00(d, J=8.2 Hz, 1H).

General Procedure J

4-[(8,8-Dimethyl-5-oxo-5,6,7,8-tetrahydro-naphthalene-2-yl-ethynyl)-phenyl]-acetic acid (Compound 5, General Formula 8)

A solution of 4-[(8,8-dimethyl-5-oxo-5,6,7,8-tetrahydro-naphthalene-2-ylethynyl)-phenyl]-acetic acid methyl ester (Compound 4, 0.1 g, 0.28 mmol) in a mixture of methanol (2 mL), tetrahydrofuran (3.5 mL) and water (1.5 mL) was treated with lithium hydroxide monohydrate (0.11 g, 2.62 mmol) and the resulting reaction mixture was stirred at ambient temperature for 3 h. The volatiles were distilled off in vacuo and the residue was diluted with water and dilute hydrochloric acid and extracted with ethyl acetate (×3). The combined organic phase was dried over anhydrous sodium sulfate, filtered and evaporated in vacuo to afford the title compound as a pale yellow solid (0.088 g, 92%).

$^1$H-NMR (300 MHz, CDCl$_3$): δ 1.41(s, 6H), 2.02(t, J=6.7 Hz, 2H), 2.74(t, J=6.8 Hz, 2H), 3.68(s, 2H), 7.28 (d, J=8.2 Hz, 2H), 7.42(dd, J=1.5, 8.2 Hz, 1H), 7.52 (d, J=8.2 Hz, 2H), 7.56 (d, J=1.5 Hz, 1H), 7.99(d, J=8.2 Hz, 1H).

4-[(5-(Cyclopropyl-amino)-8,8-dimethyl-5,6,7,8-tetrahydro-naphthalene-2-yl-ethynyl)-phenyl]-acetic acid methyl ester (Compound 6, General Formula 4)

Following general procedure G and using 4-[(8,8-dimethyl-5-oxo-5,6,7,8-tetrahydro-naphthalene-2-yl-ethynyl)-phenyl]-acetic acid methyl ester (Compound 4, 0.2 g, 0.54 mmol), dichloromethane (4 mL), acetonitrile(2 mL), cyclopropyl amine(1 mL, 14.45 mmol), acetic acid (1 mL) and sodium cyanoborohydride (0.1 6 g, 2.54 mmol) followed by flash column chromatography over silica gel (230–400 mesh) using 30% ethyl acetate in hexane as the eluent the title compound was obtained as a pale yellow oil 0.22 g, 99%).

$^1$H-NMR (300 MHz, CDCl$_3$): δ 0.38–0.60 (m, 4H), 1.26(s, 3H), 1.33(s, 3H), 1.50–1.59(m, 1H), 1.79–2.10 (m, 3H), 2.25(m, 1H), 3.63(s, 2H), 3.69(s, 3H), 3.79(t, J=4.8 Hz, 1H), 7.20–7.32 (m, 4H), 7.47(s, 1H), 7.58(d, J=8.2 Hz, 2H).

4-[(5-(Cyclopropyl-methyl-amino)-8,8-dimethyl- 5, 6,7,8-tetrahydro-naphthalene-2-yl-ethynyl)-phenyl]-acetic acid methyl ester (Compound 7, General Formula 4)

Following general procedure H and using 4-[(5-(cyclopropyl-amino)-8,8-dimethyl-5,6,7,8-tetrahydro-naphthalene-2-ylethynyl)-phenyl]-acetic acid methyl ester (Compound 6, 0.15 g, 0.37 mmol), acetone (5 mL), potassium carbonate (1.1 g, 7.95 mmol) and methyl iodide (1 mL, 16 mmol), the following work-up was used. The volatiles were distilled off in vacuo and the residue was diluted with water and extracted with dichloromethane (×2). The combined organic extract was dried over anhydrous sodium sulfate, filtered and evaporated in vacuo to afford the title compound (0.148 g, 97%).

$^1$H-NMR (300 MHz, CDCl$_3$): δ 0.38–0.58(m, 4H), 1.27(s, 3H), 1.31 (s, 3H), 1.68–1.81(m, 2H), 1.85–1.98(m, 2H), 2.08–2.15 (m, 1H), 2.12 (s, 3H), 3.62(s, 2H), 3.69(s, 3H), 3.94 (t, J=7.9 Hz, 1H), 7.24(d, J=8.2 Hz, 1H), 7.24 (d, J=8.2 Hz, 2H), 7.44–7.51(m, 4H).

4-[(5-(Cyclopropyl-methyl-amino)-8.8-dimethyl-5,6, 7,8-tetrahydro-naphthalene-2-yl-ethynyl)-phenyl]-acetic acid (Compound 8, General Formula 4)

Following general procedure J and using 4-[(5-(cyclopropyl-methyl-amino)-8,8-dimethyl-5,6,7,8-tetrahydro-naphthalene-2ylethynyl)-phenyl]-acetic acid methyl ester (Compound 7, 0.148 g, 0.357 mmol), methanol (2 mL), tetrahydrofuran (4 mL), water (1 mL) and lithium hydroxide monohydrate (0.25 g, 5.95 mmol) followed by flash column chromatography over silica gel (230–400 mesh) using 30–75% ethyl acetate in hexane as the eluent, the title compound was obtained as a white solid (0.08 g, 56%).

$^1$H-NMR (300 MHz, CDCl$_3$): δ 0.52–0.54(m, 2H), 0.68–0.70(m, 2H), 1.27(s, 3H), 1.29(s, 3H), 1.63–1.80(m, 2H), 1.95–2.17(m, 2H), 2.19–2.24(m, 1H), 2.4(s, 3H), 3.60 (s, 2H), 4.18(t, J=7.7 Hz, 1H), 7.24(dd, J=1.5, 8.2 Hz, 1H), 7.6 (d, J=8.2 Hz, 2H), 7.43 (d, J=8.2 Hz, 1H), 7.47(s, 1H), 7.47(d, J=8.2 Hz, 2H), 10.37(br s, 1H).

2-Fluoro-4-[(8.8-dimethyl-5-oxo-5,6,7,8-tetrahydro-naphthalen-2-yl-ethenyl]benzoic acid ethyl ester (Compound 9, General Formula 8)

A solution of 4,4-dimethyl-6-trifluromethylsulfonyloxy-1,2,3,4-tetrahydronaphthalene-1-one (Intermediate 11, 0.3 g, 0.9 mmol), copper(I)iodide (0.057 g, 0.3 mmol) and ethyl-2-fluoro-4-ethynyl-benzoate (Reagent D, 0.44 g, 2.27 mmol) in triethyl amine (2 mL) and tetrahydrofuran (3 mL) was sparged with argon for 5 minutes and treated with dichlorobis(triphenylphosphine)palladium(II) (0.1 35 g, 0. 192 mmol) and stirred at room temperature overnight and then refluxed for 2 h. It was then cooled to ambient temperature, diluted with diethyl ether and filtered over a bed of celite. The filtrate was evaporated in vacuo to an oil which was subjected to flash column chromatography over silica gel (230–400 mesh) using 10–15% ethyl acetate in hexane as the eluent to afford the title compound as a yellow solid (0.22 g, 67%).

$^1$H-NMR (300 MHz, CDCl$_3$): δ 1.38 (t, J=7.0 Hz, 3H), 1.39(s, 6H), 2.01(t, J=6.7 Hz, 2H), 2.71(t, J=6.7 Hz, 2H), 4.37(q, J=7 Hz, 2H), 7.28(dd, J=0.9, 10 Hz, 1H), 7.34(dd, J=0.9, 8.2 Hz, 1H), 7.41 (dd, J=1.5, 8.2 Hz, 1H), 7.57(d, J=0.9 Hz), 7.90(t, J=7.9 Hz, 1H), 7.93 (d, J=7.9 Hz, 1H).

2-Fluoro-4-(8,8-dimethyl-5-oxo-5,6,7,8-tetrahydro-naphthalen-2yl-ethynyl)-benzoic acid (Compound 10, General Formula 8)

A solution of 2-fluoro-4-(8,8-dimethyl-5-oxo-5,6,7,8-tetrahydro-naphthalen-2-ylethynyl)benzoic acid ethyl ester (Compound 9, 0.1 g, 0.274 mmol) in ethanol(4 mL), methanol (2 mL) and tetrahydrofuran (2 mL) was treated with 1M aqueous sodium hydroxide solution and heated at 70° C. for 1 h. The volatiles were distilled off in vacuo and the residue was diluted with water and dilute hydrochloric acid and extracted with ethyl acetate (×2). The combined organic extract was dried over anhydrous sodium sulfate, filtered and evaporated in vacuo to afford a solid that was recrystallized from hot aqueous acetonitrile to afford the title compound (0.025 g, 27%).

$^1$H-NMR (300 MHz, CDCl$_3$): δ 1.43(s, 6H), 2.05(t, J=6.9 Hz, 2H), 2.76(t, J=6.9 Hz, 2H), 7.26–7.47(m, 3H), 7.60(d, J=1.1 Hz, 1H), 7.99–8.05(m, 2H).

4-[5-(Cyclopropyl-amino)-8,8-dimethyl-5,6,7,8-tetrahydro-naphthalene-2-yl-ethynyl]-2-fluoro-benzoic acid ethyl ester (Compound 11, General Formula 4)

Following general procedure G and using 2-fluoro-4-(8, 8-dimethyl-5-oxo-5,6,7,8-tetrahydro-naphthalene-2-ylethynyl)-benzoic acid ethyl ester (Compound 9, 0.132 g, 0.3 mmol), dichloromethane (4 mL), acetonitrile(2 mL), cyclopropyl amine(1 mL, 14.45 mmol), acetic acid (1 mL) and sodium cyanoborohydride (0.1 8 g, 2.86 mmol) followed by flash column chromatography over silica gel (230–400 mesh) using 16–20% ethyl acetate in hexane as the eluent, the title compound was obtained as a pale yellow oil (0.1g, 82%).

$^1$H-NMR (300 MHz, CDCl$_3$): δ 0.36–0.54 (m, 4H), 1.27(s, 3H), 1.33(s, 3H), 1.40(t, J=7.0 Hz, 3H), 1.54–1.61 (m, 2H), 1.82–2.05 (m, 2H), 2.26(m, 1H), 3.79 (t, J=4.9 Hz, 1H), 4.39(q, J=7.1 Hz, 2H), 7.26–7.50(m, 4H), 7.87(s, 1H), 7.92 (t, J=7.9 Hz, 1H).

4-[5-(Cyclopropyl-methyl-amino)-8,8-dimethyl- 5,6, 7,8-tetrahydro-naphthalene-2-yl-ethynyl]-2-fluoro benzoic acid ethyl ester (Compound 12, General Formula 4)

Following general procedure H and using 4-[5-(cyclopropyl-methyl-amino)-8,8-dimethyl- 5,6,7,8-tetrahydro-naphthalene-2-ylethynyl]-2-fluoro-benzoic acid ethyl ester (Compound 11, 0.1 g, 0.246 mmol), acetone (4 mL), potassium carbonate (0.917 g, 6.63 mmol) and methyl iodide (0.8 mL, 11 mmol), the following work-up was used. The volatiles were distilled off in vacuo and the residue was diluted with water and extracted with dichloromethane (×2). The combined organic extract was dried over anhydrous sodium sulfate, filtered and evaporated in vacuo to an oil. Flash column chromatography over silica gel (230–400 mesh) using 8–10% ethyl acetate in hexane as the eluent afforded the title compound as a pale yellow oil (0.102 g, 98%).

$_1$H-NMR (300 MHz, CDCl$_3$): δ 0.39–0.62 (m, 4H), 1.29(s, 3H), 1.34(s, 3H), 1.42(t, J=6.9 Hz, 3H), 1.65–1.82 (m, 2H), 1.85–2.02 (m, 2H), 2.02–2.10(m, 1H), 2.15(s, 3H), 3.97(t, J=7.7 Hz, 1H), 4.42(q, J=7.0 Hz, 2H), 7.28–7.36 (m, 3H), 7.59(s, 1H), 7.55(d, J=7.9 Hz, 2H), 7.92 (t, J=7.5 Hz, 1H).

4-[5-(Cyclopropyl-methyl-amino)-8,8-dimethyl-5,6, 7,8-tetrahydro-naphthalene-2-yl-ethynyl]-2-fluoro benzoic acid (Compound 13, General Formula 4)

Following general procedure I and using 4-[(5-cyclopropyl-methyl-amino)-8,8-dimethyl-5,6,7,8-tetrahydro-naphthalene-2-ylethynyl]-2-fluoro-benzoic acid ethyl ester (Compound 12, 0.102 g, 0.23 mmol), ethanol (4 mL) and 1M aqueous sodium hydroxide solution (2 mL) followed by flash column chromatography over silica gel (230–400 mesh) 30% ethyl acetate in hexane as the eluent, the title compound was obtained as an off-white solid(0.01 5 g, 16%).

¹H-NMR (300 MHz, CDCl₃): δ 0.54–0.65 (m, 4H), 1.29 (s, 3H), 1.32 (s, 3H), 1.68–1.83 (m, 2H), 1.97–2.05 (m, 2H), 2.18–2.25 (m, 1H), 2.25 (s, 3H), 4.13 (t, J=6.7 Hz, 1H), 7.26–7.30 (m, 2H), 7.34 (dd, J=1.5, 7.9 Hz, 1H), 7.48 (d, J=1.8 Hz, 1H), 7.60 (d, J=8.5 Hz, 1H), 7.95 (t, J=7.9 Hz, 1H).

[2-Fluoro-4-(8,8-dimethyl-5-oxo-5,6,7,8-tetrahydro-naphthalene-2-yl-ethynyl)-phenyl]acetic acid ethyl ester (Compound 14, General Formula 8)

Following general procedure F and using 6-ethynyl-4,4-dimethyl-1,2,3,4-tetrahydro-naphthalene-1-one (Intermediate 13, 0.298 g, 1.43 mmol), 2-fluoro-4-iodo phenyl acetic acid ethyl ester (Reagent C, 0.44 g, 1.43 mmol), triethyl amine (Intermediate 13, 3 mL), anhydrous tetrahydrofuran (7 mL), copper(I)iodide (0.04 g, 0.2 mmol) and dichlorobis(triphenylphosphine)palladium(II) (0.15 g, 0.213 mmol) followed by flash column chromatography over silica gel (230–400 mesh) using 14–16% ethyl acetate in hexane as the eluent, the title compound was obtained as an oil (0.43 g, 77%).

¹H-NMR (300 MHz, CDCl₃): δ 1.26(t, J=7.2 Hz, 3H), 1.41(s, 6H), 2.04(t, J=6.7 Hz, 2H), 2.74(t, J=6.7 Hz, 2H), 3.68(s, 2H), 4.18(q, J=7.1Hz, 2H), 7.23–7.57(m, 4H), 7.59 (d, J=1.5 Hz, 1H), 7.99(d, J=7.9 Hz, 1H).

[2-Fluoro-4-(8,8-dimethyl-5-oxo-5,6,7,8-tetrahydro-naphthalene-2-yl-ethynyl)phenyl]-acetic acid (Compound 15, General Formula 8)

Following general procedure J and using [2-fluoro-4-(8,8-dimethyl-5-oxo-5,6,7,8-tetrahydro-naphthalene-2-ylethynyl)phenyl]acetic acid methyl ester (Compound 14, 0.1 8 g, 0.48 mmol), methanol (4 mL), tetrahydrofuran (8 mL), water (2 mL) and lithium hydroxide monohydrate (0.2 g, 4.76 mmol) followed by flash column chromatography over silica gel (230–400 mesh) using 50–100% ethyl acetate in hexane as the eluent, the title compound was obtained as a dirty white solid (0.068 g, 41%).

¹H-NMR (300 MHz, CDCl₃): δ 1.41(s, 6H), 2.03(t, J=6.7 Hz, 2H), 2.74(t, J=6.8 Hz, 2H), 3.73(s, 2H), 7.24–7.32(m, 3H), 7.42(dd, J=1.5, 7.9 Hz, 1H), 7.56 (s, 1H), 7.99(d, J=7.9 Hz, 1H), 9.40–10.00 (br s, 1H).

[4-(5-(Cyclopropyl-amino)-8,8-dimethyl- 5,6,7,8-tetrahydro-naphthalene-2-yl-ethynyl)-2 -fluoro-phenyl]acetic acid ethyl ester (Compound 16, General Formula 4)

Following general procedure G and using [2-fluoro-4-(8,8-dimethyl-5-oxo-5,6,7,8-tetrahydro-naphthalene-2-ylethynyl) phenyl]acetic acid ethyl ester (Compound 14, 0.258 g, 0.68 mmol), dichloromethane (4 mL), acetonitrile(2 mL), cyclopropyl amine(1 mL, 14.45 mmol), acetic acid (1 mL) and sodium cyanoborohydride (0.266 g, 4.23 mmol) followed by flash column chromatography over silica gel (230–400 mesh) using 16–20–25% ethyl acetate in hexane as the eluent, the title compound was obtained as a pale yellow oil (0.21 g, 73%).

¹H-NMR (300 MHz, CDCl₃): δ 0.35–0.54 (m, 4H), 1.25(t, J=7.1 Hz, 3H), 1.26(s, 3H), 1.32(s, 3H), 1.53–1.64 (m, 1H), 1.82–2.05 (m, 3H), 2.21–2.28(m, 1H), 3.65(s, 2H), 3.78(t, J=5.0 Hz, 1H), 4.17(q, J=7.1 Hz, 2H), 7.19–7.41 (m, 5H), 7.47(d, J=1.5 Hz, 1H).

[4-(5-(Cyclopropyl-methyl-amino)-8,8-dimethyl-5,6,7,8-tetrahydro-naphthalene-2-yl-ethynyl)-2-fluoro-phenyl]-acetic acid ethyl ester (Compound 17, General Formula 8)

Following general procedure H and using [4-((5-cyclopropyl-amino)-8,8-dimethyl-5,6,7,8-tetrahydro-naphthalene-2ylethynyl)-2-fluoro-phenyl]acetic acid ethyl ester (Compound 16, 0.21 g, 0.5 mmol), acetone (5 mL), potassium carbonate (1.13 g, 8.17 mmol) and methyl iodide (0.5 mL, 8 mmol), the following work-up was used. The volatiles were distilled off in vacuo and the residue was diluted with water and extracted with dichloromethane (×2). The combined organic extract was dried over anhydrous sodium sulfate, filtered and evaporated in vacuo to afford an oil. Flash column chromatography over silica gel (230–400 mesh) using 8% ethyl acetate in hexane as the eluent afforded the title compound (0.15 g, 69%).

¹H-NMR (300 MHz, CDCl₃): δ 0.39–0.53(m, 4H), 1.27(s, 3H), 1.31 (s, 3H), 1.66–1.81(m, 2H), 1.89–2.05(m, 2H), 2.08–2.13 (m, 1H), 2.13 (s, 3H), 3.62(s, 2H), 3.94 (t, J=8.0 Hz, 1H), 4.16(q, J=7.1 Hz, 2H), 7.20–7.29(m, 4H), 7.44(d, J=1.5 Hz, 1H), 7.51 (d, J=8.2 Hz, 1H).

[4-(5-(Cyclopropyl-methyl-amino)-8,8-dimethyl-5,6,7,8-tetrahydro-naphthalene-2-yl-ethynyl)-2-fluoro-phenyl]-acetic acid (Compound 18, General Formula 4)

Following general procedure J and using [4-(5-(cyclopropyl-methyl-amino)-8,8-dimethyl- 5,6,7,8-tetrahydro-naphthalene-2-ylethynyl)-2-fluoro-phenyl]-acetic acid ethyl ester (Compound 17, 0.025 g, 0.059 mmol), methanol (1 mL), tetrahydrofuran (1 mL), water (0.5 mL) and lithium hydroxide monohydrate (0.060 g, 1.43 mmol), the title compound was obtained as a white solid (0.023 g, 95%).

¹H-NMR (300 MHz, CDCl₃): δ 0.52–0.54(m, 2H), 0.68–0.70(m, 2H), 1.27(s, 3H), 1.29(s, 3H), 1.63–1.80(m, 2H), 1.95–2.17(m, 2H), 2.19–2.24(m, 1H), 2.24(s, 3H), 3.60(s, 2H), 4.18(t, J=7.7 Hz, 1H), 7.19–7.28(m, 4H), 7.45 (d, J=1.5 Hz, 1H), 7.49(d, J=8.2 Hz, 1H), 8.80–9.20(br s, 1H).

General Procedure K

8,8-Dimethyl-5,6,7,8-tetrahydro-naphthalene-1-one-2-carboxylic acid-4-(tert-butoxycarbonylmethyl) phenyl ester Compound 19, General Formula 8)

A solution of 4,4-dimethyl-6-trifluoromethylsulfonyloxy-1,2,3,4-tetrahydronaphthalene-1-one (Intermediate 11, 0.14 g, 0.434 mmol), t-butyl-4-hydroxy-phenyl acetate (Reagent E, 0.14 g, 0.673 mmol), palladium acetate (0.054 g, 0.24 mmol) and 1,3-bis(diphenylphosphino)propane (0.082 g, 0.2 mmol) in a mixture of dimethylsulfoxide (1 mL), 1,2-dichloroethane (1.5 mL) and triethyl amine (1 mL) was heated at 70° C. under an atmosphere of carbon monoxide overnight. The volatiles were distilled of in vacuo and the residue was diluted with water and extracted with diethyl ether (×3). The combined organic extract was dried over anhydrous magnesium sulfate, filtered and evaporated in vacuo to an oil which was subjected to flash column chromatography over silica gel (230–400 mesh) using 15% ethyl acetate in hexane as the eluent to afford the title compound (0.11 g, 53%).

¹H-NMR (300 MHz, CDCl₃): δ 1.44(s, 3H), 1.44(s, 9H), 1.46 (s, 3H), 2.07(t, J=6.9 Hz, 2H), 2.76(t, J=6.8 Hz, 2H), 3.55(s, 2H), 7.17 (d, J=8.5 Hz, 2H), 7.35(d, J=8.5 Hz, 2H), 8.05–8.13(m, 2H), 8.25 (d, J=1.5 Hz, 1H).

8,8-Dimethyl-5-oxo-5,6,7,8-tetrahydro-naphthalene-2-carboxylic acid-4-(carboxymethyl)phenyl ester (Compound 20, General Formula 8)

A solution of 8,8-dimethyl-5-oxo-5,6,7,8-tetrahydro-naphthalene-2-carboxylic acid 4-(tert-butoxycarbonylmethyl)phenyl ester (Compound 19, 0.11 g, 0.229 mmol) in dichloromethane (2 mL) was treated with trifluoroacetic acid (0.85 mL and stirred at ambient temperature for 2.5 h. The volatiles were distilled off in vacuo and the residue was diluted with water and extracted with ethyl acetate (×3). The combined organic phase was dried over anhydrous sodium sulfate, filtered and evaporated in vacuo to afford a solid which was subjected to flash column chromatography over silica gel (230–400 mesh) using ethyl acetate as the eluent to afford the title compound (0.024 g, 25%).

$^1$H-NMR (300 MHz, CDCl$_3$): δ 1.46 (s, 6H), 2.08(t, J=6.7 Hz, 2H), 2.80(t, J=6.7 Hz, 2H), 3.70(s, 2H), 7.20(d, J=8.5 Hz, 2H), 7.37(d, J=8.5 Hz, 2H), 8.08(dd, J=1.4, 8.2 Hz, 1H), 8.14 (d, J=8.2 Hz, 1H), 8.24 (d, J=1.2 Hz, 1H).

5-Methoxy-3,3-dimethyl-indane (Intermediate 15)

Following general procedure A and using titanium tetrachloride (5.5 mL, 50 mmoL), anhydrous dichloromethane (80 mL), 2M solution dimethyl zinc (50 mL) in toluene and a solution of 6-methoxy-indane-1-one (4.05 g, 25 mmol) in dichloromethane (10 mL) the title compound was obtained as an oil (3.13 g, 71%).

$^1$H-NMR (300 MHz, CDCl$_3$):δ 1.37 (s, 6H), 2.04(t, J=7.2 Hz, 2H), 2.94(t, J=7.2 Hz, 2H), 3.89(s, 3H), 6.82(d, J=2.1 Hz, 1H), 7.28(dd, J=2.1, 7.0 Hz, 1H), 7.35 (d, J=7.0 Hz, 1H).

5-Methoxy-3,3-dimethyl-indane-1-one (Intermediate 16)

Following general procedure B and using 5-methoxy-3, 3-dimethyl indane (Intermediate 15, 3.13 g, 17.78 mmol) in 20mL of glacial acetic acid and a solution of chromium trioxide (3.91 g, 39.1 mmol) in 20 mL of acetic acid and 20 mL of water the title compound was obtained as a viscous yellow oil (3.3 g, 97%).

$^1$H-NMR (300 MHz, CDCl$_3$):δ 1.37 (s, 6H), 2.54 (s, 2H), 3.87(s, 3H), 6.86–6.87 (m, 2H), 7.60 (d, J=7.0 Hz, 1H).

6-Methoxy-4,4-dimethyl-1,2,3,4-tetrahydro-isoquinoline-1-one (Intermediate 17)

A solution of 5-methoxy-3,3-dimethyl-indane-1-one (Intermediate 16, 3.3 g, 17.4 mmol) in benzene (50 mL) was treated with concentrated sulfuric acid (10 mL) and heated to 60° C. Sodium azide (1.95 g, 30 mmol) was added in small portions and after the addition was complete, the reaction mixture was heated further for 4 h. It was then cooled, diluted with water and extracted with chloroform (×3). The combined organic phase was dried over anhydrous magnesium sulfate, filtered and evaporated in vacuo to afford the title compound as a brown solid (3.5 g, quantitative by weight).

$^1$H-NMR (300 MHz, CDCl$_3$): δ 1.31 (s, 6H), 3.28 (s, 2H), 3.83(s, 3H), 6.78 (d, J=2.6 Hz, 1H), 6.82(dd, J=2.6 Hz, 8.5 Hz, 1H), 7.59 (s, 1H), 8.02 (d, J=8.2 Hz, 1H).

6-Methoxy-4,4-dimethyl-1,2,3,4-tetrahydro-isoquinoline (Intermediate 18)

A solution of 6-methoxy-4,4-dimethyl-1,2,3,4-tetrahydro-isoquinoline-1-one (Intermediate 17, 3.5 g, 17 mmol) in 100 mL of anhydrous tetrahydrofuran was treated with lithium aluminum hydride (1.3 g, 34.25 mmol) in small portions and the resulting suspension was refluxed for 3 hours under argon. The reaction mixture was then cooled in an ice bath and cautiously quenched with saturated aqueous sodium sulfate solution and the resulting slurry was filtered and the filter-cake washed well with ethyl acetate. The filtrate and washings were evaporated in vacuo to a brown oil which was dissolved in chloroform, the solution was dried over anhydrous magnesium sulfate, filtered and evaporated in vacuo to afford the title compound (3.2 g, ~100%).

$^1$H-NMR (300 MHz, CDCl$_3$): δ 1.27 (s, 6H), 2.22 (s, 1H), 2.84 (s, 2H), 3.79 (s, 3H), 3.95 (s, 2H), 6.68(dd, J=2.4 Hz, 8.3 Hz, 1H), 6.86(d, J=2.4 Hz, 1H), 6.91 (d, J=8.3 Hz, 1H).

6-Methoxy-4,4-dimethyl-1,2,3,4-tetrahydro-isoquinoline-2-carbaldehyde (Intermediate 19)

A solution of 6-methoxy-4,4-dimethyl-1,2,3,4-tetrahydro-isoquinoline (Intermediate 18, 3.2 g, 16.7 mmol) in anhydrous dichloromethane (40 mL) was treated with formic acid (1 mL, 26.5 mmol) followed 1-(3-dimethylaminopropyl)-3-ethylcarbodiimide hydrochloride (3.9 g, 20.34 mmol) and the resulting solution was stirred at ambient temperature overnight. It was then diluted with chloroform and washed with water (×1) and brine (×1), dried over anhydrous magnesium sulfate, filtered and evaporated in vacuo to afford the title compound as pale brown viscous oil (3.26 g, 90%).

$^1$H-NMR (300 MHz, CDCl$_3$): δ 1.28 (s, 6H), 3.32 (s, 0.7H), 3.54 (s, 0.3H), 3.79(s, 3H), 4.54 (s, 0.3H), 4.66(s, 0.7H), 6.71(dd, J=2.6 Hz, 8.2 Hz, 1H), 6.85–6.97(m, 1H), 7.02–7.27(m, 1H), 8.15(s, 0.7H), 8.34(s, 0.3H), 8.40–8.80 (br s, 1H).

6-Hydroxy-4,4-dimethyl-1,2,3,4-tetrahydro-isoquinoline-2-carbaldehyde (Intermediate 20)

A stirred, cooled (−78° C.) solution of 6-methoxy-4,4-dimethyl-1,2,3,4-tetrahydro-isoquinoline-2-carbaldehyde (Intermediate 19, 3.26 g, 15 mmol) in anhydrous dichloromethane (15 mL) was treated with 1M solution of boron tribromide in dichloromethane (50 mL) stirred at ambient temperature for 3 h. It was then cooled again to 78° C. and quenched carefully with saturated aqueous sodium carbonate solution, diluted with water and the aqueous phase was extracted with ethyl acetate (×2). The combined organic extract was dried over anhydrous sodium sulfate, filtered and evaporated in vacuo to afford the title compound as a solid foam (3 g, 99%).

$^1$H-NMR (300 MHz, CDCl$_3$): δ 1.23 (s, 6H), 3.31 (s, 0.7H), 3.54 (s, 0.3H), 4.51 (s, 0.3H), 4.64 (s, 0.7H), 6.70–6.75(m, 1H), 6.84–6.90(m, 2H), 7.50–7.80(br s, 1H), 8.12(s, 0.7H), 8.32(s, 0.3H).

2-Cyclopropyl-6-hydroxy-4,4-dimethyl-1,2,3,4-tetrahydro-isoquinoline (Intermediate 21)

A stirred, cooled (0° C.)solution of 6-hydroxy-4,4-dimethyl-1,2,3,4-tetrahydro-isoquinoline-2-carbaldehyde (Intermediate 20, 2.3 g, 11.21 mmol) in anhydrous tetrahydrofuran (40 mL) under argon was treated with titanium tetra-iso-propoxide (8.28 mL, 28 mmol) followed by 3M solution of ethyl magnesium bromide in diethyl ether (18.7 mL) and the reaction mixture was then heated at 55° C. overnight. It was then cooled in an ice-bath, quenched with saturated aqueous ammonium chloride solution and extracted with diethyl ether (×2). The combined organic phase was dried over anhydrous sodium sulfate, filtered and evaporated in vacuo to afford a yellow oily solid. Flash column chromatography over silica gel (230–400 mesh) using 10–20% ethyl acetate in hexane as the eluent afforded the title compound as a pale yellow solid (1.55 g, 63%).

$^1$H-NMR (300 MHz, CD$_3$COCD$_3$): δ 0.016–0.16(m, 4H), 0.847 (s, 6H), 1.37 (m, 1H), 2.20(s, 2H), 3.25 (s, 2H), 6.22(dd, J=2.4, 8.2 Hz, 1H), 6.41(d, J=2.6 Hz, 1H), 6.47(d, J=8.2 Hz, 1H), 7.62(s, 1H).

2-Cyclopropyl-4,4-dimethyl-6-trifluoromethylsulfonyloxy-1,2,3,4-tetrahydro-isoquinoline (Intermediate 22)

Following general procedure C and using 2-cyclopropyl-6-hydroxy-4,4-dimethyl-1,2,3,4-tetrahydro-isoquinoline (Intermediate 21, 1.5 g, 6.9 mmol) in anhydrous dichloromethane (30 mL), triethyl amine (1.5 mL, 10.39 mmol) and [N,N'-bis(trifluoromethylsulfonyl)amino]-5-chloropyridine (2.75 g, 7 mmol) followed by flash column chromatography over silica gel (230–400 mesh) using 8% ethyl acetate in hexane as the eluent the title compound was obtained (2.23 g, 92%) as oil. $^1$H-NMR (300 MHz, CDCl$_3$): δ 0.42–0.54(m, 4H), 1.25(s, 6H), 1.76(m, 1H), 2.62(s, 2H), 3.74(s, 2H), 6.98(dd, J=2.3, 8.4 Hz, 1H), 7.16(d, J=8.2 Hz, 1H), 7.14(d, J=2.3 Hz, 1H).

Ethyl-2-cyclopropyl-4,4-dimethyl-1,2,3,4-tetrahydroisoquinoline-6-carboxylate (Intermediate 23)

Following general procedure K and using 2-cyclopropyl-4,4-dimethyl-6-trifluoromethylsulfonyloxy-1,2,3,4-tetrahydro-isoquinoline (Intermediate 22, 1.6 g, 4.6 mmol), palladium acetate (0.127 g, 0.56 mmol), 1,3-bis(diphenylphosphino)propane (0.160 g, 0.39 mmol), dimethylsulfoxide (2 mL), 1,2-dichloroethane (5 mL), triethyl amine (2 mL), ethanol (5 mL) and an atmosphere of carbon monoxide followed by flash column chromatography over silica gel (230–400 mesh) using 10% ethyl acetate in hexane as the eluent the title compound was obtained as an oil (1 g, 79%).

$^1$H-NMR (300 MHz, CDCl$_3$):δ 0.44–0.54(m, 4H), 1.27(s, 6H), 1.38 (t, J=7 Hz, 3H), 1.73(m, 1H), 2.62(s, 2H), 3.76(s, 2H), 4.35 (q, J=7.1 Hz, 2H), 7.04(d, J=7.9 Hz, 1H), 7.74 (dd, J=1.7, 7.9 Hz, 1H), 7.97(d, J=1.8 Hz, 1H).

2-Cyclopropyl-6-hydroxymethyl-4,4-dimethyl-1,2,3,4-tetrahydroisoquinoline (Intermediate 24)

A stirred cooled (−78° C.)solution of ethyl-2-cyclopropyl-4,4-dimethyl-1,2,3,4-tetrahydro isoquinoline-6-carboxylate (Intermediate 23, 1 g, 3.66 mmol) in anhydrous dichloromethane (20 mL) under argon was treated with a 1M solution of di-iso-butyl aluminum hydride in dichloromethane (10 mL) and the reaction mixture was warmed to −20° C. over 1 h. It was then quenched with saturated aqueous ammonium chloride solution and diluted with dichloromethane and filtered over a bed of celite. The phases were separated and the aqueous phase was extracted with dichloromethane (×1). The combined organic extract was dried over anhydrous sodium sulfate, filtered and evaporated in vacuo to afford the title compound as a viscous oil (0.74 g, 87%).

$^1$H-NMR (300 MHz, CDCl$_3$): δ 0.45–0.53(m, 4H), 1.25(s, 6H), 1.72–1.82(m, 2H), 2.61(s, 2H), 3.73(s, 2H), 4.61 (d, J=5 Hz, 2H), 6.98(d, J=7.9 Hz, 1H), 7.07 (dd, J=1.5, 7.6 Hz, 1H), 7.27(s, 1H).

2-Cyclopropyl-4,4-dimethyl-1,2,3,4-tetrahydroisoquinoline-6-carbaldehyde (Intermediate 25)

A solution of 2-cyclopropyl-6-hydroxymethyl-4,4-dimethyl-1,2,3,4-tetrahydroisoquinoline (Intermediate 24, 0.74 g, 3.2 mmol) in dichloromethane (10 mL) and acetonitrile (2.5 mL) was treated sequentially with 4 A° molecular sieves powder (1.06 g), tetra-n-propyl ammonium perruthenate (0.050 g, 0.14 mmol) and N-methyl morpholine N-oxide (1.1 g, 9.8 mmol). After stirring at ambient temperature for 0.5 h, it was diluted with 5 mL of hexane and subjected to flash column chromatography over silica gel (230–400 mesh) using 10% ethyl acetate in hexane as the eluent to afford the title compound as an oil (0.27 g, 37%).

$^1$H-NMR (300 MHz, CDCl$_3$):δ 0.44–0.56(m, 4H), 1.30(s, 6H), 1.79(m, 1H), 2.66(s, 2H), 3.82(s, 2H), 7.17(d, J=7.9 Hz, 1H), 7.60 (dd, J=1.6, 7.9 Hz, 1H), 7.82(d, J=1.8 Hz, 1H), 9.95 (s, 1H).

6-(2,2-Dibromo-vinyl)-2-cyclopropyl-4,4-dimethyl-1,2,3,4-tetrahydroisoquinoline (Intermediate 26)

A stirred, cooled (ice-bath) solution of triphenyl phosphine (0.53 g, 2 mmol) in anhydrous dichloromethane was treated with carbon tetrabromide (0.35 g, 1 mmol) under argon. After 0.5 h, a solution of 2-cyclopropyl-4,4-dimethyl-1,2,3,4-tetrahydroisoquinoline-6-carboxaldehyde (Intermediate 25, 0.13 g, 0.57 mmol) in dichloromethane (2 mL) was cannulated into the reaction mixture. After 1.5 h between 0° C. and 10° C., the reaction mixture was subjected to flash column chromatography over silica gel (230–400 mesh) using 3–5% ethyl acetate in hexane as the eluent to afford the title compound as a viscous, pale yellow oil (0.18 g, 82%).

$^1$H-NMR (300 MHz, CDCl$_3$):δ 0.49–0.57(m, 4H), 1.31(s, 6H), 1.80(m, 1H), 2.67(s, 2H), 3.77(s, 2H), 7.04(d, J=7.9 Hz, 1H), 7.29 (dd, J=1.7, 7.9 Hz, 1H), 7.49 (s, 1H), 7.50(d, J=1.7 Hz, 1H).

2-Cyclopropyl-6-ethynyl-4,4-dimethyl-1,2,3,4-tetrahydroisoquinoline (Intermediate 27)

A stirred, cooled (−78° C.) solution of 6-(2,2-dibromo-vinyl)-2-cyclopropyl-4,4-dimethyl-1,2,3,4-tetrahydroisoquinoline-6-carboxaldehyde (Intermediate 26, 0.18 g, 0.47 mmol) in tetrahydrofuran (2 mL) was treated with 1.6M solution of n-butyl lithium (0.6 mL, 0.96 mmol) under argon. The reaction mixture was allowed to warm to −20° C. over 1.5 h, quenched with saturated aqueous ammonium chloride solution and extracted with diethyl ether (×2). The combined organic phase was dried over anhydrous magnesium sulfate, filtered and evaporated in vacuo to afford the title compound as an oil (0.1 g, 94%).

$^1$H-NMR (300 MHz, CDCl$_3$):δ 0.47–0.55(m, 4H), 1.28(s, 6H), 1.77(m, 1H), 2.63(s, 2H), 3.05(s, 1H), 3.67(s, 2H), 6.98(d, J=7.6 Hz, 1H), 7.26 (dd, J=1.5, 7.9 Hz, 1H), 7.46(d, J=1.5 Hz, 1H).

[4-(2-Cyclopropyl-4,4-dimethyl-1,2,3,4-tetrahydro-isoquinolin-6-yl-ethynyl)-2-fluoro-phenyl]-acetic acid ethyl ester (Compound 21, General Formula 3)

Following general procedure F and using 2-cyclopropyl-6-ethynyl-4,4-dimethyl-1,2,3,4-tetrahydro-isoquinoline (Intermediate 27, 0.13 g, 0.571 mmol), 2-fluoro-4-iodo phenyl acetic acid ethyl ester (Reagent C, 0.16 g, 0.52 mmol), triethyl amine (0.8 mL), anhydrous tetrahydrofuran (2 mL), copper(I)iodide (0.051 g, 0.27 mmol) and dichlorobis(triphenylphosphine)palladium(II) (0.1 g, 0.14 mmol) followed by flash column chromatography over silica gel (230–400 mesh) using 10% ethyl acetate in hexane as the eluent, 0.1 g of the title compound was obtained as an oil. It was further purified by preparative normal phase HPLC on a partisil-10 silica column using 10% ethyl acetate in hexane as the mobile phase (0.055 g, 24%).

¹H-NMR (300 MHz, CDCl₃):δ 0.42–0.51(m, 4H), 1.26(t, J=7.3 Hz, 3H), 1.27(s, 6H), 1.75(m, 1H), 2.61(s, 2H), 3.66(s, 2H), 3.74(s, 2H), 4.18 (q, J=7.3 Hz, 2H), 6.97 (d, J=7.9 Hz, 1H), 7.20–7.29(m, 4H), 7.45(d, J=1.5 Hz, 1H).

[4-(2-Cyclopropyl-4,4-dimethyl-1,2,3,4-tetrahydro-isoquinolin-6-yl-ethynyl)-2-fluoro-phenyl]-acetic acid (Compound 22, General Formula 3)

Following general procedure J and using [4-(2-cyclopropyl-4,4-dimethyl-1,2,3,4-tetrahydro-isoquinolin-6-ylethynyl)-2-fluoro-phenyl]-acetic acid ethyl ester (Compound 21, 0.055 g, 0.135 mmol), methanol (2 mL), tetrahydrofuran (4 mL), water (1 mL) and lithium hydroxide monohydrate (0.117 g, 2.97 mmol) the title compound was obtained as a pale yellow solid foam (0.040 g, 78%).

¹H-NMR (300 MHz, CDCl₃): δ 0.52–0.65(m, 4H), 1.27(s, 6H), 1.84(m, 1H), 2.71(s, 2H), 3.61(s, 2H), 3.85(s, 2H), 6.98(d, J=7.9 Hz, 1H), 7.06 (t, J=7.6 Hz, 1H), 7.17–7.25(m, 3H), 7.43(d, J=1.2 Hz, 1H), 8.60–9.00(br s, 1H).

[4-(2-Cyclopropyl-4,4-dimethyl-1,2,3,4-tetrahydro-isoquinolin-6-yl-ethynyl)-phenyl]-acetic acid methyl ester (Compound 23, General Formula 3)

Following general procedure F and using 2-cyclopropyl-4,4-dimethyl-6-ethynyl-1,2,3,4-tetrahydro-isoquinoline (Intermediate 27, 0.13 g, 0.571 mmol), 4-iodo phenyl acetic acid methyl ester (Reagent B, 0.16 g, 0.58 mmol), triethyl amine (0.5 mL), anhydrous tetrahydrofluran (2 mL), copper (I)iodide (0.04 g, 0.21 mmol) and dichlorobis (triphenylphosphine)palladium(II) (0.12 g, 0.17 mmol) followed by flash column chromatography over silica gel (230–400 mesh) using 10% ethyl acetate in hexane as the eluent, 0.05 g of the title compound was obtained as an oil. It was further purified by preparative normal phase HPLC on a partisil-10 silica column using 10% ethyl acetate in hexane as the mobile phase (0.01 g, 6%).

¹H-NMR (300 MHz, CDCl₃): δ 0.42–0.58(m, 4H), 1.29 (m, 6H), 1.79(m, 1H), 2.64(s, 2H), 3.67(s, 3H), 3.72(s, 2H), 3.77(s, 2H), 7.09 (d, J=7.9 Hz, 1H), 7.28(dd, J=1.5, 7.9 Hz, 1H), 7.36 (d, J=7.9 Hz, 2H), 7.50 (d, J=1.6 Hz, 1H), 7.51(d, J=7.9 Hz, 2H).

[4-(2-Cyclopropyl-4,4-dimethyl-1,2,3,4-tetrahydro-isoquinolin-6-yl-ethynyl)-phenyl]-acetic acid (Compound 24, General Formula 3)

Following general procedure J and using [4-(2-cyclopropyl-4,4-dimethyl-1,2,3,4-tetrahydro-isoquinolin-6ylethynyl)-phenyl]-acetic acid methyl ester (Compound 23, 0.01 g, 0.027 mmol), methanol (1 mL), tetrahydrofiuran (1 mL), water (0.5 mL) and lithium hydroxide monohydrate (0.042 g, 1 mmol) the title compound was obtained as a pale yellow solid foam (0.0065 g, 68%).

¹H-NMR (300 MHz, CDCl₃): δ 0.35–0.52(m, 4H), 1.24(s, 6H), 1.74(m, 1H), 2.59(s, 2H), 3.64(s, 2H), 3.71(s, 2H), 7.03 (d, J=8.2 Hz, 1H), 7.22(dd, J=1.4, 7.9 Hz, 1H), 7.33 (d, J=8.2 Hz, 2H), 7.46 (d, J=8.2 Hz, 2H), 7.47(s, 1H).

1-(Iso-propyl-methyl-amino)-6-trimethylsilanylethynyl-4,4-dimethyl-1,2,3,4-tetrahydro-naphthalene (Intermediate 28)

Following general procedure G and using a solution of 4,4-dimethyl-6-trimethylsilanylethynyl-1,2,3,4-tetrahydro-naphthalene 2-one (Intermediate 12, 0.2 g, 0.78 mmol), dichloromethane (4 mL), acetonitrile (2 mL), acetic acid (1 mL), isopropyl amine (1 mL, 11.74 mmol) and sodium cyanoborohydride (0.19 g, 3.02 mmol), after 15 days of reaction time and work up afforded an intermediate (0.14 g, 60%, 0.47 mmol) which was used following general procedure H along with acetone (2 mL), potassium carbonate (0.6 g, 4.34 mmol) and methyl iodide (0.5 mL, 8 mmol). The crude product after work up was subjected to flash column chromatography over silica gel (230–400 mesh) using 15% ethyl acetate in hexane as the eluent to afford the title compound as a pale yellow oil (0.14 g, 95%).

¹H-NMR (300 MHz, CDCl₃): δ 0.001(s, 9H), 0.85 (d, J=6.4 Hz, 6H), 0.98 (s, 3H), 1.03 (s, 3H), 1.32–1.60 (m, 4H), 1.81(s, 3H), 2.64(heptet, J=6.4 Hz, 1H), 3.65 (dd, J=6.1, 9.4 Hz, 1H), 6.97 (dd, J=1.7, 7.9 Hz, 1H), 7.13 (d, J=1.7 Hz, 1H), 7.82 (d, J=7.9 Hz, 1H).

6-Ethynyl-1-(iso-propyl-methyl-amino)-4,4-dimethyl-1,2,3,4-tetrahydro-naphthalene (Intermediate 29)

Following general procedure E and using 1-(methyl-iso-propylamino)-4,4-dimethyl-6-trimethylsilanylethynyl-1,2,3,4-tetrahydro-naphthalene (Intermediate 28, 0.14 g, 0.45 mmol), methanol (5 mL), potassium carbonate (0.61 g, 4.41 mmol) and ethyl acetate the title compound (0.092 g, 80%) was obtained as an oil.

¹H-NMR (300 MHz, CDCl₃):δ 1.11 (d, J=6.4 Hz, 6H), 1.23(s, 3H), 1.28(s, 3H), 1.51–1.87 (m, 4H), 2.09(s, 3H), 2.90 (heptet, J=6.4 Hz, 1H), 3.00(s, 1H), 3.91 (dd, J=5.8, 10.0 Hz, 1H), 7.25(dd, J=1.7, 8.2 Hz, 1H), 7.41 (d, J=1.7 Hz, 1H), 7.70(d, J=8.2 Hz, 1H).

4-[5-(Iso-propyl-methyl-amino)-8,8-dimethyl-5,6,7,8-tetrahydro-naphthalene-2-yl-ethynyl)]-benzoic acid ethyl ester (Compound 25, General Formula 4)

Following general procedure F and 6-ethynyl-1-(iso-propyl-methyl-amino)-4,4-dimethyl-1,2,3,4-tetrahydro-naphthalene (Intermediate 29, 0.092 g, 0.36 mmol), ethyl-4-iodo benzoate (Reagent A, 0.12 g, 0.48 mmol), triethyl amine (1 mL), tetrahydrofuran (2 mL), copper(I)iodide (0.028 g, 0.14 mmol) and dichlorobis(triphenylphosphine) palladium(II) (0.075 g, 0.11 mmol) followed by flash column chromatography over silica gel (230–400 mesh) using 10–15% ethyl acetate in hexane as the eluent the title compound was obtained (0.04 g, 27%).

¹H-NMR (300 MHz, CDCl₃): δ 1.12 (d, J=6.5 Hz, 6H), 1.27 (s, 3H), 1.31 (s, 3H), 1.40 (t, J=7.0 Hz, 3H), 1.62–1.89 (m, 4H), 2.10(s, 3H), 2.92 (heptet, J=6.4 Hz, 1H), 3.94(dd, J=6.1, 9.7 Hz, 1H), 4.38(q, J=7.1 Hz, 2H), 7.31(dd, J=1.4, 8.2 Hz, 1H), 7.46 (d, J=1.7 Hz, 1H), 7.58 (d, J=8.2 Hz, 2H), 7.75(d, J=8.2 Hz, 1H), 8.01(d, J=8.2 Hz, 2H).

4-[5-(Iso-propyl-methyl-amino)-8.8-dimethyl-5,6,7,8-tetrahdro-naphthalene-2-yl-ethenyl)]-benzoic acid (Compound 26, General Formula 4)

Following general procedure I and using 4-[5-(iso-propyl-methyl-amino)-8,8-dimethyl-5,6,7,8-tetrahydro-naphthalene-2-ylethynyl)]-benzoic acid ethyl ester (Compound 25, 0.04 g, 0.01 mmol), ethanol (2 mL), tetrahydrofuran (1 mL) and 1M aqueous sodium hydroxide solution (1 mL) followed by recrystallization from diethylether-hexane, the title compound was obtained as an off-white solid (0.010 g, 27%).

¹H-NMR (300 MHz, CDCl₃): δ 1.30(d, J=6.0 Hz, 6H), 1.31(s, 9H), 1.67–1.98(m, 4H), 2.35 (s, 3H), 3.19 (heptet, J=6.4 Hz, 1H), 4.36 (t, J=7.6 Hz, 1H), 7.28(dd, J=1.4, 8.2 Hz, 1H), 7.48 (d, J=1.4 Hz, 1H), 7.55 (d, J=8.2 Hz, 2H), 7.81 (d, J=8.2 Hz, 1H), 8.05 (d, J=8.2 Hz, 2H).

[4-(2,2,4,4-Tetramethyl-chroman-6-yl-ethynyl) phenyl]acetic acid methyl ester (Compound 27, General Formula 8)

Following general procedure F and using 6-ethynyl-2,2,4,4-tetramethylchroman (synthesis described in U.S. Pat. Nos. 5,045,551 and 5,616,597 incorporated herein by reference) (0.060 g, 0.28 mmol), methyl-4-iodo phenyl acetate (Reagent B, 0.078 g, 0.28 mmol), triethyl amine (4 mL), tetrahydrofuran (4 mL), copper(I)iodide (0.030 g, 0.16 mmol) and dichlorobis(triphenylphosphine)palladium(II) (0.11 g, 0.16 mmol) followed by flash column chromatography over silica gel (230–400 mesh) using 5–10% ethyl acetate in hexane as the eluent the title compound was obtained (0.047 g, 46%).

$^1$H NMR (300 MHz, CDCl$_3$): δ 7.48–7.45 (m, 3H), 7.25–7.23 (m, 3H), 6.75 (d, 1H, J=8.2 Hz), 3.70 (s, 3H), 3.62 (s, 2H), 1.84 (s, 2H), 1.36 (s, 6H), 1.35 (s, 6H).

General Procedure L

[4-(2,2,4,4-Tetramethyl-chroman-6-yl-ethynyl) phenyl]acetic acid (Compound 28, General Formula 8)

A solution of [4-(2,2,4,4-tetramethyl-chroman-6-yl-ethynyl)phenyl]acetic acid methyl ester (Compound 27, 0.047 g, 0.13 mmol) in 5 mL of methanol was treated with 1M sodium hydroxide solution (2 mL) and heated at 55° C. for 2 h. The volatiles were distilled off in vacuo and the residue was acidified with 10% hydrochloric acid and extracted with ethyl acetate (×2). The combined organic phase was washed with brine (×1), dried over anhydrous sodium sulfate, filtered and evaporated in vacuo to a residue which was purified by preparative reverse phase HPLC using 10% water in acetonitrile as the mobile phase to afford the title compound (0.034 g, 82%). $^1$H NMR (300 MHz, CDCl$_3$): δ 7.49–7.45 (m, 3H), 7.26–7.22 (m, 3H), 6.75 (d, 1H, J=8.2 Hz), 3.65 (s, 2H), 1.84 (s, 2H), 1.36 (s, 6H), 1.35 (s, 6H).

2-Fluoro-4-(2,2,4,4-tetramethyl-chroman-6-yl-ethynyl)-benzoic acid methyl ester (Compound 29, General Formula 8)

Following general procedure F and using 6-ethynyl-2,2,4,4-tetramethylchroman (0.11 g, 0.51 mmol), methyl-2-fluoro-4-iodo-benzoate (Reagent G, 0.14 g, 0.51 mmol), triethyl amine (5 mL), tetrahydrofuran(10 mL), copper(I) iodide(0.030 g, 0.16 mmol) and dichlorobis(triphenylphosphine)palladium(II) (0.110 g, 0.16 mmol) followed by flash column chromatography over silica gel (230–400 mesh) using 5–10% ethyl acetate in hexane as the eluent, the title compound was obtained (0.14 g, 79%).

$^1$H NMR (300 MHz, CDCl$_3$): δ 7.82 (t, 1H, J=7.9 Hz), 7.39 (d, 1H, J=1.8 Hz), 7.25–7.16 (m, 3H), 6.69 (d, 1H, J=8.2 Hz), 3.85 (s, 3H), 1.77 (s, 2H), 1.29 (s, 6H), 1.28 (s, 6H).

2-Fluoro-4-(2,2,4,4-tetramethyl-chroman-6-yl-ethynyl)-benzoic acid (Compound 30, General Formula 8)

Following general procedure L and using 2-fluoro-4-(2,2,4,4-tetramethyl-chroman-6-yl-ethynyl)-benzoic acid methyl ester (Compound 29, 0.14 g, 0.4 mmol), 5 mL of methanol and 1M sodium hydroxide solution (2 mL) followed by recrystallization from ethyl acetate, the title compound was obtained (0.083 g, 58%).

$^1$H NMR (300 MHz, CD$_3$COCD$_3$): δ 8.00 (t, 1H, J=7.8 Hz), 7.63 (d, 1H, J=2.1 Hz), 7.45 (dd, 1H, J=1.5, 7.9 Hz), 7.38 (dd, 1H, J=1.5, 11.4 Hz), 7.32 (dd, 1H, J=2.1, 8.2 Hz), 6.81 (d, 1H, J=8.5 Hz), 1.92 (s, 2H), 1.41 (s, 6H), 1.38 (s, 6H).

[2-Fluoro-4-(2,2,4,4-tetramethyl-chroman-6-yl-ethynyl)phenyl]acetic acid ethyl ester (Compound 31, General Formula 8)

Following general procedure F and using 6-ethynyl-2,2,4,4-tetramethylchroman (0.204 g, 0.95 mmol), ethyl-2-fluoro-4-iodo phenyl acetate (Reagent C, 0.263 g, 0.86 mmol), triethyl amine, tetrahydrofuran, copper(I)iodide (0.025 g, 0.13 mmol) and dichlorobis(triphenylphosphine) palladium(II) (0.075 g, 0.11 mmol) followed by flash column chromatography over silica gel (230–400 mesh) using 5–10% ethyl acetate in hexane as the eluent, the title compound was obtained (0.21 g, 62%).

$^1$H NMR (300 MHz, CDCl$_3$): δ 7.46 (d, 1H, J=2.1 Hz), 7.25–7.21 (m, 4H), 6.69 (d, 1H, J=8.5 Hz), 4.16 (q, 2H, J=7.1 Hz), 3.65 (s, 2H), 1.82 (s, 2H), 1.35 (s, 6H), 1.35 (s, 6H), 1.24 (t, 3H, J=7.2 Hz).

[2-Fluoro-4-(2,2,4,4-tetramethyl-chroman-6-yl-ethynyl)phenyl]acetic acid (Compound 32, General Formula 8)

Following general procedure L and using [2-fluoro-4-(2,2,4,4-tetramethyl-chroman-6-ylethynyl)phenyl]acetic acid ethyl ester (Compound 31, 0.21 g, 0.58 mmol), 5 mL of methanol and 1M sodium hydroxide solution (2 mL) followed by flash column chromatography over silica gel (230–400 mesh) using 50% ethyl acetate in hexane, the title compound was obtained as a solid (0.184 g, 93%).

$^1$H NMR (300 MHz, CDCl$_3$): δ 11.40 (br s, 1H), 7.48 (d, 1H, J=1.8 Hz), 7.46–7.16 (m, 4H), 6.76 (d, 1H, J=8.2 Hz), 3.69 (s, 2H), 1.82 (s, 2H), 1.34 (s, 12H).

3-Methyl-but-2-enoic acid 4-bromo-phenyl ester

To a stirred, cooled (ice bath) suspension of sodium hydride (2.4 g, 100 mmol) in anhydrous tetrahydrofuran (200 mL), 4-bromo phenol (17.3 g, 100 mmol) was added followed by 3,3,-dimethyl acryloyl chloride (11.14 mL, 100 mmol). After 4 hours at ambient temperature, the reaction mixture was poured into brine and extracted with diethyl ether (×2). The combined organic phase was dried over anhydrous sodium sulfate, filtered and evaporated in vacuo to afford an oil which was subjected to flash column chromatography over silica gel (230–400 mesh) using 2% ethyl acetate in hexane as the eluent to afford the title compound (15 g, 59%).

$^1$H-NMR (300 MHz, CDCl$_3$):δ 2.00(s, 3H), 2.23(s, 3H), 5.89(s, 1H), 7.00(d, J=8.8 Hz, 2H), 7.49(d, J=8.8 Hz, 2H).

6-Bromo-4,4-dimethyl-chroman-2-one

A solution of 3-methyl-but-2-enoic acid 4-bromo-phenyl ester (7 g, 27.6 mmol) in anhydrous dichloromethane (200 mL) was cooled (ice bath) and treated with aluminum chloride (6.6 g, 49.6 mmol) and the reaction mixture was stirred overnight at ambient temperature. The reaction mixture was quenched with saturated aqueous sodium bicarbonate solution and extracted with diethyl ether (×2). The combined organic extract was washed with brine (×1), dried over anhydrous sodium sulfate, filtered and evaporated in vacuo to afford an oil which was purified by flash column chromatography over silica gel (230–400 mesh) using 2.5% ethyl acetate in hexane as the eluent to afford the title compound (4.2 g, 57%).

¹H-NMR (300 MHz, CDCl₃): δ 1.36(s, 6H), 2.62(s, 2H), 6.95(d, J=8.5 Hz, 1H), 7.37(dd, J=2.4, 8.5 Hz, 1H), 7.43(d, J=2.3 Hz, 1H).

4-Bromo-2-(3-hydroxy-1,1,3-trimethyl-butyl)-phenol

A solution of 6-bromo-4,4-dimethyl-chroman-2-one (1 g, 3.92 mmol) in anhydrous tetrahydrofuran (20 mL) was treated with 3M solution of ethyl magnesium bromide (2.6 mL) and stirred at ambient temperature for 2 hours. The reaction mixture was poured into cold dilute hydrochloric acid and extracted with ethyl acetate (×2). The combined organic extract was dried over anhydrous sodium sulfate, filtered and evaporated in vacuo to afford a residue which was subjected to flash column chromatography over silica gel (230–400 mesh) using 10% ethyl acetate in hexane as the eluent to afford the title compound as a pale yellow solid (1.1 g, 100%).

¹H-NMR (300 MHz, CDCl₃): δ 1.14(s, 6H), 1.44(s, 6H), 2.20(s, 2H), 6.49(d, J=8.4 Hz, 1H), 7.15(dd, J=2.4, 8.5 Hz, 1H), 7.37(d, J=2.4 Hz, 1H).

6-Bromo-2,2,4,4-tetramethyl-chroman

A solution of 4-bromo-2-(3-hydroxy-1,1,3-trimethyl-butyl)-phenol (1.1 g, 3.92 mmol) and p-toluene sulfonic acid (0.744 g, 3.92 mmol) in benzene (20 mL) was refluxed overnight. The reaction mixture cooled to ambient temperature, filtered on silica gel and washed with 10% ethyl acetate in hexane. The filtrate and washings were evaporated in vacuo to an oil which was subjected to flash column chromatography over silica gel (230–400 mesh) using 5% ethyl acetate in hexane as the eluent to afford the title compound as a pale yellow oil (0.84 g, 80%).

¹H-NMR (300 MHz, CDCl₃): δ 1.34(s, 6H), 1.35(s, 6H), 1.82(s, 2H), 6.68(d, J=8.4 Hz, 1H), 7.16(dd, J=2.7, 8.7 Hz, 1H), 7.37(d, J=2.6 Hz, 1H).

The synthesis of this compound, as described here, is in close analogy to the synthesis of 6-bromo-2,2,4,4-tetramethylthiochroman, as described in U.S. Pat. No. 5,045,551

2,2,4,4-tetramethyl-6-(2-trimethylsilyl)ethynyl chroman

Following general procedure D and using 6-bromo-2,2,4,4-tetramethyl chroman (0.5 g, 1.87 mmol), triethyl amine (5 mL), anhydrous tetrahydrofuran (15 mL), copper(I)iodide (0.107 g, 0.156 mmol), trimethylsilyl acetylene (1.84 g, 18.7 mmol) and dichlorobis(triphenylphosphine)palladium(II) (0.39 g, 0.56 mmol) the title compound was obtained as a brown oil (0.61 g, 100%).

¹H NMR (300 MHz, CDCl₃): δ 7.43 (d, 1H, J=2.1 Hz), 7.23 (dd, 1H, J=7.9, 2.1 Hz), 6.73 (d, 1H, J=8.2 Hz), 1.83 (s, 2H), 1.36 (s, 12H), 0.28 (s, 9H).

6-Ethynyl-2,2,4,4-tetramethyl chroman

Following general procedure E and using 2,2,4,4-tetramethyl-6-(2-trimethylsilyl)ethynyl chroman (0.61 g, 1.87 mmol), potassium carbonate (1.9 g, 13.74 mmol) and methanol the title compound was obtained (0.4 g, 90%).

¹H NMR (300 MHz, CDCl₃): δ 7.47 (d, 1H, J=2.1 Hz), 7.24 (dd, 1H, J=7.9, 2.1 Hz), 6.76 (d, 1H, J=8.2 Hz), 3.01 (s, 1H), 1.85 (s, 2H), 1.37 (s, 6H), 1.36 (s, 6H).

An alternative synthesis for this compound is described in U.S. Pat. Nos. 5,045,551 and 5,616,597

General Procedure M

6-Bromo-2,2,4,4-tetramethyl-chroman-8-carbaldehyde (Intermediate 30)

A stirred, cooled (ice bath) solution of 6-bromo-2,2,4,4-tetramethyl chroman, (0.5 g, 1.865 mmol) in anhydrous dichloromethane (5 mL) was treated with a 1M solution (1.86 mL, 1.86 mmol) of titanium tetrachloride in dichloromethane followed by a,a-dichloro methyl ether (0.214 g, 1.865 mmol). The reaction mixture was allowed to warm to ambient temperature for 4 h. The reaction mixture was diluted with diethyl ether, washed with brine (×1) and dried over anhydrous sodium sulfate, filtered and evaporated in vacuo to a residue which was subjected to flash column chromatography over silica gel (230–400 mesh) using 5% ethyl acetate in hexane to afford the title compound as a yellow solid (0.52 g, 94%).

¹H NMR (300 MHz, CDCl₃): δ 10.38 (s, 1H), 7.72 (d, 1H, J=2.6 Hz), 7.57 (d, 1H, J=2.6 Hz), 1.88 (s, 2H), 1.41 (s, 6H), 1.36 (s, 6H).

General Procedure N

6-Bromo-8-vinyl-2,2,4,4-tetramethyl-chroman (Intermediate 31)

A solution of methylidene triphenyl phosphorane [generated from methyl triphenylphosphonium bromide (7 g, 20 mmol) and (11.8 mL, 19 mmol) of a 1.6M solution of n-butyl lithium in hexanes] was added 6-bromo-2,2,4,4-tetramethyl chroman-8-carbaldehyde (Intermediate 30, 0.52 g, 1.75 mmol). After 1 h the reaction mixture was diluted with hexane, washed with brine (×1), dried over anhydrous sodium sulfate, filtered and evaporated in vacuo to a clear oil which was subjected to flash column chromatography over silica gel (230–400 mesh) using 2% ethyl acetate in hexane as the eluent to afford the title compound as a clear oil (0.37 g, 72%).

¹H NMR (300 MHz, CDCl₃): δ 7.46 (d, 1H, J=2.5 Hz), 7.33 (d, 1H, J=2.5 Hz), 7.03 (dd, 1H, J=11.3, 17.9 Hz), 5.75 (dd, 1H, J=1.4, 17.9 Hz), 5.30 (dd, 1H, J=1.4, 11.3 Hz), 1.85 (s, 2H), 1.39 (s, 6H), 1.37 (s, 6H).

General Procedure O

6-Bromo-8-cyclopropyl-2,2,4,4-tetramethyl chroman (Intermediate 32)

A stirred, cooled (−30° C.) solution of 6-bromo-8-vinyl-2,2,4,4-tetramethyl chroman (Intermediate 31, 0.37 g, 1.26 mmol) in diethyl ether was treated with a solution of diazomethane in diethyl ether and catalytic amount of palladium (II)acetate (~30 mg). The reaction mixture was allowed to warm to ambient temperature and subjected to flash column chromatography over silica gel (230–400 mesh) using 2% ethyl acetate in hexane as the eluent to afford the title compound as a clear, pale yellow oil (0.376 g, 97%).

¹H NMR (300 MHz, CDCl₃): δ 7.17 (d, 1H, J=2.3 Hz), 6.73 (d, 1H, J=2.6 Hz), 2.19–2.16 (m, 1H), 1.83 (s, 2H), 1.37 (s, 6H), 1.33 (s, 6H), 0.94–0.88 (m, 2H), 0.64–0.59 (m, 2H).

8-Cyclopropyl-6-timethylsilanylethynyl-2,2,4,4-tetramethyl chroman (Intermediate 33)

Following general procedure D and using 6-bromo-8-cyclopropyl-2,2,4,4-tetramethyl chroman (Intermediate 32, 0.376 g, 1.22 mmol), (trimethylsilyl)acetylene (4 mL, 28 mmol), triethyl amine (3 mL), anhydrous tetrahydrofuran (5 mL), copper(I)iodide (0.025 g, 0.13 mmol) and dichlorobis (triphenylphosphine)palladium(II) (0.075 g, 0.11 mmol), the title compound was obtained as an oil (0.173 g, 43%).

$^1$H NMR (300 MHz, CDCl$_3$): δ 7.36 (d, 1H, J=2.2 Hz), 6.90 (d, 1H, J=1.9 Hz), 2.31–2.22 (m, 1H), 1.96 (s, 2H), 1.49 (s, 6H), 1.46 (s, 6H), 1.05–0.88 (m, 2H), 0.78–0.72 (m, 2H), 0.37 (s, 9H).

8-Cyclopropyl-6-ethynyl-2,2,4,4-tetramethyl chroman (Intermediate 34)

Following general procedure E and using 8-cyclopropyl-6-trimethylsilanylethynyl-2,2,4,4-tetramethyl chroman (Intermediate 33, 0.17 g, 0.68 mmol), methanol and potassium carbonate (0.2 g, 1.47 mmol) the title compound was obtained as an oil (0.064 g, 47%).

$^1$H NMR (300 MHz, CDCl$_3$): δ 7.38 (d, 11H, J=1.9 Hz), 6.92 (d, 1H, J=1.9 Hz), 3.08 (s, 1H), 2.32–2.23 (m, 1H), 1.96 (s, 2H), 1.50 (s, 6H), 1.46 (s, 6H), 1.05–0.99 (m, 2H), 0.77–0.72 (m, 2H).

4-(8-Cyclopropyl-2,2,4,4-tetramethyl-chroman-6-yl-ethynyl)-benzoic acid ethyl ester (Compound 33, General Formula 8)

Following general procedure F and using 8-cyclopropyl-6-ethynyl-2,2,4,4-tetramethylchroman (Intermediate 34, 0.1 g, 0.38 mmol), ethyl-4-iodo-benzoate (Reagent A, 0.1 g, 0.34 mmol), triethyl amine (5 mL), tetrahydrofuran (10 mL), copper(I)iodide (0.025 g, 0.13 mmol) and dichlorobis(triphenylphosphine)palladium(II) (0.075 g, 0.11 mmol) followed by flash column chromatography over silica gel (230–400 mesh) using 5–10% ethyl acetate in hexane as the eluent, the title compound was obtained (0.135 g, 89%).

$^1$H NMR (300 MHz, CDCl$_3$): δ 8.00 (d, 2H, J=8.2 Hz), 7.55 (d, 2H, J=8.2 Hz), 7.30 (d, 1H, J=1.8 Hz), 6.84 (d, 1H, J=2.0 Hz), 4.38 (q, 2H, J=6.9 Hz), 2.22–2.12 (m, 1H), 1.85 (s, 2H), 1.40 (t, 3H, J=6.9 Hz), 1.38 (s, 6H), 1.36 (s, 6H), 0.92–0.88 (m, 2H), 0.67–0.62 (m, 2H).

4-(8-Cyclopropyl-2,2,4,4-tetramethyl-chroman-6-yl-ethynyl)-benzoic acid (Compound 34, General Formula 8)

Following general procedure L and using 4-(8-cyclopropyl-2,2,4,4-tetramethyl-chroman-6-yl-ethynyl)-benzoic acid ethyl ester (Compound 33, 0.135 g, 0.34 mmol), 5 mL of methanol and 1M sodium hydroxide solution (2 mL) followed by preparative reverse phase HPLC using 10% water in acetonitrile as the mobile phase, the title compound was obtained as a solid (0.093 g, 73%).

$^1$H NMR (300 MHz, CDCl$_3$): δ 11.26 (br s, 1H), 8.08 (d, 2H, J=8.2 Hz), 7.59 (d, 2H, J=8.2 Hz), 7.31 (d, 1H, J=1.8 Hz), 6.85 (d, 1H, J=2.1 Hz), 2.22–2.13 (m, 1H), 1.85 (s, 2H), 1.38 (s, 6H), 1.36 (s, 6H), 0.95–0.87 (m, 2H), 0.68–0.63 (m, 2H).

[4-(8-Cyclopropyl-2,2,4,4-tetramethyl-chroman-6-yl-ethynyl)phenyl]acetic acid methyl ester (Compound 35, General Formula 8)

Following general procedure F and using 8-cyclopropyl-6-ethynyl-2,2,4,4-tetramethylchroman (Intermediate 34, 0.096 g, 0.38 mmol), methyl-4-iodo phenyl acetate (Reagent B, 0.094 g, 0.34 mmol), triethyl amine (3 mL), tetrahydrofuran (3 mL), copper(I)iodide (0.025 g, 0.13 mmol) and dichlorobis(triphenylphosphine)palladium(II) (0.075 g, 0.11 mmol) the title compound was obtained (0.137 g, 90%). $^1$H NMR (300 MHz, CDCl$_3$): δ 7.47 (d, 2H, J=7.9 Hz), 7.29 (d, 1H, J=1.8 Hz), 7.24 (d, 2H, J=7.9 Hz), 6.82 (d, 1H, J=2.1 Hz), 3.70 (s, 3H), 3.63 (s, 2H), 2.22–2.13 (m, 1H), 1.85 (s, 2H), 1.38 (s, 6H), 1.36 (s, 6H), 0.94–0.86 (m, 2H), 0.68–0.63 (m, 2H).

[4-(8-Cyclopropyl-2,2,4,4-tetramethyl-chroman-6-yl-ethynyl)phenyl]acetic acid (Compound 36, General Formula 8)

Following general procedure L and using [4-(8-cyclopropyl-2,2,4,4-tetramethyl-chroman-6-ylethynyl)phenyl]acetic acid methyl ester (Compound 35, 0.137 g, 0.30 mmol), 5 mL of methanol and 1M sodium hydroxide solution (2 mL) followed by preparative reverse phase HPLC using 10% water in acetonitrile as the mobile phase, the title compound was obtained as a solid (0.11 g, 80%).

$^1$H NMR (300 MHz, CDCl$_3$): δ 11.56 (br s, 1H), 7.47 (d, 2H, J=8.9 Hz), 7.28 (d, 1H, J=1.9 Hz), 7.23 (d, 2H, J=8.5 Hz), 6.82 (d, 1H, J=1.9 Hz), 3.62 (s, 2H), 2.21–2.12 (m, 1H), 1.83 (s, 2H), 1.36 (s, 6H), 1.34 (s, 6H), 0.93–0.82 (m, 2H), 0.72–0.62 (m, 2H).

[4-(8-Cyclopropyl-2,2,4,4-tetramethyl-chroman-6-yl-ethynyl)-2-fluorophenyl]acetic acid ethyl ester (Compound 37, General Formula 8)

Following general procedure F and using 8-cyclopropyl-6-ethynyl-2,2,4,4-tetramethylchroman (Intermediate 34, 0.096 g, 0.38 mmol), ethyl-2-fluoro-4-iodo phenyl acetate (Reagent C, 0.104 g, 0.34 mmol), triethyl amine (3 mL), tetrahydrofuran (3 mL), copper(I)iodide (0.020 g, 0.1 mmol) and dichlorobis(triphenylphosphine)palladium(II) (0.060 g, 0.085 mmol) the title compound was obtained (0.14 g, 85%).

$^1$H NMR (300 MHz, CDCl$_3$): δ 7.31 (d, 1H, J=1.9 Hz), 7.29–7.21 (m, 3H), 6.85 (d, 1H, J=1.9 Hz), 4.20 (q, 2H, J=7.1 Hz), 3.68 (s, 2H), 2.24–2.14 (m, 1H), 1.87 (s, 2H), 1.40 (s, 6H), 1.38 (s, 6H), 1.28 (t, 3H, J=7.1 Hz), 0.96–0.85 (m, 2H), 0.70–0.64 (m, 2H).

[4-(8-Cyclopropyl-2,2,4,4-tetramethyl-chroman-6-yl-ethynyl)-2-fluorophenyl]acetic acid (Compound 38, General Formula 8)

Following general procedure L and using [4-(8-cyclopropyl-2,2,4,4-tetramethyl-chroman-6-yl-ethynyl)-2-fluorophenyl]acetic acid ethyl ester (Compound 37, 0.14 g, 0.323 mmol), 5 mL of methanol and 1M sodium hydroxide solution (2 mL) followed by reverse phase HPLC using 10% water in acetonitrile as the mobile phase, the title compound was obtained as a solid (0.110 g, 80%).

$^1$H NMR (300 MHz, CDCl$_3$): δ 7.28 (d, 1H, J=2.1 Hz), 7.27–7.17 (m, 3H), 6.82 (d, 1H, J=1.8 Hz), 3.70 (s, 2H), 2.21–2.11 (m, 1H), 1.84 (s, 2H), 1.37 (s, 6H), 1.35 (s, 6H), 0.94–0.87 (m, 2H), 0.67–0.62 (m, 2H).

General Procedure P

6-Bromo-4,4-dimethyl-2-methylene chroman (Intermediate 35)

A stirred, cooled (ice bath) solution of 6-bromo-4,4-dimethyl-chroman-2-one available in accordance with U.S. Pat. No. 5,399,561 incorporated herein by reference (1 g, 3.92 mmol) in 8 mL of anhydrous tetrahydrofuran was treated with a 0.5 M solution of μ-chloro-μ-methylene-[bis(cyclopentadienyl)titanium]dimethylaluminum (Tebbe reagent) in toluene (8.23 mL, 4.12 mmol). After 10 minutes, the reaction mixture was poured into ice-water mixture containing 50 mL of 1M sodium hydroxide and extracted with hexane. The hexane extract was washed with brine (×1), filtered over a bed of celite and evaporated in vacuo to an oil which was subjected to flash column chromatography over silica gel (230–400 mesh) using hexane as the eluent to afford the title compound (0.74 g, 74%) as a clear oil.

$^1$H NMR (300 MHz, CDCl$_3$): δ 7.34 (d, 1H, J=2.3 Hz), 7.23 (dd, 1H, J=2.3,8.5 Hz), 6.77 (d, 1H, J=8.0 Hz), 4.61 (d, 1H, J=0.73 Hz), 4.17 (d, 1H, J=0.73 Hz), 2.33 (s, 2H), 1.27 (s, 6H).

General Procedure Q

6-Bromo-3,4-dihydro-4,4-dimethylspiro[2H-1-benzopyran-2,1'-cyclopropane] (Intermediate 36)

A solution of diethyl zinc in hexane (1M, 7.1 mL) was treated with diiodomethane (1.89 g, 7.1 mmol). After 5 minutes, a solution of 6-bromo-4,4-dimethyl-2-methylene chroman (Intermediate 35, 0.44 g, 1.77 mmol) in 3 mL of hexane was added and the solution was refluxed for 1 h. The reaction mixture was then cooled to ambient temperature, diluted with hexane, washed with brine (×1), dried over anhydrous sodium sulfate, filtered and evaporated in vacuo to a residue which was subjected to flash column chromatography over silica gel (230–400 mesh) using hexane as the eluent to obtain the title compound (0.44 g, 93%).

$^1$H NMR (300 MHz, CDCl$_3$): δ 7.47 (d, 1H, J=2.3 Hz), 7.23 (dd, 1H, J=2.3,8.5 Hz), 6.70 (d, 1H, J=8.0 Hz), 1.96 (s, 2H), 1.47 (s, 6H), 1.09–1.05 (m, 2H), 0.74–0.70 (m, 2H).

3,4-Dihydro-4,4-dimethyl-6-(trimethlsilanyl) ethynylspiro[2H-1-benzopyran-2,1'-cyclopropane] (Intermediate 37)

Following general procedure D and using 6-bromo-3,4-dihydro-4,4-dimethylspiro[2H-1-benzopyran-2,1'-cyclopropane] (Intermediate 36, 0.44 g, 1.65 mmol), triethyl amine (4 mL), anhydrous tetrahydrofuran (5 mL), copper(I) iodide (0.95 g, 0.5 mmol), trimethylsilyl acetylene (1.62 g, 16.5 mmol) and dichlorobis(triphenylphosphine)palladium (II) (0.4 g, 0.56 mmol), the title compound was obtained as a brown oil (0.4 g, 86%).

$^1$H NMR (300 MHz, CDCl$_3$): δ 7.44 (d, 1H, J=2.1 Hz), 7.18 (dd, 1H, J=2.1,8.5 Hz), 6.65 (d, 1H, J=8.5 Hz), 1.87 (s, 2H), 1.37 (s, 6H), 1.01–0.97 (m, 2H), 0.65–0.61 (m, 2H), 0.26 (s, 9H).

6-Ethynyl-3,4-dihydro-4,4-dimethylspiro[2H-1-benzopyran-2,1'-cyclopropane] (Intermediate 38)

Following general procedure E and using 3,4-dihydro-4,4-dimethyl-6-(trimethylsilanyl)ethynylspiro[2H-1-benzopyran-2,1'-cyclopropane] (Intermediate 37, 0.4 g, 1.42 mmol), potassium carbonate (0.98 g, 7.1 mmol) and methanol, the title compound was obtained as a yellow oil (0.3 g, 100%).

$^1$H NMR (300 MHz, CDCl$_3$): δ 7.44 (d, 1H, J=2.1 Hz), 7.18 (dd, 1H, J=2.1, 8.5 Hz), 6.65 (d, 1H, J=8.5 Hz), 2.97 (s, 1H), 1.86 (s, 2H), 1.37 (s, 6H), 1.00–0.95 (m, 2H), 0.64–0.59 (m, 2H).

Benzoic acid, 4-[(3,4-dihydro-4,4-dimethylspiro [2H-1-benzopyran-2,1'-cyclopropane]-6-yl)ethynyl]-ethyl ester (Compound 39, General Formula 1)

Following general procedure F and using 6-ethynyl-3,4-dihydro-4,4-dimethylspiro[2H-1-benzopyran-2,1'-cyclopropane] (Intermediate 38, 0.06 g, 0.28 mmol), ethyl-4-iodo-benzoate (Reagent A, 0.086 g, 0.31 mmol), triethyl amine (4 mL), tetrahydrofuran(4 mL), copper(I)iodide (0.032 g, 0.17 mmol) and dichlorobis(triphenylphosphine) palladium(II) (0.118 g, 0.17 mmol) followed by flash column chromatography over silica gel (230–400 mesh) using 5–10% ethyl acetate in hexane as the eluent, the title compound was obtained (0.07 g, 70%).

$^1$H NMR (300 MHz, CDCl$_3$): δ 8.01 (d, 2H, J=8.2 Hz), 7.56 (d, 2H, J=8.5 Hz), 7.49 (d, 1H, J=2.1 Hz), 7.24 (dd, 1H, J=2.1,8.5 Hz), 6.70 (d, 1H, J=8.5 Hz), 4.38 (q, 2H, J=7.1 Hz), 1.89 (s, 2H), 1.40 (s, 6H), 1.40 (t, 3H, J=7.0 Hz), 1.02–0.98 (m, 2H), 0.67–0.62 (m, 2H).

Benzoic acid, 4-[(3,4-dihydro-4,4-dimethylspiro [2H-1-benzopyran-2,1'-cyclopropane]-6-yl) ethynyl]—(Compound 40, General Formula 1)

Following general procedure L and using benzoic acid, 4-[(3,4-dihydro-4,4-dimethylspiro[2H-1-benzopyran-2,1'-cyclopropane]-6-yl)ethynyl]-ethyl ester (Compound 39, 0.07 g, 0.196 mmol), 5 mL of ethanol and 1M sodium hydroxide solution (2 mL) followed by preparative reverse phase HPLC using 10% water in acetonitrile as the mobile phase, the title compound was obtained as a solid (0.034 g, 52%).

$^1$H NMR (300 MHz, CD$_3$COCD$_3$): δ 8.05 (d, 2H, J=8.2 Hz), 7.64 (d, 2H, J=8.2 Hz), 7.60 (d, 1H, J=2.1 Hz), 7.28 (dd, 1H, J=2.1, 8.5 Hz), 6.73 (d, 1H, J=8.5 Hz), 1.95 (s, 2H), 1.43 (s, 6H), 0.96–0.92 (m, 2H), 0.74–0.71 (m, 2H).

Benzeneacetic acid, 4-[(3,4-dihydro-4,4-dimethylspiro[2H-1-benzopyran-2,1'-cyclopropane]-6-yl)ethynyl]-methyl ester (Compound 41, General Formula 1)

Following general procedure F and using 6-ethynyl-3,4-dihydro-4,4-dimethylspiro[2H-1-benzopyran-2,1'-cyclopropane] (Intermediate 38, 0.060 g, 0.28 mmol), methyl-4-iodo phenyl acetate (Reagent B, 0.078 g, 0.28 mmol), triethyl amine (4 mL), tetrahydroftiran (4 mL), copper(I)iodide (0.032 g, 0.17 mmol) and dichlorobis (triphenylphosphine)palladium(II) (0.118 g, 0.17 mmol) followed by flash column chromatography over silica gel (230–400 mesh) using 5% ethyl acetate in hexane as the eluent, the title compound was obtained (0.084 g, 84%).

$^1$H NMR (300 MHz, CDCl$_3$): δ 7.48–7.45 (m, 3H), 7.26–7.20 (m, 3H), 6.67 (d, 1H, J=8.5 Hz), 3.70 (s, 3H), 3.63 (s, 2H), 1.89 (s, 2H), 1.40 (s, 3H), 1.40 (s, 3H), 1.01–0.97 (m, 2H), 0.67–0.61 (m, 2H).

Benzeneacetic acid, 4-[(3,4-dihydro-4,4-dimethylspiro[2H-1-benzopyran-2,1'-cyclopropane]-6-yl)ethynyl]—(Compound 42, Formula 1)

A solution of benzeneacetic acid, 4-[(3,4-dihydro-4,4-dimethylspiro[2H-1-benzopyran-2,1'-cyclopropane]-6-yl) ethynyl]-methyl ester (Compound 41, 0.084 g, 0.24 mmol) in 5 mL of methanol was treated with 1M sodium hydroxide solution (2 mL) and heated at 55° C. for 2 h. The volatiles were distilled off in vacuo and the residue was acidified with 10% hydrochloric acid and extracted with ethyl acetate (×2). The combined organic phase was washed with brine (×1), dried over anhydrous sodium sulfate, filtered and evaporated in vacuo to a residue which was purified by preparative reverse phase HPLC using 10% water in acetonitrile as the mobile phase to afford the title compound (0.080 g, 100%).

$^1$H NMR (300 MHz, CD$_3$COCD$_3$): δ 7.49–7.46 (m, 3H), 7.25 (d, 2H, J=8.2 Hz), 7.22 (dd, 1H J=2.1,8.5 Hz), 6.68 (d, 1H, J=8.5 Hz), 3.66 (s, 2H), 1.88 (s, 2H), 1.44 (s, 6H), 1.01–0.97 (m, 2H), 0.67–0.61 (m, 2H).

2-Fluoro-benzoic acid, 4-[(3,4-dihydro-4,4-dimethylspiro[2H-1-benzopyran-2,1'-cyclopropane]-6-yl)ethynyl]-methyl ester (Compound 43, General Formula 1)

Following general procedure F and 6-ethynyl-3,4-dihydro-4,4-dimethylspiro[2H-1-benzopyran-2,1'- cyclopropane] (Intermediate 38, 0.050 g, 0.23 mmol), methyl-2-fluoro-4-iodo-benzoate (Reagent G, 0.069 g, 0.24 mmol), triethyl amine (5 mL), tetrahydrofuran(5 mL), copper(I)iodide(0.013 g, 0.07 mmol) and dichlorobis (triphenylphosphine)palladium(II) (0.049 g, 0.07 mmol) followed by flash column chromatography over silica gel (230–400 mesh) using 5–10% ethyl acetate in hexane as the eluent, the title compound was obtained (0.080 g, 100%).

$^1$H NMR (300 MHz, CDCl$_3$): δ 7.90 (t, 1H, J=7.9 Hz), 7.63 (d, 1H, J=1.8 Hz), 7.32 (dd, 1H, J=1.5, 8.2 Hz), 7.26 (dd, 1H, J=1.5,11.4 Hz), 7.24 (dd, 1H, J=2.1, 8.5 Hz), 6.71 (d, 1H, J=8.5 Hz), 1.97 (s, 2H), 1.44 (s, 6H), 0.98–0.94 (m, 2H), 0.76–0.71 (m, 2H).

2-Fluoro-benzoic acid, 4-[(3,4-dihydro-4,4-dimethylspiro[2H-1-benzopyran-2,1'-cyclopropane]-6-yl)ethynyl]—(Compound 44, General Formula 1)

Following general procedure L and using 2-fluoro-benzoic acid, 4-[(3,4-dihydro-4,4-dimethylspiro[2H-1-benzopyran-2,1'-cyclopropane]-6-yl)ethynyl]-methyl ester (Compound 43, 0.08 g, 0.23 mmol), 5 mL of methanol and 2M sodium hydroxide solution (1 mL) followed by flash column chromatography over silica gel (230–400 mesh) using ethyl acetate as the eluent, the title compound was obtained (0.020 g, 25%).

$^1$H NMR (300 MHz, CD$_3$COCD$_3$): δ 7.99 (t, 1H, J=7.9 Hz), 7.63 (d, 1H, J=2.1 Hz), 7.44 (dd, 1H, J=1.5, 7.9 Hz), 7.37 (dd, 1H, J=1.5, 11.4 Hz), 7.31 (dd, 1H, J=2.1, 8.5 Hz), 6.75 (d, 1H, J=8.2 Hz), 1.97 (s, 2H), 1.44 (s, 6H), 0.98–0.94 (m, 2H), 0.76–0.71 (m, 2H).

General Procedure R 2,2,4,4-Tetramethyl-chroman-6-carboxylic acid (Intermediate 39)

A stirred, cooled (–78° C.) solution of 6-bromo-2,2,4,4-tetramethyl chroman (1.2 g, 4.47 mmol) in 15 mL of anhydrous tetrahydrofuran was treated with a 1.7M solution of tert-butyl lithium solution in pentane (5.27 mL, 8.9 mmol). After 10 minutes at –78° C., carbon dioxide (generated from dry ice) was bubbled into the reaction mixture. The reaction mixture was allowed to warm to ambient temperature. The reaction mixture was diluted with ethyl acetate, washed with brine, dried over anhydrous sodium sulfate, filtered and evaporated in vacuo to a residue which was subjected to flash column chromatography over silica gel (230–400 mesh) using ethyl acetate as the eluent to afford the title compound as a white solid (1.1 g, 92%).

$^1$H NMR (300 MHz, CDCl$_3$): δ 12.17 (br s, 1H), 8.09 (d, 1H, J=2.1 Hz), 7.85 (dd, 1H, J=2.1, 8.5 Hz), 6.83 (d, 1H, J=8.2 Hz), 1.87 (s, 2H), 1.39 (s, 6H), 1.37 (s, 6H).

2,2,4,4-Tetramethyl-chroman-6-carboxylic acid 4-(tert-butoxycarbonylmethyl)phenyl ester (Compound 45, General Formula 8)

A solution of 2,2,4,4-tetramethyl chroman-6-carboxylic acid (0.1 g, 0.43 mmol) in thionyl chloride (10 mL) was refluxed for 2 h. The thionyl chloride was evaporated under reduced pressure and the residue was dissolved in 5 mL of dichloromethane and treated with triethyl amine (5 mL) followed by tert-butyl-4-hydroxy phenyl acetate (Reagent E, 0.088 g, 0.427 mmol). After 0.5 h, the reaction mixture was subjected to flash column chromatography over silica gel (230–400 mesh) using 5–10% ethyl acetate in hexane as the eluent to afford the title compound (0.1 g, 55%).

$^1$H NMR (300 MHz, CDCl$_3$): δ 8.15 (d, 1H, J=2.1 Hz), 7.93 (dd, 1H, J=2.1, 8.5 Hz), 7.33 (d, 2H, J=8.8 Hz), 7.16 (d, 2H, J=8.8 Hz), 6.88 (d, 1H, J=8.5 Hz), 3.54 (s, 2H), 1.89 (s, 2H), 1.45 (s, 9H), 1.41 (s, 6H), 1.40 (s, 6H).

2,2,4,4-Tetramethyl-chroman-6-carboxylic acid 4-(carboxymethyl)phenyl ester (Compound 46, General Formula 8)

A solution of 2,2,4,4-tetramethyl-chroman-6-carboxylic acid 4-(tert-butoxycarbonylmethyl)phenyl ester (Compound 45, 0.1 g, 0.23 mmol) was treated with 5 mL of trifluoroacetic acid and stirred at ambient temperature for 1 h. The trifluoroacetic acid was distilled off under reduced pressure and the residue was subjected to preparative reverse phase HPLC using 10% water in acetonitrile as the mobile phase to afford the title compound as a white solid (0.045 g, 50%).

$^1$H NMR (300 MHz, CDCl$_3$): δ 8.13 (d, 1H, J=2.1 Hz), 7.92 (dd, 1H, J=2.3, 8.5 Hz), 7.35 (d, 2H, J=8.8 Hz), 7.17 (d, 2H, J=8.5 Hz), 6.87 (d, 1H, J=8.5 Hz), 3.68 (s, 2H), 1.89 (s, 2H), 1.41 (s, 6H), 1.39 (s, 6H).

6-Bromo-8-carbaldehyde-3,4-dihydro-4,4-dimethylspiro[2H-1-benzopyran-2,1'-cyclopropane] (Intermediate 40)

Following general procedure M and using 6-bromo-3,4-dihydro-4,4-dimethylspiro[2H-1-benzopyran-2,1'-cyclopropane] (Intermediate 36, 2.3 g, 8.65 mmol), anhydrous dichloromethane (25 mL), 1M solution (8.65 mL, 8.65 mmol) of titanium tetrachloride in dichloromethane and α,α-dichloro methyl ether (1.09 g, 9.52 mmol) followed by flash column chromatography using 10% ethyl acetate in hexane as the eluent, the title compound was obtained as a yellow solid (2.06 g, 81%).

$^1$H NMR (300 MHz, CDCl$_3$): δ 10.20 (s, 1H), 7.69 (d, 1H, J=2.6 Hz), 7.58 (d, 1H, J=2.6 Hz), 1.92 (s, 2H), 1.40 (s, 6H), 1.09–1.04 (m, 2H), 0.73–0.69 (m, 2H).

6-Bromo-3,4-dihydro-4,4-dimethyl-8-vinylspiro[2H-1-benzopyran-2,1'-cyclopropane] (Intermediate 41)

Following general procedure N and using A solution of methylidene triphenyl phosphorane [generated from methyl triphenylphosphonium bromide (7 g, 20 mmol) and 1.6M solution of n-butyl lithium in hexanes (11.8 mL, 19 mmol)], 6-bromo-8-carbonyl-3,4-dihydro-4,4-dimethylspiro[2H-1-benzopyran-2,1'-cyclopropane](Intermediate 40, 2.06 g, 7 mmol) followed by flash column chromatography over silica gel (230–400 mesh) using 1–2% ethyl acetate in hexane as the eluent, the title compound was obtained as a clear oil (1.36 g, 66%).

$^1$H NMR (300 MHz, CDCl$_3$): δ 7.36 (d, 1H, J=2.3 Hz), 7.28 (d, 1H, J=2.6 Hz), 6.80 (dd, 1H, J=11.1, 17.9 Hz), 5.63 (dd, 1H, J=1.2, 17.9 Hz), 5.19 (dd, 1H, J=1.2, 11.1 Hz), 1.84 (s, 2H), 1.35 (s, 6H), 0.97 (t, 2H, J=6.3 Hz), 0.62 (d, 1H, J=5.3 Hz), 0.60 (d, 1H, J=6.2 Hz).

6-Bromo-8-cyclopropyl-3,4-dihydro-4,4-dimethylspiro[2H-1-benzopyran-2,1'-cyclopropane] (Intermediate 42)

Following general procedure O and using A 6-bromo-3,4-dihydro-4,4-dimethyl-8-vinylspiro[2H-1-benzopyran-2,1'-cyclopropane] (Intermediate 41, 1.36 g, 4.6 mmol), a solution of diazomethane in diethyl ether and palladium (II)acetate (~30 mg) followed by flash column chromatography over silica gel (230–400 mesh) using hexane as the eluent, the title compound was obtained as a clear oil (1.38 g, 100%).

$^1$H NMR (300 MHz, CDCl$_3$): δ 7.19 (d, 1H, J=2.2 Hz), 6.71 (d, 1H, J=2.2 Hz), 1.99–1.92 (m, 1H), 1.87 (s, 2H), 1.35 (s, 6H), 1.00–0.95 (m, 2H), 0.90–0.82 (m, 2H), 0.65–0.54 (m, 4H).

8-Cyclopropyl-3,4-dihydro-4,4-dimethyl-6-(trimethylsilanyl)ethynylspiro[2H-1-benzopyran-2,1'-cyclopropane] (Intermediate 43)

Following general procedure D and 6-bromo-8-cyclopropyl-3,4-dihydro-4,4-dimethylspiro[2H-1-benzopyran-2,1'-cyclopropane] (Intermediate 42, 0.74 g, 2.4 mmol), (trimethylsilyl)acetylene (4 mL, 28 mmol), triethyl amine (8 mL), anhydrous tetrahydrofuran, copper(I)iodide (0.050 g, 0.26 mmol) and dichlorobis(triphenylphosphine) palladium(II) (0.15 g, 0.22 mmol), followed by flash column chromatography over silica gel (230–400 mesh) using 1–2% ethyl acetate in hexane as the eluent, the title compound was obtained as an oil (0.62 g, 80%).

$^1$H NMR (300 MHz, CDCl$_3$): δ 7.28 (d, 1H, J=1.9 Hz), 6.77 (d, 1H, J=1.9 Hz), 2.03–1.94 (m, 1H), 1.91 (s, 2H), 1.40 (s, 6H), 1.05–0.98 (m, 2H), 0.95–0.83 (m, 2H), 0.69–0.59 (m, 4H), 0.27 (s, 9H).

8-Cyclopropyl-6-ethynyl-3,4-dihydro-4,4-dimethylspiro[2H-1-benzopyran-2,1'-cyclopropane] (Intermediate 44)

Following general procedure E, and 8-cyclopropyl-3,4-dihydro-4,4-dimethyl-6-(trimethylsilanyl)ethynylspiro[2H-1-benzopyran-2,1'-cyclopropane] (Intermediate 43, 0.62 g, 1.9 mmol), methanol and potassium carbonate (0.5 g, 3.6 mmol) followed by flash column chromatography over silica gel (230–400 mesh) using 1–2% ethyl acetate in hexane as the eluent, the title compound was obtained as an oil (0.5 g, 100%).

$^1$H NMR (300 MHz, CDCl$_3$): δ 7.30 (d, 1H, J=1.8 Hz), 6.80 (d, 1H, J=2.0 Hz), 2.97 (s, 1H), 2.04–1.95 (m, 1H), 1.91 (s, 2H), 1.39 (s, 6H), 1.20–0.90 (m, 2H), 0.90–0.84 (m, 2H), 0.75–0.58 (m, 4H).

Benzeneacetic acid, 4-[(8-cyclopropyl-3,4-dihydro-4,4-dimethylspiro[2H-1-benzopyran-2,1'-cyclopropane]-6-yl)ethynyl]-methyl ester (Compound 47, General Formula 1)

Following general procedure F and using 8-cyclopropyl-6-ethynyl-3,4-dihydro-4,4-dimethylspiro[2H-1-benzopyran-2,1'-cyclopropane] (Intermediate 44, 0.11 g, 0.43 mmol), methyl-4-iodo phenyl acetate (Reagent B, 0.114 g, 0.41 mmol), triethyl amine (5 mL), tetrahydrofuran (3 mL), copper(I)iodide (0.025 g, 0.13 mmol) and dichlorobis(triphenylphosphine)palladium(II) (0.075 g, 0.11 mmol), the title compound was obtained as a clear oil (0.096 g, 56%).

$^1$H NMR (300 MHz, CDCl$_3$): δ 7.46 (d, 2H, J=8.0 Hz), 7.31 (d, 1H, J=1.9 Hz), 7.24 (d, 2H, J=8.2 Hz), 6.81 (d, 1H, J=1.9 Hz), 3.69 (s, 3H), 3.62 (s, 2H), 2.04–1.95 (m, 1H), 1.90 (s, 2H), 1.39 (s, 6H), 1.03–0.99 (m, 2H), 0.90–0.83 (m, 2H), 0.68–0.59 (m, 4H).

Benzeneacetic acid 4-[(8-cyclopropyl-3,4-dihydro-4,4-dimethylspiro[2H-1-benzopyran-2,1'-cyclopropane]-6-yl)ethynyl]—(Compound 48, General Formula 1)

Following general procedure L and using benzeneacetic acid, 4-[(8-cyclopropyl-3,4-dihydro-4,4-dimethylspiro[2H-1-benzopyran-2,1'-cyclopropane]-6-yl)ethynyl]-methyl ester (Compound 47, 0.96 g, 0.24 mmol), 5 mL of methanol and 1M sodium hydroxide solution (2 mL) followed by flash column chromatography over silica gel (230–400 mesh) using 15% methanol in dichloromethane as the eluent, the title compound was obtained as a solid (0.084 g, 91%).

$^1$H NMR (300 MHz, CDCl$_3$): δ 10.27 (br s, 1H), 7.46 (d, 2H, J=8.2 Hz), 7.30 (d, 1H, J=1.8 Hz), 7.23 (d, 2H, J=8.2 Hz), 6.80 (d, 1H, J=1.5 Hz), 3.63 (s, 2H), 2.07–1.94 (m, 1H), 1.89 (s, 2H), 1.39 (s, 6H), 1.03–0.98 (m, 2H), 0.89–0.82 (m, 2H), 0.73–0.59 (m, 4H).

4-[(8-Cyclopropyl-3,4-dihydro-4,4-dimethylspiro[2H-1-benzopyran-2,1'-cyclopropane]-6-yl)ethynyl]-2-fluoro-benzeneacetic acid methyl ester (Compound 49, General Formula 1)

Following general procedure F and using 8-cyclopropyl-6-ethynyl-3,4-dihydro-4,4-dimethylspiro[2H-1-benzopyran-2,1'-cyclopropane] (Intermediate 44, 0.125 g, 0.5 mmol), methyl-2-fluoro-4-iodo phenyl acetate (Reagent H, 0.14 g, 0.5 mmol), triethyl amine (3 mL), tetrahydrofuran (3 mL), copper(I)iodide (0.020 g, 0.1 mmol) and dichlorobis(triphenylphosphine)palladium(II) (0.060 g, 0.085 mmol) followed by preparative normal phase HPLC using 10% ethyl acetate in hexane as the mobile phase, the title compound was obtained (0.096 g, 46%).

$^1$H NMR (300 MHz, CDCl$_3$): δ 7.30 (d, 1H, J=2.1 Hz), 7.26–7.18 (m, 3H), 6.80 (d, 1H, J=1.8 Hz), 3.71 (s, 3H), 3.67 (s, 2H), 2.04–1.94 (m, 1H), 1.90 (s, 2H), 1.40 (s, 6H), 1.18–0.99 (m, 2H), 0.90–0.83 (m, 2H), 0.68–0.59 (m, 4H).

4-[(8-Cyclopropyl-3,4-dihydro-4,4-dimethylspiro[2H-1-benzopyran-2,1'-cyclopropane]-6-yl)ethynyl]-2-fluoro-benzeneacetic acid (Compound 50, General Formula 1)

Following general procedure L and using 4-[(8-cyclopropyl-3,4-dihydro-4,4-dimethylspiro[2H-1-benzopyran-2,1'-cyclopropane]-6-yl)ethynyl]-2-fluoro-benzeneacetic acid methyl ester (Compound 49, 0.096 g, 0.23 mmol), 5 mL of methanol and 1M sodium hydroxide solution (2 mL) followed by flash column chromatography over silica gel (230–400 mesh) using 15% methanol in dichloromethane as the eluent, the title compound was obtained as a solid (0.093 g, 100%).

$^1$H NMR (300 MHz, CDCl$_3$): δ 9.50 (br s, 1H), 7.27 (d, 1H, J=2.1 Hz), 7.24–7.15 (m, 3H), 6.77 (d, 1H, J=1.5 Hz), 3.67 (s, 2H), 2.01–1.91 (m, 1H), 1.87 (s, 2H), 1.36 (s, 6H), 1.01–0.96 (m, 2H), 0.87–0.80 (m, 2H), 0.65–0.56 (m, 4H).

Benzoic acid, 4-[(8-cyclopropyl-3,4-dihydro-4,4-dimethylspiro[2H-1-benzopyran-2,1'-cyclopropane]-6-yl)ethynyl]-ethyl ester (Compound 51, General Formula 1)

Following general procedure F and using 8-cyclopropyl-6-ethynyl-3,4-dihydro-4,4-dimethylspiro[2H-1-benzopyran-2,1'-cyclopropane] (Intermediate 44, 0.05 g, 0.2 mmol), ethyl-4-iodo-benzoate (Reagent A, 0.055 g, 0.2 mmol), triethyl amine (3 mL), tetrahydrofuran (3 mL), copper(I)iodide (0.020 g, 0.1 mmol) and dichlorobis(triphenylphosphine)palladium(II) (0.060 g, 0.085 mmol), the title compound was obtained (0.06 g, 75%).

$^1$H NMR (300 MHz, CDCl$_3$): δ 8.00 (d, 2H, J=8.2 Hz), 7.55 (d, 2H, J=8.2 Hz), 7.33 (d, 1H, J=1.8 Hz), 6.83 (d, 1H, J=2.1 Hz), 4.38 (q, 2H, J=7.1 Hz), 2.04–1.95 (m, 1H), 1.91 (s, 2H), 1.40 (s, 6H), 1.40 (t, 3H, J=7.0 Hz), 1.05–0.95 (m, 2H), 0.91–0.84 (m, 2H), 0.69–0.61 (m, 4H).

Benzoic acid, 4-[(8-cyclopropyl-3,4-dihydro-4,4-dimethylspiro[2H-1-benzopyran-2,1'-cyclopropane]-6-yl)ethynyl]—(Compound 52, General Formula 1)

Following general procedure L and using benzoic acid, 4-[(8-cyclopropyl-3,4-dihydro-4,4-dimethylspiro[2H-1- benzopyran-2,1'-cyclopropane]-6-yl)ethynyl]-ethyl ester (Compound 51, 0.06 g, 0.15 mmol), 5 mL of methanol and 1M sodium hydroxide solution (2 mL) followed by preparative reverse phase HPLC using 10% water in acetonitrile as the mobile phase, the title compound was obtained as a solid (0.040 g, 72%).

$^1$H NMR (300 MHz, CDCl$_3$): δ 8.08 (d, 2H, J=8.8 Hz), 7.60 (d, 2H, J=8.8 Hz), 7.34 (d, 1H, J=1.9 Hz), 6.84 (d, 1H, J=1.9 Hz), 2.05–1.96 (m, 1H), 1.92 (s, 2H), 1.41 (s, 6H), 1.05–0.95 (m, 2H), 0.92–0.83 (m, 2H), 0.75–0.60 (m, 4H).

4-[(8-Cyclopropyl-3,4-dihydro-4,4-dimethylspiro [2H-1-benzopyran-2,1'-cyclopropane]-6-yl)ethynyl]-2-fluoro-benzoic acid methyl ester (Compound 53, General Formula 1)

Following general procedure F and using 8-cyclopropyl-6-ethynyl-3,4-dihydro-4,4-dimethylspiro[2H-1-benzopyran-2,1'-cyclopropane] (Intermediate 44, 0.03 g, 0.11 mmol), methyl-2-fluoro-4-iodo-benzoate (Reagent G, 0.025 g, 0.09 mmol), triethyl amine (3 mL), tetrahydrofuran(3 mL), copper(I)iodide(0.020 g, 0.1 mmol) and dichlorobis(triphenylphosphine)palladium(II) (0.06 g, 0.085 mmol) followed by preparative normal phase HPLC using 10% ethyl acetate in hexane as the mobile phase, the title compound was obtained as a white solid (0.019 g, 40%).

$^1$H NMR (300 MHz, CDCl$_3$): δ 7.97 (t, 1H, J=7.8 Hz), 7.34 (d, 1H, J=1.9 Hz), 7.32–7.25 (m, 2H), 6.83 (d, 1H, J=1.9 Hz), 3.95 (s, 3H), 2.06–1.96 (m, 1H), 1.93 (s, 2H), 1.42 (s, 6H), 1.06–1.02 (m, 2H), 0.91–0.86 (m, 2H), 0.71–0.61 (m, 4H).

4-[(8-Cyclopropyl-3,4-dihydro-4,4-dimethylspiro [2H-1-benzopyran-2,1'-cyclopropane]-6-yl)ethynyl]-2-fluoro-benzoic acid (Compound 54, General Formula 1)

Following general procedure L and using 4-[(8-cyclopropyl-3,4-dihydro-4,4-dimethylspiro[2H-1-benzopyran-2,1'-cyclopropane]-6-yl)ethynyl]-2-fluoro-benzoic acid methyl ester (Compound 53, 0.019 g, 0.047 mmol), 5 mL of methanol and 1M sodium hydroxide solution (2 mL) followed by preparative reverse phase HPLC using 10% water in acetonitrile as the mobile phase, the title compound was obtained as a solid (0.01 g, 56%).

$^1$H NMR (300 MHz, CDCl$_3$): δ 7.99 (t, 1H, J=8.0 Hz), 7.36–7.28 (m, 3H), 6.83 (d, 1H, J=1.9 Hz), 2.18–1.95 (m, 1H), 1.92 (s, 2H), 1.41 (s, 6H), 1.06–1.01 (m, 2H), 0.96–0.83 (m, 2H), 0.76–0.60 (m, 4H).

8-Acetyl-6-bromo-2,2,4,4-tetramethyl chroman (Intermediate 45)

A stirred, cooled (ice bath) suspension of aluminum chloride (0.99 g, 7.46 mmol) in anhydrous dichloromethane (20 mL) was treated with acetyl chloride (0.58 g, 7.46 mmol). After 5 minutes, a solution of 6-bromo-2,2,4,4-tetramethyl chroman (1 g, 3.73 mmol)in dichloromethane was added. The reaction was allowed to warm to ambient temperature and stirred for 2 h. The reaction mixture was then poured into ice containing 10% hydrochloric acid and extracted with diethyl ether (×2). The combined organic phase was washed with saturated aqueous sodium bicarbonate solution, dried over anhydrous sodium sulfate, filtered and evaporated in vacuo to a residue which was subjected to flash column chromatography over silica gel (230–400 mesh) using 5% ethyl acetate in hexane as the eluent to afford the title compound as a pale yellow oil (0.95 g, 83%). It was used as such for the next step without any characterization.

6-Bromo-8-ethyl-2,2,4,4-tetramethyl chroman (Intermediate 46)

A stirred, cooled (ice bath) solution of 8-acetyl-6-bromo-2,2,4,4-tetramenthyl chroman (Intermediate 45, 0.95 g, 3.1 mmol) in trifluoroacetic acid (10 mL) was treated with triethylsilane (10 mL) and the resulting reaction mixture was allowed to warm to ambient temperature and stirred overnight. The volatiles were distilled off in vacuo and the residue was diluted with water and extracted with hexane (×2). The combined organic phase was dried over anhydrous sodium sulfate, filtered and evaporated in vacuo to an oil which was subjected to flash column chromatography over silica gel (230–400 mesh) using hexane as the eluent to afford the title compound as a clear oil, contaminated with a small amount to triethylsilane (0.51 g, 56%).

$^1$H NMR (300 MHz, CDCl$_3$): δ 7.23 (d, 1H, J=2.3 Hz), 7.08 (d, 1H, J=2.3 Hz), 2.58 (q, 2H, J=7.6 Hz), 1.81 (s, 2H), 1.34 (s, 6H), 1.33 (s, 6H), 1.17 (t, 3H, J=7.6 Hz).

8-Ethyl-6-trimethylsilanylethynyl-2,2,4,4-tetramenthyl chroman (Intermediate 47)

Following general procedure D and using 6-bromo-8-ethyl-2,2,4,4-tetramethyl chroman (Intermediate 46, 0.5 g, 1.61 mmol), (trimethylsilyl)acetylene (1.57 g, 16.1 mmol), triethyl amine (8 mL), anhydrous tetrahydrofuran (10 mL), copper(I)iodide (0.025 g, 0.13 mmol) and dichlorobis (triphenylphosphine)palladium(II) (0.075 g, 0.11 mmol), followed by flash column chromatography over silica gel (230–400 mesh) using 5% ethyl acetate in hexane as the eluent, the title compound was obtained as an oil (0.137 g, 27%).

$^1$H NMR (300 MHz, CDCl$_3$): δ 7.27 (d, 1H, J=2.1 Hz), 7.10 (d, 1H, J=2.1 Hz), 2.55 (q, 2H, J=7.6 Hz), 1.81 (s, 2H), 1.33 (s, 6H), 1.32 (s, 6H), 1.15 (t, 3H, J=7.6 Hz), 0.24 (s, 9H).

8-Ethyl-1-6-ethynyl-2,2,4,4-tetramenthyl chroman (Intermediate 48)

Following general procedure E and using 8-ethyl-6-trimethylsilanylethynyl-2,2,4,4-tetramenthyl chroman (Intermediate 47, 0.137 g, 0.44 mmol), methanol and potassium carbonate (0.1 g, 0.72 mmol) followed by flash column chromatography over silica gel (230–400 mesh) using 5% ethyl acetate in hexane as the eluent, the title compound was obtained as an oil (0.066 g, 62%).

$^1$H NMR (300 MHz, CDCl$_3$): δ 7.33 (d, 1H, J=2.2 Hz), 7.15 (d, 1H, J=1.6 Hz), 2.99 (s, 1H), 2.59 (q, 2H, J=7.6 Hz), 1.84 (s, 2H), 1.37 (s, 6H), 1.35 (s, 6H), 1.19 (t, 3H, J=7.6 Hz).

[4-(8-Ethyl-2,2,4,4-tetramethyl-chroman-6-yl-ethynyl)phenyl] acetic acid methyl ester (Compound 55, General Formula 8)

Following general procedure F and using 8-ethyl-6-ethynyl-2,2,4,4-tetramethylchroman (Intermediate 48, 0.033 g, 0.136 mmol), methyl-4-iodophenyl acetate (Reagent B, 0.034 g, 0.12 mmol), triethyl amine (2 mL), tetrahydrofuran (2 mL), copper(I)iodide (0.025 g, 0.13 mmol) and dichlorobis(triphenylphosphine)palladium(II) (0.075 g, 0.11 mmol) the title compound was obtained (0.035 g, 73%).

$^1$H NMR (300 MHz, CDCl$_3$): δ 7.49 (d, 2H, J=7.9 Hz), 7.35 (d, 1H, J=1.8 Hz), 7.26 (d, 2H, J=7.9 Hz), 7.18 (d, 1H, J=1.9 Hz), 3.72 (s, 3H), 3.65 (s, 2H), 2.61 (q, 2H, J=7.5 Hz), 1.85 (s, 2H), 1.38 (s, 12H), 1.21 (t, 3H, J=7.5 Hz).

[4-(8-Ethyl-2,2,4,4-tetramethyl-chroman-6-yl-ethynyl)phenyl] acetic acid (Compound 56, General Formula 8)

Following general procedure L and using [4-(8-ethyl-2,2,4,4-tetramethyl-chroman-6-ylethynyl)phenyl] acetic acid methyl ester (Compound 55, 0.035 g, 0.1 mmol), 5 mL of methanol and 1M sodium hydroxide solution (1 mL) followed by preparative reverse phase HPLC using 10% water in acetonitrile as the mobile phase, the title compound was obtained as a solid (0.11 g, 25%).

$^1$H NMR (300 MHz, CDCl$_3$): δ 7.48 (d, 2H, J=8.0 Hz), 7.33 (d, 1H, J=1.9 Hz), 7.25 (d, 2H, J=8.0 Hz), 7.15 (d, 1H, J=1.9 Hz), 3.65 (s, 2H), 2.59 (q, 2H, J=7.5 Hz), 1.83 (s, 2H), 1.35 (s, 12H), 1.18 (t, 3H, J=7.4 Hz).

Spiro[2H-1-benzopyran-2,1'-cyclopropane]-6-carboxylic acid, 8-cyclopropyl-3,4-dihydro-4,4-dimethyl- (Intermediate 49)

Following general procedure R and using 6-bromo-8-cyclopropyl-3,4-dihydro-4,4-dimethylspiro[2H-1-benzopyran-2,1'-cyclopropane] (Intermediate 42, 0.45 g, 1.48 mmol), anhydrous tetrahydrofuran (5 mL), 1.7M solution of tert-butyl lithium solution in pentane (1.74 mL, 2.96 mmol) and carbon dioxide generated from dry ice, followed by flash column chromatography over silica gel (230–400 mesh) using 50% ethyl acetate in hexane as the eluent, the title compound was obtained as a white solid (0.34 g, 85%).

$^1$H NMR (300 MHz, CDCl$_3$): δ 12.43 (br s, 1H), 7.94 (d, 1H, J=2.1 Hz), 7.42 (d, 1H, J=1.8 Hz), 2.06–1.96 (m, 1H), 1.92 (s, 2H), 1.42 (s, 6H), 1.12–0.97 (m, 2H), 0.95–0.81 (m, 2H), 0.77–0.60 (m, 4H).

Spiro[2H-1-benzopyran-2,1'-cyclopropane]-6-carboxylic acid, 8-cyclopropyl-3,4-dihydro-4,4-dimethyl-, 4-(tert-butoxycarbonylmethyl)phenyl ester (Compound 57, General Formula 1)

A solution of spiro[2H-1-benzopyran-2,1'-cyclopropane]-6-carboxylic acid, 8-cyclopropyl-3,4-dihydro-4,4-dimethyl- (Intermediate 49, 0.06 g, 0.22 mmol) in anhydrous dichloromethane (5 mL) was treated with tert-butyl-4-hydroxy phenyl acetate (Reagent E, 0.05 g, 0.22 mmol) followed by 1-(3-dimethylaminopropyl)-3-ethylcarbodiimide hydrochloride (0.11 g, 0.22 mmol) and 4-dimethylaminopyridine (0.028 g, 0.22 mmol). The resulting solution was stirred at ambient temperature overnight. The reaction mixture was subjected to flash column chromatography over silica gel (230–400 mesh) using 7% ethyl acetate in hexane as the eluent to afford the title compound as a clear oil that solidified on standing (0.048 g, 48%).

$^1$H NMR (300 MHz, CDCl$_3$): δ 7.91 (d, 1H, J=2.1 Hz), 7.41 (d, 1H, J=1.8 Hz), 7.24 (d, 2H, J=8.8 Hz), 7.05 (d, 2H, J=8.5 Hz), 3.46 (s, 2H), 1.97–1.90 (m, 1H), 1.87 (s, 2H), 1.37 (s, 9H), 1.36 (s, 6H), 1.04–0.90 (m, 2H), 0.87–0.75 (m, 2H), 0.65–0.56 (m, 4H).

Spiro[2H-1-benzopyran-2,1'-cyclopropane]-6-carboxylic acid, 8-cyclopropyl-3,4-dihydro-4,4-dimethyl-, 4-(carbonymethyl)phenyl ester (Compound 58, General Formula 1)

A solution of spiro[2H-1-benzopyran-2,1'-cyclopropane]-6-carboxylic acid, 8-cyclopropyl-3,4-dihydro-4,4-dimethyl-, 4-(tert-butoxycarbonylmethyl)phenyl ester (Compound 57, 0.048 g, 0.105 mmol) was treated with 2 mL of trifluoroacetic acid and stirred at ambient temperature for 2 h. The trifluoroacetic acid was distilled off under reduced pressure and the residue was subjected to preparative reverse phase HPLC using 10% water in acetonitrile as the mobile phase to afford the title compound as a white solid (0.029 g, 55%).

$^1$H NMR (300 MHz, CDCl$_3$): δ 7.99 (d, 1H, J=2.2 Hz), 7.48 (d, 1H, J=1.9 Hz), 7.34 (d, 2H, J=8.5 Hz), 7.16 (d, 2H, J=8.5Hz), 3.67 (s, 2H), 2.07–1.97 (m, 1H), 1.95 (s, 2H), 1.44 (s, 6H), 1.09–1.04 (m, 2H), 0.93–0.85 (m, 2H), 0.79–0.64 (m, 4H).

Spiro[2H-1-benzopyran-2,1'-cyclopropane]-6-carboxylic acid, 8-cyclopropyl-3,4-dihydro-4,4-dimethyl-, 3-(tert-butoxycarbonylmethyl)phenyl ester (Compound 59, General Formula 1)

A solution of spiro[2H-1-benzopyran-2,1'-cyclopropane]-6-carboxylic acid, 8-cyclopropyl-3,4-dihydro-4,4-dimethyl- (Intermediate 49, 0.05 g, 0.18 mmol) in anhydrous dichloromethane (5 mL) was treated with tert-butyl-3-hydroxy phenyl acetate (Reagent F, 0.04 g, 0.18 mmol) followed by 1-(3-dimethylaminopropyl)-3-ethylcarbodiimide hydrochloride (0.029 g, 0.1 mmol) and 4-dimethylaminopyridine (0.022 g, 0.18 mmol). The resulting solution was stirred at ambient temperature overnight. The reaction mixture was subjected to flash column chromatography over silica gel (230–400 mesh) using 7% ethyl acetate in hexane as the eluent to afford the title compound as a clear oil that solidified on standing (0.020 g, 23%).

$^1$H NMR (300 MHz, CDCl$_3$): δ 7.98 (d, 1H, J=1.9 Hz), 7.48 (d, 1H, J=2.2 Hz), 7.38 (t, 1H, J=7.7 Hz), 7.19–7.11 (m, 3H), 3.68 (s, 2H), 2.05–1.94 (m, 1H), 1.95 (s, 2H), 1.44 (s, 15H), 1.09–1.04 (m, 2H), 0.96–0.82 (m, 2H), 0.73–0.64 (m, 4H).

Spiro[2H-1-benzopyran-2,1'-cyclopropane]-6-carboxylic acid, 8-cyclopropyl-3,4-dihydro-4,4-dimethyl-3-(carboxymethyl)phenyl ester (Compound 60, General Formula 1)

A solution of spiro[2H-1-benzopyran-2,1'-cyclopropane]-6-carboxylic acid, 8-cyclopropyl-3,4-dihydro-4,4-dimethyl-, 3-(tert-butoxycarbonylmethyl)phenyl ester (Compound 59, 0.020 g, 0.04 mmol) was treated with 2 mL of trifluoroacetic acid and stirred at ambient temperature for 2 h. The trifluoroacetic acid was distilled off under reduced pressure and the residue was subjected to preparative reverse phase HPLC using 10% water in acetonitrile as the mobile phase to afford the title compound as a white solid (0.0125 g, 62%).

$^1$H NMR (300 MHz, CDCl$_3$): δ 7.99 (d, 1H, J=2.1 Hz), 7.49 (d, 1H, J=2.1 Hz), 7.36 (t, 1H, J=7.8 Hz), 7.18–7.08 (m, 3H), 3.56 (s, 2H), 2.06–1.95 (m, 1H), 1.95 (s, 2H), 1.45 (s, 6H), 1.09–1.05 (m, 2H), 0.96–0.84 (m, 2H), 0.74–0.65 (m, 4H).

6-Bromo-4,4-dimethyl-1,2,3,4-tetrahydro-quinoline-1-carbaldehyde (Intermediate 50)

A solution of 6-bromo-4,4-dimethyl-1,2,3,4-tetrahydroquinoline, available in accordance with U.S. Pat. No. 5,089,509, the specification of which is incorporated herein by reference (1.8 g, 7.5 mmol) in 10 mL of formic acid was refluxed for 3 h. The reaction mixture was then cooled to ambient temperature and poured into ice-cold saturated aqueous sodium bicarbonate solution and extracted with diethyl ether (×2). The combined organic phase was dried over anhydrous sodium sulfate, filtered and evaporated in vacuo to a residue which was subjected to flash column chromatography over silica gel (230–400 mesh) using 15–25% ethyl acetate in hexane as the eluent to afford the title compound as a pale yellow solid (1.8 g, 90%).

$^1$H NMR (300 MHz, CDCl$_3$): δ 8.71 (s, 1H), 7.45 (d, 1H, J=2.2 Hz), 7.28 (dd, 1H, J=2.2, 8.5 Hz), 6.98 (d, 1H, J=8.5 Hz), 3.78 (t, 2H, J=6.3 Hz), 1.74 (t, 2H, J=6.3 Hz), 1.28 (s, 6H).

6-Bromo-1-cyclopropyl-4,4-dimethyl-1,2,3,4-tetrahydroquinoline (Intermediate 51)

A stirred, cooled (0° C.) solution of 6-bromo-4,4-dimethyl-1,2,3,4-tetrahydro-quinoline-1-carbaldehyde (Intermediate 50, 21.8, 6.7 mmol) in anhydrous tetrahydrofuran (20 mL) under argon was treated with titanium tetra-iso-propoxide (2.15 mL, 7.39 mmol) followed by 3M solution of ethyl magnesium bromide in diethyl ether (5.6 mL, 16.8 mmol) and the reaction mixture was then heated at 50° C. overnight. It was then cooled in an ice-bath, quenched with saturated aqueous ammonium chloride solution and extracted with diethyl ether (×2). The combined organic phase was dried over anhydrous sodium sulfate, filtered over celite and evaporated in vacuo to residue which was subjected to flash column chromatography over silica gel (230–400 mesh) using 5% ethyl acetate in hexane as the eluent to afford the title compound as an oil (1.2 g, 64%).

$^1$H NMR (300 MHz, CDCl$_3$): δ 7.24 (d, 1H, J=2.5 Hz), 7.12 (dd, 1H, J=2.2, 8.8 Hz), 7.01 (d, 1H, J=8.8 Hz), 3.20 (t, 2H, J=6.0 Hz), 2.27–2.20 (m, 1H), 1.68 (t, 2H, J=5.9 Hz), 1.24 (s, 3H), 1.23 (s, 3H), 0.83–0.77 (m, 2H), 0.60–0.55 (m, 2H).

1-Cyclopropyl-6-trimethylsilanylethynyl-4,4-dimethyl-1,2,3,4-tetrahydro-quinoline (Intermediate 52)

Following general procedure D and using 6-bromo-1-cyclopropyl-4,4-dimethyl-1,2,3,4-tetrahydro quinoline (Intermediate 51, 0.8 g, 2.86 mmol), (trimethylsilyl) acetylene (5 mL, 35 mmol), triethyl amine (10 mL), anhydrous tetrahydrofuran, copper(I)iodide (0.080 g, 0.42 mmol) and dichlorobis(triphenylphosphine)palladium(II) (0.240 g, 0.34 mmol), the title compound was obtained as an oil (0.67 g, 79%).

$^1$H NMR (300 MHz, CDCl$_3$): δ 7.33 (d, 1H, J=1.8 Hz), 7.22 (dd, 1H, J=2.1, 8.5 Hz), 7.06 (d, 1H, J=8.5 Hz), 3.27 (t, 2H, J=5.9 Hz), 2.37–2.31 (m, 1H), 1.70 (t, 2H, J=6.0 Hz), 1.28 (s, 6H), 0.89–0.82 (m, 2H), 0.66–0.60 (m, 2H), 0.28 (s, 9H).

1-Cyclopropyl-6-ethynyl-4,4-dimethyl-1,2,3,4-tetrahydroquinoline: (Intermediate 53)

Following general procedure E and using 1-cyclopropyl-6-trimethylsilanylethynyl-4,4-dimethyl-1,2,3,4-tetrahydroquinoline (Intermediate 52, 0.40 g, 1.34 mmol), methanol and potassium carbonate (0.2 g, 1.47 mmol) followed by flash column chromatography over silica gel (230–400 mesh) using 2% ethyl acetate in hexane as the eluent, the title compound was obtained as an oil (0.17 g, 56%).

$^1$H NMR (300 MHz, CDCl$_3$): δ 7.38 (d, 1H, J=2.1 Hz), 7.27 (dd, 1H, J=2.1, 8.5 Hz), 7.11 (d, 1H, J=8.5 Hz), 3.30 (t, 2H, J=6.0 Hz), 3.02 (s, 1H), 2.40–2.34 (m, 1H), 1.74 (t, 2H, J=6.0 Hz), 1.30 (s, 6H), 0.93–0.85 (m, 2H), 0.70–0.63 (m, 2H).

4-(1-Cyclopropyl-4,4-dimethyl-1,2,3,4-tetrahydro-quinolin-6-yl-ethynyl)-benzoic acid ethyl ester (Compound 61, General Formula 7)

Following general procedure F and using 1-cyclopropyl-6-ethynyl-4,4-dimethyl-1,2,3,4-tetrahydro quinoline (Intermediate 53, 0.11 g, 0.43 mmol), ethyl-4-iodo-benzoate (Reagent A, 0.11 g, 0.9 mmol), triethyl amine (3 mL), tetrahydrofuran(3 mL), copper(I)iodide(0.02 g, 0.1 mmol) and dichlorobis(triphenylphosphine)palladium(II) (0.060 g, 0.085 mmol) followed by flash column chromatography over silica gel (230–400 mesh) using 5–10% ethyl acetate in hexane as the eluent, the title compound was obtained (0.05 g, 31%).

$^1$H NMR (300 MHz, CDCl$_3$): δ 7.99 (d, 2H, J=8.2 Hz), 7.54 (d, 2H, J=8.2 Hz), 7.37 (d, 1H, J=2.1 Hz), 7.26 (dd, 1H, J=2.1, 8.5 Hz), 7.10 (d, 1H, J=8.8 Hz), 4.37 (q, 2H, J=7.1 Hz), 3.28 (t, 2H, J=6.0 Hz), 2.40–2.33 (m, 1H), 1.71 (t, 2H, J=5.8 Hz), 1.40 (t, 3H, J=7.0 Hz), 1.27 (s, 6H), 0.94–0.82 (m, 2H), 0.65–0.60 (m, 2H).

4-(1-Cyclopropyl-4,4-dimethyl-1,2,3,4-tetrahydroquinolin-6-yl-ethynyl)-benzoic acid (Compound 62, General Formula 7)

Following general procedure L and using 4-(1-cyclopropyl-4,4-dimethyl-1,2,3,4-tetrahydro-quinolin-6-ylethynyl)-benzoic acid ethyl ester (Compound 61, 0.05 g, 0.13 mmol), 5 mL of ethanol and 5M sodium hydroxide solution (2 mL) followed by recrystallization from hot ethyl acetate, the title compound was obtained as a solid (0.030 g, 64%).

$^1$H NMR (300 MHz, DMSO-d$_6$): δ 7.92 (d, 2H, J=8.2 Hz), 7.57 (d, 2H, J=8.2 Hz), 7.33 (d, 1H, J=1.9 Hz), 7.23 (dd, 1H, J=1.9, 8.5 Hz), 7.06 (d, 1H, J=8.8 Hz), 3.25 (t, 2H, J=5.8 Hz), 2.41–2.34 (m, 1H), 1.64 (t, 2H, J=5.6 Hz), 1.21 (s, 6H), 0.87–0.81 (m, 2H), 0.59–0.54 (m, 2H).

[4-(1-Cyclopropyl-4,4-dimethyl-1,2,3,4-tetrahydro-quinolin-6-yl-ethynyl)phenyl] acetic acid methyl ester (Compound 63, General Formula 7)

Following general procedure F and using 1-cyclopropyl-6-ethynyl-4,4-dimethyl-1,2,3,4-tetrahydro quinoline (Intermediate 53, 0.05 g, 0.22 mmol), methyl-4-iodo-phenyl acetate (Reagent B, 0.055 g, 0.2 mmol), triethyl amine (5 mL), tetrahydrofuran, copper(I)iodide(0.025 g, 0.13 mmol) and dichlorobis(triphenylphosphine)palladium(II) (0.75 g, 0.11 mmol) followed preparative normal phase HPLC using 10% ethyl acetate in hexane as the mobile phase, the title compound was obtained (0.089 g, 100%).

$^1$H NMR (300 MHz, CDCl$_3$): δ 7.47 (d, 2H, J=8.8 Hz), 7.45 (d, 1H, J=1.8 Hz), 7.35–7.22 (m, 2H), 7.10 (d, 2H, J=8.8 Hz), 3.70 (s, 3H), 3.63 (s, 2H), 3.27 (t, 2H, J=6.0 Hz), 2.37–2.31 (m, 1H), 1.71 (t, 2H, J=6.0 Hz), 1.27 (s, 6H), 0.89–0.81 (m, 2H), 0.65–0.60 (m, 2H).

[4-(1-Cyclopropyl-4,4-dimethyl-1,2,3,4-tetrahydro-quinolin-6-yl-ethynyl)-2-fluoro-phenyl] acetic acid ethyl ester (Compound 64, General Formula 7)

Following general procedure F and using 1-cyclopropyl-6-ethynyl-4,4-dimethyl-1,2,3,4-tetrahydro quinoline (Intermediate 53, 0.11 g, 0.49 mmol), ethyl-2-fluoro-4-iodo-phenyl acetate (Reagent C, 0.11 g, 0.9 mmol), triethyl amine (3 mL), tetrahydrofuran(3 mL), copper(I)iodide(0.06 g, 0.32 mmol) and dichlorobis(triphenylphosphine)palladium(II) (0.25 g, 0.36 mmol) followed by flash column chromatography over silica gel (230–400 mesh) using 10% ethyl acetate in hexane as the eluent, the title compound was obtained (0.1 g, 51%).

$^1$H NMR (300 MHz, CDCl$_3$): δ 7.34 (d, 1H, J=2.1 Hz), 7.25–7.17 (m, 3H), 7.09 (d, 2H, J=8.8 Hz), 4.17 (q, 2H, J=7.1 Hz), 3.65 (s, 2H), 3.27 (t, 2H, J=6.0 Hz), 2.38–2.31 (m, 1H), 1.69 (t, 2H, J=6.0 Hz), 1.27 (s, 6H), 1.25 (t, 3H, J=7.1 Hz), 0.88–0.81 (m, 2H), 0.65–0.59 (m, 2H).

N-(4-Bromophenyl)-N-methyl-3-methyl-2-butenamide (Intermediate 54)

3,3-Dimethylacryloyl chloride (3 mL, 27 mmol) was added to a solution of 4-bromo-N-methyl-aniline (4.55 g, 25 mmol) in 150 mL of dichloromethane followed after 5 minutes by triethyl amine (5 mL, 33 mmol). After 2.5 h at ambient temperature, the reaction mixture was washed with water and the organic phase was dried over anhydrous sodium sulfate and evaporated in vacuo to afford the title product as a brown oil in quantitative yield.

$^1$H-NMR (300 MHz, CDCl$_3$): d 1.71 (s, 3H), 2.1 1(s, 3H), 3.28(s, 3H), 5.47(s, 1H), 7.05(d, J=8.5 Hz, 2H), 7.50(d, J=8.2 Hz, 2H).

6-Bromo-1,4,4-trimethyl-2-oxo-1,2,3,4-tetrahydroquinoline (Intermediate 55)

N-(4-bromophenyl)-N-methyl-3-methyl-2-butenamide (Intermediate 54, 6.42 g, 24 mmol) was heated to 130° C. and aluminum chloride (5 g, 37.4 mmol) was added in portions over 0.5 h. The reaction mixture was stirred for 1 hour at the same temperature and then cooled to room temperature. Ice was added cautiously to the solid, followed by ~200 mL of iced water. The reaction mixture was then extracted with ether (×2) and dichloromethane (×1) and the combined organic phase was dried over anhydrous magnesium sulfate and evaporated in vacuo to yield a brown solid. The solid was treated with hexane-dichloromethane and filtered to afford 1.7 g of product. The mother liquor was evaporated and purified by flash column chromatography on silica gel (230–400 mesh) to afford 2.9 g of the title compound as a solid (total 72%).

$^1$H-NMR (300 MHz, CDCl$_3$): δ 1.29(s, 6H), 2.49(s, 2H), 3.36(s, 3H), 6.87(d, J=8.2 Hz, 1H), 7.36(dd, J=2.0, 8.5 Hz, 1H), 7.39(d, J=2.0 Hz, 1H).

6-Bromo-1,4,4-trimethylspiro[2H-1-1,2,3,4-tetrahydroquinoline-2,1'-cyclopropane] (Intermediate 56)

A stirred, cooled (−78° C.) 3M solution of ethyl magnesium bromide in ether (8.1 mL, 24.25 mmol) under argon was treated with anhydrous tetrahydrofuran (20 mL) followed by a solution of titanium tetra-iso-propoxide (3.15 mL, 10.2 mmol) in tetrahydrofuran (10 mL). A solution of 6-bromo-1,4,4-trimethyl-2-oxo-1,2,3,4-tetrahydroquinoline (Intermediate 55, 2.6 g, 9.7 mmol) was cannulated into the reaction mixture and the solution was allowed to warm to room temperature overnight. It was then cooled in an ice-bath, quenched with saturated aqueous ammonium chloride solution, filtered over celite and the aqueous phase was extracted with diethyl ether (×2). The combined organic phase was dried over anhydrous magnesium sulfate, filtered and evaporated in vacuo to afford an orange oil. Flash column chromatography over silica gel (230–400 mesh) using 2–4% ethyl acetate in hexane as the eluent afforded the title compound as an oil which was ~70% pure (1.7 g, 63%) and 0.5 g of recovered starting material.

$^1$H-NMR (300 MHz, CDCl$_3$): δ 0.58(t, J=6.0 Hz, 2H), 0.91(t, J=6.0 Hz, 2H), 1.35 (s, 6H), 1.70(s, 2H), 2.68 (s, 3H), 6.59 (d, J=8.8 Hz, 1H), 7.16(dd, J=2.3, 8.8 Hz, 1H), 7.33(d, J=2.3 Hz, 1H).

1,4,4-Trimethyl-6-(trimethylsilanyl)ethynylspiro [2H-1-1,2,3,4-tetrahydroquinoline-2,1'-cyclopropane] (Intermediate 57)

Following general procedure D and using 6-bromo-1,4,4-trimethylspiro[2H-1-1,2,3,4-tetrahydroquinoline-2,1'-cyclopropane] (Intermediate 56, 0.56 g, 2 mmol), (trimethylsilyl)acetylene (1.13 mL, 8 mmol), triethylamine (4 mL), anhydrous tetrahydrofuran (5 mL), copper(I)iodide (0.08 g, 0.4 mmol) and dichlorobis(triphenylphosphine) palladium(II) (0.28 g, 0.4 mmol), followed by flash column chromatography over silica gel (230–400 mesh) using hexane-2% ethyl acetate in hexane as the eluent, the title compound was obtained as an oil (0.42 g, 70%).

$^1$H NMR (300 MHz, CDCl$_3$): δ 0.023(s, 9H), 0.33(t, J=6.1 Hz, 2H), 0.71(t, J=6.1Hz, 2H), 1.10(s, 6H), 1.45(s, 2H), 2.41 (s, 3H), 6.31(d, J=8.5 Hz, 1H), 6.96 (dd, J=2.1, 8.5 Hz, 1H), 7.10(d, J=2.1 Hz, 1H).

Benzoic acid, 4-[(1,4,4-trimethylspiro[2H-1-1,2,3,4-tetrahydroquinoline-2,1'-cyclopropane]-6-yl) ethynyl]-ethyl ester (Compound 65, General Formula 1)

Following general procedure E and using a solution of 1,4,4-trimethyl-6-(trimethylsilanyl)ethynylspiro[2H-1-1,2,3,4-tetrahydroquinoline-2,1'-cyclopropane] (Intermediate 57, 0.416 g, 1.4 mmol), methanol (10 mL), ethyl acetate (2 mL) and potassium carbonate (1.08 g, mmol) a silyl deprotected acetylenic intermediate was obtained which was used directly for the next step (0.25 g, 79%). Following general procedure F and using part of the acetylenic intermediate obtained as above (0.11 g, 0.5 mmol), ethyl-4-iodo benzoate (Reagent A, 0.112 g, 0.4 mmol), triethylamine (1 mL), tetrahydrofuran (2.5 mL), copper(I)iodide (0.050 g, 0.26 mmol) and tetrakis(triphenylphosphine)palladium(0)(0.096 g, 0.17 mmol) followed by flash column chromatography over silica gel (230–400 mesh) using 8% ethyl acetate in hexane as the eluent and preparative HPLC on Partisil 10 silica column using 10% ethyl acetate in hexane as the mobile phase, the title compound was obtained as a yellow oil (0.048 g, 26%).

$^1$H-NMR (300 MHz, CDCl$_3$): δ 0.60 (t, J=6.1 Hz, 2H), 0.99(t, J=6.1 Hz, 2H), 1.37(s, 6H), 1.42(t, J=7.0 Hz, 3H), 1.73(s, 2H), 2.68(s, 3H), 4.40 (q, J=7.0 Hz, 2H), 6.61(d, J=8.8 Hz, 1H), 7.28 (dd, J=2.1, 8.5 Hz, 1H), 7.42 (d, J=2.1 Hz, 1H), 7.57(d, J=8.2 Hz, 2H), 8.01(d, J=8.2 Hz, 2H).

Benzoic acid, 4-[(1,4,4-trimethylspiro[2H-1-1,2,3,4-tetrahydroquinoline-2,1'-cyclopropane]-6-yl) ethynyl]- (Compound 66, General Formula 1)

Following general procedure I and using benzoic acid, 4-[(1,4,4-trimethylspiro[2H-1-1,2,3,4-tetrahydroqunoline-2,1'-cyclopropane]-6-yl)ethynyl]-ethyl ester (Compound 65, 0.03 g, 0.08 mmol), ethanol (2 mL), tetrahydrofuran (2 mL) and 1M aqueous sodium hydroxide solution (1 mL), the title compound was obtained as a yellow solid (0.020 g, 67%).

$^1$H-NMR (300 MHz, CD$_3$COCD$_3$): δ 0.60 (t, J=5.8 Hz, 2H), 1.03(t, J=5.8 Hz, 2H), 1.34(s, 6H), 1.74(s, 2H), 2.69(s, 3H), 6.60(d, J=8.5 Hz, 1H), 7.23 (dd, J=2.0, 8.4 Hz, 1H), 7.39 (d, J=2.0 Hz, 1H), 7.58(d, J=8.2 Hz, 2H), 8.01(d, J=8.2 Hz, 2H).

Esterification Methods
Method A

The carboxylic acid was combined with a solution of the desired alcohol and concentrated sulfuric acid (20 to 1 v/v) and the resulting mixture or solution (0.75 to 1.0 M) heated to reflux overnight. The solution was cooled to room temperature, diluted with Et$_2$O, and washed with H$_2$O, saturated aqueous NaHCO$_3$, and saturated aqueous NaCl before being dried over MgSO$_4$. Concentration of the dry solution under reduced pressure afforded the desired carboxylic ester of sufficient purity to be used directly in the next reaction.

Method B

To a solution (0.67 to 1.0 M) of the carboxylic acid in acetone was added 1.1 equivalents of the desired alkyl halide and 1.0 equivalents of solid potassium carbonate. The resulting mixture was heated to reflux for 2 h and then allowed to stir at room temperature overnight. The mixture was filtered and the filtrate concentrated under reduced pressure. The product was isolated from the residue by column chromatography using silica gel as the solid phase.

Method C

A solution (1M) of the carboxylic acid in thionyl chloride was heated at reflux until analysis of a reaction aliquot by IR spectroscopy showed the absence of the aryl carboxylic acid carbonyl band (1705–1680 cm$^{-1}$). The solution was cooled to room temperature and concentrated under reduced pressure to give the crude acyl chloride.

The acyl chloride was dissolved in $CH_2Cl_2$ and the resulting solution (0.5 to 0.75M) treated with 1.1 equivalents the desired alcohol and 2.0 equivalents of pyridine. After stirring overnight at room temperature the solution was diluted with $Et_2O$ and washed with $H_2O$, 10% aqueous HCl, saturated aqueous $NaHCO_3$, and saturated aqueous NaCl before being dried over $Na_2SO_4$. Concentration of the dry solution under reduced pressure followed by column chromatography afforded the desired ester.

General Procedure 1 (Preparation of Enol Ethers)

A solution (0.35 M) of the aryl ester in anhydrous THF was cooled to 0° C. and treated with 1.0 equivalents of Tebbe's Reagent ([$\mu$-chloro-$\mu$-methylene[bis (cyclopentadienyl)titanium]-dimethylaluminum] 0.5 M in toluene). After 30 minutes the solution was warmed to room temperature and stirred for 30 minutes before being carefully added to a 0.1 N NaOH solution at 0° C. This mixture was treated with hexanes and the solids removed by filtration through a pad of Celite. The solids were washed with hexanes and the filtrate passed through a second pad of Celite to remove any newly formed solids. The organic layer was dried ($Na_2SO_4$) and concentrated under reduced pressure. The desired enol ether was isolated from the residue by column chromatography using 1–2% of $Et_3N$ added to the eluant. (note: prolonged exposure of the product to the column can result in hydrolysis and formation of the corresponding methyl ketone.)

General Procedure 2 (Cyclopropanation of the Enol Ethers)

To a solution (0.3 M) of the enol ether in anhydrous $Et_2O$ was added 2.0 equivalent of $Et_2Zn$ (as a solution in hexanes) and 2.0 equivalents of $CH_2I_2$. The resulting solution was heated to reflux until analysis of a reaction aliquot (by TLC or $^1$H NMR) indicated that all of the starting enol ether had been consumed. (note: Additional equal amounts of $Et_2Zn$ and $CH_2I_2$ can be added to drive the reaction to completion.) Upon cooling to room temperature the reaction was carefully quenched by the addition of saturated aqueous $NH_4Cl$. The resulting mixture is extracted with $Et_2O$ and the combined organic layers washed with $H_2O$ and saturated aqueous NaCl before being dried over $Na_2SO_4$ and concentrated under reduced pressure. The product is isolated from the residue by column chromatography.

1-Bromo-4-(1-methoxyvinyl)-benzene: (Intermediate 58)

Using General Procedure 1; methyl 4-bromo-benzoate (600.0 mg, 2.78 mmols), and 5.6 mL of Tebbe's Reagent (794.0 mg, 2.78 mmols) afforded 420.0 mg (70%) of the title compound as a colorless oil after column chromatography (100% hexanes).

$^1$H NMR (CDCl$_3$) δ: 7.48–7.45 (4H, m), 4.64 (1H, d, J=2.9 Hz), 4.23 (1H, d, J=2.9 Hz), 3.73 (3H, s).

1-Bromo-4-(1-methoxycyclopropyl)-benzene (Intermediate 59)

Using General Procedure 2; 1-bromo-4-(1-methoxyvinyl)-benzene (Intermediate 58, 410. 0 mg, 1.92 mmols), $Et_2Zn$ (711.3 mg, 5.76 mmols), and $CH_2I_2$ (1.54 g, 5.76 mmols) in 4.0 mL $Et_2O$ afforded 300.0 mg (69%) of the title compound as a colorless oil after chromatography (0–3% EtOAc-hexanes).

$^1$H NMR (CDCl$_3$) δ: 7.46 (2H, d, J=8.5 Hz), 7.18 (2H, d, J=8.5 Hz), 3.21 (3H, s), 1.19 (2H, m), 0.94 (2H, m).

[4-(1-Methoxycyclopropyl)-phenylethynyl]-trimethylsilane (Intermediate 60)

Using General Procedure D; 1-bromo-4-(1-methoxycyclopropyl)-benzene (Intermediate 59, 300.0 mg, 1.32 mmol) in triethylamine (4 mL) and anhydrous tetrahydrofuiran (4 mL) was treated with copper(I)iodide (93.0 mg, 0.13 mmol) and then sparged with argon for 5 minutes. Trimethylsilyl acetylene (1.39 g, 14.2 mmols) was then added followed by dichlorobis(triphenylphosphine) palladium(II) (93.0 mg, 0.13 mmol). The resulting reaction mixture was heated to 70° C. for 60 h. The title compound (286.0 mg, 90%) was isolated by chromatography (0–3% EtOAc-hexanes).

$^1$H NMR (CDCl$_3$) δ: 7.35 (2H, d, J=7.2 Hz), 7.14 (2H, d, J=7.2 Hz), 3.14 (3H, s), 1.14 (2H, m), 0.88 (2H, m), 0.17 (9H, s).

1-Ethynyl-4-(1-methoxycyclopropyl)-benzene (Intermediate 61)

Using General Procedure E; [4-(1-methoxycyclopropyl) phenylethynyl]-trimethylsilane (Intermediate 60, 285.0 mg, 1.18 mmols) in methanol (10 mL) was treated with potassium carbonate (100.0 mg, 0.72 mmol) and stirred overnight at ambient temperature. The crude alkyne (220 mg, 100%) was used directly in the next reaction.

$^1$H NMR (CDCl$_3$) δ: 7.46 (2H, d, J=8.2 Hz), 7.24 (2H, d, J=8.2 Hz), 3.23 (3H, s), 3.06 (1H, s), 1.22 (2H, m), 0.98 (2H, m).

Ethyl 4-[4-(1-methoxycyclopropyl)-phenylethynyl]-benzoate (Compound 67, General Formula 2)

Using General Procedure F; 1-ethynyl-4-(1-methoxycyclopropyl)-benzene (Intermediate 61, 100.0 mg, 0.47 mmol) and ethyl-4-iodo benzoate (Reagent A, 141.0 mg, 0.51 mmol) in triethyl amine (6 mL) was treated with copper(I)iodide (30.0 mg, 0.16 mmol) and sparged with argon for 5 minutes. Dichlorobis(triphenylphosphine) palladium(II) (109 mg, 0.16 mmol) was added and the reaction mixture was stirred overnight at room temperature. Column chromatography (2–5% EtOAc-hexanes) afforded 135.0 mg (90%) of the title compound as an orange solid.

$^1$H NMR (CDCl$_3$) δ: 8.02 (2H, d, J=8.2 Hz), 7.58 (2H, d, J=8.8 Hz), 7.52 (2H, d, J=8.2 Hz), 7.28 (2H, d, J=8.8 Hz), 4.39 (2H, q, J=7.1 Hz), 3.25 (3H, s), 1.40 (3H, t, J=7.1 Hz), 1.23 (2H, m), 1.00 (2H, m).

Methyl {4-[4-(1-methoxycyclopropyl)-phenylethynyl]-phenyl}-acetate (Compound 68, General Formula 2)

Using General Procedure F; 1-ethynyl-4-(1-methoxycyclopropyl)-benzene (Intermediate 61, 120.0 mg, 0.56 mmol) and methyl-(4-iodophenyl)acetate (Reagent B, 154.0 mg, 0.56 mmol) in triethyl amine (6 mL) was treated with copper(I)iodide (35.0 mg, 0.19 mmol) and sparged with argon for 5 minutes. Dichlorobis(triphenylphosphine) palladium(II) (130 mg, 0.19 mmol) was added and the reaction mixture was stirred overnight at room temperature. Column chromatography (2–8% EtOAc-hexanes) afforded 140.0 mg (78%) of the title compound as an orange solid.

¹H NMR (CDCl₃) δ: 7.50 (4H, d, J=8.1 Hz), 7.28 (4H, d, J=8.1 Hz), 3.76 (3H, s), 3.64 (2H, s), 3.25 (3H, s), 1.22 (2H, m), 0.99 (2H, m).

4-[4-(1-Methoxycyclopropyl)-phenylethynyl]-benzoic acid (Compound 69, General Formula 2)

Using General Procedure I; a solution of ethyl 4-[4-(1-methoxycyclopropyl)-phenylethynyl]-benzoate (Compound 67, 110.0 mg, 0.34 mmol) in ethanol (3 mL) and tetrahydrofuran (3 mL) was treated with NaOH (160.0 mg, 4.0 mmols, 2.0 mL of a 2N aqueous solution) and stirred overnight at room temperature. Work-up afforded 85.0 mg (86%) of the title compound as an orange solid.

¹H NMR (CDCl₃) δ: 8.05 (2H), 7.66 (2H), 7.56 (2H, d, J=8.5 Hz), 7.35 (2H, d, J=8.6 Hz), 3.22 (3H, s), 1.21 (2H, m), 1.01 (2H, m).

{4-[4-(1-Methoxacyclopropyl)-phenylethynyl]-phenyl}-acetic acid (Compound 70, General Formula 2)

Using General Procedure I; a solution of methyl {4-[4-(1-methoxycyclopropyl)-phenylethynyl]-phenyl}-acetate (Compound 68, 100.0 mg, 0.31 mmol) in ethanol (3 mL) and tetrahydrofuran (3 mL) was treated with NaOH (160.0 mg, 4.0 mmols, 2.0 mL of a 2N aqueous solution) and stirred overnight at room temperature. Work-up afforded 80.0 mg (84%) of the title compound as an orange solid.

¹H NMR (CDCl₃) δ: 7.49 (4H), 7.27 (4H), 3.66 (2H, s), 3.25 (3H, s), 1.22 (2H, m), 0.99 (2H, m).

Isopropyl 4-bromobenzoate (Intermediate 62)

Using General Esterification Procedure A; 4-bromobenzoic acid (1.50 g, 7.46 mmols) was combined with isopropyl alcohol to give 1.76 g (97%) of the title compound as a colorless oil.

¹H NMR (CDCl₃) δ: 7.90 (2H, d, J=8.5 Hz), 7.57 (2H, d, J=8.5 Hz), 5.24 (1H, septet, J=6.2 Hz), 1.37 (6H, d, J=6.2 Hz).

1-Bromo-4-(1-isopropoxyvinyl)-benzene (Intermediate 63)

Using General Procedure 1; isopropyl 4-bromobenzoate (Intermediate 62, 780.0 mg, 3.20 mmols) and 6.4 mL of Tebbe's Reagent (910.7 mg, 3.20 mmols) afforded 328.0 mg (43%) of the title compound as a colorless oil after column chromatography (100% hexanes).

¹H NMR (CDCl₃) δ: 7.46 (4H, m), 4.66 (1H, d, J=2.6 Hz), 4.40 (1H, septet, J=6.2 Hz), 4.21 (1H, d, J=2.6 Hz), 1.34 (6H, d, J=6.2 Hz).

1-Bromo-4-(1-isopropoxycyclopropyl)-benzene (Intermediate 64)

Using General Procedure 2; 1-bromo-4-(1-isopropoxyvinyl)-benzene (Intermediate 63, 328.0 mg, 1.36 mmols), Et₂Zn (335.9 mg, 2.72 mmols), and CH₂I₂ (728.0 mg, 2.72 mmols) in 4.0 mL Et₂O afforded 240.0 mg (70%) of the title compound as a colorless oil after chromatography (3% EtOAc-hexanes).

¹H NMR (CDCl₃) δ: 7.43 (2H, d, J=8.5 Hz), 7.27 (2H, d, J=8.5 Hz), 3.70 (1H, septet, J=6.2 Hz), 1.18 (2H, m), 1.06 (6H, d, J=6.2 Hz), 0.91 (2H, m).

[4-(1-Isopropoxycyclopropyl)-phenylethynyl]-trimethylsilane (Intermediate 65)

Using General Procedure D; 1-bromo-4-(1-isopropoxycyclopropyl)-benzene (Intermediate 64, 240.0 mg, 0.94 mmol) in triethylamine (8 mL) was treated with copper(I)iodide (18.0 mg, 0.094 mmol) and then sparged with argon for 5 minutes. Trimethylsilyl acetylene (0.70 g, 7.1 mmols) was then added followed by dichlorobis-(triphenylphosphine)palladium(II) (66.0 mg, 0.094 mmol). The resulting reaction mixture was heated to 70° C. for 5 days. The title compound (250.0 mg, 98%) was isolated by chromatography (0–3% EtOAc-hexanes) as an orange oil.

1H NMR (CDCl₃) δ: 7.41 (2H, d, J=7.9 Hz), 7.31 (2H, d, J=7.9 Hz), 3.70 (1H, septet, J=6.2 Hz), 1.18 (2H, m), 1.05 (6H, d, J=6.2 Hz), 0.93 (2H, m), 0.94 (9H, s).

1-Ethynyl-4-(1-isopropoxycyclopropyl)-benzene (Intermediate 66)

Using General Procedure E; [4-(1-isopropoxycyclopropyl)phenylethynyl]-trimethylsilane (Intermediate 65, 260.0 mg, 0.96 mmol) in methanol (10 mL) was treated with potassium carbonate (100.0 mg, 0.72 mmol) and stirred overnight at ambient temperature. The crude alkyne (220 mg, 100%) was used directly in the next reaction.

¹H NMR (CDCl₃) δ: 7.45 (2H, d, J=8.8 Hz), 7.35 (2H, d, J=8.8 Hz), 3.72 (1H, septet, J=6.2 Hz), 3.06 (1H, s), 1.20 (2H, m), 1.07 (6H, d, J=6.2 Hz), 0.95 (2H, m).

Ethyl 4-[4-(1-isopropoxacyclopropyl)-phenylethynyl]-benzoate (Compound 71, General Formula 2)

Using General Procedure F; 1-ethynyl-4-(1-isopropoxycyclopropyl)-benzene (Intermediate 66, 114.0 mg, 0.57 mmol) and ethyl-4-iodo benzoate (Reagent A, 731.0 mg, 0.63 mmol) in triethylamine (8 mL) was treated with copper(I)iodide (36.0 mg, 0.19 mmol) and sparged with argon for 5 minutes. Dichlorobis(triphenylphosphine) palladium(II) (133 mg, 0.19 mmol) was added and the reaction mixture was stirred overnight at room temperature. Column chromatography (2–4% EtOAc-hexanes) afforded 151.0 mg (76%) of the title compound as an orange solid.

¹H NMR (CDCl₃) δ: 8.02 (2H, d, J=7.6 Hz), 7.58 (2H, d, J=7.6 Hz), 7.50 (2H, d, J=7.8 Hz), 7.39 (2H, d, J=7.8 Hz), 4.39 (2H, q, J=7.1 Hz), 3.74 (1H, septet, J=6.2 Hz), 1.40 (3H, t, J=7.1 Hz), 1.22 (2H, m), 1.08 (6H, d, J=6.2 Hz), 0.97 (2H, m).

Methyl {4-[4-(1-isopropoxycyclopropyl)-phenylethynyl]-phenyl}-acetate (Compound 72, General Formula 2)

Using General Procedure F; 1-ethynyl-4-(1-isopropoxycyclopropyl)-benzene (Intermediate 66, 95.0 mg, 0.45 mmol) and methyl-(4-iodophenyl)acetate (Reagent B, 131.0 mg, 0.45 mmol) in triethylamine (6 mL) was treated with copper(I)iodide (30.0 mg, 0.16 mmol) and sparged with argon for 5 minutes. Dichlorobis(triphenylphosphine) palladium(II) (111 mg, 0.16 mmol) was added and the reaction mixture was stirred overnight at room temperature. Column chromatography (2–8% EtOAc-hexanes) afforded 110.0 mg (70%) of the title compound as an orange oil.

¹H NMR (CDCl₃) δ: 7.20 (4H), 7.08 (2H, d, J=7.0 Hz), 6.97 (2H, d, J=7.9 Hz), 3.45 (1H, septet, J=6.2 Hz), 3.41 (3H, s), 3.35 (2H, s), 0.91 (2H, m), 0.79 (6H, d, J=6.2 Hz), 0.68 (2H, m).

4-[4-(1-Isopropoxycyclopropyl)-phenylethynyl]-benzoic acid (Compound 73, General Formula 2)

Using General Procedure I; a solution of ethyl 4-[4-(1-isopropoxycyclopropyl)-phenylethynyl]-benzoate (Compound 71, 110.0 mg, 0.32 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up afforded 89.0 mg (88%) of the title compound as a yellow solid.

$^1$H NMR (CDCl$_3$) δ: 8.06 (2H, d, J=8.2 Hz), 7.66 (2H, d, J=8.2 Hz), 7.55 (2H, d, J=8.2 Hz), 7.46 (2H, d, J=8.2 Hz), 3.73 (1H, septet, J=6.2 Hz), 1.18 (2H, m), 1.04 (6H, d, J=6.2 Hz), 0.99 (2H, m).

{4-[4-(1-Isopropoxycyclopropyl)-phenylethynyl]-phenyl}-acetic acid (Compound 74, General Formula 2)

Using General Procedure I; a solution of methyl {4-[4-(1-isopropoxycyclopropyl)-phenylethynyl]-phenyl}-acetate (Compound 72, 80.0 mg, 0.23 mmol) in ethanol (3 mL) and tetrahydrofuran (3 mL) was treated with NaOH (80.0 mg, 2.0 mmols, 2.0 mL of a 1N aqueous solution) and stirred overnight at room temperature. Work-up afforded 48.0 mg (56%) of the title compound as a solid.

$^1$H NMR (CDCl$_3$) δ: 7.20 (2H, d, J=8.2 Hz), 7.19 (2H, d, J=8.8 Hz), 7.09 (2H, d, J=8.8 Hz), 6.98 (2H, d, J=8.2 Hz), 3.46 (1H, septet, J=6.2 Hz), 3.37 (2H, s), 0.92 (2H, m), 0.79 (6H, d, J=6.2 Hz), 0.67 (2H, m).

Benzyl 4-bromobenzoate (Intermediate 67)

Using General Esterification Method B; 4-bromobenzoic acid (2.01 g, 10.0 mmols), benzyl bromide (1.89 g, 11.1 mmols), and K$_2$CO$_3$ (1.40 g, 10.0 mmols) afforded 2.33 g (80%) of the title compound as a colorless solid after column chromatography (3–10% EtOAc-hexanes).

$^1$H NMR (CDCl$_3$) δ: 7.89 (2H, d, J=8.5 Hz), 7.52 (2H, d, J=8.5 Hz), 7.43–7.31 (5H), 5.33 (2H, s).

1-Bromo-4-(1-benzyloxyvinyl)-benzene (Intermediate 68)

Using General Procedure 1; benzyl 4-bromobenzoate (Intermediate 67, 920.0 mg, 3.16 mmols) and 6.3 mL of Tebbe's Reagent (897.0 mg, 3.16 mmols) afforded 640.0 mg (70%) of the title compound after column chromatography (100% hexanes).

$^1$H NMR (CDCl$_3$) δ: 7.55–7.35 (9H), 4.95 (2H, s), 4.73 (1H, d, J=2.9 Hz), 4.34 (1H, d, J=2.9 Hz).

1-Bromo-4-(1-benzyloxycyclopropyl)-benzene (Intermediate 69)

Using General Procedure 2; 1-bromo-4-(1-benzyloxyvinyl)-benzene (Intermediate 68, 280. 0 mg, 0.97 mmol), Et$_2$Zn (247.0 mg, 2.0 mmols), and CH$_2$I$_2$ (536.0 mg, 2.0 mmols) in 2.0 mL Et$_2$O afforded 159.0 mg (53%) of the title compound as a colorless solid after chromatography (2–5% EtOAc-hexanes).

$^1$H NMR (CDCl$_3$) δ: 7.49–7.24 (9H), 4.41 (2H, s), 1.29 (2H, m), 1.00 (2H, m).

[4-(1-Benzyloxycyclopropyl)-phenylethynyl]-trimethylsilane (Intermediate 70)

Using General Procedure D; 1-bromo-4-(1-benzyloxycyclopropyl)-benzene (Intermediate 69, 160.0 mg, 0.53 mmol) in triethylamine (5 mL) was treated with copper(I)iodide (10.0 mg, 0.05 mmol) and then sparged with argon for 5 minutes. Trimethylsilylacetylene (0.70 g, 7.1 mmols) was then added followed by dichlorobis-(triphenylphosphine)palladium(II) (37.0 mg, 0.05 mmol). The resulting reaction mixture was heated to 70° C. for 5d. The title compound (150.0 mg, 83%) was isolated by chromatography (0–3% EtOAc-hexanes) as a pale-yellow oil.

$^1$H NMR (CDCl$_3$) δ: 7.21 (3H, m), 7.09–7.01 (6H, m), 4.18 (2H, s), 1.07 (2H, m), 0.79 (2H, m), 0.02 (9H, s).

1-Ethynyl-4-(1-benzyloxycyclopropyl)-benzene (Intermediate 71)

Using General Procedure E; [4-(1-benzyloxycyclopropyl)-phenylethynyl]-trimethylsilane (Intermediate 70, 150.0 mg, 0.47 mmols) in methanol (6 mL) was treated with potassium carbonate (100.0 mg, 0.72 mmol) and stirred overnight at ambient temperature. The crude alkyne (115 mg, 100%) was used directly in the next reaction.

$^1$H NMR (CDCl$_3$) δ: 7.67–7.50 (2H, d, J=8.2 Hz), 7.34–7.26 (7H, m), 4.43 (2H, s), 3.07 (1H, s), 1.32 (2H, m), 1.04 (2H, m).

Ethyl 4-[4-(1-benzyloxycyclopropyl)-phenylethynyl]-benzoate (Compound 75, General Formula 2)

Using General Procedure F; 1-ethynyl-4-(1-benzyloxycyclopropyl)-benzene (Intermediate 71, 60.0 mg, 0.24 mmol) and ethyl-4-iodo benzoate (Reagent A, 72.0 mg, 0.26 mmol) in triethylamine (4 mL) was treated with copper (I)iodide (17.0 mg, 0.09 mmol) and sparged with argon for 5 minutes. Dichlorobis(triphenylphosphine)palladium(II) (61 mg, 0.09 mmol) was added and the reaction mixture was stirred overnight at room temperature. Column chromatography (2–4% EtOAc-hexanes) afforded 85.0 mg (91%) of the title compound as an orange oil.

$^1$H NMR (CDCl$_3$) δ: 8.03 (2H, d, J=8.2 Hz), 7.62–7.54 (4H, m), 7.39–7.26 (7H, m), 4.47 (2H, s), 4.40 (2H, q, J=7.1 Hz), 1.42 (3H, t, J=7.1 Hz), 1.36 (2H, m), 1.07 (2H, m).

Methyl {4-[4-(1-benzyloxycyclopropyl)-phenylethynyl]-phenyl}-acetate (Compound 76, General Formula 2)

Using General Procedure F; 1-ethynyl-4-(1-benzyloxycyclopropyl)-benzene (Intermediate 71, 60.0 mg, 0.20 mmol) and methyl-(4-iodophenyl)-acetate (Reagent B, 66.0 mg, 0.24 mmol) in triethylamine (5 mL) was treated with copper(I)iodide (15.0 mg, 0.08 mmol) and sparged with argon for 5 minutes. Dichlorobis(triphenylphosphine) palladium(II) (56 mg, 0.08 mmol) was added and the reaction mixture was stirred overnight at room temperature. Column chromatography (2–7% EtOAc-hexanes) afforded 64.0 mg (81%) of the title compound as a yellow oil.

$^1$H NMR (CDCl$_3$) δ: 7.52–7.47 (4H, m), 7.37–7.25 (9H, m), 4.44 (2H, s), 3.70 (3H, s), 3.64 (2H, s), 1.32 (2H, m), 1.06 (2H, m).

4-[4-(1-Benzyloxycyclopropyl)-phenylethynyl]-benzoic acid (Compound 77, General Formula 2)

Using General Procedure I; a solution of ethyl 4-[4-(1-benzyloxycyclopropyl)-phenylethynyl]-benzoate (Compound 75, 78.0 mg, 0.20 mmol) in ethanol (3 mL) and tetrahydrofiran (3 mL) was treated with NaOH (80.0 mg, 2.0 mmols, 2.0 mL of a 1N aqueous solution) and stirred overnight at room temperature. Work-up afforded 65.0 mg (89%) of the title compound as a solid.

$^1$H NMR (CDCl$_3$) δ: 7.97 (2H, d, J=8.5 Hz), 7.67 (2H, d, J=8.7 Hz), 7.58 (2H, d, J=8.5 Hz), 7.41–7.28 (7H, m), 4.44 (2H, s), 1.33 (2H, m), 1.12 (2H, m).

{4-[4-(1-Benzyloxycyclopropyl)-phenylethnyl]-phenyl}-acetic acid (Compound 78, General Formula 2)

Using General Procedure I; a solution of methyl {4-[4-(1-benzyloxycyclopropyl)-phenylethynyl]-phenyl}-acetate (Compound 76,45.0 mg, 0.11 mmol) in ethanol (3 mL) and tetrahydrofuran (3 mL) was treated with NaOH (80.0 mg, 2.0 mmols, 2.0 mL of a 1N aqueous solution) and stirred overnight at room temperature. Work-up afforded 35.0 mg (81%) of the title compound as a pale-yellow solid.

$^1$H NMR (CDCl$_3$) δ: 7.49 (4H, m), 7.37–7.25 (9H, m), 4.44 (2H, s), 3.66 (2H, s), 1.32 (2H, m), 1.05 (2H, m).

Benzyl 4-bromo-2-methylbenzoate (Intermediate 72)

Using General Esterification Method C; 2-methyl-4-bromo-benzoic acid (2.15 g, 10.0 mmols) was refluxed for 3 h with 10 mL SOCl$_2$. The resulting solution concentrated under reduced pressure and the crude acyl chloride was combined with benzyl alcohol (1.08 g, 10.0 mmols) and pyridine (1.6 mL, 20.0 mmols) to give the title compound (2.4 g, 80%) after work-up and column chromatography (2–5% EtOAc-hexanes) as a colorless oil.

$^1$H NMR (CDCl$_3$) δ: 7.81 (1H, d, J=8.5 Hz), 7.41–7.33 (7H, m), 5.32 (2H, s), 2.57 (3H, s).

4-Bromo-1-(1-benzyloxyvinyl)-2-methylbenzene (Intermediate 73)

Using General Procedure 1; benzyl 4-bromo-2-methylbenzoate (Intermediate 72, 840.0 mg, 2.77 mmols) and 5.4 mL of Tebbe's Reagent (788.0 mg, 2.77 mmols) afforded 640.0 mg (76%) of the title compound after column chromatography (100% hexanes).

$^1$H NMR (CDCl$_3$) δ: 7.38–7.19 (8H, m), 4.88 (2H, s), 4.45 (1H, d, J=2.6 Hz), 4.25 (2H, d, J=2.6 Hz), 2.35 (3H, s).

4-Bromo-1-(1-benzyloxycyclopropyl)-2-methyl-benzene (Intermediate 74)

Using General Procedure 2; 4-bromo-1-(1-benzyloxyvinyl)-2-methyl-benzene (Intermediate 73, 400.0 mg, 1.32 mmols), Et$_2$Zn (325.0 mg, 2.63 mmols), and CH$_2$I$_2$ (704.0 mg, 2.63 mmols) in 4 mL Et$_2$O afforded 380.0 mg (90%) of the title compound as a colorless oil after chromatography (2–5% EtOAc-hexanes).

$^1$H NMR (CDCl$_3$) δ: 7.42–7.20 (8H, m), 4.31 (2H, s), 2.58 (3H, s), 1.25 (2H, m), 0.94 (2H, m).

[4-(1-Benzyloxycyclopropyl)-3-methyl-phenylethynyl]-trimethylsilane (Intermediate 75)

Using General Procedure D; 4-bromo-1-(1-benzyloxycyclopropyl)-2-methyl-benzene (Intermediate 74, 320.0 mg, 1.00 mmol) in triethylamine (8 mL) was treated with copper(I)iodide (19.0 mg, 0.1 mmol) and then sparged with argon for 5 minutes. Trimethylsilylacetylene (0.70 g, 7.1 mmols) was then added followed by dichlorobis-(triphenylphosphine)palladium(II) (70.0 mg, 0.05 mmol). The resulting reaction mixture was heated to 70° C. for 5d. The title compound (300.0 mg, 89%) was isolated by chromatography (0–2% EtOAc-hexanes).

$^1$H NMR (CDCl$_3$) δ: 7.34–7.13 (8H, m), 4.24 (2H, s), 2.52 (3H, s), 1.20 (2H, m), 0.88 (2H, m), 0.25 (9H, s).

4-Ethynyl-1-(1-benzyloxycyclopropyl)-2-methyl-benzene (Intermediate 76)

Using General Procedure E; [4-(1-benzyloxycyclopropyl)-3-methyl-phenylethynyl]-trimethylsilane (Intermediate 75, 300.0 mg, 0.95 mmols) in methanol (6 mL) was treated with potassium carbonate (120.0 mg, 0.87 mmol) and stirred overnight at ambient temperature. The crude alkyne (185 mg, 79%) was used directly in the next reaction.

$^1$H NMR (CDCl$_3$) δ: 7.37–7.16 (8H, m), 4.27 (2H, s), 3.07 (1H, s), 2.55 (3H, s), 1.21 (2H, m), 0.92 (2H, m).

Ethyl 4-[4-(1-benzyloxycaclopropyl)-3-methyl-phenylethynyl]-benzoate (Compound 79, General Formula 2)

Using General Procedure F; 1-ethynyl-4-(1-benzyloxycyclopropyl)-3-methyl-benzene (Intermediate 76, 90.0 mg, 0.34 mmol) and ethyl-4-iodo benzoate (Reagent A, 95.0 mg, 0.34 mmol) in triethylamine (6 mL) was treated with copper(I)iodide (23.0 mg, 0.12 mmol) and sparged with argon for 5 minutes. Dichlorobis(triphenylphosphine)palladium(II) (80 mg, 0.11 mmol) was added and the reaction mixture was stirred overnight at room temperature. Column chromatography (2–4% EtOAc-hexanes) afforded 68.0 mg (54%) of the title compound.

$^1$H NMR (CDCl$_3$) δ: 8.03 (2H, d, J=8.2 Hz), 7.58 (2H, d, J=8.2 Hz), 7.33–7.16 (8H, m), 4.39 (2H, q, J=7.1 Hz), 4.29 (2H, s), 2.57 (3H, s), 1.40 (3H, t, J=7.1 Hz), 1.22 (2H, m), 0.93 (2H, m).

Methyl {4-[4-(1-benzyloxycyclopropyl)-3-methyl-phenylethynyl]-phenyl}-acetate (Compound 80, General Formula 2)

Using General Procedure F; 1-ethynyl-4-(1-benzyloxycyclopropyl)-3-methyl-benzene (Intermediate 76, 90.0 mg, 0.34 mmol) and methyl-(4-iodophenyl)-acetate (Reagent B, 95.0 mg, 0.34 mmol) in triethylamine (5 mL) was treated with copper(I)iodide (22.0 mg, 0.11 mmol) and sparged with argon for 5 minutes. Dichlorobis(triphenylphosphine)palladium(II) (80 mg, 0.11 mmol) was added and the reaction mixture was stirred overnight at room temperature. Column chromatography (2–4% EtOAc-hexanes) afforded 90.0 mg (71%) of the title compound as a pale-yellow oil.

$^1$H NMR (CDCl$_3$) δ: 7.49 (2H, d, J=8.2 Hz), 7.32–7.16 (10H, m), 4.28 (2H, s), 3.70 (3H, s), 3.64 (2H, s), 2.56 (3H, s), 1.22 (2H, m), 0.92 (2H, m).

4-[4-(1-Benzyloxacyclopropyl)-3-methyl-phenylethynyl]-benzoic acid (Compound 81, General Formula 2)

Using General Procedure I; a solution of ethyl 4-[4-(1-benzyloxycyclopropyl)-3-methyl-phenylethynyl]-benzoate (Compound 79, 68.0 mg, 0.17 mmol) in ethanol (3 mL) and tetrahydrofuran (3 mL) was treated with NaOH (360.0 mg, 9.0 mmols, 3.0 mL of a 3N aqueous solution) and stirred overnight at room temperature. Work-up afforded 48.0 mg (76%) of the title compound as a solid.

$^1$H NMR (CDCl$_3$) δ: 8.10 (2H, d, J=8.1 Hz), 7.63 (2H, d, J=8.1 Hz), 7.44–7.16 (8H, m), 4.29 (2H, m), 2.58 (3H, s), 1.24 (2H, m), 0.94 (2H, m).

{4-[4-(1-Benzyloxycaclopropyl)-3-methyl-phenylethynyl]-phenyl}-acetic acid (Compound 82, General Formula 2)

Using General Procedure I; a solution of methyl {4-[4-(1-benzyloxycyclopropyl)-3-methyl-phenylethynyl]-phenyl}-acetate (Compound 80, 75.0 mg, 0.18 mmol) in ethanol (3 mL) and tetrahydrofuiran (3 mL) was treated with NaOH (120.0 mg, 3.0 mmols, 3.0 mL of a 1N aqueous solution) and stirred overnight at room temperature. Work-up afforded 30.0 mg (40%) of the title compound.

$^1$H NMR (CDCl$_3$) δ: 7.51 (2H, d, J=8.2 Hz), 7.42 (1H, s), 7.33–7.17 (9H, m), 4.36 (2H, s), 3.67 (2H, s), 2.57 (3H, s), 1.23 (2H, m), 0.94 (2H, m).

Isopropyl 3-methyl-4-bromobenzoate
(Intermediate 77)

Using General Esterification Procedure A; 4-bromo-2-methylbenzoic acid (1.6 g, 7.4 mmols) was combined with isopropyl alcohol to give 1.5 g (79%) of the title compound as a colorless oil.

$^1$H NMR (CDCl$_3$) δ: 7.76 (1H, d, J=8.2 Hz), 7.40 (1H, d, J=7.4 Hz), 7.37 (1H, dd, J=1.4, 8.2 Hz), 5.23 (1H, septet, J=6.2 Hz), 2.57 (3H, s), 1.37 (6H, d, J=6.2 Hz).

4-Bromo-1-(1-isopropoxyvinyl)-2-methyl-benzene
(Intermediate 78)

Using General Procedure 1; isopropyl 2-methyl-4-bromobenzoate (Intermediate 77, 800.0 mg, 3.11 mmols) and 6.2 mL of Tebbe's Reagent (885.2 mg, 3.11 mmols) afforded 595.0 mg (75%) of the title compound as a colorless oil after column chromatography (100% hexanes).

$^1$H NMR (CDCl$_3$) δ: 7.31–7.25 (2H, m), 7.16 (1H, d, J=8.2 Hz), 4.34 (1H, septet, J=6.0 Hz), 4.31 (1H, d, J=2.1 Hz), 4.18(1H, d, J=2.1 Hz), 2.33 (3H, s), 1.31 (6H, d, J=6.0 Hz).

4-Bromo-1-(1-isopropoxycyclopropyl)-2-methyl-benzene (Intermediate 79)

Using General Procedure 2; 4-bromo-1-(1-isopropoxyvinyl)-2-methyl-benzene (Intermediate 78, 389.0 mg, 1.53 mmols), Et$_2$Zn (376.6 mg, 3.05 mmols), and CH$_2$I$_2$ (817.0 mg, 3.05 mmols) in 3.0 mL Et$_2$O afforded 340.0 mg (84%) of the title compound as a colorless oil after chromatography (3% EtOAc-hexanes).

$^1$H NMR (CDCl$_3$) δ: 7.33 (1H, d, J=2.3 Hz), 7.24 (1H, dd, J=2.3, 8.2 Hz), 7.13 (1H, d, J=8.2 Hz), 3.57 (1H, septet, J=6.1 Hz), 2.49 (3H, s), 1.00 (2H, m), 0.97 (6H, d, J=6.1 Hz), 0.82 (2H, m).

[4-(1-Isopropoxycyclopropyl)-3-methyl-phenylethynyl]-trimethylsilane (Intermediate 80)

Using General Procedure D; 4-bromo-1-(1-isopropoxycyclopropyl)-2-methyl-benzene (Intermediate 79, 250.0 mg, 0.95 mmol) in triethylamine (8 mL) was treated with copper(I)iodide (19.0 mg, 0.10 mmol) and then sparged with argon for 5 minutes. Trimethylsilylacetylene (0.70 g, 7.1 mmols) was then added followed by dichlorobis-(triphenylphosphine)palladium(II) (70.0 mg, 0.1 mmol). The resulting reaction mixture was heated to 70° C. for 5d. The title compound (250.0 mg, 91%) was isolated by chromatography (0–3% EtOAc-hexanes).

$^1$H NMR (CDCl$_3$) δ: 7.32–7.17 (3H, m), 3.56 (1H, septet, J=6.2 Hz), 2.48 (3H, s), 1.00 (2H, m), 0.95 (6H, d, J=6.2 Hz), 0.83 (2H, m), 0.24 (9H, s).

4-Ethynyl-1-(1-isopropoxycyclopropyl)-2-methyl-benzene (Intermediate 81)

Using General Procedure E; [4-(1-isopropoxycyclopropyl)-3-methyl-phenylethynyl]-trimethylsilane (Intermediate 80, 250.0 mg, 0.87 mmol) in methanol (10 mL) was treated with potassium carbonate (100.0 mg, 0.72 mmol) and stirred overnight at ambient temperature. The crude alkyne (180 mg, 98%) was used directly in the next reaction.

$^1$H NMR (CDCl$_3$) δ: 7.32 (1H, s), 7.23 (2H, m), 3.57 (1H, septet, J=6.2 Hz), 3.05 (1H, s), 2.50 (3H, s), 1.11 (2H, m), 0.96 (6H, d, J=6.2 Hz), 0.83 (2H, m).

Ethyl 4-[4-(1-isopropoxycyclopropyl)-3-methyl-phenylethynyl]-benzoate (Compound 83, General Formula 2)

Using General Procedure F; 4-ethynyl-1-(1-isopropoxycyclopropyl)-3-methyl-benzene (Intermediate 81, 80.0 mg, 0.13 mmol) and ethyl-4-iodo benzoate (Reagent A, 100.0 mg, 0.36 mmol) in triethylamine (5 mL) was treated with copper(I)iodide (25.0 mg, 0.13 mmol) and sparged with argon for 5 minutes. Dichlorobis (triphenylphosphine)-palladium(II) (91 mg, 0.13 mmol) was added and the reaction mixture was stirred overnight at room temperature. Column chromatography (2–4% EtOAc-hexanes) afforded 75.0 mg (56%) of the title compound as an orange solid.

$^1$H NMR (CDCl$_3$) δ: 8.02 (2H, d, J=8.2 Hz), 7.57 (2H, d, J=8.2 Hz), 7.39 (1H, s), 7.29–7.20 (2H, m), 4.39 (2H, q, J=7.1 Hz), 3.60 (1H, septet, J=6.2 Hz), 1.40 (3H, t, J=7.1 Hz), 1.13 (2H, m), 0.97 (6H, d, J=6.2 Hz), 0.87 (2H, m).

Methyl {4-[4-(1-isopropoxycyclopropyl)-3-methyl-phenylethynyl]-phenyl}-acetate (Compound 84, General Formula 2)

Using General Procedure F; 1-ethynyl-4-(1-isopropoxycyclopropyl)-3-methyl-benzene (Intermediate 81, 100.0 mg, 0.47 mmol) and methyl-(4-iodophenyl)-acetate (Reagent B, 129.0 mg, 0.45 mmol) in triethylamine (6 mL) was treated with copper(I)iodide (30.0 mg, 0.16 mmol) and sparged with argon for 5 minutes. Dichlorobis (triphenylphosphine)palladium(II) (110 mg, 0.16 mmol) was added and the reaction mixture was stirred overnight at room temperature. Column chromatography (2–4% EtOAc-hexanes) afforded 120.0 mg (71%) of the title compound.

$^1$H NMR (CDCl$_3$) δ: 7.48 (2H, d, J=8.5 Hz), 7.36 (1H, s), 7.29–7.22 (4H, m), 3.70 (3H, s), 3.63 (2H, s), 3.60 (1H, septet, J=6.2 Hz), 2.52 (3H, s), 1.09 (2H, m), 0.97 (6H, d, J=6.2 Hz), 0.86 (2H, m).

4-[4-(1-Isopropoxycyclopropyl)-3-methyl-phenylethynyl]-benzoic acid (Compound 85, General Formula 2)

Using General Procedure I; a solution of ethyl 4-[4-(1-isopropoxycyclopropyl)-3-methyl-phenylethynyl]-benzoate (Compound 83, 60.0 mg, 0.17 mmol) in ethanol (2 mL) and tetrahydrofuran (2 mL) was treated with NaOH (80.0 mg, 2.0 mmols, 2.0 mL of a 1N aqueous solution) and stirred overnight at room temperature. Work-up afforded 38.0 mg (69%) of the title compound as a colorless solid.

$^1$H NMR (d$_6$-acetone) δ: 8.06 (2H, d, J=8.5 Hz), 7.66 (2H, d, J=8.5 Hz), 7.42 (1H, s), 7.35 (2H, m), 3.59 (1H, septet, J=6.2 Hz), 2.52 (3H, s), 1.07 (2H, m), 0.93 (6H, d, J=6.2 Hz), 0.88 (2H, m).

{4-[4-(1-Isopropoxycyclopropyl)-3-methyl-phenylethynyl]-phenyl}-acetic acid (Compound 86, General Formula 2)

Using General Procedure I; a solution of methyl {4-[4-(1-isopropoxycyclopropyl)-3-methyl-phenylethynyl]-phenyl }-acetate (Compound 84, 100.0 mg, 0.28 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up afforded 60.0 mg (62%) of the title compound as a colorless solid.

$^1$H NMR (CDCl$_3$) δ: 7.48 (2H, d, J=7.6 Hz), 7.36 (1H, s), 7.25 (4H, m), 3.65 (2H, s), 3.60 (1H, septet, J=6.2 Hz), 2.51 (3H, s), 1.12 (2H, m), 0.97 (6H, d, J=6.2 Hz), 0.86 (2H, m).

2,2-Dimefhylpropyl 2-methyl-4-bromobenzoate (Intermediate 82)

Using General Esterification Method C; 2-methyl-4-bromo-benzoic acid (1.82 g, 8.47 mmols) was refluxed for 3 h with 10 mL SOCl$_2$. The resulting solution was concentrated under reduced pressure and the crude acyl chloride combined with 2,2-dimethylpropanol (0.75 g, 8.47 mmols) and pyridine (1.4 mL, 16.9 mmols) to give the title compound (1.64 g, 68%) after work-up and column chromatography (2–5% EtOAc-hexanes) as a colorless oil.

$^1$H NMR (CDCl$_3$) δ: 7.81 (1H, d, J=8.2 Hz), 7.42 (1H, d, J=2.0 Hz), 7.39 (1H, dd, J=2.0, 8.2 Hz), 3.99 (2H, s), 2.60 (3H, s), 1.03 (9H, s).

4-Bromo-1-[1-(2,2-dimethylpropyloxy)-vinyl]-2-methyl-benzene (Intermediate 83)

Using General Procedure 1; 2,2-dimethylpropyl 2-methyl-4-bromobenzoate (Intermediate 82, 820.0 mg, 2.87 mmols) and 5.8 mL of Tebbe's Reagent (817.0 mg, 2.87 mmols) afforded 800.0 mg (98%) of the title compound as a colorless oil after column chromatography (100% hexanes).

$^1$H NMR (CDCl$_3$) δ: 7.32 (1H, d, J=2.0 Hz), 7.28 (1H, dd, J=2.0, 8.2 Hz), 7.18 (1H, d, J=8.2 Hz), 4.27 (1H, d, J=2.1 Hz), 4.10 (1H, d, J=2.1 Hz), 3.43 (2H, s), 2.33 (3H, s), 0.98 (9H, s).

4-Bromo-1-[1-(2,2-dimethylpropyloxy)-cyclopropyl]-2-methyl-benzene (Intermediate 84)

Using General Procedure 2; 4-bromo-1-[1-(2,2-dimethylpropyloxy)-cyclopropyl]-2-methyl-benzene (Intermediate 83, 400. 0 mg, 1.43 mmols), Et$_2$Zn (353.2 mg, 2.86 mmols), and CH$_2$I$_2$ (760.0 mg, 2.86 mmols) in 3.0 mL Et$_2$O afforded 370.0 mg (87%) of the title compound as a colorless oil after chromatography (3% EtOAc-hexanes).

$^1$H NMR (CDCl$_3$) δ: 7.36 (1H, s),7.27 (1H, d, J=8.5 Hz), 7.09 (1H, d, J=7.9 Hz), 2.86 (2H, s), 2.52 (3H, s), 1.08 (2H, m), 0.83 (2H, m), 0.80 (9H, s).

[4-[1-[1-(2,2-Dimethylpropyloxy)-cyclopropyl]-3-methyl-phenylethynyl]]-trimethylsilane (Intermediate 84a)

Using General Procedure D; 4-bromo-1-[1-(2,2-dimethylpropyloxy)-cyclopropyl]-2-methyl-benzene (Intermediate 84, 255.0 mg, 0.86 mmol) in triethylamine (8 mL) was treated with copper(I)iodide (17.0 mg, 0.09 mmol) and then sparged with argon for 5 minutes. Trimethylsilylacetylene (0.70 g, 7.1 mmols) was then added followed by dichlorobis-(triphenylphosphine)palladium(II) (63.0 mg, 0.09 mmol). The resulting reaction mixture was heated to 70° C. for 5d. The title compound (220.0 mg, 81%) was isolated by chromatography (1–2% EtOAc-hexanes).

$^1$H NMR (CDCl$_3$) δ: 7.30 (1H, s), 7.21 (1H, d, J=7.6 Hz), 7.12 (1H, d, J=8.6 Hz), 2.80 (2H, s), 2.47 (3H, s), 1.05 (2H, m), 0.82 (2H, m), 0.75 (9H, 0.24 (9H, s).

4-Ethynyl-1-[1-(2,2-dimethylpropyloxy)-cyclopropyl]-2-metlhyl-benzene (Intermediate 85)

Using General Procedure E; [4-[1-[1-(2,2-dimethylpropyloxy)-cyclopropyl]]-3-methyl-phenylethynyl]-trimethylsilane (Intermediate 84a, 220.0 mg, 0.83 mmol) in methanol (10 mL) was treated with potassium carbonate (80.0 mg, 0.58 mmol) and stirred overnight at ambient temperature. The crude alkyne (155 mg, 76%) was used directly in the next reaction.

$^1$H NMR (CDCl$_3$) δ: 7.32 (1H, s), 7.24 (1H, d, J=7.1 Hz), 7.15 (1H, d, J=7.1 Hz), 3.04 (1H, s), 2.83 (2H, s), 2.49 (3H, s), 1.06 (2H, m), 0.83 (2H, m), 0.76 (9H, s).

Ethyl 4-[4-[1-(2,2-dimethylpropyloxy)-cyclopropyl]-3-methyl-phenylethynyl]-benzoate (Compound 87, General Formula 2)

Using General Procedure F; 4-ethynyl-1-[1-(2,2-dimethylpropyloxy)-cyclopropyl]-3-methyl-benzene (Intermediate 85, 75.0 mg, 0.31 mmol) and ethyl-4-iodo benzoate (Reagent A, 86.0 mg, 0.31 mmol) in triethylamine (5 mL) was treated with copper(I)iodide (21.0 mg, 0.11 mmol) and sparged with argon for 5 minutes. Dichlorobis(triphenylphosphine)-palladium(II) (78 mg, 0.11 mmol) was added and the reaction mixture was stirred overnight at room temperature. Column chromatography (2–4% EtOAc-hexanes) afforded 60.0 mg (50%) of the title compound as an orange solid.

$^1$H NMR (CDCl$_3$) δ: 8.02 (2H, d, J=8.4 Hz), 7.56 (2H, d, J=8.4 Hz), 7.38 (1H, s), 7.30 (1H, dd, J=1.1, 8.0 Hz), 7.20 (1H, d, J=8.0 Hz), 4.38 (2H, q, J=7.1 Hz), 2.84 (2H, s), 2.52 (3H, s), 1.40 (3H, t, J=7.1 Hz), 1.07 (2H, m), 0.84 (2H, m), 0.77 (9H, s).

Methyl {4-[4-[1-(2,2-dimethylpropyloxy)-cyclopropyl]-3-methyl-phenylethynyl]-phenyl}-acetate (Compound 88, General Formula 2)

Using General Procedure F; 4-ethynyl-1-[1-(2,2-dimethylpropyloxy)-cyclopropyl]-3-methyl-benzene (Intermediate 85, 75.0 mg, 0.31 mmol) and methyl-(4-iodophenyl)-acetate (Reagent B, 86.0 mg, 0.31 mmol) in triethylamine (6 mL) was treated with copper(I)iodide (21.0 mg, 0.11 mmol) and sparged with argon for 5 minutes. Dichlorobis(triphenylphosphine)palladium(II) (78 mg, 0.11 mmol) was added and the reaction mixture was stirred overnight at room temperature. Column chromatography (2–4% EtOAc-hexanes) afforded 100.0 mg (83%) of the title compound.

$^1$H NMR (CDCl$_3$) δ: 7.48 (2H, d, J=7.9 Hz), 7.36–7.24 (4H, m), 7.18 (1H, d, J=7.9 Hz), 3.70 (3H, s), 3.63 (2H, s), 2.84 (2H, s), 2.51 (3H, s), 1.07 (2H, m), 0.83 (2H, m), 0.77 (9H, s).

4-[4-[1-(2,2-Dimethylpropyloxy)-cyclopropl]-3-methyl-phenylethynyl]-benzoic acid (Compound 89, General Formula 2)

Using General Procedure I; a solution of ethyl 4-[4-[1-(2,2-dimethylpropyloxy)-cyclopropyl]-3-methyl-phenylethynyl]-benzoate (Compound 87, 60.0 mg, 0.15 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up afforded 24.0 mg (43%) of the title compound as a colorless solid.

$^1$H NMR (CDCl$_3$) δ: 8.06 (2H, d, J=7.9 Hz), 7.65 (2H, d, J=7.9 Hz), 7.42 (1H, s), 7.33 (2H, m), 2.89 (2H, s), 2.53 (3H, s), 1.07 (2H, m), 0.90 (2H, m), 0.77 (9H, s).

{4-[4-[1-(2,2-Dimethylpropyloxy)-cyclopropyl]-3-methyl-phenylethynyl]-phenyl}-acetic acid (Compound 90, General Formula 2)

Using General Procedure I; a solution of methyl {4-[4-[1-(2,2-dimethylpropyloxy)-cyclopropyl]-3-methyl-phenylethynyl]-phenyl}-acetate (Compound 88, 95.0 mg, 0.24 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up afforded 49.0 mg (53%) of the title compound as a colorless solid.

$^1$H NMR (CDCl$_3$) δ: 7.49 (2H, d, J=8.2 Hz), 7.36 (1H, s), 7.27 (3H, m), 7.18 (1H, d, J=7.9 Hz), 3.66 (2H, s), 2.84 (2H, s), 2.51 (3H, s), 1.07 (2H, m), 0.83 (2H, m), 0.77 (9H, s).

Benzyl 4-bromo-2-ethyl-benzoate (Intermediate 86)

Using General Esterification Method B; 4-bromo-2-ethyl-benzoic acid (0.98 g, 4.25 mmols), benzyl bromide (0.80 g, 4.68 mmols), and K$_2$CO$_3$ (0.64 g, 4.68 mmols) afforded 1.0 g (74%) of the title compound after column chromatography (0–3% EtOAc-hexanes).

$^1$H NMR (CDCl$_3$) δ: 7.76 (1H, d, J=8.5 Hz), 7.41–7.33 (7H, m), 5.32 (2H, s), 2.95 (2H, q, J=7.6 Hz), 1.20 (3H, t, J=7.6 Hz).

4-Bromo-1-(1-benzyloxyinyl)-2-ethyl-benzene (Intermediate 87)

Using General Procedure 1; benzyl 4-bromo-2-ethylbenzoate (Intermediate 86, 1.20 g, 3.78 mmols) and 7.6 mL of Tebbe's Reagent (1.08 g, 3.78 mmols) afforded 800.0 mg (66%) of the title compound after column chromatography (100% hexanes).

$^1$H NMR (CDCl$_3$) δ: 7.37–7.17 (8H, m), 4.88 (2H, s), 4.43 (1H, d, J=2.1 Hz), 4.25 (1H, d, J=2.1 Hz), 2.71 (2H, q, J=7.6 Hz), 1.18 (3H, t, J=7.6 Hz).

4-Bromo-1-(1-benzyloxycyclopropyl)-2-ethyl-benzene (Intermediate 88)

Using General Procedure 2; 4-bromo-1-(1-benzyloxyvinyl)-2-ethyl-benzene (Intermediate 87, 330.0 mg, 1.04 mmols), Et$_2$Zn (257.0 mg, 2.08 mmols), and CH$_2$I$_2$ (557.0 mg, 2.08 mmols) in 4 mL Et$_2$O afforded 241.0 mg (70%) of the title compound as a colorless oil after chromatography (2–5% EtOAc-hexanes).

$^1$H NMR (CDCl$_3$) δ: 7.43–7.15 (8H, m), 4.27 (2H, s), 3.00 (2H, q, J=7.6 Hz), 1.29–1.21 (5H, m), 0.90 (2H, m).

[4-(1-Benzyloxycyclopropyl)-3-ethyl-phenylethynyl]-trimethylsilane (Intermediate 89)

Using General Procedure D; 4-bromo-1-(1-benzyloxycyclopropyl)-2-ethyl-benzene (Intermediate 88, 220.0 mg, 0.66 mmol) in triethylamine (8 mL) was treated with copper(I)iodide (14.0 mg, 0.07 mmol) and then sparged with argon for 5 minutes. Trimethylsilylacetylene (0.70 g, 7.1 mmols) was then added followed by dichlorobis-(triphenylphosphine)palladium(II) (50.0 mg, 0.07 mmol). The resulting reaction mixture was heated to 70° C. for 5 d. The title compound was isolated by chromatography (0–2% EtOAc-hexanes).

$^1$H NMR (CDCl$_3$) δ: 7.41–7.13 (8H, m), 4.24 (2H, s), 2.98 (2H, q, J=7.6 Hz), 1.25 (3H, t, J=7.6 Hz), 1.20 (2H, m), 0.90 (2H, m), 0.26 (9H, s).

4-Ethynyl-1-(1-benzyloxycyclopropyl)-2-ethyl-benzene (Intermediate 90)

Using General Procedure E; [4-(1-benzyloxycyclopropyl)-3-ethyl-phenylethynyl]-trimethylsilane (Intermediate 89, 240 mg, 0.69 mmol) in methanol (6 mL) was treated with potassium carbonate (10.0 mg, 0.72 mmol) and stirred overnight at ambient temperature. The crude alkyne (190 mg, 99%) was used directly in the next reaction. $^1$H NMR (CDCl$_3$) δ: 7.43–7.15 (8H, m), 4.27 (2H, s), 3.08 (1H, s), 3.01 (2H, q, J=7.6 Hz), 1.26 (3H, t, J=7.6 Hz), 1.22 (2H, m), 0.92 (2H, m).

Ethyl 4-[4-(1-benzyloxycyclopropyl)-3-ethyl-phenylethynyl]-benzoate (Compound 91, General Formula 2)

Using General Procedure F; 1-ethynyl-4-(1-benzyloxycyclopropyl)-3-ethyl-benzene (Intermediate 90, 90.0 mg, 0.33 mmol) and ethyl-4-iodo benzoate (Reagent A, 100.0 mg, 0.36 mmol) in triethylamine (5 mL) was treated with copper(I)iodide (21.0 mg, 0.11 mmol) and sparged with argon for minutes. Dichlorobis(triphenylphosphine)palladium(II) (77 mg, 0.11 mmol) was added and the reaction mixture was stirred overnight at room temperature. Column chromatography (2–4% EtOAc-hexanes) afforded 100.0 mg (72%) of the title compound.

$^1$H NMR (CDCl$_3$) δ: 8.03 (2H, d, J=7.9 Hz), 7.59 (2H, d, J=7.9 Hz), 7.49 (1H, s), 7.36–7.16 (7H, m), 4.38 (2H, q, J=7.1 Hz), 4.28 (2H, s), 3.04 (2H, q, J=7.6 Hz), 1.40 (3H, t, J=7.1 Hz), 1.29 (3H, t, J=7.6 Hz), 1.23 (2H, m), 0.94 (2H, m).

Methyl {4-[4-(1-benzyloxycyclopropyl)-3-ethyl-phenylethynyl]-phenyl}-acetate (Compound 92, General Formula 2)

Using General Procedure F; 1-ethynyl-4-(1-benzyloxycyclopropyl)-3-ethyl-benzene (Intermediate 90, 107.0 mg, 0.39 mmol) and methyl-(4-iodophenyl)-acetate (Reagent B, 110.0 mg, 0.39 mmol) in triethylamine (5 mL) was treated with copper(I)iodide (25.0 mg, 0.13 mmol) and sparged with argon for 5 minutes. Dichlorobis(triphenylphosphine)palladium(II) (91 mg, 0.13 mmol) was added and the reaction mixture was stirred overnight at room temperature. Column chromatography (2–4% EtOAc-hexanes) afforded 130.0 mg (79%) of the title compound as a pale-yellow oil.

$^1$H NMR (CDCl$_3$) δ: 7.49 (3H, m), 7.32–7.16 (9H, m), 4.28 (2H, s), 3.71 (3H, s), 3.64 (2H, s), 3.03 (2H, q, J=7.6 Hz), 1.32–1.23 (5H, m), 0.94 (2H, m).

4-[4-(1-Benzyloxycyclopropyl)-3-ethyl-phenylethynyl]-benzoic acid (Compound 93, General Formula 2)

Using General Procedure I; a solution of ethyl 4-[4-(1-benzyloxycyclopropyl)-3-ethyl-phenylethynyl]-benzoate (Compound 91, 100.0 mg, 0.24 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up and purification by HPLC (Partisil 10-pac, 10% H$_2$O/CH$_3$CN) afforded the title compound as a colorless solid.

$^1$H NMR (CDCl$_3$) δ: 8.10 (2H, d, J=8.5 Hz), 7.64 (2H, d, J=8.5 Hz), 7.50 (1H, s), 7.35–7.16 (7H, m), 4.29 (2H, s), 3.04 (2H, q, J=7.6 Hz), 1.30 (3H, t, J=7.6 Hz), 1.25 (2H, m), 0.95 (2H, m).

{4-[4-(1-Benzyloxacyclopropyl)-3-ethyl-phenylethynyl]-phenyl}-acetic acid (Compound 94, General Formula 2)

Using General Procedure I; a solution of methyl {4-[4-(1-benzyloxycyclopropyl)-3-ethyl-phenylethynyl]-phenyl}- acetate (Compound 92, 130.0 mg, 0.31 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up and purification by HPLC (Partisil 10-pac, 10% $H_2O/CH_3CN$) afforded the title compound.

$^1$H NMR (CDCl$_3$) δ: 7.49 (3H, m), 7.31–7.16 (9H, m), 4.28 (2H, s), 3.66 (2H, s), 3.02 (2H, q, J=7.6 Hz), 1.29 (3H, t, J=7.6 Hz), 1.23 (2H, m), 0.94 (2H, m).

Isopropyl 2-ethyl-4-bromobenzoate (Intermediate 91)

Using General Esterification Procedure A; 4-bromo-2-ethyl-benzoic acid (2.25 g, 9.9 mmols) was combined with isopropyl alcohol to give the title compound as a colorless oil after column chromatography (2% EtOAc-hexanes).

$^1$H NMR (CDCl$_3$) δ: 7.69 (1H, d, J=8.5 Hz), 7.41 (1H, s), 7.36 (1H, d, J=8.5 Hz), 5.23 (1H, septet, J=6.2 Hz), 2.95 (2H, q, J=7.6 Hz), 1.37 (6H, d, J=6.2 Hz), 1.23 (3H, t, J=7.6 Hz).

4-Bromo-1-(1-isopropoxyvinyl)-2-ethyl-benzene (Intermediate 92)

Using General Procedure 1; isopropyl 2-ethyl-4-bromobenzoate (Intermediate 91, 1.21 g, 4.46 mmols) and 8.9 mL of Tebbe's Reagent (1.27 g, 4.46 mmols) afforded 570.0 mg (75%) of the title compound after column chromatography (100% hexanes).

$^1$H NMR (CDCl$_3$) δ: 7.36 (1H, d, J=2.0 Hz), 7.28 (1H, dd, J=2.0, 8.0 Hz), 7.17 (1H, d, J=8.0 Hz), 4.39 (1H, septet, J=6.2 Hz), 4.31 (1H, d, J=2.1 Hz), 4.26 (1H, d, J=2.1 Hz), 2.73 (2H, q, J=7.6 Hz), 1.35 (6H, d, J=6.2 Hz), 1.24 (3H, t, J=7.6 Hz).

4-Bromo-1-(1-isopropoxycyclopropyl)-2-ethyl-benzene (Intermediate 93)

Using General Procedure 2; 4-bromo-1-(1-isopropoxyvinyl)-2-ethyl-benzene (Intermediate 92, 570.0 mg, 2.11 mmols), Et$_2$Zn (521.0 mg, 4.22 mmols), and CH$_2$I$_2$ (1.13 g, 4.22 mmols) in 7.0 mL Et$_2$O afforded 500.0 mg (85%) of the title compound as a colorless oil after chromatography (3% EtOAc-hexanes).

$^1$H NMR (CDCl$_3$) δ: 7.39 (1H, d, J=2.1 Hz), 7.25 (1H, dd, J=2.1, 8.1 Hz), 7.15 (1H, d, J=8.1 Hz), 3.59 (1H, septet, J=6.2 Hz), 2.97 (2H, q, J=7.6 Hz), 1.27 (3H, t, J=7.6 Hz), 1.11 (2H, m), 0.97 (6H, d, J=6.2 Hz), 0.83 (2H, m).

[4-(1-Isopropoxycyclopropyl)-3-ethyl-phenylethynyl]-trimethylsilane (Intermediate 94)

Using General Procedure D; 4-bromo-1-(1-isopropoxycyclopropyl)-2-ethyl-benzene (Intermediate 93, 300.0 mg, 1.07 mmol) in triethylamine (8 mL) was treated with copper(I)iodide (20.0 mg, 0.11 mmol) and then sparged with argon for 5 minutes. Trimethylsilylacetylene (0.70 g, 7.1 mmols) was then added followed by dichlorobis-(triphenylphosphine)palladium(II) (75.0 mg, 0.11 mmol). The resulting reaction mixture was heated to 70° C. for 5 d. The title compound (320.0 mg, 99%) was isolated by chromatography (0–2% EtOAc-hexanes as an orange oil.

$^1$H NMR (CDCl$_3$) δ: 7.37–7.21 (3H, m), 3.56 (1H, septet, J=6.2 Hz), 2.96 (2H, q, J=7.6 Hz), 1.27 (3H, t, J=7.6 Hz), 1.10 (2H, m), 0.94 (6H, d, J=6.2 Hz), 0.84 (2H, m), 0.25 (9H, s).

4-Ethynyl-1-(1-isopropoxycyclopropyl)-2-ethyl-benzene (Intermediate 95)

Using General Procedure E; [4-(1-isopropoxycyclopropyl)-3-ethyl-phenylethynyl]-trimethylsilane (Intermediate 94, 330.0 mg, 1.10 mmols) in methanol (10 mL) was treated with potassium carbonate (150.0 mg, 1.10 mmol) and stirred overnight at ambient temperature. The crude alkyne (238 mg, 95%) was used directly in the next reaction.

$^1$H NMR (CDCl$_3$) δ: 7.40–7.22 (3H, m), 3.59 (1H, septet, J=6.2 Hz), 3.07 (1H, s), 2.97 (2H, q, J=7.6 Hz), 1.28 (3H, t, J=7.6 Hz), 1.12 (2H, m), 0.96 (6H, d, J=6.2 Hz), 0.85 (2H, m).

Ethyl 4-[4-(1-isopropoxycyclopropyl)-3-ethyl-phenylethynyl]-benzoate (Compound 95, General Formula 2)

Using General Procedure F; 4-ethynyl-1-(1-isopropoxycyclopropyl)-3-ethyl-benzene (Intermediate 95, 108.0 mg, 0.47 mmol) and ethyl-4-iodo benzoate (Reagent A, 130.0 mg, 0.47 mmol) in triethylamine (5 mL) was treated with copper(I)iodide (30.0 mg, 0.16 mmol) and sparged with argon for 5 minutes. Dichlorobis (triphenylphosphine)-palladium(II) (110 mg, 0.16 mmol) was added and the reaction mixture was stirred overnight at room temperature. Column chromatography (2–4% EtOAc-hexanes) afforded 125.0 mg (71%) of the title compound as an oil.

$^1$H NMR (CDCl$_3$) δ: 8.02 (2H, d, J=8.2 Hz), 7.59 (2H, d, J=8.2 Hz), 7.46 (1H, s), 7.33–7.26 (2H, m), 4.39 (2H, q, J=7.1 Hz), 3.62 (1H, septet, J=6.2 Hz), 3.01 (2H, q, J=7.6 Hz), 1.41 (3H, t, J=7.1 Hz), 1.31 (3H, t, J=7.1 Hz) 1.14 (2H, m), 0.97 (6H, d, J=6.2 Hz), 0.88 (2H, m).

Methyl {4-[4-(1-isopropoxycyclopropyl)-3-ethyl-phenylethynyl]-phenyl}-acetate (Compound 96, General Formula 2)

Using General Procedure F; 1-ethynyl-4-(1-isopropoxycyclopropyl)-3-ethyl-benzene (Intermediate 95, 130.0 mg, 0.57 mmol) and methyl-(4-iodophenyl)-acetate (Reagent B, 157.0 mg, 0.57 mmol) in triethylamine (5 mL) was treated with copper(I)iodide (36.0 mg, 0.19 mmol) and sparged with argon for 5 minutes. Dichlorobis (triphenylphosphine)palladium(II) (133 mg, 0.19 mmol) was added and the reaction mixture was stirred overnight at room temperature. Column chromatography (2–5% EtOAc-hexanes) afforded 150.0 mg (70%) of the title compound as an orange oil.

$^1$H NMR (CDCl$_3$) δ: 7.50–7.44 (3H, m), 7.27 (4H, m), 3.70 (3H, s), 3.64 (2H, s), 3.62 (1H, septet, J=6.2 Hz), 3.00 (2H, q, J=7.6 Hz), 1.30 (3H, t, J=7.6 Hz), 1.13 (2H, m), 0.97 (6H, d, J=6.2 Hz), 0.87 (2H, m).

4-[4-(1-Isopropoxycyclopropyl)-3-ethyl-phenylethynyl]-benzoic acid (Compound 97, General Formula 2)

Using General Procedure I; a solution of ethyl 4-[4-(1-isopropoxycyclopropyl)-3-ethyl-phenylethynyl]-benzoate (Compound 95, 110.0 mg, 0.29 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up and isolation by HPLC (partisil 10-pac, 10% $H_2O/CH_3CN$) afforded the title compound as a colorless solid.

$^1$H NMR (d$_6$-acetone) δ: 8.06 (2H, d, J=8.2 Hz), 7.67 (2H, d, J=8.2 Hz), 7.49 (1H, s), 7.40–7.34 (2H, m), 3.61 (1H, septet, J=6.2 Hz), 3.01 (2H, q, J=7.6 Hz), 1.29 (3H, t, J=7.6 Hz), 1.08 (2H, m), 0.93 (6H, d, J=6.2 Hz), 0.88 (2H, m).

{4-[4-(1-Isopropoxycyclopropyl)-3-ethyl-phenylethynyl]-phenyl}-acetic acid (Compound 98, General Formula 2)

Using General Procedure I; a solution of methyl {4-[4-(1-isopropoxycyclopropyl)-3-ethyl-phenylethynyl]- phenyl}-acetate (Compound 96, 156.0 mg, 0.41 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up and isolation by HPLC (partisil 10-pac, 10% $H_2O$/$CH_3CN$) afforded 85.0 mg (57%) of the title compound.

$^1$H NMR (CDCl$_3$) δ: 7.54–7.48 (3H, m), 7.34–7.27 (4H, m), 3.68 (2H, s), 3.66 (1H, septet, J=6.2 Hz), 3.03 (2H, q, J=7.6 Hz), 1.33 (2H, t, J=7.6 Hz), 1.17 (2H, m), 1.01 (6H, d, J=6.2 Hz), 0.90 (2H, m).

(4-Bromo-3-isopropyl-phenoxy)-triisopropyl-silane (Intermediate 96)

To a solution of 4-bromo-3-isopropylphenol (880.0 mg, 4.09 mmols) and imidazole (417.0 mg, 6.13 mmols) in 10 mL DMF was added chloro-triisopropylsilane (946.0 mg, 4.90 mmols). After stirring overnight at room temperature the solution was diluted with $H_2O$ and extracted with EtOAc. The combined organic layers were washed with $H_2O$ and saturated aqueous NaCl before being dried (MgSO$_4$) and concentrated under reduced pressure. The title compound, 1.30 g (92%), was isolated by column chromatography (1–2% EtOAc-hexanes) as a colorless oil.

$^1$H NMR (CDCl$_3$) δ: 7.34 (1H, d, J=8.5 Hz), 6.81 (1H, d, J=2.9 Hz), 6.59 (1H, dd, J=2.9, 8.5 Hz), 3.31 (1H, septet, J=7.0 Hz), 1.33–1.21 (3H, m), 1.24 (6H, d, J=7.0 Hz), 1.13 (18H, d, J=7.0 Hz).

Ethyl 2-isopropyl-4-triisopropylsilanyloxy-benzoate (Intermediate 97)

To a solution of (4-bromo-3-isopropyl-phenoxy)-triisopropyl-silane (Intermediate 96, 1.3 g, 3.8 mmols) in 15 mL Et$_2$O cooled to −78° C. was added 4.9 mL of tert-butyllithium in pentane (532.0 mg, 8.3 mmols; 1.7 M). After stirring for 30 minutes ethyl chloroformate (832.0 mg, 7.8 mmols) was added. The resulting solution was warmed to room temperature and quenched by the addition of saturated aqueous NH$_4$Cl. The mixture was extracted with EtOAc and the combined organic layers dried (MgSO$_4$) concentrated under reduced pressure and the residue chromatographed (4% EtOAc-hexanes) to give 1.09 g (85%) of the title compound as a colorless oil.

$^1$H NMR (CDCl$_3$) δ: 7.72 (1H, d, J=8.5 Hz), 6.87 (1H, d, J=2.3 Hz), 6.69 (1H, dd, J=2.3, 8.5 Hz), 3.88 (1H, septet; J=7.1 Hz), 4.30 (2H, q, J=7.1 Hz), 1.36 (3H, t, J=7.1 Hz), 1.31–1.17 (9H, m), 1.09 (18H).

[4-(1-Ethoxyvinyl)-3-isopropyl-phenoxy]-triisopropyl-silane (Intermediate 98)

Using General Procedure 1; ethyl 2-isopropyl-4-triisopropylsilanyloxy-benzoate (Intermediate 97, 450.0 mg, 1.34 mmols) and 2.0 mL of Tebbe's Reagent (398.0 mg, 1.40 mmols) afforded the title compound after column chromatography (100% hexanes).

$^1$H NMR (CDCl$_3$) δ: 7.11 (1H, d, J=8.2 Hz), 6.78 (1H, d, J=2.3 Hz), 6.63 (1H, dd, J=2.3, 8.2 Hz), 4.23 (1H, d, J=1.7 Hz), 4.10 (1H, d, J=1.7 Hz), 3.86 (2H, q, J=7.0 Hz), 3.16 (1H, septet, J=7.0 Hz), 1.35 (3H, t, J=7.1 Hz), 1.28–1.19 (3H, m), 1.19 (6H, d, J=7.0 Hz), 1.11 (18H).

[4-(1-Ethoxycyclopropyl)-3-isopropyl-phenoxy]-triisopropyl-silane (Intermediate 99)

Using General Procedure 2; [4-(1-ethoxyvinyl)-3-isopropyl-phenoxy]-triisopropyl-silane (Intermediate 98, 300.0 mg, 0.83 mmols), Et$_2$Zn (325.0 mg, 2.63 mmols), and CH$_2$I$_2$ (704.0 mg, 2.63 mmols) in 5.0 mL Et$_2$O afforded 270.0 mg (86%) of the title compound as a colorless oil after chromatography (0.5–2.5% EtOAc-hexanes).

$^1$H NMR (CDCl$_3$) δ: 7.06 (1H, d, J=8.2 Hz), 6.81 (1H, d, J=2.6 Hz), 6.59 (1H, dd, J=2.6, 8.2 Hz), 3.76 (1H, septet, J=7.0 Hz), 3.25 (2H, q, J=7.0 Hz), 1.30–1.20 (3H, m), 1.19 (6H, d, J=7.0 Hz), 1.15 (2H, m), 1.10 (18H), 1.02 (2H, t, J=7.0 Hz), 0.82 (2H, m).

4-(1-Ethoxycyclopropyl)-3-isopropyl-phenol (Intermediate 100)

To a solution of [4-(1-ethoxycyclopropyl)-3-isopropyl-phenoxy]-triisopropyl-silane (Intermediate 99, 360.0 mg, 0.96 mmol) in 3 mL THF at 0° C. was added tetrabutylammonium fluoride (625.0 mg, 2.39 mmols, 2.4 mL of a 1 M solution in THF). The solution was stirred at 0° C. for 30 minutes and then quenched by the addition of $H_2O$. The mixture was extracted with EtOAc and the combined organic layers were washed with $H_2O$ and saturated aqueous NaCl before being dried (MgSO$_4$) and concentrated under reduced pressure. The title compound (180 mg, 86%) was isolated from the residue by column chromatography (4–10% EtOAc-hexanes) as a colorless solid.

$^1$H NMR (CDCl$_3$) δ: 7.13 (1H, d, J=8.2 Hz), 6.79 (1H, d, J=2.6 H), 6.57 (1H, dd, J=2.6, 8.2 Hz), 5.48 (1H, s), 3.79 (1H, septet, J=7.0 Hz), 3.32 (2H, q, J=7.0 Hz), 1.21 (6H, d, J=7.0 Hz), 1.12 (2H, m), 1.05 (3H, t, J=7.0 Hz), 0.84 (2H, m).

4-(1-Ethoxycyclopropyl)-3-isopropyl-phenyl 1,1,1-trifluoromethansulfonate (Intermediate 101)

A solution of 4-(1-ethoxycyclopropyl)-3-isopropyl-phenol (Intermediate 100, 172.0 mg, 0.78 mmol) in 5 mL of CH$_2$Cl$_2$ was cooled to 0° C. and to it was added 2-[N,N-bis(trifluoromethylsulfonyl)amino]-5-chloropyridine (321.0 mg, 0.82 mmol) and triethylamine (240.0 mg, 2.4 mmols). The resulting solution was warmed to room temperature and stirred overnight. The reaction was quenched by the addition of $H_2O$ and the mixture extracted with EtOAc and the combined organic layers were washed with 10% aqueous HCl, saturated aqueous NaHCO$_3$, $H_2O$, and saturated aqueous NaCl. The solution was dried (MgSO$_4$) and concentrated under reduced pressure. The title compound was isolated by column chromatography (2–4% EtOAc-hexanes) as a colorless oil, 240.0 mg, 87%.

$^1$H NMR (CDCl$_3$) δ: 7.31 (1H, d, J=8.6 Hz), 7.18 (1H, d, J=2.6 Hz), 7.00 (1H, dd, J=2.6, 8.6 Hz), 3.87 (1H, septet, J=7.0 Hz), 2.38 (2H, q, J=7.0 Hz), 1.24 (6H, d, J=7.0 Hz), 1.15 (2H, m), 1.04 (3H, t, J=7.0 Hz), 0.86 (2H, m).

[4-(1-Ethoxycyclopropyl)-3-isopropyl-phenylethynyl]-trimethylsilane (Intermediate 102)

Using General Procedure D; 4-(1-ethoxycyclopropyl)-3-isopropyl-phenyl 1,1,1-trifluoromethansulfonate (Intermediate 101, 240.0 mg, 0.68 mmol) in triethylamine (2 mL) and DMF (6 mL) was sparged with argon for 5 minutes. Trimethylsilylacetylene (0.70 g, 7.1 mmols) was then added followed by dichlorobis-(triphenylphosphine)palladium(II) (38.0 mg, 0.05 mmol). The resulting reaction mixture was heated to 95° C. for 5 d. The title compound, 200.0 mg (99%), was isolated by chromatography (0–2% EtOAc-hexanes) as an orange oil.

$^1$H NMR (CDCl$_3$) δ: 7.43 (1H, d, J=1.7 Hz), 7.25 (1H, dd, J=1.7, 7.9 Hz), 7.16 (1H, d, J=7.9 Hz), 3.80 (1H, septet, J=6.8 Hz), 3.26 (2H, q, J=7.0 Hz), 1.24 (6H, d, J=6.8 Hz), 1.24–1.10 (2H, m), 1.03 (3H, t, J=7.0 Hz), 0.87 (2H, s), 0.26 (9H, s).

1-(1-Ethoxycyclopropyl)-4-ethnyl-2-isopropylbenzene (Intermediate 103)

Using General Procedure E; [4-(1-ethoxycyclopropyl)-3-isopropyl-phenylethynyl]-trimethylsilane (Intermediate 102, 210.0 mg, 0.70 mmol) in methanol (10 mL) was treated with potassium carbonate (100.0 mg, 0.72 mmol) and stirred overnight at ambient temperature. The crude alkyne was used directly in the next reaction.

$^1$H NMR (CDCl$_3$) δ: 7.47 (1H, d, J=1.7 Hz), 7.23 (1H, dd, J=1.7, 7.6 Hz), 7.19 (1H, d, J=7.6 Hz), 3.80 (1H, septet, J=7.0 Hz), 3.27 (1H, q, J=7.0 Hz), 3.07 (1H, s), 1.23 (6H, d, J=7.0 Hz), 1.13 (2H, m), 1.03 (3H, t, J=7.0 Hz), 0.85 (2H, m).

Ethyl 4-[4-(1-ethoxycyclopropyl)-3-isopropyl-phenylethynyl]-benzoate (Compound 99, General Formula 2)

Using General Procedure F; 1-(1-ethoxycyclopropyl)-4-ethynyl-2-isopropylbenzene (Intermediate 103, 50.0 mg, 0.22 mmol) and ethyl-4-iodo benzoate (Reagent A, 60.0 mg, 0.22 mmol) in triethylamine (5 mL) was treated with copper (I)iodide (14.0 mg, 0.07 mmol) and sparged with argon for 5 minutes. Dichlorobis(triphenylphosphine)-palladium(II) (51 mg, 0.07 mmol) was added and the reaction mixture was stirred overnight at room temperature. Column chromatography (1–2% EtOAc-hexanes) afforded 28.0 mg (34%) of the title compound.

$^1$H NMR (CDCl$_3$) δ: 8.01 (2H, d, J=8.2 Hz), 7.59 (2H, d, J=8.2 Hz), 7.51 (1H, d J=1.7 Hz), 7.28 (1H, dd, J=1.7, 7.9 Hz), 7.21 (1H, d, J=7.9 Hz), 4.38 (2H, q, J=7.1 Hz), 3.83 (1H, septet, J=6.7 Hz), 3.29 (2H, q, J=7.0 Hz), 1.40 (3H, t, J=7.1 Hz), 1.26 (6H, d, J=6.7 Hz), 1.14 (2H, m), 1.04 (3H, t, J=7.0 Hz), 0.87 (2H, m).

Methyl {4-[4-(1-ethoxycyclopropyl)-3-isopropyl-phenylethynyl]-phenyl}-acetate (Compound 100, General Formula 2)

Using General Procedure F; 1-(1-ethoxycyclopropyl)-4-ethynyl-2-isopropylbenzene (Intermediate 103, 120.0 mg, 0.52 mmol) and methyl-(4-iodophenyl)-acetate (Reagent B, 150.0 mg, 0.52 mmol) in triethylamine (8 mL) was treated with copper(I)iodide (32.0 mg, 0.17 mmol) and sparged with argon for 5 minutes. Dichlorobis(triphenylphosphine) palladium(II) (121 mg, 0.17 mmol) was added and the reaction mixture was stirred overnight at room temperature. Column chromatography (2–5% EtOAc-hexanes) afforded 140.0 mg (71%) of the title compound as a pale-yellow oil.

$^1$H NMR (CDCl$_3$) δ: 7.53 (3H, m), 7.31–7.23 (4H, m), 3.86 (1H, septet, J=6.7 Hz), 3.73 (3H, s), 3.67 (2H, s), 3.33 (2H, q, J=7.0 Hz), 1.30 (6H, d, J=6.7 Hz), 1.15 (2H, m), 1.08 (3H, t, J=7.0 Hz), 0.90 (2H, m).

4-[4-(1-Ethoxycyclopropyl)-3-isopropyl-phenylethnyl]-benzoic acid (Compound 101, General Formula 2)

Using General Procedure I; A solution of ethyl 4-[4-(1-ethoxycyclopropyl)-3-isopropyl-phenylethynyl]-benzoate (Compound 99, 28.0 mg, 0.07 mmol) in ethanol (2 mL) and tetrahydrofuran (2 mL) was treated with NaOH (80.0 mg, 2.0 mmols, 2.0 mL of a 1N aqueous solution) and stirred overnight at room temperature. Work-up afforded 24 mg (92%) the title compound as a pale-yellow solid.

$^1$H NMR (d$_6$-acetone) δ: 8.06 (2H, d, J=8.2 Hz), 7.66 (2H, d, J=8.2 Hz), 7.58 (1H, s), 7.33 (2H, m), 3.87 (1H, m), 2.27 (2H, q, J=7.0 Hz), 1.26 (6H, d, J=6.7 Hz), 1.09 (2H, m), 0.99 (3H, t, J=7.0 Hz), 0.88 (2H, m).

{4-[4-(1-Ethoxycyclopropyl)-3-isopropyl-phenylethynyl]-phenyl}-acetic acid (Compound 102, General Formula 2)

Using General Procedure I; a solution of methyl {4-[4-(1-ethoxycyclopropyl)-3-isopropyl-phenylethynyl]-phenyl}-acetate (Compound 100, 130.0 mg, 0.35 mmol) in ethanol (5 mL) and tetrahydrofuran (5 mL) was treated with NaOH (120.0 mg, 3.0 mmols, 3.0 mL of a 1N aqueous solution) and stirred at 50° C. for 4 h. Work-up and isolation by HPLC (Partisil 10-pac, 10% H$_2$O/CH$_3$CN) afforded 88.0 mg (70%) of the title compound.

$^1$H NMR (CDCl$_3$) δ: 7.50 (3H, m), 7.28–7.19 (4H, m), 3.82 (1H, m), 3.65 (2H, s), 3.29 (2H, q, J=7.0 Hz), 1.25 (6H, d, J=6.7 Hz), 1.14 (2H, m), 1.04 (3H, t, J=7.0 Hz), 0.86 (2H, m).

4-Bromo-3-tert-butylphenol (Intermediate 104)

To a mixture of 3-tert-butyl-methoxy benzene (1.00 g, 6.09 mmols) in CCl$_4$ (20 mL), molecular sieves, and silica gel was added N-bromosuccinimide (1.19 g, 6.70 mmols). This mixture was stirred at 55° C. for 48 h. The resulting mixture was cooled to room temperature, filtered to remove the solids, and the filtrate diluted with EtOAc. This solution was washed with H$_2$O, 10% aqueous HCl, H$_2$O, saturated aqueous NaHCO$_3$ and saturated aqueous NaCl before being dried (MgSO$_4$) and concentrated under reduced pressure. Column chromatography (2.5% EtOAc-hexanes) afforded 1.15 g (78%) of a 3 to 1 mixture of 1-bromo-2-tert-butyl methoxy benzene and 1-bromo-2-methoxy-4-tert-butyl benzene as a colorless oil.

A solution of the isomeric methoxy compounds in 10 mL of CH$_2$Cl$_2$ was cooled to 0° C. and treated with a solution (18.5 mL) of BBr$_3$ in CH$_2$Cl$_2$ (4.63 g, 18.5 mmols). After 10 minutes the solution was warmed to room temperature, stirred for 1 h, and then quenched with H$_2$O. The mixture was extracted with EtOAc and the combined organic layers washed with saturated aqueous NaCl, dried (MgSO$_4$), and concentrated under reduced pressure. The title compound was isolated, 1.17 g (59%), by column chromatography (2.5–5% EtOAc-hexanes).

$^1$H NMR (CDCl$_3$) δ: 7.39 (1H, d, J=8.5 Hz), 6.96 (1H, d, J=2.9 Hz), 6.54 (1H, dd, J=2.9, 8.5 Hz), 1.46 (9H, s).

(4-Bromo-3-tert-butyl-phenoxy)-triisopropyl-silane (Intermediate 105)

To a solution of 4-bromo-3-tert-butylphenol (Intermediate 104, 1.17 g, 5.10 mmols) and imidazole (520.0 mg, 7.65 mmols) in 10 mL DMF was added chloro-triisopropylsilane (1.18 g, 6.10 mmols). After stirring overnight at room temperature the solution was diluted wirth H$_2$O and extracted with EtOAc. The combined organic layers were washed with H$_2$O and saturated aqueous NaCl before being dried (MgSO$_4$) and concentrated under reduced pressure. The title compound, 1.80 g (92%), was isolated by column chromatography (0–1.5% EtOAc-hexanes) as a colorless oil.

$^1$H NMR (CDCl$_3$) δ: 7.38 (1H, d, J=8.0 Hz), 6.97 (1H, d, J=2.9 Hz), 6.56 (1H, dd, J=2.9, 8.5 Hz), 1.47 (9H, s), 1.29–1.24 (3H, m), 1.09 (18H, d, J=6.7 Hz).

Ethyl 2-tert-butyl-4-triisopropylsilanyloxy-benzoate (Intermediate 106)

To a solution of (4-bromo-3-tert-butyl-phenoxy)-triisopropyl-silane (Intermediate 105, 1.00 g, 2.60 mmols) in 15 mL Et$_2$O cooled to −78° C. was added 3.6 mL of tert-butyllithium, 1.7 M in pentane (395.0 mg, 6.2 mmols).

After stirring for 30 minutes ethyl chloroformate (607.6 mg, 5.6 mmols) was added. The resulting solution was warmed to room temperature and quenched by the addition of saturated aqueous NH$_4$Cl. The mixture was extracted with EtOAc and the combined organic layers dried (MgSO$_4$) concentrated under reduced pressure The residue was chromatographed (2–5% EtOAc-hexanes) to give 1.23 g (88%) of the title compound as a colorless oil.

$^1$H NMR (CDCl$_3$) δ: 7.24 (1H, d, J=8.2 Hz), 6.97 (1H, d, J=2.6 Hz), 6.69 (1H, dd, J=2.6, 8.2 Hz), 4.33 (2H, q, J=7.1 Hz), 1.39 (9H, s), 1.37 (3H, t, J=7.1 Hz), 1.29–1.21 (3H, m), 1.10 (18H, d, J=6.7 Hz).

[4-(1-Ethoxyvinyl)-3-tert-butyl-phenoxy]-triisopropyl-silane (Intermediate 107)

Using General Procedure 1; ethyl 2-tert-butyl-4-triisopropylsilanyloxy-benzoate (Intermediate 106, 1.30 g, 3.44 mmols) and 7.2 mL of Tebbe's Reagent (1.03 g, 3.61 mmols) were reacted. The reaction required 7 days at room temperature to go to completion. The standard work-up afforded 1.29 g (78%) of the title compound after column chromatography (1–2% EtOAc-hexanes).

$^1$H NMR (CDCl$_3$) δ: 7.05 (1H, d, J=8.2 Hz), 6.94 (1H, d, J=2.6 Hz), 6.63 (1H, dd, J=2.6, 8.2 Hz), 4.20 (1H, d, J=1.7 Hz), 4.08 (1H, d, J=1.7 Hz), 3.83 (2H, q, J=7.1 Hz), 1.37 (9H, s), 1.36 (3H, t, J=7.1 Hz), 1.27–1.20 (3H, m), 1.10 (18H, d, J=6.7 Hz).

[4-(1-Ethoxycyclopropyl)-3-tert-butyl-phenoxy]-triisopropyl-silane (Intermediate 108)

Using General Procedure 2; [4-(1-ethoxyvinyl)-3-tert-butyl-phenoxy]-triisopropyl-silane (Intermediate 107, 320.0 mg, 0.85 mmols), Et$_2$Zn (325.0 mg, 2.63 mmols), and CH$_2$I$_2$ (704.0 mg, 2.63 mmols) in 5.0 mL Et$_2$O afforded 257.0 mg (66%) of the title compound as a colorless oil after chromatography (1–2.5% EtOAc-hexanes).

$^1$H NMR (CDCl$_3$) δ: 7.24 (1H, d, J=8.5 Hz), 7.06 (1H, d, J=2.6 Hz), 6.60 (1H, dd, J=2.6, 8.5 Hz), 3.24 (2H, q, J=7.1 Hz), 1.50 (9H, s), 1.29–1.21 (3H, m), 1.11 (18H, d, J=6.7 Hz), 1.04 (3H, t, J=7.1 Hz).

4-(1-Ethoxycyclopropyl)-3-tert-butyl-phenol (Intermediate 109)

To a solution of [4-(1-ethoxycyclopropyl)-3-tert-butyl-phenoxy]-triisopropyl-silane (Intermediate 108, 600.0 mg, 1.54 mmol) in 3 mL THF at 0° C. was added tetrabutylammonium fluoride (802.8.0 mg, 3.07 mmols; 3.1 mL of a 1 M solution in THF). The solution was stirred at 0° C. for 30 minutes and then quenched by the addition of H$_2$O. The mixture was extracted with EtOAc and the combined organic layers were washed with H$_2$O and saturated aqueous NaCl before being dried (MgSO$_4$) and concentrated under reduced pressure. The title compound (400 mg, 88%) was isolated from the residue by column chromatography (4–10% EtOAc-hexanes) as a colorless solid.

$^1$H NMR (CDCl$_3$) δ: 7.29 (1H, d, J=8.2 Hz), 7.01 (1H, d, J=2.6 Hz), 6.57 (1H, dd, J=2.6, 8.2 Hz), 3.29 (2H, q, J=7.1 Hz), 1.59 (9H, s), 1.08–1.04 (7H, m).

4-(1-Ethoxycyclopropyl)-3-tert-butyl-phenyl 1,1,1-trifluoromethansulfonate (Intermediate 110)

A solution of 4-(1-ethoxycyclopropyl)-3-tert-butyl-phenol (Intermediate 109, 400.0 mg, 1.71 mmol) in 10 mL of CH$_2$Cl$_2$ was cooled to 0° C. and to it was added 2-[N,N-bis(trifluoromethylsulfonyl)amino]-5-chloropyridine (705.0 mg, 1.79 mmol) and triethylamine (522.0 mg, 5.1 mmols). The resulting solution was warmed to room temperature and stirred overnight. The reaction was quenched by the addition of H$_2$O and the mixture extracted with EtOAc and the combined organic layers were washed with 10% aqueous HCl, saturated aqueous NaHCO$_3$, H$_2$O, and saturated aqueous NaCl. The solution was dried (MgSO$_4$) and concentrated under reduced pressure. The title compound was isolated by column chromatography (2–4% EtOAc-hexanes) as a colorless oil, 542.0 mg (87%).

$^1$H NMR (CDCl$_3$) δ: 7.48 (1H, d, J=8.5 Hz), 7.39 (1H, d, J=2.6 Hz), 7.01 (1H, dd, J=2.6, 8.5 Hz), 3.26 (2H, q, J=7.1 hz), 1.52 (9H, s), 1.12 (2H, bs), 1.08–1.04 (5H, m).

[4-(1-Ethoxycyclopropyl)-3-tert-butyl-phenylethynyl]-trimethylsilane (Intermediate 111)

Using General Procedure D; 4-(1-ethoxycyclopropyl)-3-tert-butyl-phenyl 1,1,1-trifluoromethansulfonate (Intermediate 110, 260.0 mg, 0.71 mmol) in triethylamine (4 mL) and DMF (6 mL) was sparged with argon for 5 minutes. Trimethylsilylacetylene (0.70 g, 7.1 mmols) was then added followed by dichlorobis-(triphenylphosphine)palladium(II) (40.0 mg, 0.06 mmol). The resulting reaction mixture was heated to 95° C. for 18 hours. The title compound, 215.0 mg (96%), was isolated by chromatography (0–2% EtOAc-hexanes) as an orange oil.

$^1$H NMR (CDCl$_3$) δ: 7.63 (1H, d, J=1.7 Hz), 7.32 (1H, d, J=7.9 Hz), 7.19 (1H, dd, J=1.7, 7.9 Hz), 3.24 (2H, q, J=7.1 Hz), 1.51 (9H, s), 1.10 (2H, bs), 1.06–1.01 (5H, m), 0.25 (9H, s).

1-(1-Ethoxycyclopropyl)-4-ethynyl-2-tert-butylbenzene (Intermediate 112)

Using General Procedure E; [4-(1-ethoxycyclopropyl)-3-tert-butyl-phenylethynyl]-trimethylsilane (Intermediate 111, 215.0 mg, 0.69 mmol) in methanol (10 mL) was treated with potassium carbonate (80.0 mg, 0.58 mmol) and stirred overnight at ambient temperature. The crude alkyne, 169 mg, was used directly in the next reaction.

$^1$H NMR (CDCl$_3$) δ: 7.68 (1H, d, J=1.8 Hz), 7.36 (1H, d, J=7.9 Hz), 7.23 (1H, dd, J=1.8, 7.9 Hz), 3.26 (2H, q, J=7.1 Hz), 3.06 (1H, s), 1.51 (9H, s), 1.11 (2H, bs), 1.07–1.02 (5H, m).

Ethyl 4-[4-(1-ethoxycyclopropyl)-3-tert-butyl-phenylethynyl]-benzoate (Compound 103, General Formula 2)

Using General Procedure F; 1-(1-ethoxycyclopropyl)-4-ethynyl-2-tert-butylbenzene (Intermediate 112, 70.0 mg, 0.30 mmol) and ethyl-4-iodo benzoate (Reagent A, 85.0 mg, 0.30 mmol) in triethylamine (5 mL) was treated with copper (I)iodide (19.0 mg, 0.01 mmol) and sparged with argon for 5 minutes. Dichlorobis(triphenylphosphine)-palladium(II) (70 mg, 0.01 mmol) was added and the reaction mixture was stirred overnight at room temperature. Column chromatography (1–2% EtOAc-hexanes) afforded 70.0 mg (73%) of the title compound.

$^1$H NMR (CDCl$_3$) δ: 8.02 (2H, d, J=8.8 Hz), 7.72 (1H, d, J=1.7 Hz), 7.59 (2H, d, J=8.8 Hz), 7.40 (1H, d, J=7.9 Hz), 7.28 (1H, dd, J=1.7, 7.9 Hz), 4.39 (2H, q, J=7.1 Hz), 3.28 (2H, q, J=7.1 Hz), 1.55 (9H, s), 1.40 (3H, t, J=7.1 Hz), 1.12 (2H, bs), 1.08–1.04 (5H, m).

Methyl {4-[4-(1-ethoxycyclopropyl)-3-tert-butyl-phenylethynyl]-phenyl}-acetate (Compound 104, General Formula 2)

Using General Procedure F; 1-(1-ethoxycyclopropyl)-4-ethynyl-2-tert-butylbenzene (Intermediate 112, 95.0 mg, 0.39 mmol) and methyl-(4-iodophenyl)-acetate (Reagent B, 108.0 mg, 0.39 mmol) in triethylamine (8 mL) was treated with copper(I)iodide (25.0 mg, 0.13 mmol) and sparged with argon for 5 minutes. Dichlorobis(triphenylphosphine) palladium(II) (91 mg, 0.13 mmol) was added and the reaction mixture was stirred overnight at room temperature. Column chromatography (2–5% EtOAc-hexanes) afforded 100.0 mg (72%) of the title compound.

$^1$H NMR (CDCl$_3$) δ: 7.70 (1H, d, J=1.5 Hz), 7.50 (2H, d, J=7.9 Hz), 7.38 (1H, d, J=7.9 Hz), 7.27 (3H, m), 3.70 (3H, s), 3.64 (2H, s), 3.28 (2H, q, J=7.1 Hz), 1.54 (9H, s), 1.12 (2H, bs), 1.08–1.03 (5H, m).

4-[4-(1-Ethoxycyclopropyl)-3-tert-butyl-phenylethynyl]-benzoic acid (Compound 105, General Formula 2)

Using General Procedure I; a solution of ethyl 4-[4-(1-ethoxycyclopropyl)-3-tert-butyl-phenylethynyl]-benzoate (Compound 103, 70.0 mg, 0.18 mmol) in ethanol (3 mL) and tetrahydrofuran (3 mL) was treated with NaOH (240.0 mg, 6.0 mmols, 3.0 mL of a 2N aqueous solution) and stirred overnight at room temperature. Work-up afforded 40 mg (62%) the title compound as a pale-yellow solid.

$^1$H NMR (d$_6$-acetone) δ: 8.06 (2H, d, J=8.7 Hz), 7.76 (1H, d, J=1.8 Hz), 7.67 (2H, d, J=8.7 Hz), 7.50 (1H, d, J=7.9 Hz), 7.33 (1H, dd, J=1.8, 7.9 Hz), 3.28 (2H, q, J=7.3 Hz), 1.54 (9H, s), 1.13 (2H, bs), 1.10 (2H, m), 1.02 (3H, t, J=7.3 Hz).

{4-[4-(1-Ethoxycyclopropyl)-3-tert-butyl-phenylethynyl]-phenyl}-acetic acid (Compound 106, General Formula 2)

Using General Procedure I; a solution of methyl {4-[4-(1-ethoxycyclopropyl)-3-tert-butyl-phenylethynyl]-phenyl}-acetate (Compound 104, 100.0 mg, 0.26 mmol) in ethanol (4 mL) and tetrahydrofuran (4 mL) was treated with NaOH (240.0 mg, 6.0 mmols, 3.0 mL of a 2N aqueous solution) and stirred at 50° C. for 4 h. Work-up and isolation by HPLC (Partisil 10-pac, 10% H$_2$O/CH$_3$CN) afforded 70.0 mg (73%) of the title compound.

$^1$H NMR (CDCl$_3$) δ: 7.73 (1H, d, J=1.3 Hz), 7.53 (2H, d, J=7.9 Hz), 7.41 (1H, d, J=7.9 Hz), 7.28 (3H, m), 3.69 (2H, s), 3.31 (2H, q, J=7.1 Hz), 1.56 (9H, s), 1.15 (2H, bs), 1.11–1.05 (5H, m).

1-(4-Bromophenyl)-cyclopropanecarbonitrile (Intermediate 113)

To a 50% aqueous NaOH solution (40.0 g, wt/wt) was added benzyl triethylammonium chloride (1.0 g, 4.4 mmols), 4-bromobenzonitrile (19.6 g, 0.10 mol), and 1,2-dibromoethane (56.4 g, 0.30 mol). The mixture was stirred overnight at room temperature and then diluted with 100 mL of H$_2$O. This mixture was extracted with EtOAc and the combined extracts were washed with saturated aqueous NaHS$_2$O$_3$, H$_2$O, and saturated aqueous NaCl before being dried (MgSO$_4$) and concentrated under reduced pressure. Bulb-to-bulb distillation afforded 18.8 g (85%) of the title compound as a colorless solid.

$^1$H NMR (CDCl$_3$) δ: 7.48 (2H, d, J=8.6 Hz), 7.17 (2H, d, J=8.6 Hz), 1.75 (2H, dd, J=5.2, 7.6 Hz), 1.39 (2H, dd, J=5.2, 7.6 Hz).

1-(4-Bromophenyl)-cyclopropanecarboxylic acid (Intermediate 114)

To a solution of KOH (6.06 g, 0.11 mol) in 10 mL of H$_2$O was added 40 mL of ethylene glycol and 1-(4-bromophenyl)-cyclopropanecarbonitrile (Intermediate 113, 10.0 g, 0.45 mol). This solution was heated to 135–140° C. for 4 h, cooled to room temperature, and then poured into a mixture of 100 mL ice and 10% aqueous HCl. The resulting mixture was allowed to stand overnight at 5° C., the solid was collected by filtration and washed with H$_2$O. The colorless solid was dried under reduced pressure to give 10.6 g (97%) of the title compound.

$^1$H NMR (CDCl$_3$) δ: 7.43 (2H, d, J=8.5 Hz), 7.21 (2H, d, J=8.5 Hz), 1.68 (2H, dd, J=4.0, 7.1 Hz), 1.24 (2H, dd, J=4.0, 7.1 Hz).

Tert-butyl [1-(4-bromophenyl)-cyclopropyl]-carbamate (Intermediate 115)

A solution of 1-(4-bromophenyl)-cyclopropanecarboxylic acid (Intermediate 114, 2.32 g, 9.62 mmols), diphenylphosphoryl azide (2.65 g, 9.62 mmols), triethylamine (973.0 mg, 9.62 mmols) in 40 mL tert-BuOH (distilled from Na°) was heated to reflux for 17 h. The solution was concentrated under reduced pressure and the residue dissolved in EtOAc and washed with 5% aqueous HCl, H$_2$O, saturated aqueous NaHCO$_3$, and saturated aqueous NaCl before being dried over MgSO$_4$. Concentration of the dry solution under reduced pressure and column chromatography (5–10% EtOAc-hexanes) afforded 2.01 g (67%) of the title compound as a colorless solid.

$^1$H NMR (CDCl$_3$) δ: 7.39 (2H, d, J=8.3 Hz), 7.08 (2H, d, J=8.3 Hz), 5.35 (1H, bs), 1.43 (9H, s), 1.26 (2H, m), 1.17 (2H, m).

1-(4-Bromophenyl)-cyclopropylamine (Intermediate 116)

To a solution of tert-butyl [1-(4-bromophenyl)-cyclopropyl]-carbamate (Intermediate 115, 1.08 g, 3.40 mmols) in 20 mL MeOH and 20 mL THF was added 20 mL of 3M aqueous HCl. The solution was warmed to 35° C. for 3 hours and then stirred for 17 h at 25° C. The reaction was quenched by adjusting the pH of the solution to 12 with 3M aqueous NaOH. The mixture was extracted with Et$_2$O and the combined organic layers were washed with H$_2$O and saturated aqueous NaCl before being dried (MgSO$_4$) and concentrated under reduced pressure. The title compound 613 mg (85%) was used without further purification.

$^1$H NMR (CDCl$_3$) δ: 7.43 (2H, d, J=8.3 Hz), 7.17 (2H, d, J=8.3 Hz), 1.89 (2H, bs), 1.07 (2H, m), 0.95 (2H, m).

N-[1-(4-bromophenyl)-cyclopropyl]-propionamide (Intermediate 117)

To a solution of 1-(4-bromophenyl)-cyclopropylamine (Intermediate 116, 84 mg, 0.4 mmol) in 4 mL CH$_2$Cl$_2$ at room temperature was added propionyl chloride (43.0 mg, 0.47 mmol) and pyridine (56.0 mg, 0.71 mmol). After stirring 17 hours at room temperature the reaction was quenched by the addition of H$_2$O and extracted with EtOAc. The combined extracts were washed with 10% aqueous HCl, saturated aqueous NaHCO$_3$, and saturated aqueous NaCl before being dried (MgSO$_4$) and concentrated under reduced pressure. The title compound 85.0 mg (67%), was isolated by column chromatography (20–50% EtOAc-hexanes) as a colorless solid.

$^1$H NMR (CDCl$_3$) δ: 7.48 (2H, d, J=8.5 Hz), 7.09 (2H, d, J=8.5 Hz), 6.40 (1H, s), 2.19 (2H, q, J=7.2 Hz), 1.18–1.24 (4H, m), 1.12 (3H, t, J=7.2 Hz).

[1-(4-Bromophenyl)-cyclopropyl]-propylamine (Intermediate 118)

To a solution of N-[1-(4-bromophenyl)-cyclopropyl]-propionamide (Intermediate 117, 85.0 mg, 0.32 mmol) in THF (5 mL) at 0° C. was added BH$_3$—Me$_2$S (48.0 mg, 0.63 mmol; 0.31 mL of a 2M solution in THF). The solution was heated to 55° C. for 17 hours, cooled to room temperature, saturated aqueous NaHCO$_3$ was added and the resulting mixture was stirred for 2 hours. This mixture was extracted with EtOAc and the combined organic layers were washed with H$_2$O and saturated aqueous NaCl before being dried (MgSO$_4$) and concentrated under reduced pressure. The title compound was isolated by column chromatography (10–30% EtOAc-hexanes).

$^1$H NMR (CDCl$_3$) δ: 7.42 (2H, d, J=8.5 Hz), 7.19 (2H, d, J=8.5 Hz), 2.46 (2H, t, J=7.3 Hz), 1.40 (2H, m), 0.98 (2H, m), 0.86 (5H, m).

Propyl-[1-(4-trimethylsilanylethynyl-phenyl)-cyclopropyl]-amine (Intermediate 119)

Using General Procedure D; [1-(4-bromophenyl)-cyclopropyl]-propylamine (Intermediate 118, 100.0 mg, 0.39 mmol) in triethylamine (8 mL) was treated with copper (I)iodide (13.0 mg, 0.06 mmol) and then sparged with argon for 5 minutes. Trimethylsilyl acetylene (0.70 g, 7.1 mmols) was then added followed by dichlorobis (triphenylphosphine)palladium(II) (48.0 mg, 0.06 mmol). The resulting reaction mixture was heated to 70° C. for 5 days. The title compound (80.0 mg, 75%) was isolated by chromatography (0–10% EtOAc-hexanes) as an orange oil.

$^1$H NMR (CDCl$_3$) δ: 7.41 (2H, d, J=8.5 Hz), 7.21 (2H, d, J=8.5 Hz), 2.45 (2H, t, J=7.3 Hz), 1.39 (2H, m), 0.98 (2H, m), 0.87 (2H, m), 0.84 (3H, t, J=7.3 Hz), 0.24 (9H, s).

[1-(4-Ethynylphenyl)-cyclopropyl]-propylamine (Intermediate 120)

Using General Procedure E; propyl-[1-(4-trimethylsilanylethynyl-phenyl)-cyclopropyl]-amine (Intermediate 119, 80.0 mg, 0.30 mmols) in methanol (8 mL) was treated with potassium carbonate (80.0 mg, 0.59 mmol) and stirred overnight at ambient temperature. The crude alkyne (58 mg, 100%) was used directly in the next reaction.

$^1$H NMR (CDCl$_3$) δ: 7.44 (2H, d, J=8.5 Hz), 7.24 (2H, d, J=8.5 Hz), 3.05 (1H, s), 2.46 (2H, t, J=7.3 Hz), 1.41 (2H, m), 1.00 (2H, m), 0.90 (2H, m), 0.86 (3H, t, J=7.3 Hz).

Ethyl 4-[4-(1-propylamino-cyclopropyl)-phenylethynyl]-benzoate (Compound 107, General Formula 2)

Using General Procedure F; [1-(4-ethynylphenyl)-cyclopropyl]-propylamine (Intermediate 120, 38.0 mg, 0.19 mmol) and ethyl-4-iodo benzoate (Reagent A, 58.0 mg, 0.21 mmol) in triethyl amine (6 mL) was treated with copper(I) iodide (8.0 mg, 0.04 mmol) and sparged with argon for 5 minutes. Dichlorobis(triphenylphosphine)palladium(II) (27 mg, 0.04 mmol) was added and the reaction mixture was stirred overnight at room temperature. Column chromatography (5–15% EtOAc-hexanes) afforded 40.0 mg (61%) of the title compound as an orange oil.

$^1$H NMR (CDCl$_3$) δ: 8.01 (2H, d, J=8.5 Hz), 7.57 (2H, d, J=8.5 Hz), 7.49 (2H, d, J=8.5 Hz), 7.28 (2H, d, J=8.5 Hz), 4.39 (2H, q, J=7.1 Hz), 2.49 (2H, t, J=7.3 Hz), 1.46 (2H, m), 1.41 (3H, t, J=7.1 Hz), 1.01 (2H, m), 0.89 (2H, m), 0.87 (3H, t, J=7.3 Hz).

4-[4-(1-Propylamino-cyclopropyl)-phenylethynyl]-benzoic acid (Compound 108, General Formula 2)

Using General Procedure I; a solution of ethyl 4-[4-(1-propylamino-cyclopropyl)-phenylethynyl]-benzoate (Compound 107, 40.0 mg, 0.12 mmol) in ethanol (3 mL) and tetrahydrofuran (3 mL) was treated with NaOH (160.0 mg, 4.0 mmols, 2.0 mL of a 2N aqueous solution) and stirred overnight at room temperature. Work-up afforded 25.0 mg (69%) of the title compound as a solid.

$^1$H NMR (d$_6$-DMSO) δ: 7.97 (2H, d, J=8.5 Hz), 7.65 (2H, d, J=8.5 Hz), 7.50 (2H, d, J=8.5 Hz), 7.36 (2H, d, J=8.5 Hz), 2.39 (2H, t, J=7.3 Hz), 1.37 (2H, m), 1.00 (2H, m), 0.93 (2H, m), 0.84 (3H, t, J=7.3 Hz).

[1-(4-Bromophenyl)-cyclopropyl]-dipropylamine (Intermediate 121)

To a solution of 1-(4-bromophenyl)-cyclopropylamine (Intermediate 116) in CH$_3$CN/HOAc (5 mL, 9:1, v/v) and THF 3 mL at 0° C. was added propionaldehyde (277.0 mg, 4.95 mmols) and NaCNBH$_3$ (153.0 mg, 2.47 mmols). The reaction was warmed to room temperature and after 5 hours quenched with H$_2$O. The pH of the solution was adjusted to 8–9 using aqueous NaOH and extracted with EtOAc. The combined extracts were washed with H$_2$O and saturated aqueous NaCl, dried (MgSO$_4$) and concentrated under reduced pressure. The title compound, 190.0 mg (56%), was isolated by column chromatography (2–5% EtOAc-hexanes).

$^1$H NMR (CDCl$_3$) δ: 7.42 (2H, d, J=8.3 Hz), 7.18 (2H, d, J=8.3 Hz), 2.39 (4H, t, J=7.3 Hz), 1.62–1.40 (4H, m), 0.96 (2H, m), 0.86 (6H, t, J=7.3 Hz), 0.80 (2H, m).

Dipropyl-[1-(4-trimethylsilanylethynyl-phenyl)-cyclopropyl]-amine (Intermediate 122)

Using General Procedure D; [1-(4-bromophenyl)-cyclopropyl]-dipropylamine (Intermediate 121, 150.0 mg, 0.50 mmol) in triethylamine (5 mL) was treated with copper (I)iodide (10.0 mg, 0.05 mmol) and then sparged with argon for 5 minutes. Trimethylsilyl acetylene (0.70 g, 7.1 mmols) was then added followed by dichlorobis (triphenylphosphine)palladium(II) (35.0 mg, 0.05 mmol). The resulting reaction mixture was heated to 70° C. for 5 d. The title compound was isolated by chromatography (0–3% EtOAc-hexanes).

$^1$H NMR (CDCl$_3$) δ: 7.35 (2H, d, J=8.3 Hz), 7.24 (2H, d, J=8.3 Hz), 2.39 (4H, t, J=7.3 Hz), 1.55–1.42 (4H, m), 0.96 (2H, m), 0.88–0.79 (8H, m), 0.25 (9H, s).

[1-(4-Ethynylphenyl)-cyclopropyl]-dipropylamine (Intermediate 123)

Using General Procedure E; dipropyl-[1-(4-trimethylsilanylethynyl-phenyl)-cyclopropyl]-amine (Intermediate 122, 45.0 mg, 0.14 mmols) in methanol (5 mL) was treated with potassium carbonate (50.0 mg, 0.37 mmol) and stirred overnight at ambient temperature. The crude alkyne (34 mg, 100%) was used directly in the next reaction.

$^1$H NMR (CDCl$_3$) δ: 7.42 (2H, d, J=8.3 Hz), 7.28 (2H, d, J=8.3 Hz), 2.40(4H, t, J=7.3 Hz), 1.53–1.40 (4H, m), 0.96 (2H, m), 0.90–0.79 (8H, m).

Ethyl 4-[4-(1-dipropylamino-cyclopropyl)-phenylethynyl]-benzoate (Compound 109, General Formula 2)

Using General Procedure F; [1-(4-ethynylphenyl)-cyclopropyl]-dipropylamine (Intermediate 123, 34.0 mg, 0.16 mmol) and ethyl-4-iodo benzoate (Reagent A, 59.0 mg, 0.21 mmol) in triethyl amine (6 mL) was treated with copper(I)iodide (13.0 mg, 0.07 mmol) and sparged with argon for 5 minutes. Dichlorobis(triphenylphosphine) palladium(II) (49 mg, 0.07 mmol) was added and the reaction mixture was stirred overnight at room temperature. Column chromatography (2–4% EtOAc-hexanes) afforded the title compound as a yellow oil.

$^1$H NMR (CDCl$_3$) δ: 8.03 (2H, d, J=8.2 Hz), 7.58 (2H, d, J=8.2 Hz), 7.49 (2H, d, J=8.2 Hz), 7.30 (2H, d, J=8.2 Hz), 4.39 (2H, q, J=7.1 Hz), 2.43 (4H, t, J=7.3 Hz), 1.52–1.42 (4H, m), 1.41 (3H, t, J=7.1 Hz), 0.99 (2H, m), 0.88–0.83 (8H, m).

4-[4-(1-Dipropylamino-cyclopropyl)-phenylethynyl]-benzoic acid (Compound 110, General Formula 2)

Using General Procedure I; a solution of ethyl 4-[4-(1-dipropylamino-cyclopropyl)-phenylethynyl]-benzoate (Compound 109, 51.0 mg, 0.13 mmol) in ethanol (3 mL) and tetrahydrofuran (3 mL) was treated with NaOH (80.0 mg, 2.0 mmols, 2.0 mL of a 1N aqueous solution) and stirred overnight at room temperature. Work-up afforded 32.0 mg (70%) of the title compound as a colorless solid.

$^1$H NMR (d$_6$-DMSO) δ: 7.98 (2H, d, J=8.3 Hz), 7.67 (6H, m), 3.05–2.89 (4H, m), 1.98 (2H, m), 1.72 (4H, m), 1.23 (2H, m), 0.88 (6H, t, J=7.3 Hz).

Benzyl-[1-(4-bromophenyl)-cyclopropyl]-amine (Intermediate 124) and Dibenzyl-[1-(4-bromophenyl)-cyclopropyl]-amine (Intermediate 125)

A solution of 1-(4-bromophenyl)-cyclopropylamine (Intermediate 116, 244.0 mg, 1.15 mmols) and benzyl bromide (255.0 mg, 1.50 mmols) in 4 mL DMF was stirred at 85° C. for 6 hours, cooled to room temperature and stirred overnight. The solution was diluted with H$_2$O and the pH adjusted to 8–9 with aqueous NaOH. The solution was extracted with EtOAc and the combined organic layers were washed with H$_2$O and saturated aqueous NaCl, dried (MgSO$_4$) and concentrated under reduced pressure. Column chromatography (5–10% EtOAc-Hexanes) afforded 110 mg (32%) of the N-benzyl amine.

$^1$H NMR (CDCl$_3$) δ: 7.48 (2H, d, J=8.4 Hz), 7.30–7.23 (7H, m), 3.68 (2H, s), 1.07 (2H, m), 0.93 (2H, m); and 100 mg (22%) of the N,N-dibenzyl amine, $^1$H NMR (CDCl$_3$) δ: 7.55 (2H, d, J=8.3 Hz), 7.40–7.19 (12H, m), 3.61 (4H, s), 0.87 (2H, m), 0.71 (2H, m).

Benzyl-[1-(4-trimethylsilanylethynyl-phenyl)-cyclopropyl]-amine (Intermediate 126)

Using General Procedure D; benzyl-[1-(4-bromophenyl)-cyclopropyl]-amine (Intermediate 124, 110.0 mg, 0.36 mmol) in triethylamine (8 mL) was treated with copper(I) iodide (10.0 mg, 0.05 mmol) and then sparged with argon for 5 minutes. Trimethylsilyl acetylene (0.70 g, 7.1 mmols) was then added followed by dichlorobis(triphenylphosphine) palladium(II) (38.0 mg, 0.05 mmol). The resulting reaction mixture was heated to 70° C. for 5 d. The title compound 85 mg (74%) was isolated by chromatography (1–10% EtOAc-hexanes).

$^1$H NMR (CDCl$_3$) δ: 7.46 (2H, d, J=8.3 Hz), 7.31–7.22 (7H, m), 3.67 (2H, s), 1.06 (2H, m), 0.94 (2H, m), 0.26 (9H, s).

Benzyl-[1-(4-ethynylphenyl)-cyclopropyl]-amine (Intermediate 127)

Using General Procedure E; benzyl-[1-(4-trimethylsilanylethynyl-phenyl)-cyclopropyl]-amine (Intermediate 126, 85.0 mg, 0.27 mmol) in methanol (5 mL) was treated with potassium carbonate (50.0 mg, 0.37 mmol) and stirred overnight at ambient temperature. The crude alkyne (65 mg, 100%) was used directly in the next reaction.

$^1$H NMR (CDCl$_3$) δ: 7.49 (2H, d, J=7.9 Hz), 7.32 (2H, d, J=7.9 Hz), 7.23 (5H, m), 3.68 (2H, s), 3.08 (1H, s), 1.07 (2H, m), 0.95 (2H, m).

Ethyl 4-[4-(1-benzylamino-cyclopropyl)-phenylethynyl]-benzoate (Compound 111, General Formula 2)

Using General Procedure F; benzyl-[1-(4-ethynylphenyl)-cyclopropyl]-amine (Intermediate 127, 65.0 mg, 0.27 mmol) and ethyl-4-iodo benzoate (Reagent A, 68.0 mg, 0.27 mmol) in triethyl amine (8 mL) was treated with copper(I)iodide (16.0 mg, 0.08 mmol) and sparged with argon for 5 minutes. Dichlorobis(triphenylphosphine)palladium(II) (58 mg, 0.08 mmol) was added and the reaction mixture was stirred overnight at room temperature. Column chromatography (2–5% EtOAc-hexanes) afforded 90 mg (90%) of the title compound as an orange solid.

$^1$H NMR (CDCl$_3$) δ: 8.05 (2H, d, J=8.3 Hz), 7.61 (2H, d, J=8.3 Hz), 7.55 (2H, d, J=8.1 Hz), 7.43 (2H, d, J=8.1 Hz), 7.32–7.22 (5H, m), 4.40 (2H, q, J=7.1 Hz), 3.72 (2H, s), 1.42 (2H, t, J=7.1 Hz), 1.01 (2H, m), 0.99 (2H, m).

4-[4-(1-Benzylamino-cyclopropyl)-phenylethynyl]-benzoic acid (Compound 112, General Formula 2)

Using General Procedure I; a solution of ethyl 4-[4-(1-benzylamino-cyclopropyl)-phenylethynyl]-benzoate (Compound 111, 75.0 mg, 0.19 mmol) in ethanol (4 mL) and tetrahydrofuran (4 mL) was treated with NaOH (80.0 mg, 2.0 mmols, 2.0 mL of a 1N aqueous solution) and stirred overnight at room temperature. Work-up afforded 35.0 mg (50%) of the title compound as a colorless solid.

$^1$H NMR (CD$_3$OD) δ: 7.93 (2H, d, J=8.3 Hz), 7.61–7.51 (6H, m), 7.32–7.23 (5H, m), 3.98 (2H, s), 1.33(2H, m), 1.19 (2H, m).

Dibenzyl-[1-(4-trimethylsilanylethynyl-phenyl)-cyclopropyl]-amine (Intermediate 128)

Using General Procedure D; dibenzyl-[1-(4-bromophenyl)-cyclopropyl]-amine (Intermediate 125, 45.0 mg, 0.11 mmol) in triethylamine (8 mL) was treated with copper(I)iodide (10.0 mg, 0.05 mmol) and then sparged with argon for 5 minutes. Trimethylsilyl acetylene (0.35 g, 3.6 mmols) was then added followed by dichlorobis (triphenylphosphine)palladium(II) (35.0 mg, 0.05 mmol). The resulting reaction mixture was heated to 70° C. for 5 d. The title compound 40 mg (88%) was isolated by chromatography (hexanes).

$^1$H NMR (CDCl$_3$) δ: 7.52 (2H, d, J=8.3 Hz), 7.36–7.24 (12H, m), 3.60 (4H, s), 0.87 (2H, m), 0.67 (2H, m), 0.29 (9H, s).

Dibenzyl-[1-(4-ethynylphenyl)-cyclopropyl]-amine (Intermediate 129)

Using General Procedure E; dibenzyl-[1-(4-trimethylsilanylethynyl-phenyl)-cyclopropyl]-amine (Intermediate 128, 100.0 mg, 0.26 mmol) in methanol (5 mL) was treated with potassium carbonate (60.0 mg, 0.44 mmol) and stirred overnight at ambient temperature. The crude alkyne (80 mg, 99%) was used directly in the next reaction.

$^1$H NMR (CDCl$_3$) δ: 7.53 (2H, d, J=7.9 Hz), 7.36 (2H, d, J=7.9 Hz), 7.28–7.25 (10H, m), 3.62 (4H, s), 3.11 (1H, s), 0.88 (2H, m), 0.68 (2H, m).

Ethyl 4-[4-(1-dibenzylamino-cyclopropyl)-phenylethynyl]-benzoate (Compound 113, General Formula 2)

Using General Procedure F; dibenzyl-[1-(4-ethynylphenyl)-cyclopropyl]-amine (Intermediate 129, 40.0 mg, 0.12 mmol) and ethyl-4-iodo benzoate (Reagent A, 60.0 mg, 0.22 mmol) in triethylamine (5 mL) was treated with copper(I)iodide (8.0 mg, 0.04 mmol) and sparged with argon for 5 minutes. Dichlorobis(triphenylphosphine)palladium (II) (27 mg, 0.04 mmol) was added and the reaction mixture was stirred overnight at room temperature. Column chromatography (2–5% EtOAc-hexanes) afforded the title compound as an oil.

$^1$H NMR (CDCl$_3$) δ: 8.04 (2H, d, J=8.5 Hz), 7.79 (4H, m), 7.42 (2H, d, J=7.9 Hz), 7.29–7.17 (10H, m), 4.40 (2H, q, J=7.1 Hz), 3.63 (4H, s), 1.42 (3H, t, J=7.1 Hz), 0.88 (2H, m), 0.73 (2H, m).

4-[4-(1-Dibenzylamino-cyclopropyl)-phenylethynyl]-benzoic acid (Compound 114, Formula 2)

Using General Procedure I; a solution of ethyl 4-[4-(1-dibenzylamino-cyclopropyl)-phenylethynyl]-benzoate (Compound 113, 48.0 mg, 0.10 mmol) in ethanol (2 mL) and tetrahydrofuran (2 mL) was treated with NaOH (80.0 mg, 2.0 mmols, 2.0 mL of a 1N aqueous solution) and stirred overnight at room temperature. Work-up afforded 42.0 mg (93%) of the title compound as a colorless solid.

$^1$H NMR (d$_6$-DMSO) δ: 7.98 (2H, d, J=8.2 Hz), 7.67 (2H, d, J=8.2 Hz), 7.64 (2H, d, J=7.9 Hz), 7.47 (2H, d, J=7.9 Hz), 7.28–7.20 (10H, m), 3.57 (4H, s), 0.84 (2H, m), 0.69 (2H, m).

Benzyl-[1-(4-bromophenyl)-cyclopropyl]-methylamine (Intermediate 130)

To a solution of benzyl-[1-(4-bromophenyl)-cyclopropyl]-amine (Intermediate 124, 100.0 mg, 0.33 mmol) in 5 mL of acetone was added K$_2$CO$_3$ (91 mg, 0.66 mmol) and iodomethane (2.28 g, 16.1 mmols). The resulting mixture was stirred at 25° C. for 20 hours, diluted with Et$_2$O, and washed with H$_2$O and saturated aqueous NaCl. The solution was dried (MgSO$_4$) and concentrated under reduced pressure to give 90 mg (86%) of the title compound.

$^1$H NMR (CDCl$_3$) δ: 7.47 (2H, d, J=8.5 Hz), 7.29–7.18 (7H, m), 3.53 (2H, s), 2.07 (3H, s), 1.07 (2H, m), 0.86 (2H, m).

Benzyl-[1-(4-trimethylsilanylethynyl-phenyl)-cyclopropyl]-methylamine (Intermediate 131)

Using General Procedure D; benzyl-[1-(4-bromophenyl)-cyclopropyl]-methylamine (Intermediate 130, 90.0 mg, 0.28 mmol) in triethylamine (8 mL) was treated with copper(I) iodide (6.0 mg, 0.03 mmol) and then sparged with argon for 5 minutes. Trimethylsilyl acetylene (0.70 g, 7.1 mmols) was then added followed by dichlorobis(triphenylphosphine) palladium(II) (20.0 mg, 0.03 mmol). The resulting reaction mixture was heated to 70° C. for 5 days. The title compound 80 mg (84%) was isolated by chromatography (0–2% EtOAc-hexanes).

$^1$H NMR (CDCl$_3$) δ: 7.46 (2H, d, J=8.2 Hz), 7.32–7.18 (7H, m), 3.52 (2H, s), 2.06 (3H, s), 1.06 (2H, m), 0.87(2H, m), 0.26 (9H, s).

Benzyl-[1-(4-ethynylphenyl)-cyclopropyl]-methylamine (Intermediate 132)

Using General Procedure E; benzyl-[1-(4-trimethylsilanylethynyl-phenyl)-cyclopropyl]-methylamine (Intermediate 131, 80.0 mg, 0.24 mmol) in methanol (5 mL) was treated with potassium carbonate (80.0 mg, 0.59 mmol) and stirred overnight at ambient temperature. The crude alkyne (60 mg, 99%) was used directly in the next reaction.

$^1$H NMR (CDCl$_3$) δ: 7.49 (2H, d, J=8.2 Hz), 7.33–7.21 (7H, m), 3.55 (2H, s), 3.08 (1H, s), 2.08 (3H, s), 1.07 (2H, m), 0.89 (2H, m).

Ethyl 4-{4-[1-(benzyl-methylamino)-cyclopropyl]-phenylethynyl}-benzoate (Compound 115, General Formula 2)

Using General Procedure F; benzyl-[1-(4-ethynylphenyl)-cyclopropyl]-methylamine (Intermediate 132, 70.0 mg, 0.28 mmol) and ethyl-4-iodo benzoate (Reagent A, 77.0 mg, 0.28 mmol) in triethylamine (5 mL) was treated with copper(I) iodide (18.0 mg, 0.10 mmol) and sparged with argon for 5 minutes. Dichlorobis(triphenylphosphine)palladium(II) (65 mg, 0.10 mmol) was added and the reaction mixture was stirred overnight at room temperature. Column chromatography (2–5% EtOAc-hexanes) afforded 86 mg (75%) of the title compound as an oil.

$^1$H NMR (CDCl$_3$) δ: 8.03 (2H, d, J=8.5 Hz), 7.59 (2H, d, J=8.5 Hz), 7.53 (2H, d, J=8.2 Hz), 7.36 (2H, d, J=8.2 Hz), 7.25 (5H, m), 4.39 (2H, q, J=7.1 Hz), 3.57 (2H, s), 2.10 (3H, s), 1.41 (3H, t, J=7.1 Hz), 1.10 (2H, m), 0.92 (2H, m).

4-[4-(1-Benzylmethylamino-cyclopropyl)-phenylethynyl]-benzoic acid (Compound 116, General Formula 2)

Using General Procedure I; a solution of ethyl 4-{4-[1-(benzyl-methylamino)-cyclopropyl]-phenylethynyl}-benzoate (Compound 115, 65.0 mg, 0.16 mmol) in ethanol (3 mL) and tetrahydrofuran (3 mL) was treated with NaOH (80.0 mg, 2.0 mmols, 2.0 mL of a 1N aqueous solution) and stirred overnight at room temperature. Work-up afforded 45.0 mg (75%) of the title compound as a solid.

$^1$H NMR (d$_6$-DMSO) δ: 7.96 (2H, d, J=8.3 Hz), 7.66 (2H, d, J=8.3 Hz), 7.58 (2H, d, J=8.2 Hz), 7.42 (2H, d, J=8.2 Hz), 7.29–7.18 (5H, m), 3.52 (2H, s), 2.00 (3H, s),1.02 (2H, m), 0.87 (2H, m).

(4-Bromo-2-methyl-phenyl)-methanol (Intermediate 133)

A solution of methyl 4-bromo-2-methyl-benzoate (1.05 g, 4.58 mmols) in 10 mL of Et$_2$O was cooled to 0° C. and treated with LiAlH$_4$ (177.0 mg, 4.58 mmols), stirred for 3 hours, and then carefully quenched with H$_2$O. The mixture was extracted with Et$_2$O and the combined organic layers were washed with H$_2$O and saturated aqueous NaCl, dried (MgSO$_4$), and concentrated under reduced pressure. The title compound, 830.0 mg (90%), was isolated by column chromatography (10–30% EtOAc-hexanes) as a colorless oil.

$^1$H NMR (CDCl$_3$) δ: 7.30 (2H, m), 7.18 (1H, d, J=8.8 Hz), 4.57 (2H, d, J=5.5 Hz), 2.27 (3H, s), 2.13 (1H, t, J=5.5 Hz).

(4-Bromo-2-methyl-benzyloxy)-trimethylsilane (Intermediate 134)

To a solution of (4-bromo-2-methyl-phenyl)-methanol (Intermediate 133, 500.0 mg, 2.48 mmols), in 10 mL THF was added triethylamine (374.0 mg, 3.70 mmols) and chlorotrimethylsilane (297.0 mg, 2.70 mmols). The resulting solution was stirred for 17 hours at 25° C. and then treated with H$_2$O and extracted with Et$_2$O. The combined organic layers were washed with H$_2$O, 10% aqueous HCl, saturated NaHCO$_3$, and saturated NaCl before being dried (MgSO$_4$) and concentrated under reduced pressure. The title compound, 550.0 mg (81%), was isolated by column chromatography (5% EtOAc-hexanes) as a colorless oil.

$^1$H NMR (CDCl$_3$) δ: 7.35–7.28 (3H, m), 4.64 (2H, s), 2.29 (3H, s), 0.20 (9H, s).

2-Methyl-4-trimethylsilanylethynyl-1-trimethylsilanyloxymethyl-benzene (Intermediate 135)

Using General Procedure D; (4-bromo-2-methyl-benzyloxy)-trimethylsilane (Intermediate 134, 550.0 mg, 2.01 mmol) in triethylamine (8 mL) was treated with copper (I)iodide (38.0 mg, 0.20 mmol) and then sparged with argon for 5 minutes. Trimethylsilyl acetylene (1.05 g, 10.6 mmols) was then added followed by dichlorobis(triphenylphosphine)palladium(II) (142.0 mg, 0.20 mmol). The resulting reaction mixture was heated to 70° C. for 5 days. The title compound (380.0 mg, 65%) was isolated by chromatography (0–2% EtOAc-hexanes) as an orange oil.

$^1$H NMR (CDCl$_3$) δ: 7.31 (3H, m), 4.64 (2H, s), 2.24 (3H, s), 0.24 (9H, s), 0.15 (9H, s).

(4-Ethynyl-2-methyl-phenyl)-methanol (Intermediate 136)

Using General Procedure E; 2-methyl-4-trimethylsilanylethynyl-1-trimethylsilananyloxymethyl-benzene (Intermediate 135, 380.0 mg, 1.30 mmols) in methanol (10 mL) was treated with potassium carbonate (180.0 mg, 1.3 mmol) and stirred overnight at ambient temperature. The crude alkyne was purified by column chromatography (5–20% EtOAc-hexanes) to give 100.0 mg (34%) of the title compound.

$^1$H NMR (CDCl$_3$) δ: 7.06 (3H, m), 4.42 (2H, d, J=5.2 Hz), 2.81 (1H, s), 2.05 (3H, s), 1.59 (1H, t, J=5.2 Hz).

Ethyl 4-(4-hydroxymethyl-3-methyl-phenylethynyl)-benzoate (Compound 117, General Formula 6)

Using General Procedure F; (4-ethynyl-2-methyl-phenyl)-methanol (Intermediate 136, 100.0 mg, 0.44 mmol) and ethyl-4-iodo benzoate (Reagent A, 125.0 mg, 0.45 mmol) in triethyl amine (4 mL) was treated with copper(I) iodide (29 mg, 0.15 mmol) and sparged with argon for 5 minutes. Dichlorobis(triphenylphosphine)palladium(II) (102 mg, 0.15 mmol) was added and the reaction mixture was stirred overnight at room temperature. Column chromatography (20–40% EtOAc-hexanes) afforded 130.0 mg (99%) of the title compound as an orange solid.

$^1$H NMR (CDCl$_3$) δ: 7.98 (2H, d, J=8.2 Hz), 7.56 (2H, d, J=8.2 Hz), 7.36 (3H, m), 4.65 (2H, s), 4.36 (2H, q, J=7.1 Hz), 2.40 (1H, s), 2.30 (3H, s), 1.39 (3H, t, J=7.1 Hz).

Ethyl 4-(4-bromomethyl-3-methyl-phenylethynyl)-benzoate (Intermediate 137)

A solution of ethyl 4-(4-hydroxymethyl-3-methyl-phenylethynyl)-benzoate (Compound 117, 130.0 mg, 0.44 mmol) and triphenylphosphine (150.0 mg, 0.57 mmol) in 5 mL CH$_2$Cl$_2$ was cooled to 0° C. and N-bromosuccinimide (101.0 mg, 0.57 mmol) was added in 5 portions over 20 minutes. The solution was warmed to 25° C. and stirred for 17 hours. The reaction was quenched by the addition of dilute aqueous NaHCO$_3$. The resulting mixture was extracted with Et$_2$O and the combined organic layers were washed with H$_2$O and saturated aqueous NaCl before being dried (Na$_2$SO$_4$) and concentrated under reduced pressure. The title compound, 120.0 mg (76%), was isolated by column chromatography (2–5% EtOAc-hexanes) as a colorless solid.

$^1$H NMR (CDCl$_3$) δ: 8.01 (2H, d, J=8.1 Hz), 7.56 (2H, d, J=8.1 Hz), 7.32 (3H, m), 4.48 (2H, s), 4.38 (2H, q, J=7.1 Hz), 2.40 (3H, s), 1.39 (3H, t, J=7.1 Hz).

Ethyl 4-(4-imidazol-1-yl-methyl-3-methyl-phenylethynyl)-benzoate (Compound 118, General Formula 6)

A solution of imidazole (30.0 mg, 0.44 mmol) in 2 mL DMF was treated with NaH (11.0 mg, 0.44 mmol) and heated to 90° C. After 1 h a solution of ethyl 4-(4-bromomethyl-3-methyl-phenylethynyl)-benzoate (Intermediate 137, 120.0 mg, 0.34 mmol) in 2 mL DMF was added and stirring at 90° C. continued for 1 hour. The solution was cooled to room temperature and concentrated under reduced pressure. The title compound, 90.0 mg (71%) was isolated by column chromatography (20–100% EtOAc-hexanes) as a colorless solid.

$^1$H NMR (CDCl$_3$) δ: 8.02 (2H, d, J=8.5 Hz), 7.57 (2H, d, J=8.5 Hz), 7.51 (1H, s), 7.40 (1H, s), 7.36 (1H, dd, J=1.2, 7.9 Hz), 7.10 (1H, s), 6.93 (1H, d, J=7.9 Hz), 6.88 (1H, t, J=1.7 Hz), 5.12 (2H, s), 4.38 (2H, q, J=7.1 Hz), 2.27 (3H, s), 1.40 (3H, t, J=7.1 Hz).

4-(4-Imidazol-1-yl-methyl-3-methyl-phenylethynyl)-benzoic acid (Compound 119, General Formula 6)

Using General Procedure I; a solution of ethyl 4-(4-imidazol-1-ylmethyl-3-methyl-phenylethynyl)-benzoate (Compound 118, 82.0 mg, 0.24 mmol) in ethanol (3 mL) and tetrahydrofuran (3 mL) was treated with NaOH (120.0 mg, 3.0 mmols, 3.0 mL of a 1N aqueous solution) and stirred overnight at room temperature. Work-up afforded 51.0 mg (68%) of the title compound as a solid.

$^1$H NMR (d$_6$-DMSO) δ: 9.20 (1H, s), 7.97 (2H, d, J=8.2 Hz), 7.73 (2H, m), 7.65 (2H, d, J=8.2 Hz), 7.52 (1H, s), 7.46 (1H, d, J=7.9 Hz), 7.13 (1H, d, J=7.9 Hz), 5.50 (2H, s), 2.32 (3H, s).

4-Bromo-1-bromomethyl-2-methyl-benzene (Intermediate 138)

A solution of (4-bromo-2-methyl-phenyl)-methanol (Intermediate 133, 319.0 mg, 1.58 mmol) and triphenylphosphine (466.0 mg, 1.74 mmol) in 5 mL CH$_2$Cl$_2$ was cooled to 0° C. and N-bromosuccinimide (309.0 mg, 1.74 mmol) was added in 5 portions over 20 minutes. The solution was warmed to 25° C. and stirred for 17 hours. The reaction was quenched by the addition of dilute aqueous NaHCO$_3$. The resulting mixture was extracted with Et$_2$O and the combined organic layers were washed with H$_2$O and saturated aqueous NaCl before being dried (Na$_2$SO$_4$) and concentrated under reduced pressure. The title compound, 350.0 mg (84%), was isolated by column chromatography (2–3% EtOAc-hexanes) as a colorless oil.

$^1$H NMR (CDCl$_3$) δ: 7.32 (1H, d, J=2.0 Hz), 7.29 (1H, dd, J=2.0, 7.9 Hz), 7.15 (1H, d, J=7.9 Hz), 4.43 (2H, s), 2.37 (3H, s).

1-(4-Bromo-2-methyl-benzyl)-1H-imidazole (Intermediate 139)

A solution of imidazole (58.0 mg, 0.86 mmol) in 3 mL DMF was treated with NaH (20.0 mg, 0.86 mmol) and heated to 90° C. After 1 h a solution of 4-bromo-1-bromomethyl-2-methyl-benzene (Intermediate 138, 190.0 mg, 0.72 mmol) in 3 mL DMF was added and stirring at 90° C. continued for 1 hour. The solution was cooled to room temperature and concentrated under reduced pressure. The title compound, 160.0 mg (88%) was isolated by column chromatography (5% MeOH-EtOAc) as a colorless solid.

$^1$H NMR (CDCl$_3$) δ: 7.46 (1H, s), 7.34 (1H, dd, J=1.8 Hz), 7.30 (1H, dd, J=1.8, 8.2 Hz), 7.08 (1H, t, J=1.2 Hz), 6.83 (1H, t, J=1.2 Hz), 6.80 (1H, d, J=8.2 Hz), 5.03 (2H, s), 2.23 (3H, s).

1-(2-Methyl-4-trimethylsilanylethynyl-benzyl)-1H-imidazole (Intermediate 140)

Using General Procedure D; 1-(4-bromo-2-methyl-benzyl)-1H-imidazole (Intermediate 139, 160.0 mg, 0.64 mmol) in triethylamine (8 mL) was treated with copper(I) iodide (12.0 mg, 0.07 mmol) and then sparged with argon for 5 minutes. Trimethylsilyl acetylene (0.70 g, 0.71 mmols) was then added followed by dichlorobis(triphenylphosphine)palladium(II) (45.0 mg, 0.07 mmol). The resulting reaction mixture was heated to 70° C. for 5 days. The title compound (140.0 mg, 82%) was isolated by chromatography (5% MeOH-EtOAc) as an orange oil.

$^1$H NMR (CDCl$_3$) δ: 7.53 (1H, s), 7.38 (1H, s), 7.34 (1H, d, J=8.0 Hz), 7.15 (1H, s), 6.94 (1H, s), 6.91 (1H, d, J=8.0 Hz), 5.14 (2H, s), 2.29 (3H, s), 0.31 (9H, s).

1-(4-Ethynyl-2-methyl-benzyl)-1H-imidazole (Intermediate 141)

Using General Procedure E; 1-(2-methyl-4-trimethylsilanylethynyl-benzyl)-1H-imidazole (Intermediate 140, 140.0 mg, 0.53 mmols) in methanol (5 mL) was treated with potassium carbonate (100.0 mg, 0.72 mmol) and stirred overnight at ambient temperature. The crude alkyne (105 mg, 100%) was used directly in the next reaction.

$^1$H NMR (CDCl$_3$) δ: 7.49 (1H, s), 7.35 (1H, s), 7.31 (1H, dd, J=1.7, 7.9 Hz), 7.10 (1H, s), 6.69 (1H, d, J=7.9 Hz), 6.85 (1H, t, J=1.2 Hz), 5.14 (2H, s), 3.08 (1H, s), 2.26 (3H, s).

Methyl [4-(4-imidazol-1-yl-methyl-3-methyl-phenylethynyl)-phenyl]-acetate (Compound 120, General Formula 6)

Using General Procedure F; 1-(4-ethynyl-2-methyl-benzyl)-1H-imidazole (Intermediate 141, 101.0 mg, 0.53 mmol) and methyl-(4-iodophenyl)-acetate (Reagent B, 145.0 mg, 0.53 mmol) in triethylamine (5 mL) was treated with copper(I)iodide (34.0 mg, 0.18 mmol) and sparged with argon for 5 minutes. Dichlorobis(triphenylphosphine)palladium(II) (124 mg, 0.18 mmol) was added and the reaction mixture was stirred overnight at room temperature. Column chromatography (5% MeOH-EtOAc) afforded 45.0 mg (25%) of the title compound as an orange oil.

$^1$H NMR (CDCl$_3$) δ: 7.47 (3H, m), 7.35 (3H, m), 7.27 (3H, m), 6.91 (1H, d, J=7.3 Hz), 5.11 (2H, s), 3.70 (3H, s), 3.64 (2H, s), 2.26 (3H, s).

[4-(4-Imidazol-1-yl-methyl-3-methyl-phenylethynyl)-phenyl]-acetic acid (Compound 121, General Formula 6)

Using General Procedure I; a solution of methyl [4-(4-imidazol-1-ylmethyl-3-methyl-phenylethynyl)-phenyl]-acetate (Compound 120, 45.0 mg, 0.13 mmol) in ethanol (2 mL) and tetrahydrofuran (2 mL) was treated with NaOH (80.0 mg, 2.0 mmols, 2.0 mL of a 1N aqueous solution) and stirred overnight at room temperature. Work-up afforded 30.0 mg (70%) of the title compound as a pale-orange solid.

$^1$H NMR (d$_4$-MeOH) δ: 8.97 (1H, s), 7.60 (2H, d J=8.8 Hz), 7.47 (3H, m), 7.41 (1H, d, J=7.9 Hz), 7.30 (2H, d, J=7.9 Hz), 7.23 (1H, d, J=7.9 Hz), 5.51 (2H, s), 3.64 (2H, s), 2.33 (3H, s).

1-Isopropyl-3-methoxy-benzene (Intermediate 142)

To a solution of 3-isopropyl-phenol (5.00 g, 36.2 mmols) in 50 mL of acetone was added K$_2$CO$_3$ (7.50 g, 54.3 mmols) and iodomethane (10.3 g, 72.5 mmols). The resulting solution was heated to 50° C. and stirred for 18 hours, cooled to room temperature, and concentrated under reduced pressure. The residual oil was dissolved in Et$_2$O and washed with H$_2$O, saturated aqueous NaHCO$_3$, and saturated aqueous NaCl before being dried (MgSO$_4$) and concentrated under reduced pressure. The crude methyl ether was used without further purification.

$^1$H NMR (CDCl$_3$) δ: 7.22 (1H, t, J=8.1 Hz), 6.84–6.72 (3H, m), 3.81 (3H, s), 2.88 (1H, septet, J=7.0 Hz), 1.25 (6H, d, J=7.0 Hz).

1-Bromo-2-isopropyl-4-methoxy-benzene (Intermediate 143)

A mixture of 1-isopropyl-3-methoxy-benzene (Intermediate 142, 3.50 g, 23.3 mmols), molecular sieves, and silica gel in 150 mL CCl$_4$ was treated with N-bromosuccinimide (4.98 g, 28.0 mmols) at 35° C. for 18 hours. An additional portion of N-bromosuccinimide (830.0 mg, 4.46 mmols) was added and stirring continued for 6 hours. The mixture was cooled to room temperature, H$_2$O was added, and the mixture was filtered to remove the solids. The mixture was extracted with E$_2$O and the combined organic layers were washed with 10% aqueous HCl, H$_2$O, saturated aqueous NaHCO$_3$, and saturated NaCl before being dried (MgSO$_4$) and concentrated under reduced pressure. Column chromatography (2.5% EtOAc-hexanes) afforded 4.34 g (81%) of the title compound as a pale-yellow oil.

$^1$H NMR (CDCl$_3$) δ: 7.41 (1H, d, J=8.8 Hz), 6.82 (1H, d, J=2.6 Hz), 6.61 (1H, dd, J=2.6, 8.8 Hz), 3.79 (3H, s), 3.31 (1H, septet, J=6.7 Hz), 123 (6H, d, J=6.7 Hz).

4-Bromo-3-isopropyl-phenol (Intermediate 144)

To a solution of 1-bromo-2-isopropyl-4-methoxy-benzene (Intermediate 143, 2.20 g, 9.60 mmols) in 50 mL CH$_2$Cl$_2$ at −78° C. was added BBr$_3$ (4.81 g, 19.2 mmols; 19.2 mL of a 1M solution in CH$_2$Cl$_2$). After stirring for 3 hours at −78° C. the solution was warmed to 0° C. for 3 hours and then at 25° C. for 1 hour before being quenched with H$_2$O. The mixture was diluted with Et$_2$O and washed with H$_2$O and saturated aqueous NaCl, dried (Na$_2$SO$_4$) and concentrated under reduced pressure. Column chromatography (2.5–10% EtOAc-hexanes) afforded the title compound as a colorless oil.

$^1$H NMR (CDCl$_3$) δ: 7.38 (1H, d, J=8.5 Hz), 6.79 (1H, d, J=2.9 Hz), 6.57 (1H, dd, J=2.9, 8.5 Hz), 3.31 (1H, septet, J=7.0 Hz), 1.22 (6H, d, J=7.0 Hz).

(4-Bromo-3-isopropyl-phenoxy)-tert-butyl-dimethyl-silane (Intermediate 145)

A solution of 4-bromo-3-isopropyl-phenol (Intermediate 144, 1.13 g, 5.25 mmols), chloro-tert-butyl-dimethylsilane (0.95 g, 6.30 mmols), and imidazole (428.0 mg, 6.3 mmols) in 10 mL DMF was stirred at 25° C. for 3 hours. The solution was diluted with H$_2$O and extracted with Et$_2$O and the combined organic layers were washed with H$_2$O, saturated aqueous NaCl, and dried (MgSO$_4$) before being concentrated under reduced pressure. Column chromatography (1–2% EtOAc-hexanes) afforded 1.50 g (87%) of the title compound as a colorless oil.

$^1$H NMR (CDCl$_3$) δ: 7.32 (1H, d, J=8.8 Hz), 6.73 (1H, d, J=3.0 Hz), 6.52 (1H, dd, J=3.0, 8.8 Hz), 3.26 (1H, septet, J=6.7 Hz), 1.19 (6H, d, J=6.7 Hz), 0.96 (9H, s), 0.17 (6H, s).

4-(Tert-butyl-dimethyl-silanyloxy)-2-isopropyl-benzaldehyde (Intermediate 146)

A solution of (4-bromo-3-isopropyl-phenoxy)-tert-butyl-dimethyl-silane (Intermediate 145, 1.03 g, 3.13 mmols) in 25 mL E$_2$O was cooled to –78° C. and treated with tert-butyllithium (401.0 mg, 6.26 mmols; 3.7 mL of a 1.7M solution in pentane). After 30 minutes the reaction was quenched with DMF (913.0 mg, 12.5 mmols) and warmed to room temperature. The solution was diluted with H$_2$O, extracted with Et$_2$O and the combined organic layers washed with H$_2$O and saturated aqueous NaCl before being dried (MgSO$_4$) and concentrated under reduced pressure. Column chromatography (2% EtOAc-hexanes) afforded 480.0 mg (55%) of the title compound as a colorless oil.

$^1$H NMR (CDCl$_3$) δ: 10.19 (1H, s), 7.72 (1H, d, J=8.5 Hz), 6.85 (1H, d, J=2.3 Hz), 6.77 (1H, dd, J=2.3, 8.5 Hz), 3.97 (1H, septet, J=6.7 Hz), 1.27 (6H, d, J=6.7 Hz), 1.00 (9H, s), 0.25 (6H, s).

4-Hydroxy-2-isopropyl-benzaldehyde (Intermediate 147)

To a solution of 4-(tert-butyl-dimethyl-silanyloxy)-2-isopropyl-benzaldehyde (Intermediate 146, 880.0 mg, 3.17 mmols) in 6 mL THF at 0° C. was added tetrabutylammonium fluoride (1.66 g, 6.33 mmols; 6.3 mL of a 1M solution in THF). The pale-yellow solution was stirred for 30 minutes and quenched by the addition of ice cold H$_2$O. The mixture was extracted with Et$_2$O and the combined organic layers were washed with H$_2$O and saturated aqueous NaCl before being dried (Na$_2$SO$_4$) and concentrated under reduced pressure. Column chromatography (20% EtOAc-hexanes) afforded 500.0 mg (96%) of the title compound as a colorless solid.

$^1$H NMR (CDCl$_3$) δ: 10.15 (1H, s), 7.79 (1H, d, J=8.5 Hz), 6.95 (1H, d, J=2.3 Hz), 6.86 (1H, dd, J=2.3, 8.5 Hz), 3.96 (1H, septet, J=6.7 Hz), 1.29 (6H, d, J=6.7 Hz).

4-Formyl-3-isopropyl-phenyl 1,1,1-trifluoro-methansulfonate (Intermediate 148)

A solution of 4-hydroxy-2-isopropyl-benzaldehyde (Intermediate 147, 300.0 mg, 1.83 mmol) in 10 mL of CH$_2$Cl$_2$ was cooled to 0° C. and to it was added 2-[N,N-bis(trifluoromethylsulfonyl)amino]-5-chloropyridine (754.0 mg, 1.92 mmol) and triethylamine (592.0 mg, 5.85 mmols). The resulting solution was warmed to room temperature and stirred for 4.5 hours. The reaction was quenched by the addition of H$_2$O and the mixture extracted with EtOAc and the combined organic layers were washed with 10% aqueous HCl, saturated aqueous NaHCO$_3$, H$_2$O, and saturated aqueous NaCl. The solution was dried (MgSO$_4$) and concentrated under reduced pressure. The title compound was isolated by column chromatography (5–10% EtOAc-hexanes) as a colorless oil, 470.0 mg (87%).

$^1$H NMR (CDCl$_3$) δ: 10.37 (1H, s), 7.94 (1H, d, J=8.5 Hz), 7.33 (1H, d, J=2.3 Hz), 7.26 (1H, dd, J=2.3, 8.5 Hz), 4.00 (1H, septet, J=6.7 Hz), 1.33 (6H, d, J=6.7 Hz), 4-Hydroxymethyl-3-isopropyl-phenyl 1,1,1-trifluoro-methansulfonate (Intermediate 149)

To a solution of 4-formyl-3-isopropyl-phenyl 1,1,1-trifluoro-methansulfonate (Intermediate 148, 540.0 mg, 1.82 mmols) in 7 mL MeOH at 0° C. was added NaBH$_4$ (72.0 mg, 1.91 mmols). After stirring 2 hours at 0° C. the reaction was carefully quenched with H$_2$O and extracted with Et$_2$O. The combined organic layers were washed with H$_2$O and saturated aqueous NaCl, dried (MgSO$_4$), and concetrated under reduced pressure. The title compound was isolated by column chromatography (5–10% EtOAc-hexanes) as a colorless oil, 355.0 mg (90%).

$^1$H NMR (CDCl$_3$) δ: 7.45 (1H, d, J=8.5 Hz), 7.17 (1H, d, J=2.7 Hz), 7.08 (1H, dd, J=2.7, 8.5 Hz), 4.74 (2H, d, J=5.3 Hz), 3.21 (1H, septet, J=7.0 Hz), 2.12 (1H, t, J=5.3 Hz), 1.24 (6H, d, J=7.0 Hz).

4-(Tert-butyl-dimethyl-silanyloxymethyl)-3-isopropyl-phenyl 1,1,1-trifluoro-methansulfonate (Intermediate 150)

A solution of 4-hydroxymethyl-3-isopropyl-phenyl 1,1,1-trifluoro-methansulfonate (Intermediate 149, 760.0 mg, 2.55 mmols), chloro-tert-butyl-dimethylsilane (470.0 mg, 3.18 mmols), and imidazole (225.0 mg, 3.25 mmols) in 6 mL DMF was stirred at 25° C. for 17 hours. The solution was diluted with H$_2$O and extracted with Et$_2$O and the combined organic layers were washed with 10% aqueous HCl, saturated aqueous NaHCO$_3$, H$_2$O, and saturated aqueous NaCl, and dried (MgSO$_4$) before being concentrated under reduced pressure. Column chromatography (2–5% EtOAc-hexanes) afforded 970.0 mg (92%) of the title compound as a colorless oil.

$^1$H NMR (CDCl$_3$) δ: 7.49 (1H, d, J=8.5 Hz), 7.10 (1H, d, J=2.3 Hz), 7.06 (1H, dd, J=2.3, 8.5 Hz), 4.75 (2H, s), 3.10 (1H, septet, J=6.7 Hz), 1.21 (6H, d, J=6.7 Hz), 0.93 (9H, s), 0.10 (6H, s).

1-(Tert-butyl-dimethyl-silanyloxymethyl)-2-isopropyl-4-trimethylsilanylethynyl-benzene (Intermediate 151)

To a solution of 4-(tert-butyl-dimethyl-silanyloxymethyl)-3-isopropyl-phenyl 1,1,1-trifluoro-methansulfonate (Intermediate 150, 970.0 mg, 2.35 mmols) in triethylamine (2 mL) and 6 mL DMF was sparged with argon for 15 minutes. Trimethylsilyl acetylene (1.00 g, 10.6 mmols) was then added followed by dichlorobis (triphenylphosphine)palladium(II) (66.0 mg, 0.09 mmol). The resulting reaction mixture was heated to 95° C. for 20 hours. The solution was cooled to room temperature and concentrated under reduced pressure. The title compound (200.0 mg, 78%) was isolated by chromatography (0–25% EtOAc-hexanes) as an orange oil.

$^1$H NMR (CDCl$_3$) δ: 7.37–7.25 (3H, m), 4.75 (2H, s), 3.08 (1H, septet, J=7.0 Hz), 1.21 (6H, d, J=7.0 Hz), 0.92 (9H, s), 0.25 (9H, s), 0.09 (6H, s).

Tert-butyl-(4-ethynyl-2-isopropyl-benzyloxyy-dimethyl-silane (Intermediate 152)

Using General Procedure E; 1-(tert-butyl-dimethyl-silanyloxymethyl)-2-isopropyl-4-trimethylsilanylethynyl-benzene (Intermediate 151, 850.0 mg, 2.36 mmols) in methanol (25 mL) was treated with potassium carbonate (250.0 mg, 1.81 mmols) and stirred overnight at ambient temperature. The crude alkyne (650 mg, 95%) was used directly in the next reaction.

$^1$H NMR (CDCl$_3$) δ: 7.41–7.25 (3H, m), 4.77 (2H, s), 3.07 (1H, septet, J=7.0 Hz), 3.05 (1H, s), 1.22 (6H, d, J=7.0Hz), 0.94 (9H, s), 0.11 (6H, s).

Ethyl 4-[4-(tert-butyl-dimethyl-silanyloxymethyl)-3-isopropyl-phenylethynyl]-benzoate (Intermediate 153)

Using General procedure F; tert-butyl-(4-ethynyl-2-isopropyl-benzyloxy)-dimethyl-silane (Intermediate 152, 300.0 mg, 1.04 mmols) and ethyl-4-iodo benzoate (Reagent A, 287.0 mg, 1.04 mmols) in triethylamine (8 mL) was treated with copper(I)iodide (50.0 mg, 0.26 mmol) and sparged with argon for 5 minutes. Dichlorobis (triphenylphosphine)palladium(II) (182 mg, 0.26 mmol) was added and the reaction mixture was stirred overnight at room temperature. Column chromatography (2–4% EtOAc-hexanes) afforded 310.0 mg (68%) of the title compound as an orange solid.

$^1$H NMR (CDCl$_3$) δ: 8.03 (2H, d, J=8.5 Hz), 7.60 (2H, d, J=8.5 Hz), 7.48–7.37 (3H, m), 4.80 (2H, s), 4.39 (2H, q, J=7.1 Hz), 3.14 (1H, septet, J=6.8 Hz), 1.40 (3H, t, J=7.1 Hz), 1.27 (6H, d, J=6.8 Hz), 0.96 (9H, s), 0.12 (6H, s).

Methyl {4-[4-(tert-butyl-dimethyl-silanyloxymethyl)-3-isopropyl-phenylethynyl]-phenyl}-acetate (Intermediate 154)

Using General Procedure F; tert-butyl-(4-ethynyl-2-isopropyl-benzyloxy)-dimethyl-silane (Intermediate 152, 355.0 mg, 1.26 mmols) and methyl-(4-iodophenyl)-acetate (Reagent B, 349.0 mg, 1.26 mmols) in triethylamine (8 mL) was treated with copper(I)iodide (60.0 mg, 0.32 mmol) and sparged with argon for 5 minutes. Dichlorobis (triphenylphosphine)palladium(II) (222 mg, 0.32 mmol) was added and the reaction mixture was stirred overnight at room temperature. Column chromatography (2–5% EtOAc-hexanes) afforded 288.0 mg (66%) of the title compound as an orange oil.

$^1$H NMR (CDCl$_3$) δ: 7.49 (2H, d, J=8.5 Hz), 7.43–7.35 (3H, m), 7.25 (2H, d, J=8.5 Hz), 4.77 (2H, s), 3.69 (3H, s), 3.63 (2H, s), 3.11 (1H, septet, J=6.7 Hz), 1.25 (6H, d, J=6.7 Hz), 0.94 (9H, s), 0.10 (6H, s).

Ethyl [4-(4-hydroxymethyl-3-isopropyl-phenylethynyl)-benzoate (Compound 122, General Formula 6)

To a solution of ethyl 4-[4-(tert-butyl-dimethyl-silanyloxymethyl)-3-isopropyl-phenylethynyl]-benzoate (Intermediate 153, 310.0 mg, 0.71 mmol) in 4 mL THF at 0° C. was added tetrabutylammonium fluoride (371.0 mg, 1.42 mmols; 1.4 mL of a 1M solution in THF). The pale-yellow solution was stirred for 10 minutes and quenched by the addition of ice cold H$_2$O. The mixture was extracted with Et$_2$O and the combined organic layers were washed with H$_2$O and saturated aqueous NaCl before being dried (Na$_2$SO$_4$) and concentrated under reduced pressure. Column chromatography (20–30% EtOAc-hexanes) afforded 200.0 mg (87%) of the title compound as a colorless solid.

$^1$H NMR (CDCl$_3$) δ: 7.98 (2H, d, J=8.5 Hz), 7.58 (2H, d, J=8.5 Hz), 7.48 (1H, s), 7.35 (2H, m), 4.71 (2H, s), 4.35 (2H, q, J=7.1 Hz), 3.19 (1H, septet J=7.0 Hz), 2.51 (1H, s), 1.39 (3H, t, J=7.1 Hz), 1.25 (6H, d, J=7.0 Hz).

Methyl [4-(4-hydroxymethyl-3-isopropyl-phenylethynyl)-phenyl]-acetate (Compound 123, General Formula 6)

To a solution of methyl {4-[4-(tert-butyl-dimethyl-silanyloxymethyl)-3-isopropyl-phenylethynyl]-phenyl}-acetate (Intermediate 154, 288.0 mg, 0.66 mmol) in 5 mL THF at 0° C. was added tetrabutylammonium fluoride (471.0 mg, 1.80 mmols; 1.8 mL of a 1M solution in THF). The pale-yellow solution was stirred for 15 minutes and quenched by the addition of ice cold H$_2$O. The mixture was extracted with Et$_2$O and the combined organic layers were washed with H$_2$O and saturated aqueous NaCl before being dried (Na$_2$SO$_4$) and concentrated under reduced pressure. Column chromatography (5–10% EtOAc-hexanes) afforded 180.0 mg (85%) of the title compound as a colorless solid.

$^1$H NMR (CDCl$_3$) δ: 7.48 (3H, m), 7.32 (2H, m), 7.24 (2H, d, J=8.5 Hz), 4.69 (2H, s), 3.68 (3H, s), 3.62 (2H, s), 3.18 (1H, septet, J=7.0 Hz), 2.21 (1H, s), 1.25 (6H, d, J=7.0Hz).

Ethyl [4-(4-bromomethyl-3-isopropyl-phenylethynyl)-benzoate (Intermediate 155)

A solution of ethyl [4-(4-hydroxymethyl-3-isopropyl-phenylethynyl)-benzoate (Compound 122, 200.0 mg, 0.62 mmol) and triphenylphosphine (211.0 mg, 0.81 mmol) in 5 mL CH$_2$Cl$_2$ was cooled to 0° C. and N-bromosuccinimide (144.0 mg, 0.81 mmol) was added in 5 portions over 20 minutes. The solution was warmed to 25° C. and stirred for 17 hours. The reaction was quenched by the addition of dilute aqueous NaHCO$_3$. The resulting mixture was extracted with Et$_2$O and the combined organic layers were washed with H$_2$O and saturated aqueous NaCl before being dried (Na$_2$SO$_4$) and concentrated under reduced pressure. The title compound, 220.0 mg (93%), was isolated by column chromatography (5% EtOAc-hexanes) as a pale-yellow solid.

$^1$H NMR (CDCl$_3$) δ: 8.03 (2H, d, J=8.2 Hz), 7.59 (2H, d, J=8.2 Hz), 7.48 (1H, s), 7.31 (2H, m) 4.55 (2H, s), 4.39 (2H, q, J=7.1 Hz), 3.29 (1H, septet, J=7.0 Hz), 1.40 (3H, t, J=7.1 Hz), 1.30 (6H, d, J=7.0 Hz).

Methyl [4-(4-bromomethyl-3-isopropyl-phenylethynyl)-phenyl]-acetate (Intermediate 156)

A solution of methyl [4-(4-hydroxymethyl-3-isopropyl-phenylethynyl)-phenyl]-acetate (Compound 123, 180.0 mg, 0.56 mmol) and triphenylphosphine (190.0 mg, 0.73 mmol) in 5 mL CH$_2$Cl$_2$ was cooled to 0° C. and N-bromosuccinimide (130.0 mg, 0.73 mmol) was added in 5 portions over 20 minutes. The solution was warmed to 25° C. and stirred for 17 hours. The reaction was quenched by the addition of dilute aqueous NaHCO$_3$. The resulting mixture was extracted with Et$_2$O and the combined organic layers were washed with H$_2$O and saturated aqueous NaCl before being dried (Na$_2$SO$_4$) and concentrated under reduced pressure. The title compound, 212.0 mg (98%), was isolated by column chromatography (5–10% EtOAc-hexanes) as a pale-yellow oil.

$^1$H NMR (CDCl$_3$) δ: 7.48 (3H, m), 7.28 (4H, m), 4.55 (2H, s), 3.69 (3H, s), 3.63 (2H, s), 3.28 (1H, septet, J=7.0 Hz), 1.30 (6H, d, J=7.0 Hz).

Ethyl [4-(4-imidazol-1-yl-methyl-3-isopropyl-phenylethynyl)-phenyl]-benzoate (Compound 124, General Formula 6)

A solution of ethyl [4-(4-bromomethyl-3-isopropyl-phenylethynyl)-benzoate (Intermediate 155, 120.0 mg, 0.31 mmol) and 1-acetylimidazole (36.0 mg, 0.33 mmol) in 5 mL CH$_3$CN was heated at 65° C. for 4 hours and then at 55° C. for 16 hours. The solution was cooled to room temperature, diluted with H$_2$O and made basic by addition of Na$_2$CO$_3$, and extracted with EtOAc. The combined organic layers were washed with H$_2$O and saturated aqueous NaCl, dried (MgSO$_4$), and concentrated under reduced pressure. Column chromatography (1% Et$_3$N in 5% MeOH-EtOAc) afforded 75.0 mg (65%) of the title compound as a colorless solid.

$^1$H NMR (CDCl$_3$) δ: 8.03 (2H, d, J=8.5 Hz), 7.60 (2H, d, J=8.5 Hz), 7.53 (1H, d, J=1.5 Hz), 7.49 (1H, s), 7.35 (1H, dd,

J=1.5, 7.9 Hz), 7.09 (1H, bs), 6.98 (1H, d, J=7.9 Hz), 6.85 (1H, bs), 5.19 (2H, s), 4.39 (2H, q, J=7.1 Hz), 3.08 (1H, septet, J=6.8 Hz), 1.40 (3H, t, J=7.1 Hz), 1.20 (6H, d, J=6.8 Hz).

Methyl [4-(4-imidazol-1-yl-methyl-3-isopropyl-phenylethynyl)-phenyl]-acetate (Compound 125, General Formula 6)

A solution of methyl [4-(4-bromomethyl-3-isopropyl-phenylethynyl)-phenyl]-acetate (Intermediate 156, 72.0 mg, 0.19 mmol) and 1-acetylimidazole (22.0 mg, 0.20 mmol) in 5 mL $CH_3CN$ was heated at 65° C. for 8 h and then at 55° C. for 16 hours. The solution was cooled to room temperature, diluted with $H_2O$ and made basic by addition of $Na_2CO_3$, and extracted with EtOAc. The combined organic layers were washed with $H_2O$ and saturated aqueous NaCl, dried ($MgSO_4$), and concentrated under reduced pressure. Column chromatography (0.5% $Et_3N$ in 5% MeOH-EtOAc) afforded 40.0 mg (58%) of the title compound as a colorless solid.

$^1$H NMR ($CDCl_3$) δ: 7.49 (4H, m), 7.33 (1H, dd, J=1.5, 7.9 Hz), 7.28 (2H, d, J=8.5 Hz), 7.08 (1H, t, J=1.2 Hz), 6.95 (1H, d, J=7.9 Hz), 6.84 (1H, t, J=1.2 Hz), 5.17 (2H, s), 3.70 (3H, s), 3.64 (2H, s), 3.06 (1H, septet, J=6.8 Hz), 1.20 (6H, d, J=6.8 Hz).

[4-(4-Imidazol-1-yl-methyl-3-isopropyl-phenylethynyl)-phenyl]-benzoic acid (Compound 126, General Formula 6)

Using General Procedure I; a solution of ethyl [4-(4-imidazol-1-ylmethyl-3-isopropyl-phenylethynyl)-phenyl]-benzoate (Compound 124, 75.0 mg, 0.20 mmol) in ethanol (4 mL) and tetrahydrofuran (1 mL) was treated with NaOH (120.0 mg, 3.0 mmols, 3.0 mL of a 1N aqueous solution) and stirred overnight at room temperature. Work-up afforded 68.0 mg (88%) of the title compound as a colorless solid.

$^1$H NMR ($d_4$-MeOH) δ: 9.01 (1H, s), 8.01 (2H, d, J=8.2 Hz), 7.63–7.57 (5H, m), 7.44 (1H, d, J=7.9 Hz), 7.29 (1H, d, J=7.9 Hz), 5.59 (2H, s), 3.17 (1H, septet, J=6.8 Hz), 1.20 (6H, d, J=6.8 Hz).

[4-(4-Imidazol-1-yl-methyl-3-isopropyl-phenylethynyl)-phenyl]-acetic acid (Compound 127, General Formula 6)

Using General Procedure I; a solution of methyl [4-(4-imidazol-1-ylmethyl-3-isopropyl-phenylethynyl)-phenyl]-acetate (Compound 125, 40.0 mg, 0.11 mmol) in ethanol (4 mL) and tetrahydrofuiran (1 mL) was treated with NaOH (120.0 mg, 3.0 mmols, 3.0 mL of a 1N aqueous solution) and stirred overnight at room temperature. Work-up afforded 22.0 mg (52%) of the title compound as a colorless solid.

$^1$H NMR ($d_4$-MeOH) δ: 9.02 (1H, bs), 7.62 (1H, t, J=1.4 Hz), 7.58 (2H, m), 7.49 (2H, d, J=8.2 Hz), 7.43 (1H, dd, J=1.5, 7.9 Hz), 7.31 (3H, m), 5.58 (2H, s), 3.68 (2H, s), 3.16 (1H, septet, J=6.7 Hz), 1.18 (6H, d, J=6.7 Hz).

4-Bromo-N-cyclopropyl-2-methyl-benzamide (Intermediate 157)

A solution of 4-bromo-2-methylbenzoic acid and $SOCl_2$ was refluxed for 3 hours, cooled to room temperature and concentrated under reduced pressure. The residue was dissolved in 30 mL $CH_2Cl_2$ and combined with cyclopropyl amine (810.0 mg, 14.3 mmols) and pyridine (2.05 g, 26.0 mmols). The solution was stirred for 18 hours and then diluted with EtOAc before being washed with 5% aqueous HCl, saturated $NaHCO_3$, and saturated aqueous NaCl. The solution was dried ($MgSO_4$) and concentrated under reduced pressure leaving the title compound as a colorless solid.

$^1$H NMR ($CDCl_3$) δ: 7.34 (1H, d, J=2.3 Hz), 7.28 (1H, dd, J=2.3, 8.2 Hz), 7.13 (1H, d, J=8.2 Hz), 6.10 (1H, bs), 2.85 (1H, m), 2.37 (3H, s), 0.85 (2H, m), 0.59 (2H, m).

(4-Bromo-2-methyl-benzyl)-cyclopropyl-amine (Intermediate 158)

To a solution of 4-bromo-N-cyclopropyl-2-methyl-benzamide (Intermediate 157, 1.81 g, 7.12 mmols) in THF (12 mL) was added $BH_3.SMe_2$ (1.08 g, 14.24 mmols). The solution was heated to 60° C. for 6 hours, cooled to room temperature and carefully treated with saturated aqueous $Na_2CO_3$ (30 mL) and stirred for 17 hours. This mixture was extracted with EtOAc and the combined organic layers were washed with $H_2O$, saturated aqueous NaCl before being dried ($MgSO_4$) and concentrated under reduced pressure. The title compound was isolated by column chromatography (10–15% EtOAc-hexanes).

$^1$H NMR ($CDCl_3$) δ: 7.26 (2H, m), 7.12 (1H, d, J=7.9 Hz), 3.76 (2H, s), 2.31 (3H, s), 2.14 (1H, m), 0.44 (2H, m), 0.36 (2H, m).

(4-Bromo-2-methyl-benzyl)-cyclopropyl-ethyl-amine (Intermediate 159)

A mixture of (4-bromo-2-methyl-benzyl)-cyclopropyl-amine (Intermediate 158, 600.0 mg, 2.49 mmols), ethyl iodide (1.56 g, 10.0 mmols), and $K_2CO_3$ (690.0 mg, 5.00 mmols) in 10 mL acetone was heated at 60° C. for 18 hours. The mixture was cooled to room temperature, diluted with $H_2O$, and extracted with EtOAc. The combined organic layers were washed with $H_2O$ and saturated aqueous NaCl before being dried ($MgSO_4$) and concentrated under reduced pressure. The title compound was isolated by column chromatography (2.5% EtOAc-hexanes).

$^1$H NMR ($CDCl_3$) δ: 7.23 (2H, m), 7.12 (1H, d, J=7.6 Hz), 3.62 (2H, s), 2.56 (2H, q, J=7.3 Hz), 2.29 (31H, s), 1.75 (1H, m), 1.04(3H, t, J=7.3 Hz), 0.39 (2H, m), 0.30 (2H, m).

Cyclopropyl-ethyl-(2-methyl-4-trimethylsilanylethynyl-benzyl)-amine (Intermediate 160)

Using General Procedure D; (4-bromo-2-methyl-benzyl)-cyclopropyl-ethyl-amine (Intermediate 159, 620.0 mg, 2.31 mmols) in triethylamine (8 mL) was treated with copper(I) iodide (44.0 mg, 0.23 mmol) and then sparged with argon for 15 minutes. Trimethylsilylacetylene (1.04 g, 10.6 mmols) was then added followed by dichlorobis-(triphenylphosphine)palladium(II) (162.0 mg, 0.23 mmol). The resulting reaction mixture was heated to 70° C. for 5 days. The title compound (650.0 mg, 98%) was isolated by chromatography (1–4% EtOAc-hexanes).

$^1$H NMR ($CDCl_3$) δ: 7.32 (1H, s), 7.20 (2H, m), 3.65 (2H, s), 2.55 (2H, q, J=7.3 Hz), 2.28 (3H, s), 1.74 (1H, m), 1.03 (3H, t, J=7.3 Hz), 0.36 (2H, m), 0.27 (2H, m), 0.24 (9H, s).

Cyclopropyl-ethyl-(4-ethynyl-2-methyl-benzyl)-amine (Intermediate 161)

Using General Procedure E; cyclopropyl-ethyl-(2-methyl-4-trimethylsilanylethynyl-benzyl)-amine (Intermediate 160, 650.0 mg, 2.30 mmols) in methanol (10 mL) was treated with potassium carbonate (100.0 mg, 0.72 mmol) and stirred overnight at ambient temperature. The crude alkyne (495 mg, 99%) was used directly in the next reaction.

¹H NMR (CDCl₃) δ: 7.32 (1H, s), 7.21 (2H, m), 3.66 (2H, s), 3.01 (1H, s), 2.56 (2H, q, J=7.3 Hz), 2.29 (3H, s), 1.76 (1H, m), 1.04 (3H, t, J=7.3 Hz), 0.40 (2H, m), 0.29 (2H, m).

Ethyl 4-{4-[(cyclopropyl-ethyl-amino)-methyl]-3-methyl-phenylethynyl}-benzoate (Compound 128, General Formula 6)

Using General Procedure F; cyclopropyl-ethyl-(4-ethynyl-2-methyl-benzyl)-amine (Intermediate 161, 190.0 mg, 0.89 mmol) and ethyl-4-iodo benzoate (Reagent A, 245.0 mg, 0.89 mmol) in triethylamine (5 mL) was treated with copper(I)iodide (56.0 mg, 0.30 mmol) and sparged with argon for 15 minutes. Dichlorobis(triphenylphosphine)-palladium(II) (208 mg, 0.30 mmol) was added and the reaction mixture was stirred overnight at room temperature. Column chromatography (3–5% EtOAc-hexanes) afforded the title compound.

¹H NMR (CDCl₃) δ: 8.01 (2H, d, J=8.2 Hz), 7.56 (2H, d, J=8.2 Hz), 7.31–7.24 (3H, m), 4.38 (2H, q, J=7.1 Hz), 3.68 (2H, s), 2.58 (2H, q, J=7.3 Hz), 2.32 (3H, s), 1.77 (1H, m), 1.39 (3H, t, J=7.1 Hz), 1.05 (3H, t, J=7.3 Hz), 0.39 (2H, m), 0.31 (2H, m).

Methyl (4-{4-[(cyclopropyl-ethyl-amino)-methyl]-3-methyl-phenylethynyl}-phenyl)-acetate) (Compound 129, General Formula 6)

Using General Procedure F; cyclopropyl-ethyl-(4-ethynyl-2-methyl-benzyl)-amine (Intermediate 161, 300.0 mg, 1.41 mmols) and methyl-(4-iodophenyl)-acetate (Reagent B, 388.0 mg, 1.41 mmols) in triethylamine (8 mL) was treated with copper(I)iodide (67.0 mg, 0.35 mmol) and sparged with argon for 15 minutes. Dichlorobis(triphenylphosphine)palladium(II) (246 mg, 0.35 mmol) was added and the reaction mixture was stirred overnight at room temperature. Column chromatography (5–7% EtOAc-hexanes) afforded 270.0 mg (53%) of the title compound as a pale-yellow oil.

¹H NMR (CDCl₃) δ: 7.47 (2H, d, J=7.9 Hz), 7.30–7.22 (5H, m), 3.70 (3H, s), 3.68 (2H, s), 3.63 (2H, s), 2.58 (2H, q, J=7.3 Hz), 2.32 (3H, s), 1.77 (1H, m), 1.05 (3H, t, J=7.3 Hz), 0.39 (2H, m), 0.30 (2H, m).

4-{4-[(Cyclopropyl-ethyl-amino)-methyl]-3-methyl-phenylethynyl}-benzoic acid: (Compound 130, General Formula 6)

Using General Procedure I; a solution of ethyl 4-{4-[(cyclopropyl-ethyl-amino)-methyl]-3-methyl-phenylethynyl}-benzoate (Compound 128, 130.0 mg, 0.36 mmol) in ethanol (5 mL) and tetrahydrofuran (5 mL) was treated with NaOH (360.0 mg, 9.0 mmols, 3.0 mL of a 3N aqueous solution) and stirred overnight at room temperature. Work-up afforded 115.0 mg (96%) of the title compound as a colorless solid.

¹H NMR (d₆-acetone) δ: 8.05 (2H, d, J=8.2 Hz), 7.64 (2H, d, J=8.2 Hz), 7.32 (3H, m), 3.73 (2H, s), 2.59 (2H, q, J=7.3 Hz), 2.35 (3H, s), 1.83 (1H, m), 1.05 (3H, t, J=7.3 Hz), 0.38 (2H, m), 0.27 (2H, m).

(4-{4-[(Cyclopropyl-ethyl-amino)-methyl]-3-methyl-phenylethynyl}-phenyl)-acetic acid (Compound 131, General Formula 6)

Using General Procedure I; a solution of methyl (4-{4-[(cyclopropyl-ethyl-amino)-methyl]-3-methyl-phenylethynyl}-phenyl)-acetate (Compound 129, 140.0 mg, 0.39 mmol) in ethanol (5 mL) and tetrahydrofuran (5 mL) was treated with NaOH (360.0 mg, 9.0 mmols, 3.0 mL of a 3N aqueous solution) and stirred overnight at room temperature. Work-up followed by HPLC (Partisil-10 pac 10% H₂O—CH₃CN) afforded the title compound.

¹H NMR (CDCl₃) δ: 7.45 (2H, d, J=8.2 Hz), 7.25 (5H, m), 4.16 (2H, m), 3.82 (2H, s), 3.56 (2H, s), 2.75 (2H, q, J=7.3 Hz), 2.30 (3H, s), 1.86 (1H, m), 1.14 (3H, t, J=7.3 Hz), 0.54 (2H, m), 0.46 (2H, m).

Ethyl {4-(4-cyclopropylaminomethyl-3-isopropyl-phenylethynyl}-benzoate (Compound 132, General Formula 6)

A solution of ethyl [4-(4-bromomethyl-3-isopropyl-phenylethynyl)-benzoate (Intermediate 155, 110.0 mg, 0.29 mmol) and cyclopropylamine (420.0 mg, 7.4 mmols) in EtOH (5 mL) was stirred at 25° C. for 6 hours and then concentrated under reduced pressure. The residue was dissolved in EtOAc and washed with saturated aqueous NaHCO₃, H₂O and saturated aqueous NaCl. The solution was dried (MgSO₄) and concentrated under reduced pressure to give 103 mg (99%) of the title compound as an orange oil.

¹H NMR (CDCl₃) δ: 8.01 (2H, d, J=8.5 Hz), 7.59 (2H, d, J=8.5 Hz), 7.47 (1H, s), 7.30 (2H, m), 4.38 (2H, q, J=7.1 Hz), 3.89 (2H, s), 3.26 (1H, septet, J=7.0 Hz), 2.17 (1H, m), 1.40 (3H, t, J=7.1 Hz), 1.26 (6H, d, J=7.0 Hz), 0.45 (2H, m), 0.39 (2H, m).

Ethyl 4-{4-[(cyclopropyl-ethyl-amino)-methyl]-3-isopropyl-phenylethynyl}-benzoate (Compound 133, General Formula 6)

To a solution of ethyl {4-(4-cyclopropylaminomethyl-3-isopropyl-phenylethynyl}-benzoate (Compound 132, 103.0 mg, 0.29 mmol) in 6 mL of acetone was added ethyl iodide (67.0 mg, 0.43 mmol) and K₂CO₃ (79.0 mg, 0.57 mmol). The mixture was stirred at 60° C. for 6 hours, cooled to room temperature and quenched by the addition of H₂O. The mixture was extracted with EtOAc and the combined organic layers were washed with H₂O and saturated aqueous NaCl before being dried (MgSO₄) and concentrated under reduced pressure. Column chromatography (4–5% EtOAc-hexanes) afforded 68.0 mg (59%) of the title compound.

¹H NMR (CDCl₃) δ: 8.01 (2H, d, J=8.6 Hz), 7.58 (2H, d, J=8.6 Hz), 7.44 (1H, s), 7.28 (2H, m), 4.39 (2H, q, J=7.1 Hz), 3.73 (2H, s), 3.55 (1H, septet, J=6.6 Hz), 2.57 (2H, q, J=7.3 Hz), 1.75 (1H, m), 1.40 (3H, t, J=7.1 hz), 1.22 (6H, d, J=6.6 Hz), 1.05 (3H, t, J=7.3 Hz), 0.37 (2H, m), 0.28 (2H, m).

4-{4-[(Cyclopropyl-ethyl-amino)-methyl]-3-isopropyl-phenylethynyl}-benzoic acid (Compound 134, General Formula 6)

Using General Procedure I; a solution of ethyl 4-{4-[(cyclopropyl-ethyl-amino)-methyl]-3-isopropyl-phenylethynyl}-benzoate (Compound 133, 68.0 mg, 0.17 mmol) in ethanol (3 mL) and tetrahydrofuran (3 mL) was treated with NaOH (600.0 mg,15.0 mmols, 3.0 mL of a 5N aqueous solution) and stirred overnight at room temperature and then at 55° C. for 9 hours. Work-up followed by crystallization of the solid residue from hot CH₃CN afforded 45.0 mg (72%) of the title compound as a pale-yellow solid.

¹H NMR (d₆-acetone δ: 8.05 (2H, d, J 8.1 Hz), 7.66 (2H, d, J=8.1 Hz), 7.49 (1H, s), 7.32 (2H, m), 3.78 (2H, s), 3.44 (1H, septet, J=6.7 Hz), 2.59 (2H, q, J=7.3 Hz), 1.80 (1H, m), 1.21 (6H, d, J=6.7 Hz), 1.05 (3H, t, J=7.3 Hz), 0.40 (2H, m), 0.26 (2H, m).

Methyl [4-(8,8-dimethyl-5-oxo-5,6,7,8-tetrahydro-naphthalen-2-yl-ethynyl)-phenyl]-acetate (Compound 4, General Formula 8)

Using General Procedure F; 6-ethynyl-4,4-dimethyl-3,4-dihydro-2H-naphthalen-1-one (Intermediate 13, 190.0 mg, 0.96 mmol) and methyl-(4-iodophenyl)-acetate (Reagent B, 245.0 mg, 0.96 mmol) in triethyl amine (8 mL) was treated with copper(I)iodide (46 mg, 0.24 mmol) and sparged with argon for 15 minutes. Dichlorobis(triphenylphosphine) palladium(II) (168 mg, 0.24 mmol) was added and the reaction mixture was stirred overnight at room temperature. Column chromatography (10–20% EtOAc-hexanes) afforded 250.0 mg (75%) of the title compound as a pale-yellow solid.

$^1$H NMR (CDCl$_3$) δ: 7.99 (1H, d, J=7.9 Hz), 7.57 (1H, d, J=1.5 Hz), 7.51 (2H, d, J=8.5 Hz), 7.43 (1H, dd, J=1.5, 7.9 Hz), 7.29 (2H, d, J=8.5 Hz), 3.70 (3H, s), 3.65 (2H, s), 2.73 (2H, t, J=7.0 Hz), 2.04 (2H, t, J=7.0 Hz), 1.41 (6H, s).

Methyl [4-(5-hydroxy-8,8-dimethyl-5,6,7,8-tetrahydro-naphthalen-2-yl-ethynyl)-phenyl]-acetate (Compound 135, General Formula 4)

To a solution of methyl [4-(8,8-dimethyl-5-oxo-5,6,7,8-tetrahydro-naphthalen-2-yl-ethynyl)-phenyl]-acetate (Compound 4) in 5 mL MeOH at 0° C. was added NaBH$_4$ (18.0 mg, 0.48 mmol). The reaction was stirred at 0° C. for 2 hours and then quenched by the addition of H$_2$O. The solution was diluted with Et$_2$O and washed with H$_2$O and saturated aqueous NaCl before being dried (MgSO$_4$) and the solvents were removed under reduced pressure. Column chromatography (20–40% EtOAc-hexanes) afforded 140.0 mg (87%) of the title compound as a colorless oil.

$^1$H NMR (CDCl$_3$) δ: 7.49 (3H, m), 7.39 (1H, d, J=7.9 Hz), 7.31 (1H, dd, J=1.5, 7.9 Hz), 7.25 (2H, d, J=8.2 Hz), 4.58 (1H, bs), 3.68 (3H, s), 3.62 (2H, s), 2.05 (1H, m), 1.79 (2H, m), 1.60 (1H, m), 1.33 (3H, s), 1.26 (3H, s).

Methyl [4-(5-imidazol-1-yl-8,8-dimethyl-5,6,7,8-tetrahydro-naphthalen-2-ylethynyl)-phenyl]-acetate (Compound 136, General Formula 4)

A solution of methyl [4-(5-hydroxy-8,8-dimethyl-5,6,7,8-tetrahydro-naphthalen-2-ylethynyl)-phenyl]-acetate (Compound 135, 140.0 mg, 0.40 mmol) and carbonyldiimidazole (136.0 mg, 0.84 mmol) in 5 mL THF was heated to 65° C. for 48 hours. The solution was cooled to room temperature and concentrated under reduced pressure. The residue was dissolved in Et$_2$O and washed with 5% aqueous NaOH, H$_2$O, and saturated aqueous NaCl before being dried (Na$_2$SO$_4$) and concentrated under reduced pressure. Column chromatography (5% MeOH—CH$_2$Cl$_2$) afforded 50.0 mg (31%) of the title compound as a colorless solid.

$^1$H NMR (CDCl$_3$) δ: 7.57 (1H, d, J=1.5 Hz), 7.52–7.45 (3H, m), 7.27 (3H, m), 7.08 (1H, s), 6.81 (2H, m), 5.30 (1H, t, J=5.8 Hz), 3.71 (3H, s), 3.65 (2H, s), 2.20 (2H, m), 1.75 (2H, m), 1.40 (3H, s), 1.36 (3H, s).

[4-(5-Imidazol-1-yl-8,8-dimethyl-5,6,7,8-tetrahydro-naphthalen-2-yl-ethynl)-phenyl]-acetic acid (Compound 137, General Formula 4)

Using General Procedure I; a solution of methyl [4-(5-imidazol-1-yl-8,8-dimethyl-5,6,7,8-tetrahydro-naphthalen-2-yl-ethynyl)-phenyl]-acetate (Compound 136, 50.0 mg, 0.13 mmol) in ethanol (4 mL) was treated with NaOH (120.0 mg, 3.0 mmols, 3.0 mL of a 1N aqueous solution) and stirred overnight at room temperature. Work-up afforded 40.0 mg (83%) of the title compound as a pale-orange solid.

$^1$H NMR (d$_4$-MeOH δ: 8.93 (1H, s), 7.68 (1H, s), 7.61 (1H, s), 7.54 (1H, s), 7.47 (2H, d, J 8.2 Hz), 7.31 (3H, m), 6.95 (1H, d, J 8.2 Hz), 5.83 (1H, t, J=5.8 Hz), 3.68 (1H, s), 3.63 (1H, s), 2.38 (1H, m), 2.26 (1H, m), 1.76 (2H, m), 1.45 (3H, s), 1.36 (3H, s).

Ethyl [4-(5-imidazol-1-yl-8,8-dimethyl-5,6,7,8-tetrahydro-naphthalen-2-yl-ethynyl)-benzoate (Compound 138, General Formula 4)

A solution of ethyl [4-(5-hydroxy-8,8-dimethyl-5,6,7,8-tetrahydro-naphthalen-2-yl-ethynyl)-benzoate (180.0 mg, 0.52 mmol) and carbonyldiimidazole (176.0 mg, 1.08 mmol) in 5 mL THF was heated to 65° C. for 21 hours. The solution was cooled to room temperature and concentrated under reduced pressure. The residue was dissolved in Et$_2$O and washed with 55 aqueous NaOH, H$_2$O, and saturated aqueous NaCl before being dried (Na$_2$SO$_4$) and concentrated under reduced pressure. Column chromatography (5% MeOH—CH$_2$Cl$_2$) afforded 50.0 mg (24%) of the title compound as a colorless solid.

$^1$H NMR (CDCl$_3$) δ: 8.03 (2H, d, J=7.9 Hz), 7.59 (3H, m), 7.46 (1H, s), 7.29 (1H, dd, J=1.5, 8.3 Hz), 7.09 (1H, s), 6.82 (1H, d, J=8.2 Hz), 6.81 (1H, s), 5.31 (1H, t, J=5.8 Hz), 4.39 (2H, q, J=7.1 Hz), 2.20 (2H, m), 1.75 (2H, m), 1.40 (9H, m).

[4-(5-Imidazol-1-yl-8,8-dimethyl-5,6,7,8-tetrahydro-naphthalen-2-yl-ethynyl)-benzoic acid (Compound 139, General Formula 4)

Using General Procedure I; a solution of ethyl [4-(5-imidazol-1-yl-8,8-dimethyl-5,6,7,8-tetrahydro-naphthalen-2-yl-ethynyl)-benzoate (Compound 138, 50.0 mg, 0.13 mmol) in ethanol (3 mL) and tetrahydrofuran (1 mL) was treated with NaOH (120.0 mg, 3.0 mmols, 3.0 mL of a 1N aqueous solution) and stirred overnight at room temperature. Work-up afforded 40.0 mg (87%) of the title compound as a colorless solid.

$^1$H NMR (d$_4$-MeOH δ: 8.92 (1H, s), 8.04 (2H, d, J=8.2 Hz), 7.74 (1H, d, J=1.5 Hz), 7.62 (3H, m), 7.57 (1H, t, J=1.5 Hz), 7.38 (1H, dd, J=1.5, 7.9 Hz), 6.97 (1H, d, J=7.9 Hz), 5.83 (1H, t, J=5.8 Hz), 2.33(2H, m), 1.78 (2H, m), 1.47 (3H, s), 1.39 (3H, s).

2-Isopropyl-4-trifluoromethanesulfonyloxy-benzyl acetate (Intermediate 162)

To a solution of 4-hydroxymethyl-3-isopropylphenyl 1,1,1-trifluoromethanesulfonate (Intermediate 149, 190.0 mg, 0.64 mmol) in 5 mL CH$_2$Cl$_2$ was added acetyl chloride (75.0 mg, 0.96 mmol) and pyridine(101.0 mg, 1.38 mmols). After stirring for 3 hours at 25° C. the reaction was quenched by the addition of H$_2$O and the resulting mixture extracted with EtOAc. The combined organic layers were washed with H$_2$O and saturated aqueous NaCl, dried (MgSO$_4$) and concentrated under reduced pressure. The title compound, 182 mg (84%), was isolated from the residual oil by column chromatography (5–10% EtOAc-hexanes) as a colorless oil.

$^1$H NMR (CDCl$_3$) δ: 7.43 (1H, d, J=8.7 Hz), 7.19 (1H, d, J=2.7 Hz), 7.09 (1H, dd, J=2.7, 8.5 Hz), 5.17 (2H, s), 3.18 (1H, septet, J=6.7 Hz), 2.10 (3H, s), 1.26 (6H, d, J=6.7 Hz).

4-Isopropenyloxymethyl-3-isopropyl-phenyl 1,1,1-trifluoromethanesulfonate (Intermediate 163)

Using General Procedure 1; 2-isopropyl-4-trifluoromethanesulfonyloxy-benzyl acetate (Intermediate 162, 182.0 mg, 0.54 mmols), and 1.1 mL of Tebbe's Reagent (159.0 mg, 0.56 mmols) afforded 130.0 mg (72%) of the title compound as a colorless oil after column chromatography (2–5% EtOAc-hexanes).

¹H NMR (CDCl₃) δ: 7.43 (1H, d, J=8.5 Hz), 7.18 (1H, d, J=2.6 Hz), 7.09 (1H, dd, J=2.6, 8.5 Hz), 4.75 (2H, s), 3.98 (2H, s), 3.12 (1H, septet, J=6.7 Hz), 1.88 (3H, s), 1.25 (6H, d, J=Hz).

3-Isopropyl-4-(1-methyl-cyclopropoxymethyl)-phenyl 1,1,1-trifluoromethanesulfonate (Intermediate 164)

Using General Procedure 2; 4-isopropenyloxymethyl-3-isopropylphenyl 1,1,1-trifluoromethanesulfonate (Intermediate 163, 130.0 mg, 0.39 mmol), Et₂Zn (272.0 mg, 2.2 mmols), and CH₂I₂ (702.0 mg, 2.6 mmols) in 3.0 mL Et₂O afforded 120.0 mg (89%) of the title compound as a colorless oil after column chromatography (4–5% EtOAc-hexanes).

¹H NMR (CDCl₃) δ: 7.39 (1H, d, J=8.5 Hz), 7.13 (1H, d, J=2.7 Hz), 7.05 (1H, dd, J=2.7, 8.5 Hz), 4.54 (2H, s), 3.16 (1H, septet, J=6.7 Hz), 1.47 (3H, s), 1.24 (6H, d, J=6.7 Hz), 0.86 (2H, m), 0.48 (2H, m).

[3-Isopropyl-4-(1-methyl-cyclopropoxymethyl)-phenylethynyl]-trimethylsilane (Intermediate 165)

Using General Procedure D; 3-isopropyl-4-(1-methyl-cyclopropoxymethyl)-phenyl 1,1,1-trifluoromethanesulfonate (Intermediate 164, 120.0 mg, 0.34 mmol) in triethylamine (2 mL) and anhydrous DMF (5 mL) was sparged with argon for 5 minutes. Trimethylsilyl acetylene (700.0 mg, 0.71 mmol) was then added followed by dichlorobis(triphenylphosphine)palladium(II) (24.0 mg, 0.03 mmol). The resulting reaction mixture was heated to 95° C. for 60 hours. The title compound 110.0 mg, (99%) was isolated by chromatography (0–1% EtOAc-hexanes).

¹H NMR (CDCl₃) δ: 7.36 (1H, s), 7.24 (2H, bs), 4.53 (2H, s), 3.11 (1H, septet, J=6.7 Hz), 1.45 (3H, s), 1.22 (6H, d, J=6.7 Hz), 0.85 (2H, m), 0.44 (2H, 0.25 (9H, s).

4-Ethynyl-2-isopropyl-1-(1-methyl-cyclopropoxymethyl)-benzene (Intermediate 166)

Using General Procedure E; [3-isopropyl-4-(1-methyl-cyclopropoxymethyl)-phenylethynyl]-trimethylsilane (Intermediate 165, 110.0 mg, 0.37 mmol) in methanol (6 mL) was treated with potassium carbonate (80.0 mg, 0.58 mmol) and stirred overnight at ambient temperature. The crude alkyne (84 mg, 100%) was used directly in the next reaction.

¹H NMR (CDCl₃) δ: 7.55 (1H, s), 7.41 (2H, m), 4.68 (2H, s), 3.26 (1H, septet, J=6.8 Hz), 3.18 (1H, s), 1.60 (3H, s), 1.37 (6H, d, J=6.8 Hz), 0.99 (2H, m), 0.59 (2H, m).

Methyl {4-[3-isopropyl-4-(1-methyl-cyclopropoxymethyl)-phenylethynyl]-phenyl}-acetate (Compound 140, General Formula 6)

Using General Procedure F; 4-ethynyl-2-isopropyl-1-(1-methyl-cyclopropoxymethyl)-benzene (Intermediate 166, 78.0 mg, 0.34 mmol) and methyl-(4-iodophenyl)-acetate (Reagent B, 94.0 mg, 0.34 mmol) in triethylamine (8 mL) was treated with copper(I)iodide (22.0 mg, 0.11 mmol) and sparged with argon for 5 minutes. Dichlorobis(triphenylphosphine)palladium(II) (79 mg, 0.11 mmol) was added and the reaction mixture was stirred at room temperature for 3.5 hours. Column chromatography (2–5% EtOAc-hexanes) afforded 77.0 mg (60%) of the title compound as a yellow oil.

¹H NMR (CDCl₃) δ: 7.49 (2H, d, J=8.2 Hz), 7.43 (1H, d, J=1.5 Hz), 7.33–7.24 (4H, m), 4.55 (2H, s), 3.70 (3H, s), 3.63 (2H, s), 3.14 (1H, septet, J=6.8 Hz), 1.47 (3H, s), 1.25 (6H, d, J=6.8 Hz), 0.86 (2H, m), 0.46 (2H, m).

{4-[3-Isopropyl-4-(1-methyl-cyclopropoxymethyl)-phenylethynyl-phenyl}-acetic acid (Compound 141, Formula 6)

Using General Procedure I; a solution methyl {4-[3-isopropyl-4-(1-methyl-cyclopropoxymethyl)-phenylethynyl]-phenyl}-acetate (Compound 140, 70.0 mg, 0.19 mmol) in ethanol (3 mL) and tetrahydrofuran (3 mL) was treated with NaOH (240.0 mg, 6.0 mmols, 2.0 mL of a 3N aqueous solution) and stirred overnight at room temperature. Work-up and purification by HPLC (Partisil 10-pac, 10% H₂O/CH₃CN) afforded of the title compound as a colorless solid.

¹H NMR (CDCl₃) δ: 7.50 (2H, d, J=8.2 Hz), 7.43 (1H, s), 7.33–7.24 (4H, m), 4.55 (2H, s), 3.65 (2H, s), 3.14 (1H, septet, J=6.7 Hz), 1.47 (3H, s), 1.25 (6H, d, J=6.7 Hz), 0.87 (2H, m), 0.46 (2H, m).

2,6-Di-tert-butyl-4-trimethylsilanylethynyl-phenol: (Intermediate 167)

Following General Procedure D and using 4-bromo-2,6-di-t-butyl-phenol (1.43 g, 5 mmol), triethyl amine (15 mL), anhydrous tetrahydrofuran (15 mL), copper(I)iodide (0.06 g, 0.3 1 mmol), trimethylsilyl acetylene (4.9 g, 50 mmol) and dichlorobis(triphenylphosphine)palladium(II) (0.1 8 g, 0.26 mmol) followed by flash column chromatography over silica gel (230–400 mesh) using hexane as eluent, the title compound was obtained (1.35 g, 90%).

¹H NMR (300 MHz, CDCl₃): δ 7.29 (s, 2H), 5.35 (s, 1H), 1.42 (s, 18H), 0.24 (s, 9H).

(3,5-Di-tert-butyl-4-methoxy-phenylethynyl)-trimethyl-silane: (Intermediate 168)

A solution 2,6-di-tert-butyl-4-trimethylsilanylethynyl-phenol (Intermediate 167, 0.302 g, 1 mmol) in acetone (5 mL) was treated with potassium carbonate (0.13 g, 1 mmol) and methyl iodide (0.142 g, 1 mmol) and stirred overnight at room temperature. The volatiles were distilled off in vacuo and the residue was purified by flash column chromatography on silica gel (230–400 mesh) using ethyl acetate as the eluent to afford the title compound as a white solid (0.28 g, 90%).

¹H NMR (300 MHz, CDCl₃): δ 7.41 (s, 2H), 3.70 (s, 3H), 1.49 (s, 18H), 0.30 (s, 9H).

1,3-Di-tert-butyl-5-ethynyl-2-methoxy-benzene: (Intermediate 169)

Following General Procedure E and (3,5-di-tert-butyl-4-methoxy-phenylethynyl)-trimethyl-silane (Intermediate 168, 0.28 g, 0.9 mmol), potassium carbonate (0.98 g, 7.1 mmol) and methanol (10 mL) followed by flash column chromatography over silica gel (230–400 mesh) using hexane as the eluent, the title compound was obtained (0.23 g, 100%).

¹H NMR (300 MHz, CDCl₃): δ 7.46 (s, 2H), 3.75 (s, 3H), 3.05 (s, 1H), 1.49 (s, 18H).

[4-(3,5-Di-tert-butyl-4-methoxy-phenylethynyl)-phenyl]-acetic acid methyl ester: (Compound 142, General Formula 5)

Following General Procedure F and using 1,3-di-tert-butyl-5-ethynyl-2-methoxy-benzene (Intermediate 169, 0.094 g, 0.36 mmol), methyl-4-iodo phenyl acetate (Reagent B, 0.09 g, 0.32 mmol), triethyl amine (5 mL), anhydrous tetrahydrofuran (5 mL), copper(I)iodide (0.02 g, 0.1 mmol) and dichlorobis(triphenylphosphine)palladium(II) (0.06 g, 0.085 mmol) followed by flash column chromatography over silica gel (230–400 mesh) using 10% ethyl acetate in hexane as the eluent, the title compound (0.11 4 g, 81%) was obtained as an oil.

$^1$H NMR (300 MHz, CDCl$_3$): δ 7.52 (d, 2H, J=8.0 Hz), 7.46 (s, 2H), 7.28 (d, 2H, J=8.2 Hz), 3.72 (s, 3H), 3.71(s, 3H), 3.66 (s, 2H), 1.47 (s, 18H).

[4-(3,5-Di-tert-butyl-4-methoxy-phenylethynyl)-phenyl]-acetic acid: (Compound 143, General Formula 5)

Following General Procedure I and using [4-(3,5-di-tert-butyl-4-methoxy-phenylethynyl)-phenyl]-acetic acid methyl ester (Compound 142, 0.114 g, 0.29 mmol), 5M aqueous sodium hydroxide solution (2 mL) and ethanol (4 mL), followed by preparative reverse phase HPLC using 10% water in acetonitrile as the mobile phase, the title compound was obtained as a white solid (0.097 g, 88%).

$^1$H NMR (300 MHz, CDCl$_3$): δ 7.55(d, 2H, J=8.0 Hz), 7.48 (s, 2H), 7.30 (d, 2H, J=8.2 Hz), 3.74 (s, 3H), 3.69 (s, 2H), 1.49 (s, 18H).

[4-(3,5-Di-tert-butyl-4-methoxy-phenylethynyl)-2-fluoro-phenyl-acetic acid methyl ester: (Compound 144, General Formula 5)

Following General Procedure F and using 1,3-di-tert-butyl-5-ethynyl-2-methoxy-benzene (Intermediate 169, 0.087 g, 0.33 mmol), methyl-2-fluoro-4-iodo phenyl acetate (Reagent H, 0.088 g, 0.30 mmol), triethyl amine (5 mL), anhydrous tetrahydrofuran (10 mL), copper(I)iodide (0.02 g, 0. 1 mmol) and dichlorobis(triphenylphosphine)palladium (II) (0.06 g, 0.085 mmol) followed by flash column chromatography over silica gel (230–400 mesh) using 10% ethyl acetate in hexane as the eluent, the title compound (0. 122 g, 89%) was obtained.

$^1$H NMR (300 MHz, CDCl$_3$): δ 7.46 (s, 2H), 7.33–7.24 (m, 3H), 3.75 (s, 3H), 3.73(s, 3H), 3.72 (s, 2H), 1.48 (s, 18H).

4-(3,5-Di-tert-butyl-4-methoxy-phenylethynyl)-2-fluoro-phenyl]-acetic acid: (Compound 145, General Formula 5)

Following General Procedure I and using [4-(3,5-di-tert-butyl-4-methoxy-phenylethynyl)-2-fluoro-phenyl]-acetic acid methyl ester (Compound 144, 0.122 g, 0.29 mmol), 5M aqueous sodium hydroxide solution (1 mL) and ethanol (4 mL), followed preparative reverse phase HPLC using 10% water in acetonitrile as the mobile phase, the title compound was obtained as a white solid (0.077 g, 65%).

$^1$H NMR (300 MHz, CDCl$_3$): δ 7.42 (s, 2H), 7.29–7.19 (m, 3H), 3.71 (s, 2H), 3.69 (s, 3H), 1.43 (s, 18H).

What is claimed is:
1. A compound of the formula

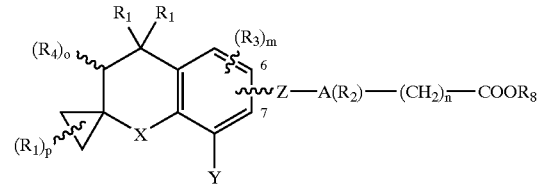

wherein

A is selected from a group consisting of pyridazinyl, pyrimidinyl and pyrazinyl, said groups being unsubstituted or substituted with one or two R$_2$ groups;

X is NR where R is H, alkyl of 1 to 6 carbons or benzyl;

Y is H, alkyl of 1 to 10 carbons, benzyl, lower alkyl or halogen substituted benzyl, fluoro-substituted alkyl of 1 to 10 carbons, cycloalkyl of 3 to 6 carbons, lower alkyl substituted cycloalkyl of 3 to 6 carbons, Cl, Br, or I;

Z is
—C≡C—,
—(CR$_1$=CR$_1$)$_{n'}$ where n' is an integer having the value 1–5,
—CO—NR$_1$—,
NR$_1$—CO—;
—CO—O—,
—O—CO—,
—CS—NR$_1$—,
NR$_1$—CS—,
—CO—S—,
—S—CO—,
—N=N—;

R$_1$ is independently H or alkyl of 1 to 6 carbons;

p is an integer having the values of 0 to 4;

R$_2$ is independently H, alkyl of 1 to 6 carbons, F, Cl, Br, I, CF$_3$, fluoro substituted alkyl of 1 to 6 carbons, alkoxy of 1 to 6 carbons, or alkylthio of 1 to 6 carbons;

R$_3$ is independently alkyl of 1 to 6 carbons, F, Cl, Br, I, fluoro substituted alkyl of 1 to 6 carbons, OH, SH, alkoxy of 1 to 6 carbons, alkylthio of 1 to 6 carbons or benzyl;

m is an integer having the values 0 to 2;

R$_4$ is independently H, alkyl of 1 to 6 carbons, or F; fluorosubstituted alkyl of 1 to 6 carbons, or halogen;

o is an integer having the values of 0 to 2;

n is an integer having the values of 0 to 4, and

R$_8$ is H, alkyl of 1 to 6 carbons, —CH$_2$O(C$_{1-6}$-alkyl), or a cation of a pharmaceutically acceptable base.

2. A compound in accordance with claim 1 where n is 0, 1 or 2.

3. A compound in accordance with claim 1 where Z is —C≡C—, —CO—NR$_1$—, —CO—O—, or —(CR$_1$=CR$_1$)$_{n'}$, where n' is 1.

4. A compound in accordance with claim 1 where the Z group is attached to the 6-position of the bicyclic moiety.

5. A compound in accordance with claim 1 where Y is H, lower alkyl of 1 to 3 carbons or cyclopropyl.

6. A compound in accordance with claim 1 where Z is —C≡C—, or CO—O.

7. A compound in accordance with claim 6 where Y is H or cyclopropyl.

8. A compound in accordance with claim 1 where A is pyridazinyl.

9. A compound in accordance with claim 7 where A is pyridazinyl.

10. A compound in accordance with claim 1 where A is pyrimidinyl.

11. A compound in accordance with claim 7 where A is pyrimidinyl.

12. A compound in accordance with claim 1 where A is pyrazinyl.

13. A compound in accordance with claim 7 where A is pyrazinyl.

\* \* \* \* \*

UNITED STATES PATENT AND TRADEMARK OFFICE
CERTIFICATE OF CORRECTION

PATENT NO.  : 6,531,599 B2
DATED       : March 11, 2003
INVENTOR(S) : Vasudevan et al.

It is certified that error appears in the above-identified patent and that said Letters Patent is hereby corrected as shown below:

Column 8,
Line 6, "—C≡—C—" should be -- -C≡C- --.

Column 11,
Line 10, "usefull" should be -- useful --.

Column 22,
Line 27, Formula 10,

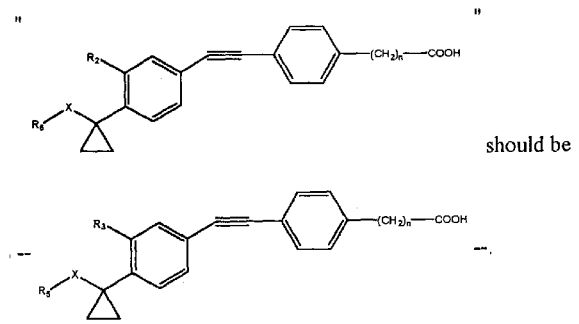

Column 26,
Line 44, Reaction Scheme 1, Reagent H,

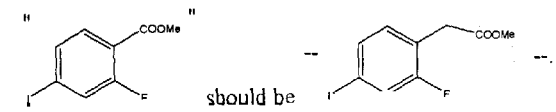

Line 51, Reaction Scheme 1, Intermediate 4,

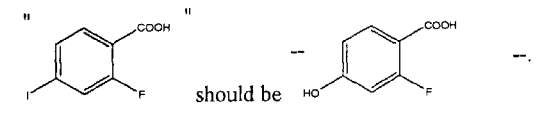

Column 31,
Line 55, Reaction Scheme 4, Intermediate 25 → Intermediate 26, above the arrow "CHCl$_2$" should be -- CH$_2$Cl$_2$ --.

Column 32,
Line 32, Reaction Scheme 4, above "Reaction Scheme 5" insert
-- TPAP = tetra-n-propyl ammonium peruthenate
    NMO = N-methylmorpholine N-Oxide
    reference 1 Tomita et al. J. Chem. Soc. (c), 1969, 183-188
    reference 2 Chaplinski et al. Angew. Chem. Int. Edn. Engl., 1996, 35, 413-414 --.

UNITED STATES PATENT AND TRADEMARK OFFICE
CERTIFICATE OF CORRECTION

PATENT NO. : 6,531,599 B2
DATED : March 11, 2003
INVENTOR(S) : Vasudevan et al.

It is certified that error appears in the above-identified patent and that said Letters Patent is hereby corrected as shown below:

Column 32 (cont'd),
Line 38, Reaction Scheme 5, above the arrow, "NEt$_2$" should be -- NEt$_3$ --.

Column 45,
Line 6, Reaction Scheme 13, Intermediate 133,

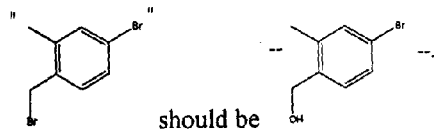

Line 64, Reaction Scheme 14, Intermediate 143 → Intermediate 146, below the arrow, "t-Buli" should be -- t-BuLi --.

Column 51,
Line 64, "2 mL" should be -- 20 mL --.

Column 52,
Line 33, "9.2" should be -- 19.2 --.

Column 58,
Line 48, "0.1 6" should be -- 0.16 --.

Column 59,
Line 28, "2.4" should be -- 2.24 --.
Line 30, "7.6" should be -- 7.26 --.
Line 33, "8.8" should be -- 8,8 --.
Line 34, "ethenyl" should be -- ethynyl --.
Line 42, "0.1 35" should be -- 0.135 --.

Column 60,
Line 20, "0.1 8" should be -- 0.18 --.
Line 49, "$_1$H" should be -- $^1$H --.

Column 61,
Line 31, "0.1 8" should be -- 0.18 --.

UNITED STATES PATENT AND TRADEMARK OFFICE
CERTIFICATE OF CORRECTION

PATENT NO. : 6,531,599 B2
DATED : March 11, 2003
INVENTOR(S) : Vasudevan et al.

It is certified that error appears in the above-identified patent and that said Letters Patent is hereby corrected as shown below:

Column 68,
Line 51, "8.8" should be -- 8,8 --.
Line 52, "tetrahdro" should be -- tetrahydro --.
Line 52, "ethenyl" should be -- ethynyl --.

Column 72,
Line 9, "a,a-" should be -- α,α- --.

Column 73,
Line 16, "11H" should be -- 1H --.

Column 76,
Line 32, "tetrahydroftiran" should be -- tetrahydrofuran --.

Column 79,
Line 45, "tetrahydroffiran" should be -- tetrahydrofuran --.

Column 82,
Lines 22, 35 and 38, "tetramenthyl" should be -- tetramethyl --.

Column 87,
Line 7, "2.1 1" should be -- 2.11 --.

Column 90,
Lines 12-13, "tetrahydrofuiran" should be -- tetrahydrofuran --.

Column 91,
Line 18, "Methoxacyclopropyl" should be -- Methoxycyclopropyl --.

Column 92,
Line 9, "1H" should be -- $^1$H --.
Line 26, "isopropoxacyclopropyl" should be -- isopropoxycyclopropyl --.

Column 94,
Line 61, "tetrahydrofiran" should be -- tetrahydrofuran --.

Column 96,
Line 9, "benzyloxycaclopropyl" should be -- benzyloxycyclopropyl --.
Line 46, "Benzyloxacyclopropyl"" should be -- Benzyloxycyclopropyl --.

UNITED STATES PATENT AND TRADEMARK OFFICE
CERTIFICATE OF CORRECTION

PATENT NO. : 6,531,599 B2
DATED : March 11, 2003
INVENTOR(S) : Vasudevan et al.

It is certified that error appears in the above-identified patent and that said Letters Patent is hereby corrected as shown below:

Column 97,
Line 67, "tetrahydrofuiran" should be -- tetrahydrofuran --.

Column 99,
Line 10, "Dimefylpropyl" should be -- Dimethylpropyl --.
Line 67, "(9H," should be -- (9H, s), --.

Column 100,
Line 53, "cyclopropl" should be -- cyclopropyl --.

Column 102,
Line 17, "for minutes" should be -- for 5 minutes --.
Line 24, "(2H)," should be -- (2H, --.
Line 63, , "Benzyloxacyclopropyl"" should be -- Benzyloxycyclopropyl --.

Column 107,
Line 54, "phenylethnyl" should be -- phenylethynyl --.

Column 123,
Line 55, "$H_2$ O" should be -- $H_2O$ --.

Column 124,
Line 50, "benzyloxyy" should be -- benzyloxy --.
Line 64, "phenylethenyl" should be -- phenylethynyl --.

Column 127,
Line 50, "tetrahydrofuiran" should be -- tetrahydrofuran --.

Column 128,
Line 39, "(31H" should be -- (3H --.

Column 130,
Line 63, "acetone" should be -- acetone) --.
Line 63, "J 8.1" should be -- J = 8.1 --.

UNITED STATES PATENT AND TRADEMARK OFFICE
CERTIFICATE OF CORRECTION

PATENT NO. : 6,531,599 B2
DATED : March 11, 2003
INVENTOR(S) : Vasudevan et al.

It is certified that error appears in the above-identified patent and that said Letters Patent is hereby corrected as shown below:

Column 131,
Line 1, "8.8" should be -- 8,8 --.
Line 59, "ethynl" should be -- ethynyl --.

Column 132,
Lines 1 and 38, "MeOH" should be -- MeOH) --.
Lines 2 and 3, "J 8.2" should be -- J = 8.2 --.

Column 133,
Line 38, "(2H, 0.25" should be -- (2H, m), 0.25 --.

Column 134,
Line 28, "0.3 1" should be -- 0.31 --.
Line 29, "0.1 8" should be -- 0.18 --.
Line 41, "0.13" should be -- 0.138 --.

Column 135,
Line 7, "0.11 4" should be -- 0.114 --.
Line 43, "0. 1" should be -- 0.1 --.
Line 46, "0. 122" should be -- 0.122 --.

Signed and Sealed this

Twentieth Day of April, 2004

JON W. DUDAS
*Acting Director of the United States Patent and Trademark Office*